United States Patent [19]

Koh et al.

[11] Patent Number: 5,442,062
[45] Date of Patent: Aug. 15, 1995

[54] IMIDAZOLE DERIVATIVES AND PHARMACEUTICAL COMPOSITIONS CONTAINING THE SAME

[75] Inventors: Keiko Koh; Mikio Taniguchi, both of Tsukuba; Noriie Itoh, Inashiki; Hiroshi Kushida, Shimodate; Osamu Morita; Hiroyoshi Yamada, both of Tsukuba; Kiyotaka Munesada, Shimotsuma; Kazuo Tsuzuki; Mineo Kunihara, both of Tsukuba; Yoshiji Fujita, Abiko, all of Japan

[73] Assignee: The Upjohn Company, Kalamazoo, Mich.

[21] Appl. No.: 122,446

[22] PCT Filed: Oct. 14, 1992

[86] PCT No.: PCT/US92/08584

§ 371 Date: Apr. 22, 1994

§ 102(e) Date: Apr. 22, 1994

[87] PCT Pub. No.: WO93/08193

PCT Pub. Date: Apr. 29, 1993

[30] Foreign Application Priority Data

| Oct. 24, 1991 | [JP] | Japan | 3-277537 |
| Dec. 7, 1991 | [JP] | Japan | 3-323474 |
| Apr. 15, 1992 | [JP] | Japan | 4-095191 |
| Aug. 14, 1992 | [JP] | Japan | 4-216809 |

[51] Int. Cl.$^6$ .............. C07D 237/26; C07D 237/32; C07D 257/04
[52] U.S. Cl. .................. 544/234; 544/238; 544/240; 548/254
[58] Field of Search .......... 544/234, 238, 251, 264, 544/269, 240; 548/254, 143, 146, 215

[56] References Cited

U.S. PATENT DOCUMENTS

| 3,562,271 | 2/1971 | Doebel et al. | 544/234 |
| 3,704,300 | 11/1972 | Hardtmann | 544/234 |
| 4,004,009 | 1/1977 | Anderson | 544/234 |
| 4,228,164 | 10/1980 | Szebeni et al. | 544/251 |
| 4,250,180 | 2/1981 | Kane et al. | 424/250 |
| 4,391,807 | 7/1983 | Alexander et al. | 544/234 |
| 4,472,400 | 9/1984 | Tully et al. | 544/251 |
| 4,495,187 | 1/1985 | Sarges | 514/250 |
| 4,526,890 | 7/1985 | Peet et al. | 544/234 |
| 4,690,930 | 9/1987 | Takada et al. | 544/234 |
| 4,722,701 | 9/1988 | Attwood et al. | 544/235 |
| 4,722,929 | 2/1988 | Austel et al. | 514/303 |
| 5,270,316 | 12/1993 | Suzuki et al. | 544/251 |
| 5,369,104 | 11/1994 | Miyake et al. | 544/234 |

FOREIGN PATENT DOCUMENTS

| 094095 | 11/1983 | European Pat. Off. ... C07D 487/04 |
| 149200 | 7/1985 | European Pat. Off. ... C07D 487/04 |
| 245637 | 11/1987 | European Pat. Off. ... C07D 471/04 |
| 399731 | 12/1990 | European Pat. Off. ... C07D 471/04 |
| 400974 | 12/1990 | European Pat. Off. ... C07D 471/04 |
| 401030 | 12/1990 | European Pat. Off. ... C07D 403/10 |
| 407102 | 1/1991 | European Pat. Off. ... C07D 495/04 |
| 426021 | 5/1991 | European Pat. Off. ... C07D 471/04 |
| 430300 | 6/1991 | European Pat. Off. ... C07D 473/00 |
| 461040 | 12/1991 | European Pat. Off. ... C07D 235/08 |
| 0668275 | 8/1989 | U.S.S.R. |
| 91/11999 | 8/1991 | WIPO ......... A61K 31/395 |
| 91/19715 | 12/1991 | WIPO ......... C07D 487/04 |

OTHER PUBLICATIONS

Suzuki et al., Adenosin A$_1$ Antagonists . . . , J. Med. Chem., vol. 35, No. 16, pp. 3066–3075, 1992.

Primary Examiner—Richard L. Raymond
Assistant Examiner—Deborah Lambkin
Attorney, Agent, or Firm—Lawrence T. Welch

[57] ABSTRACT

The present invention provides a novel imidazole derivative having the chemical formula

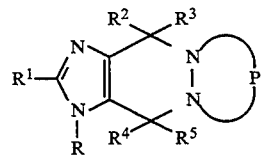

These compounds are useful for preventing or treating hypertension or congestive heart failure and have high activity, rapid action upon intravenous injection, good oral absorbtion, low toxicity, and long-lasting action. Also provided are pharmaceutical compositions which contain these compounds.

12 Claims, No Drawings

IMIDAZOLE DERIVATIVES AND PHARMACEUTICAL COMPOSITIONS CONTAINING THE SAME

This application is the national phase of international application PCT/US92/08584, filed 14 Oct. 1992, which claims the benefit of Japanese Patent Application Ser. No. 216809/92, filed 14 Aug. 1992, Japanese Patent Application Ser. No. 095191/92, filed 15 Apr. 1992, Japanese Patent Application Ser. No. 323474/91, filed 7 Dec. 1991, and Japanese Patent Application Ser. No. 277537/91, filed 24 Oct. 1991.

FIELD OF THE INVENTION

The present invention relates to a novel imidazole derivative or a pharmacologically acceptable ester or salt thereof and a pharmaceutical composition for preventing or treating hypertension, congestive heart failure, renal failure, glaucoma or hyperuricemia which contains the same as an active ingredient.

BACKGROUND OF THE INVENTION

It is widely known that Renin-Angiotensin-Aldosterone system is closely connected with hypertensive pathogenesis through control of blood pressure and the water/electrolyte balance. Prevention and treatment of hypertension including essential hypertension and further congestive heart failure by controlling this system have been studied for a long time. As the controlling methods, there are i) inhibition of synthesis or secretion of renin which is thought to be situated at the most upstream position of the system, ii) renin-inhibition of the conversion of the renin substrate (angiotensinogen) to angiotensin (I), iii) inhibition of the angiotensin converting enzyme (ACE) which converts angiotensin (I) into angiotensin (II) having strong vasoconstriction action, aldosterone secretion stimulating action, sympathetic nerve function promoting action and the like, iv) blockade of angiotensin (II) receptor, v) activation of angiotensinase to accelerate the degradation of the produced angiotensin (II).

Among them, the study of ACE inhibitors is most advanced, and many drugs have been used for preventing or treating hypertension or congestive heart failure. However, since the ACE inhibitors are not selective and act toward other systems such as kalliklein-kinin system and the like, there is a clinical problem in that side effects such as skin rash and dry cough occur frequently. For this reason, many attempts to develop a renin inhibitor which is thought to be more selective have been tried but none have been successfully marketed.

On the other hand, since salarasin obtained by modifying the terminal part of angiotensin (II) has been found to have the antagonism to the receptor of angiotensin (II) by D. T. Pals et al., the study on a receptor antagonist (hereinafter referred to as Ang-II antagonist) has begun. Studies are directed to search for a nonpeptidic compound without partial agonist activity which can be administered orally, and has long-lasting action. The first reports are found in JP-A 54-148788, JP-A 56-71073, JP-A 57-98270 and JP-A 58-157768, but the pharmacological activity is about 1/10000 of the practical level. An increase in this activity to a practical level was first reported in EP-A 0253310 and EP-A 0291969, and the compound called as Dup753 is currently in clinical tests.

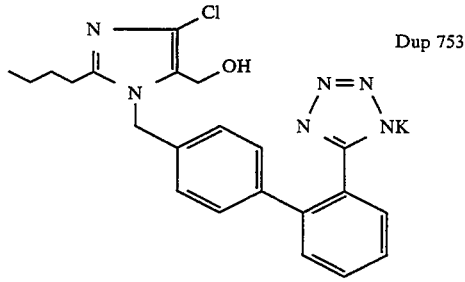

However, since this compound is usually produced as a mixture of regio-isomers (where the ratio depends on the reaction conditions), Dup753 can not be selectively synthesized unless a special process is used, and this is thought to be a problem for mass production. On the other hand, it has been recognized that an addition of a hydrophilic group on the 5-position of the imidazole ring is effective for increasing the pharmacological activity. This working hypothesis was compelled to be significantly modified by the finding of benzimidazoles shown in EP-A 039231717 (also reported in EP-A 0400835 and EP-A 0399732 later) and imidazopyridines (see EP-A 0399731, EP-A 0400974 and EP-A 01415886).

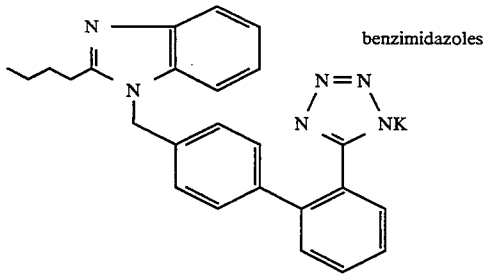

In addition, the present inventors have found that imidazobenzoquinones shown by the following formula have higher angiotensin (II) antagonist action and also have the vasodepressor activity in vivo tests, and filed a patent application (Japanese patent application No. 3-102639, 3-140057 and 3-205879).

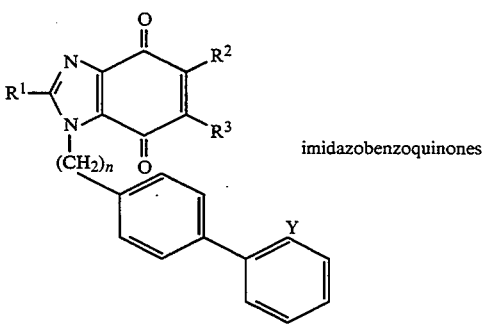

On the other hand, them have been reported many compounds possessing a fused imidazole structure with a nitrogen containing saturated and/or unsaturated cyclic compound. For example, Warner Lambert has been reported the following compound (EP-A 245637).

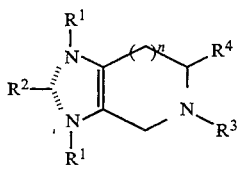

R⁴=—CH₂OR,—CH₂NR₂,—CHO,—CN,—CO₂R

However, WL-19 reported therein has the selective affinity to different type Ang-II receptors and the vasopressor activity is far from practical use [Chang et al., Mol. Pharmacology, 24, 347 (1990)]. Merck has been reported a wide group of compounds as shown in the following (EP-A 400974, WO91/11999), and further a 7-membered (EP-A 401030) or 5-membered (EP-A 407102) nitrogen containing saturated compound.

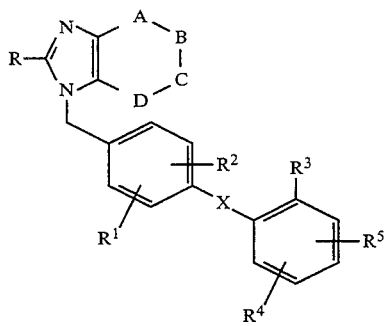

In particular, the compound wherein the fused ring is of the formula:

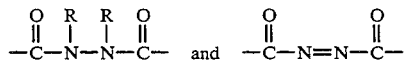

which is disclosed in EP-A 4430974 and WO91/11999 has a problem both in terms of stability and activity, in particular, in vivo activity, oral absorbability, weak hypotensive action and short duration of action, etc.

Takeda has been reported the following compound including a compound wherein the fused ring is of the formula:

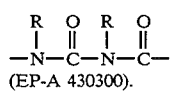

(EP-A 430300).

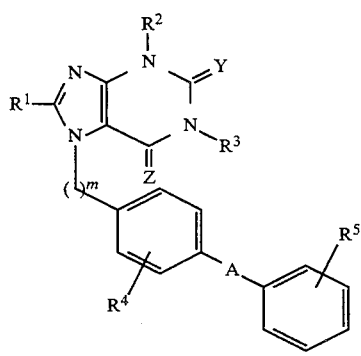

Searle has been reported the following imidazopyridazine derivatives (WO91/19715). However, when R¹ and/or R² are hydroxy group in the compound, formation of

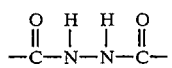

bond via keto + enol tautomerism can be also considered. The structure of the Searle compounds is as follows:

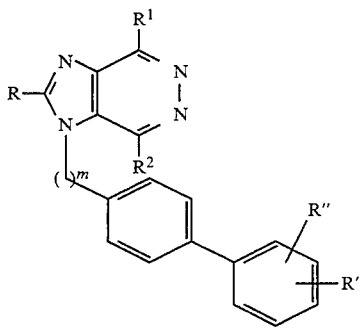

The following compound reported by Roussel Uclaf (EP-A 46 1040) includes

as the A ring. Also in this case, formation of

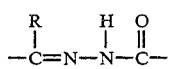

via keto ⇌ enol tautormerism can be considered.

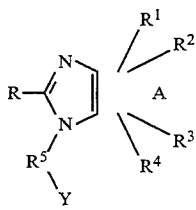

PROBLEMS TO BE SOLVED BY THE INVENTION

The present inventors have attempted to find a novel Ang-II antagonist as an agent for preventing or treating hypertension, congestive heart failure, renal failure, glaucoma or hyperuricemia, and studied drugs which have good stability, high activity, rapid manifestation of action upon intravenous injection, good oral absorbtion, low toxicity and long-lasting action. As a result, it has been found that novel imidazole derivatives having certain bridgehead hydrazine derivatives are effective. Thus, the present invention has been completed.

INFORMATION DISCLOSURE

As described above, there have been reported many compounds possessing a fused imidazole structure with a nitrogen containing saturated and/or unsaturated cyclic compound, see, EPA 245637; EPA 400974; WO 91/11999; EPA 401030; EPA 407102; EPA 430300; WO 91/19715 and EPA 461040.

SUMMARY OF THE INVENTION

The present invention provides an imidazole derivative represented by the general formula I:

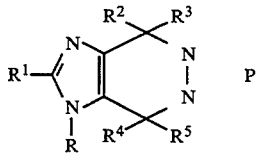

wherein
R¹ is
(a) hydrogen atom,
(b) $C_1$-$C_8$ alkyl group,
(c) $C_1$-$C_8$ alkoxy group,
(d) $C_1$-$C_8$ alkylthio group,
(e) $C_1$-$C_8$ alkylamino group,
(f) $C_1$-$C_8$ alkenyl group,
(g) $C_1$-$C_8$ alkynyl group,
(h) —$CF_3$ group,
(i) $C_6$-$C_{10}$ aryl group, or
(j) $C_6$-$C_{10}$ aralkyl group;
R is
(a) hydrogen atom, or
(b) a group selected from the following groups;

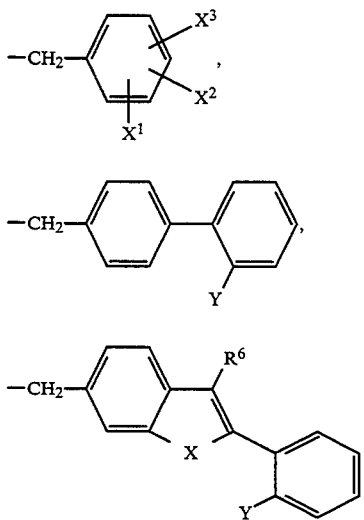

wherein
each occurrence of $X^1$, $X^2$ and $X^3$ is independently selected from
(a) hydrogen atom,
(b) halogen atom,
(c) $C_1$-$C_8$ alkyl group,
(d) $C_1$-$C_8$ alkoxy group,
(e) nitro group,
(f) cyano group,
(g) 1H-tetrazol-5-yl group or an alkali metal salt thereof,
(h) —$CO_2R^7$ group,
(i) —$CONR'R''$ group,
(j) —$CONHSO_2R^8$ group,
(k) an amino group,
(l) —$NHSO_2CF_3$ group
(m) —$SO_3H$ group, or
(n) a moiety selected from the following:

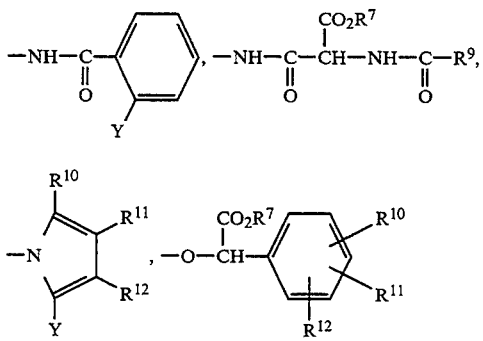

wherein
Y is
(a) cyano group,
(b) 1H-tetrazol-5-yl group or alkali metal salt thereof,
(C) —$CO_2R^7$ group,
(d) —$CONR'R''$ group,
(e) —$CONHSO_2R^8$ group,
(f) an amino group,
(g) —$NHSO_2CF_3$ group, or
(h) —$SO_3H$ group;
wherein
each occurrence of $R^2$, $R^3$, $R^4$ and $R^5$ is independently selected from
(a) hydrogen atom or
(b) $C_1$-$C_8$ alkyl group, or
(c) $R^2$ and $R^3$, or $R^4$ and $R^5$ taken together form a =O bond;
$R^6$ is
(a) hydrogen atom,
(b) halogen atom,
(c) $C_1$-$C_8$ alkyl group,
(d) —$CF_3$ group, or
(e) —$CF_2CF_3$ group;
$R^7$ is
(a) hydrogen atom,
(b) alkali metal atom, or
(c) $C_1$-$C_8$ alkyl group;
wherein
each occurrence of R' and R'' is independently
(a) hydrogen atom, or
(b) $C_1$-$C_8$ alkyl group, or
(c) R' and R'' are taken together to form an alicyclic structure;
$R^8$ is
(a) $C_1$-$C_8$ alkyl group,
(b) $C_6$-$C_{10}$ cycloalkyl group, or
(c) $C_6$-$C_{10}$ aryl group;
$R^9$ is
(a) $C_1$-$C_8$ alkyl group,
(b) $C_1$-$C_8$ alkoxy group,
(c) $C_6$-$C_{10}$ cycloalkyl group,
(d) $C_6$-$C_{10}$ cycloalkoxy group,
(e) $C_6$-$C_{10}$ aryl group, or
(f) $C_6$-$C_{10}$ aryloxy group;
$R^{10}$, $R^{11}$ and $R^{12}$ are independently
(a) hydrogen atom,
(b) halogen atom,
(c) $C_1$-$C_8$ alkyl group, (d) $C_1-C_8$ alkoxy group,
(e) nitro group,
(f) cyano group,
(g) —$CO_2R^7$ group, or
(h) —$CONR'R''$ group;

—P— is
(a) A—B—C—D—,
(b) A—B=C—D, or
(c) A=B—C=D; wherein A or D may be absent or present and wherein A—B—C—D, A—B=C—D or A=B—C=D represents, when A or D is not present, B—C—D, B=C—D, B—C=D, A—B—C, A—B=C or A=B—C, wherein these moieties are:
(a) —$CH(R^{13})$—$CH(R^{14})$—$CH(R^{15})$—,
(b) —$C(R^{13})$=$C(R^{14})$—$C(R^{15})$—,
(c) —$CH(R^{13})$—$C(R^{14})$=$C(R^{15})$—,
(d) —$CH(R^{13})$—$CH(R^{14})$—$C(=O)$—,
(e) —$C(=O)$—$CH(R^{14})$—$CH(R^{15})$—, or
(f) —$CH(R^{13})$—$C(=O)$—$CH(R^{15})$—, or represents, when A and D are present, as A—B—C—D—, A—B=C—D or A=B—C=D, wherein these moieties are:
(a) —$C(R^{13})(R^{16})$—$CH(R^{14})$—$CH(R^{15})$—$C(R^{17})(R^{18})$—,
(b) —$C(R^{13})(R^{16})$—$C(R^{14})$=$C(R^{15})$—$C(R^{17})(R^{18})$—,
(c) —$C(R^{13})$=$C(R^{14})$—$CH(R^{15})$=$C(R^{17})$—,
(d) —$C(=O)$—$CH(R^{14})$—$CH(R^{15})$—$C(R^{17})(R^{18})$—,
(e) —$C(R^{13})(R^{16})$—$C(=O)$—$CH(R^{15})$—$C(R^{17})(R^{18})$—,
(f) —$C(R^{13})(R^{16})$—$CH(R^{14})$—$C(=O)$—$C(R^{17})(R^{18})$—, or
(g) —$C(R^{13})(R^{16})$—$CH(R^{14})$—$CH(R^{15})$—$C(=O)$—;

wherein
each occurrence of $R^{13}$, $R^{14}$, $R^{15}$, $R^{16}$, $R^{17}$ and $R^{18}$ is independently
(a) hydrogen atom,
(b) $C_1-C_8$ alkyl group,
(c) $C_1-C_8$ fluoroalkyl group,
(d) —$C(R')(R'')$—$OR^{19}$ group,
(e) —$(CH_2)_j$—$CO_2R^7$ group,
(f) —$(CH_2)_j$—CN group,
(g) —$(CH_2)_j$—$C(=O)R'$ group,
(h) —$(CH_2)_j$$CONR'R''$ group, or
(i) —$(CH_2)_j$—Aryl group wherein j is 0, 1 or 2, or
(j) wherein $R^{16}$ and $R^{18}$ may be taken together to form —$(CH_2)_i$— group, wherein i is 1, 2 or 3; wherein Aryl is
(a) phenyl group,
(b) pyridyl group,
(c) pyrimidinyl,
(d) pyridazinyl group,
(e) furyl group,
(f) thienyl group,
(g) pyrazolinyl group,
(h) oxazolyl group,
(i) thiazolyl group,
(j) oxadiazolyl group or
(k) isoxazolyl group; or
(l) any of the foregoing groups substituted with
(i) halogen atom,
(ii) $C_1-C_8$ alkyl group,
(iii) hydroxy group,
(iv) $C_1-C_8$ alkoxy group,
(v) nitro group, or
(vi) cyano group;

wherein
$R^{19}$ is
(a) hydrogen atom, or
(b) $C_1-C_8$ alkyl group optionally substituted with hydroxy group or ether group;

or a pharmacologically acceptable ester or salt thereof, as well as a pharmaceutical composition for preventing or treating hypertension congestive heart failure, renal failure, glaucoma or hyperuricemia which comprises as an active ingredient an imidazole derivative of the general formula [I] or a pharmacologically acceptable ester or salt thereof.

EFFECT OF THE INVENTION

Surprisingly, the present invention provides novel imidazole derivatives which can be used for preventing or treating hypertension, congestive heart failure, renal failure, glaucoma or hyperuricemia. The pharmaceutical compositions of the present invention which contain these compounds have high activity, rapidly manifested action upon intravenous injection, good absorbability into the body upon oral administration, low toxicity, and long-lasting action.

The general formula [I] can be represented depending upon the group —P—, by the following formula [Ia], [Ib] or [Ic].

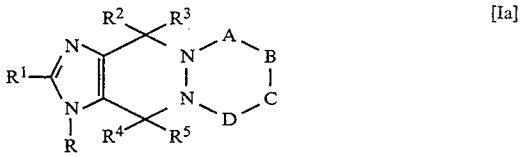

[Ia]

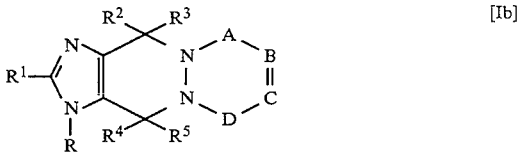

[Ib]

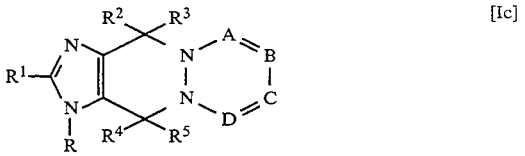

[Ic]

An imidazole derivative wherein R is hydrogen, represented by the general formula [Ia], [Ib] or [IIc]:

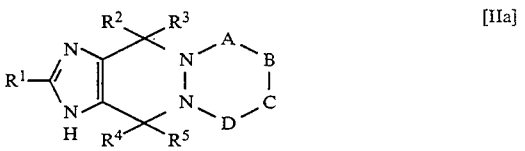

[IIa]

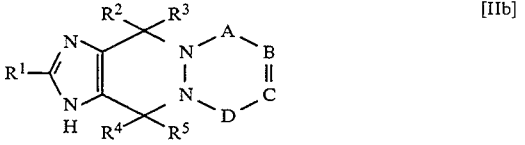

[IIb]

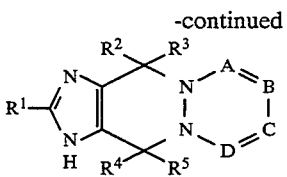

wherein $R^1$, $R^2$, $R^3$, $R^4$, $R^5$ and A—B—C—D are as defined above, is useful as an intermediate for synthesizing the compound represented by the general formula [I] because the intermediate can be reacted with various substituted or unsubstituted benzyl halide or biphenylmethyl halide and the like in the presence of a base.

In addition, an imidazole derivative wherein R is substituted or unsubstituted phenylmethyl group, represented by the general formula [IIIa], [IIIb] or [IIIc]:

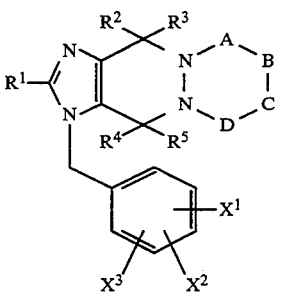

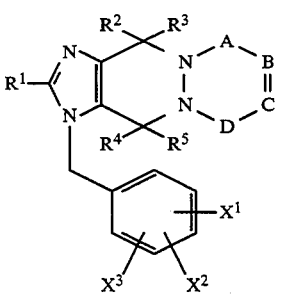

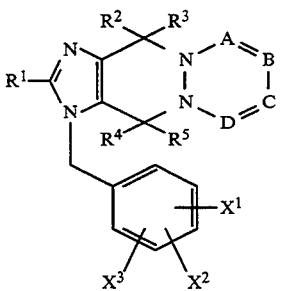

wherein $R^1$, $R^2$, $R^3$, $R^4$, $R^5$, $X^1$, $X^2$, $X^3$ and A—B—C—D are as defined above, is a useful intermediate for synthesizing the compound represented by the general formula [I] because the intermediate can be debenzylated into the compound represented by the general formula [IIa], [IIb] or [IIc] wherein R is hydrogen using various methods, for example, by hydrogenolysis, metal reduction, oxidative degradation and the like.

The carbon atom content of the carbon containing moieties is indicated by a prefix "$C_i$-$C_j$" wherein "i" is the lowest number of carbon atoms and "j" is the highest number of carbon atoms.

As the lower alkyl group represented by $R^1$ in the general formula [I], there are alkyl groups having from 1 to 8 carbon atoms, for example, methyl, ethyl, n-propyl, isopropyl, n-butyl, isobutyl, t-butyl, n-pentyl, isoamyl, n-hexyl, n-heptyl, n-octyl and the like. As the lower alkoxy group represented by $R^1$, having from 1 to 8 carbon atoms there are methoxy, ethoxy, n-propoxy, isopropoxy, n-butoxy, isobutoxy, t-butoxy, n-pentoxy, isoamyloxy, n-hexyloxy, n-heptyloxy, n-octyloxy and the like. As the lower alkylthio groups having from 1 to 8 carbon atoms represented by $R^1$, there are methylthio, ethylthio, n-propylthio, isopropylthio, n-butylthio, n-pentylthio, n-hexylthio, n-heptylthio, n-octylthio and the like. As the lower alkylamino group having from 1 to 8 carbon atoms represented by $R^1$, there are methylamino, dimethylamino, ethylamino, diethylamino, n-propylamino, di(n-propyl)amino, isopropylamino, n-butylamino, n-pentylamino, pyrrolidino, piperidino, piperazino, morpholino and the like. As the lower alkenyl group having from 1 to 8 carbon atoms represented by $R^1$, there are vinyl, 1-propenyl, 2-propenyl, 2-methyl-1-propenyl, 1-butenyl, 2-butenyl, 1-pentenyl, 2-pentenyl, 1-hexenyl, 1-heptenyl, 1-octenyl and the like. As the lower alkynyl group having from 1 to 8 carbon atoms represented by $R^1$, there are an acetylene group, 1-propynyl, 2-propynyl, 1-butynyl, 2-butynyl, 1-pentynyl, 2-pentynyl, 1-hexynyl, 1-heptynyl, 1-octynyl and the like. As the aryl group or aralkyl group represented by $R^1$, there are aryl groups or aralkyl groups having from 6 to 10 carbon atoms, for example, phenyl, naphthyl, benzyl, phenethyl, 3-phenylpropyl, 4-phenylbutyl and the like. These aryl or aralkyl groups may be optionally substituted by substituents such as lower alkyl group or lower alkoxy group described above, or halogen atom, nitro group, cyano group and the like.

In the general formula [I] of the compound of the present invention, when R is substituted or unsubstituted phenylmethyl group, the examples of halogen atom defined by $X^1$, $X^2$ and $X^3$ are fluorine, chlorine, bromine and iodine and the examples of lower alkyl group and lower alkoxy group are as defined above. When $X^1$, $X^2$ and $X^3$ are 1H-tetrazol-5-yl group, the examples of alkali metal salt thereof are sodium salt, potassium salt and the like. When $X^1$, $X^2$ and $X^3$ are —$CO_2R^7$ group, the examples of $R^7$ in the group are hydrogen atom, alkali metal such as lithium, sodium, potassium and the like, and alcohol ester group of the above defined lower alkyl group and the like. When $X^1$, $X^2$ and $X^3$ are —CONR'R", the examples of —NR'R" in the group are amino, methylamino, dimethylamino, ethylamino, diethylamino, n-propylamino, di(n-propyl)amino, diisopropylamino, dibutylamino, pyrrolidinyl, piperazino, morpholino and the like. The examples of $R^8$ in the —$CONHSO_2R^8$ group are methyl, trifluoromethyl, ethyl, n-propyl, n-butyl, isobutyl, t-butyl, cyclopentyl, cyclohexyl, phenyl and the like. When $X^1$, $X^2$ and $X^3$ are a group selected from the following groups:

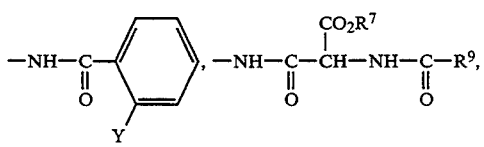

-continued

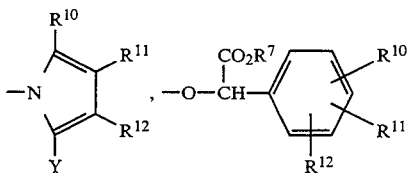

Y and $R^7$ are as defined above. The lower alkyl group and lower alkoxy group represented by $R^9$ are as defined above. When $R^9$ is cycloalkyl group or cycloalkoxy group, 5 to 7—membered ring compounds such as cyclopentyl, cyclohexyl, cycloheptyl are included. The examples of aryl group and aryloxy group represented by $R^9$ are the substituted or unsubstituted phenyl compounds such as phenyl, p-hydroxyphenyl, p-carboxyphenyl, o-nitrophenyl and the like. When $R^{10}$, $R^{11}$ and $R^{12}$ are lower alkyl group, lower alkoxy group, —$CO_2R^7$ group or —$CONR'R''$ group, the examples of them are as defined above. When R is substituted biphenylmethyl group in the general formula [I], the examples of alkali metal salt of 1H-tetrazol-5-yl as a substituent Y are sodium salt, potassium salt and the like. When Y is —$CO_2R^7$ group, —$CONR'R''$ group or —$CONHSO_2R^8$ group, $R^7$, —$NR'R''$ and $R^8$ in these groups are as defined above. When R is represented by the following formula:

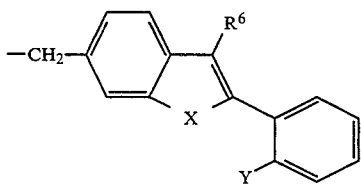

in the general formula [I], the examples of halogen atom and lower alkyl group represented by $R^6$, alkali metal salt of 1H-tetrazol-5-yl represented by Y, and $R^7$, $NR'R''$ and $R^8$ in —$CO^2R^7$ group, —$CONR'R''$ group and —$CONHSO_2R^8$ group represented by Y are as defined above.

In the general formula [I] in the present invention, when $R^2$, $R^3$, $R^4$ and $R^5$ are lower alkyl group, the examples of them are an alkyl group having 1 to 8 carbon atoms, for example, methyl, ethyl, n-propyl, isopropyl, n-butyl, isobutyl, t-butyl, n-pentyl, isoamyl, n-hexyl, n-heptyl, n-octyl and the like.

In the general formula [I] in the present invention, when $R^{13}$, $R^{14}$, $R^{15}$, $R^{16}$, $R^{17}$ and $R^{18}$ in the A—B—C—D group are a lower alkyl group, examples of them are an alkyl group having from 1 to 8 carbon atoms, for example, methyl, ethyl, n-propyl, isopropyl, n-butyl, isobutyl, t-butyl, n-pentyl, isoamyl, n-hexyl, n-heptyl, n-octyl and the like. When $R^{13}$, $R^{14}$, $R^{15}$, $R^{16}$, $R^{17}$ and $R^{18}$ are lower fluoroalkyl group, the examples of them are trifluoromethyl, 2,2,2-trifluoroethyl, pentafluoroethyl and the like. When $R^{13}$, $R^{14}$, $R^{15}$, $R^{16}$, $R^{17}$ and $R^{18}$ are —$(CH_2)_j$—$CO_2R^7$, —$(CH_2)_j$—$C(=O)R'$, —$C(R')(R'')$—$OR^{19}$ or —$(CH_2)_j$—$CONR'R''$, $R^7$, $R'$ and $R''$ in these groups are as defined above.

Examples of compounds represented by the general formula [1] are as follows:

1) 2-methyl-6,7-dimethyl-5,6,7,8-tetrahydro-1H-1,3,4a,8a-tetraza-cyclopentanaphthalene-4,9-dione,
2) 2-ethyl-6,7-dimethyl-5,6,7,8-tetrahydro-1H-1,3,4a,8a-tetraza-cyclopentanaphthalene-4,9-dione,
3) 2-n-propyl-6,7-dimethyl-5,6,7,8-tetrahydro-1H-1,3,4a,8a-tetraza-cyclopentanaphthalene-4,9-dione,
4) 2-n-butyl-6,7-dimethyl-5,6,7,8-tetrahydro-1H-1,3,4a,8a-tetraza-cyclopentanaphthalene-4,9-dione,
5) 2-n-pentyl-6,7-dimethyl-5,6,7,8-tetrahydro-1H-1,3,4a,8a-tetraza-cyclopentanaphthalene-4,9-dione,
6) 2-n-hexyl-6,7-dimethyl-5,6,7,8-tetrahydro-1H-1,3,4a,8a-tetraza-cyclopentanaphthalene-4,9-dione,
7) 2-methyl-5,8-dihydro-6,7-dimethyl-1H-1,3,4a,8a-tetraza-cyclopentanaphthalene-4,9-dione,
8) 2-ethyl-5,8-dihydro-6,7-dimethyl-1H-1,3,4a,8a-tetraza-cyclopentanaphthalene-4,9-dione,
9) 2-n-propyl-5,8-dihydro-6,7-dimethyl-1H-1,3,4a,8a-tetraza-cyclopentanaphthalene-4,9-dione,
10) 2-n-butyl-5,8-dihydro-6,7-dimethyl-1H-1,3,4a,8a-tetraza-cyclopentanaphthalene-4,9-dione,
11) 5,8-dihydro-6,7-dimethyl-2-n-pentyl-1H-1,3,4a,8a-tetraza-cyclopentanaphthalene-4,9-dione
12) 5,8-dihydro-6,7-dimethyl-2-n-hexyl-1H-1,3,4a,8a-tetraza-cyclopentanaphthalene-4,9-dione
13) 2-ethyl-5,4,7,8,-tetrahydro-1H-1,3,4a,8a-tetraza-cyclopentanaphthalene-4,9-dione,
14) 2-n-propyl-5,6,7,8-tetrahydro-1H-1,3,4a,8a-tetraza-cyclopentanaphthalene-4,9-dione,
15) 2-n-butyl-5,6,7,8-tetrahydro-1H-1,3,4a,8a-tetraza-cyclopentanaphthalene-4,9-dione,
16) 2-n-pentyl-5,6,7,8-tetrahydro-1H-1,3,4a,8a-tetraza-cyclopentanaphthalene-4,9-dione,
17) 5,8-dihydro-2-ethyl-1H-1,3,4a,8a-tetraza-cyclopentanaphthalene-4,9-dione,
18) 5,8-dihydro-2-n-propyl-1H-1,3,4a,8a-tetraza-cyclopentanaphthalene-4,9-dione,
19) 2-n-butyl-5,8-dihydro-1H-1,3,4a,8a-tetraza-cyclopentanaphthalene-4,9-dione,
20) 5,8-dihydro-2-n-pentyl-1H-1,3,4a,8a-tetraza-cyclopentanaphthalene-4,9-dione,
21) 4,9-dioxo-2-n-propyl-5,6,7,8-tetrahydro-1H-1,3,4a,8a-tetraza-cyclopentanaphthalene-8-carboxylic acid,
22) 2-n-butyl-1,9-dioxo-5,6,7,8-tetrahydro-1H-1,3,4a,8a-tetraza-cyclopentanaphthalene-8-carboxylic acid,
23) 4,9-dioxo-2-n-pentyl-5,6,7,8-tetrahydro-1H-1,3,4a,8a-tetraza-cyclopentanaphthalene-8-carboxylic acid,
24) ethyl 4,9-dioxo-2-n-propyl-5,6,7,8-tetrahydro-1H-1,3,4a,8a-tetraza-cyclopentanaphthalene-8-carboxylate,
25) ethyl 2-n-butyl-1,9-dioxo-5,6,7,8-tetrahydro-1H-1,3,4a,8a-tetraza-cyclopentanaphthalene-8-carboxylate,
26) ethyl 4,9-dioxo-2-n-pentyl-5,6,7,8-tetrahydro-1H-1,3,4a,8a-tetraza-cyclopentanaphthalene-8-carboxylate,
27) ethyl 4,9-dioxo-2-ethyl-5-methyl-5,6,7,8-tetrahydro-1H-1,3,4a,8a-tetraza-cyclopentanaphthalene-8-carboxylate,
28) ethyl 4,9-dioxo-5-methyl-2-n-propyl-5,6,7,8-tetrahydro-1H-1,3,4a,8a-tetraza-cyclopentanaphthalene-8-carboxylate,
29) ethyl 2-n-butyl-1,9-dioxo-5-methyl-5,6,7,8-tetrahydro-1H-1,3,4a,8a-tetraza-cyclopentanaphthalene-8-carboxylate,
30) ethyl 4,9-dioxo-2-ethyl-5-methyl-1H-1,3,4a,8a-tetraza-cyclopentanaphthalene-8-carboxylate, 31) ethyl 4,9-dioxo-5-methyl-2-n-propyl-1H-1,3,4a,-8a-tetraza-cyclopentanaphthalene-carboxylate,
32) ethyl 2-n-butyl-1,9-dioxo-5-methyl-1H-1,3,4a,8a-tetraza-cyclopentanaphthalene-carboxylate,
33) 5,8-dihydro-4,9-dioxo-2-ethyl-1H-1,3,4a,8a-tetraza-cyclopentanaphthalene-7-carboxylic acid,
34) 5,8-dihydro-4,9-dioxo-2-n-propyl-1H-1,3,4a,8a-tetraza-cyclopentanaphthalene-7-carboxylic acid,
35) 2-n-butyl-5,8-dihydro-4,9-dioxo-1H-1,3,4a,8a-tetraza-cyclopentanaphthalene-7-carboxylic acid,
36) 5,8-dihydro-4,9-dioxo-2-n-pentyl-1H-1,3,4a,8a-tetraza-cyclopentanaphthalene-7-carboxylic acid,
37) ethyl 5,8-dihydro-4,9-dioxo-2-n-propyl-1H-1,3,4a,8a-tetraza-cyclopentanaphthalene-7-carboxylate,
38) ethyl 2-n-butyl-5,8-dihydro4,9-dioxo-1H-1,3,4a,-8a-tetraza-cyclopentanaphthalene-7-carboxylate,
39) ethyl 4,9-dioxo-2-ethyl-5,6,7,8-tetrahydro-1H-1,3,4a,8a-tetraza-cyclopentanaphthalene-7-carboxylate,
40) ethyl 4,9-dioxo-2-n-propyl-5,6,7,8-tetrahydro-1H-1,3,4a,8a-tetraza-cyclopentanaphthalene-7-carboxylate,
41) ethyl 2-n-butyl-1,9-dioxo-5,6,7,8-tetrahydro-1H-1,3,4a,8a-tetraza-cyclopentanaphthalene-7-carboxylate,
42) ethyl 4,9-dioxo-2-n-propyl-1H-1,3,4a,8a-tetraza-cyclopentanaphthalene-7-carboxylate,
43) ethyl 2-n-butyl-1,9-dioxo-1H-1,3,4a,8a-tetraza-cyclopentanaphthalene-7-carboxylate,
44) 2-methyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
45) 2-ethyl-5,6,7,8-tetrahydro-1-[(2'-(1H-tetrazol-5-yl)biphenyl-4-yl)methyl]-1H-3,4a,8 a-tetraza-cyclopentanaphthalene -4,9-dione,
46) 2-n-propyl-5,6,7, 8-tetrahydro-1-[(2'-(1H-tetrazol-5-yl)biphenyl-4-yl)methyl]-1H-3,4a,8a-tetraza-cyclopentanaphthalene-4,9-dione,
47) 2-n-butyl-5,6,7,8-tetrahydro-1-[(2'-(1H-tetrazol-5-yl)biphenyl-4-yl)methyl 1H, 3,4a,8a-tetraza-cyclopentanaphthalene-4,9-dione,
48) 2-n-pentyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
49) 6,7-dimethyl-2-ethyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
50) 6,7-dimethyl-2-n-propyl-5,6,7,8-tetrahydro-1-[(2'-(1H-tetrazol-5-yl)biphenyl-4yl)methyl]-1H-1,3,4a,-8a-tetraza-cyclopentanaphthalene-4,9-dione,
51) 2-n-butyl-6,7-dimethyl-5,6,7,8-tetrahydro-1-[(2'-(1H-tetrazol-5-yl)biphenyl-4yl)methyl]-1H-1,3,4a,-8a-tetraza-cyclopentanaphthalene-4,9-dione,
52) 4,9-dioxo-2-ethyl-5,6,7,8-tetrahydro-1-[(2'-(1H-tetrazol-5-yl)biphenyl-4-yl)methyl]-1H-1,3,4a,8a-tetraza-cyclopentanaphthalene-7-carboxylic acid,
53) 4,9-dioxo-2-n-propyl-5,6,7,8-tetrahydro-1-[(2'-(1H-tetrazol-5-yl)biphenyl-4-yl)methyl-1H-1,3,4a,-8a-tetraza-cyclopentanaphthalene-7-carboxylic acid,
54) 2-n-butyl-1,9-dioxo-5,6,7,8-tetrahydro-1-[(2'-(1H-tetrazol-5-yl)biphenyl-4-yl)methyl]-1H-1,3,4a,8a-tetraza-cyclopentanaphthalene-7-carboxylic acid,
55) 4,9-dioxo-2-ethyl-5-methyl-5,6,7,8-tetrahydro-1-[(2'-(1H-tetrazol-5-yl)biphenyl-4-yl)methyl]-1H-1,3,4a,8a-tetraza-cyclopentanaphthalene-8-carboxylic acid,
56) 4,9-dioxo-5-methyl-2-n-propyl-5,6,7,8-tetrahydro-1-[(2'-(1H-tetrazol-5-yl)biphenyl-4-yl)methyl]-1H-3-4a,8a-tetraza-cyclopentanaphthalene-8-carboxylic acid,
57) 2-n-butyl-4,9-dioxo-5-methyl-5,6,7,8-tetrahydro-1-[(2'-(1H-tetrazol-5-yl)biphenyl-1-yl)methyl]-1H-1,3,4a,8a-tetraza-cyclopentanaphthalene-8-carboxylic acid,
58) 4,9-dioxo-5-methyl-2-n-pentyl-5,6,7,8-tetrahydro-1-[(2'-(1H-tetrazol-5-yl)biphenyl-1-yl)methyl]-1H-1,3,4a,8a-tetraza-cyclopentanaphthalene-8-carboxylic acid,
59) 5,8-dihydro-4,9-dioxo-2-ethyl-5-methyl-1-[(2'-(1H-tetrazol-5-yl)biphenyl-4-yl)methyl]-1H-1,3,4a,8a-tetraza-cyclopentanaphthalene-8-carboxylic acid,
60) 5,8-dihydro-4,9-dioxo-5-methyl-2-n-propyl-1-[(2'-(1H-tetrazol-5-yl)biphenyl-4-yl)methyl]-1H-1,3,4a,8a-tetraza-cyclopentanaphthalene-8-carboxylic acid,
61) 2-n-butyl-5,8-dihydro-4,9-dioxo-5-methyl-1-[(2'-(1H-tetrazol-5-yl)biphenyl-4-yl)methyl]-1H-1,3,4a,8a-tetraza-cyclopentanaphthalene-8-carboxylic acid,
62) 5,8-dihydro-4,9-dioxo-5-methyl-2-n-pentyl-1-[(2'-(1H-tetrazol-5-yl)biphenyl-4-yl)methyl]-1H-1,3,4a,8a-tetraza-cyclopentanaphthalene-8-carboxylic acid,
63) 5,8-dihydro-4,9-dioxo-2-n-propyl-1-[(2'-(1H-tetrazol-5-yl)biphenyl-4-yl)methyl]-1H-1,3,4a,8a-tetraza-cyclopentanaphthalene-7-carboxylic acid,
64) 2-n-butyl-5,8-dihydro-4,9-dioxo-1-[(2'-(1H-tetrazol-5-yl)biphenyl-4-yl)methyl]-1H-1,3,4a,8a-tetraza-cyclopentanaphthalene-7-carboxylic acid,
65) 5,8-dihydro-4,9-dioxo-2-n-pentyl-1-[(2'-(1H-tetrazol-5-yl)biphenyl-4-yl)methyl]-1H-1,3,4a,8a-tetraza-cyclopentanaphthalene-7-carboxylic acid,
66) 5,8-dihydro-6,7-dimethyl-2-ethyl-1-[(2'-(1H-tetrazol-5-yl)biphenyl-4-yl)methyl]-1H-1,3,4a,8a-tetraza-cyclopentanaphthalene-4,9-dione,
67)-5,8-dihydro-6,7-dimethyl-2-n-propyl-1-[(2'-(1H-tetrazol-5-yl)biphenyl-4-yl)methyl]-1H-1,3,4a,8a-tetraza-cyclopentanaphthalene-4,9-dione,
68) 2-n-butyl-5,8-dihydro-6,7-dimethyl-1-[(2'-(1H-tetrazol-5-yl)biphenyl-4-yl)methyl]-1H-1,3,4a,8a-tetraza-cyclopentanaphthalene-4,9-dione,
69) 5,8-dihydro-6,7-dimethyl-2-n-pentyl-1-[(2'-(1H-tetrazol-5-yl)biphenyl-4-yl)methyl]-1H-1,3,4a,8a-tetraza-cyclopentanaphthalene-4,9-dione,
70) 5,8-dihydro-2-n-propyl-1-[(2'-(1H-tetrazol-5-yl)biphenyl-4-yl)methyl]-1H-1,3,4a,8a-tetraza-cyclopentanaphthalene-4,9-dione,
71) 2-n-butyl-5,8-dihydro-1-[(2'-(1H-tetrazol-5-yl)biphenyl-4-yl)methyl]-1H-1,3,4a,8a-tetraza-cyclopentanaphthalene-4,9-dione,
72) 5,8-dihydro-2-n-pentyl-1-[(2'-(1H-tetrazol-5-yl)biphenyl-4-yl)methyl]-1H-1,3,4a,8a-tetraza-cyclopentanaphthalene-4,9-dione,
73) 2-n-propyl-1-[(2'-(1H-tetrazol-5-yl)biphenyl-4-yl)methyl]-1H-1,3,4a,8a-tetraza-cyclopentanaphthalene-4,9-dione,
74) 2-n-butyl-1-[(2'-(1H-tetrazol-5-yl)biphenyl-4-yl)methyl]-1H-1,3,4a,8a-tetraza-cyclopentanaphthalene-4,9-dione,
75) 2-n-pentyl-1-[(2'-(1H-tetrazol-5-yl)biphenyl-4-yl)methyl]-1H-1,3,4a,8a-tetraza-cyclopentanaphthalene-4,9-dione, 76) 6,7-dimethyl-2-ethyl-1-[(2'-(1H-tetrazol-5-yl)biphenyl-4-yl)methyl]-1H-1,3,4a,8a-tetraza-cyclopentanaphthalene-4,9-dione,
77) 6,7-dimethyl-2-n-propyl-1-[(2'-(1H-tetrazol-5-yl)biphenyl-4-yl)methyl]-1H-1,3,4a,8a-tetraza-cyclopentanaphthalene-4,9-dione,
78) 2-n-butyl-6,7-dimethyl-1-[(2'-(1H-tetrazol-5-yl)biphenyl-4-yl)methyl]-1H-1,3,4a,8a-tetraza-cyclopentanaphthalene-4,9-dione,
79) 6,7-dimethyl-2-n-pentyl-1-[(2'-(1H-tetrazol-5-yl)biphenyl-4-yl)methyl]-1H-1,3,4a,8a-tetraza-cyclopentanaphthalene-4,9-dione,
80) 4,9-dioxo-2-n-propyl-1-[(2'-(1H-tetrazol-5-yl)biphenyl-4-yl)methyl]-1H-1,3,4a,8a-tetraza-cyclopentanaphthalene-7-carboxylic acid,
81) 2-n-butyl-4,9-dioxo-1-[(2'-(1H-tetrazol-5-yl)biphenyl-4-yl)methyl]-1H-1,3,4a,8a-tetraza-cyclopentanaphthalene-7-carboxylic acid,
82) 4,9-dioxo-2-n-pentyl-1-[(2'-(1H-tetrazol-5-yl)biphenyl-4-yl)methyl]-1H-1,3,4a,8a-tetraza-cyclopentanaphthalene-7-carboxylic acid,
83) 4,9-dioxo-5-methyl-2-n-propyl-1-[(2'-(1H-tetrazol-5-yl)biphenyl-4-yl)methyl]-1H-1,3,4a,8a-tetraza-cyclopentanaphthalene-8-carboxylic acid,
84) 2-n-butyl-4,9-dioxo-5-methyl-1-[(2'-(1H-tetrazol-5-yl)biphenyl-4-yl)methyl]-1H-1,3,4a,8a-tetraza-cyclopentanaphthalene-8-carboxylic acid,
85) 4,9-dioxo-5-methyl-2-n-pentyl-1-[(2'-(1H-tetrazol-yl-5)biphenyl-4-yl)methyl]-1H-1,3,4a,8a-tetraza-cyclopentanaphthalene-8-carboxylic acid,
86) 2-ethyl-1,5,6,8-tetrahydro-1-[(2'-(1H-tetrazol-5-yl)biphenyl-4-yl)methyl]-1H-1,3,4a,7a-tetraza-s-indacene-4,8-dione,
87) 2-n-propyl-1,5,6,8-tetrahydro-1-[(2'-(1H-tetrazol-5-yl)biphenyl-4-yl)methyl]-1H-1,3,4a,7a-tetraza-s-indacene-4,8-dione,
88) 2-n-butyl-1,5,6,8-tetrahydro-1-[(2'-(1H-tetrazol-5-yl)biphenyl-4-yl)methyl]-1H-1,3,4a,7a-tetraza-s-indacene-4,8-dione,
89) 2-n-pentyl-1,5,6,8-tetrahydro-1-[(2'-(1H-tetrazol-5-yl)biphenyl-4-yl)methyl]-1H-1,3,4a,7a-tetraza-s-indacene-4,8-dione,
90) 5-t-butyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
91) 2-n-butyl-5-t-butyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
92) 5-t-butyl-2-n-pentyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
93) 5-t-butyl-5,8-dihydro-2-n-propyl-1-[(2'-(1H-tetrazol-5-yl)biphenyl-4-yl)methyl]-1H-1,3,4a,8a-tetraza-cyclopentanaphthalene-4,9-dione,
94) 2-n-butyl-5-t-butyl-5,8-dihydro-1-[(2'-(1H-tetrazol-5-yl)biphenyl-4-yl)methyl]-1H-1,3,4a,8a-tetraza-cyclopentanaphthalene-4,9-dione,
95) 5-t-butyl-5,8-dihydro-2-n-pentyl-1-[(2'-(1H-tetrazol-5-yl)biphenyl-4-yl)methyl]-1H-1,3,4a,8a-tetraza-cyclopentanaphthalene-4,9-dione,
96) 5-t-butyl-2-n-propyl-1-[(2'-(1H-tetrazol-5-yl)biphenyl-4-yl)methyl]-1H-1,3,4a,8a-tetraza-cyclopentanaphthalene-4,9-dione,
97) 2-n-butyl-5-t-butyl-1-[(2'-(1H-tetrazol-5-yl)biphenyl-4-yl)methyl]-1H-1,3,4,a8a-tetraza-cyclopentanaphthalene-4,9-dione,
98) 5-t-butyl-2-n-pentyl-1-[(2'-(1H-tetrazol-5-yl)biphenyl-4-yl)methyl]-1H-1,3,4a,8a-tetraza-cyclopentanaphthalene-4,9-dione,
99) 5,8-methano-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
100) 2-n-butyl-5,8-methano-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
101) 5,8-methano-2-n-pentyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
102) 5,8-dihydro-5,8-methano-2-n-propyl-1-[(2'-(1H-tetrazol-5-yl)biphenyl-4-yl)methyl]-1H-1,3,4a,8a-tetraza-cyclopentanaphthalene-4,9-dione,
103) 2-n-butyl-5,8-dihydro-5,8-methano-1-[(2'-(1H-tetrazol-5-yl)biphenyl-4-yl)methyl]-1H-1,3,4a,8a-tetraza-cyclopentanaphthalene-4,9-dione,
104) 5,8-dihydro-5,8-methano-2-n-pentyl-1-[(2'-(1H-tetrazol-5-yl)biphenyl-4-yl)methyl]-1H-1,3,4a,8a-tetraza-cyclopentanaphthalene-4,9-dione,
105) 5,8-dihydro-5,8-ethano-2-n-propyl-1-[(2'-(1H-tetrazol-5-yl)biphenyl-4-yl)methyl]-1H-1,3,4a,8a-tetraza-cyclopentanaphthalene-4,9-dione,
106) 2-n-butyl-5,8-dihydro-5,8-ethano-1-[(2'-(1H-tetrazol-5-yl)biphenyl-4-yl)methyl]-1H-1,3,4a,8a-tetraza-cyclopentanaphthalene-4,9-dione,
107) 5,8-dihydro-5,8-ethano-2-n-pentyl-1-[(2'-(1H-tetrazol-5-yl)biphenyl-4-yl)methyl]-1H-1,3,4a,8a-tetraza-cyclopentanaphthalene-4,9-dione,
108) 5,8-ethano-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
109) 2-n-butyl-5,8-ethano-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
110) 5,8-ethano-2-n-pentyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione,
111) 4,9-dioxo-8-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-5-carboxylic acid,
112) 2-n-butyl-4,9-dioxo-8-methyl-5,6,7,8-tetrahydro-1-[(2'-(1H-tetrazol-5-yl)biphenyl-4-yl)methyl]-1H-1,3,4a,8a-tetraza-cyclopentanaphthalene-5-carboxylic acid,
113) 4,9-dioxo-8-methyl-2-n-pentyl-5,6,7,8-tetrahydro-1-[(2'-(1H-tetrazol-5-yl)biphenyl-4-yl)methyl]-1H-1,3,4a,8a-tetraza-cyclopentanaphthalene-5-carboxylic acid,
114) 5,8-dihydro-4,9-dioxo-8-methyl-2-n-propyl-1-[(2'-(1H-tetrazol-5-yl)biphenyl-4-yl)methyl]-1H-1,3,4a,8a-tetraza-cyclopentanaphthalene-5-carboxylic acid,
115) 2-n-butyl-5,8-dihydro-4,9-dioxo-8-methyl-1-[(2'-(1H-tetrazol-5-yl)biphenyl-4-yl)methyl]-1H-1,3,4a,8a-tetraza-cyclopentanaphthalene-5-carboxylic acid,
116) 5,8-dihydro-4,9-dioxo-8-methyl-2-n-pentyl-1-[(2'-(1H-tetrazol-5-yl)biphenyl-4-yl)methyl]-1H-1,3,4a,8a-tetraza-cyclopentanaphthalene-5-carboxylic acid,
117) 4,9-dioxo-8-methyl-2-n-propyl-1-[(2'-(1H-tetrazol-5-yl)biphenyl-4-yl)methyl]-1H-1,3,4a,8a-tetraza-cyclopentanaphthalene-5-carboxylic acid, 118) 2-n-butyl-4,9-dioxo-8-methyl-1-[(2'-(1H-tetrazol-5-yl)biphenyl-4-yl)methyl]-1H-1,3,4a,8a-tetraza-cyclopentanaphthalene-5-carboxylic acid,
119) 4,9-dioxo-8-methyl-2-n-pentyl-1-[(2'-(1H-tetrazol-5-yl)biphenyl-4-yl)methyl]-1H-1,3,4a,8a-tetraza-cyclopentanaphthalene-5-carboxylic acid,
120) 1-[(4-carboxyphenyl)methyl]-4,9-dioxo-5-methyl-2-n-propyl-5,6,7,8-tetrahydro-1H-1,3,4a,8a-tetraza-cyclopentanaphthalene-8-carboxylic acid,
121) 2-n-butyl-1-[(4-carboxyphenyl)methyl]-4,9-dioxo-5-methyl-5,6,7,8-tetrahydro-1H-1,3,4a,8a-tetraza-cyclopentanaphthalene-8-carboxylic acid,
122) 1-[(4-carboxyphenyl)methyl]-4,9-dioxo-5-methyl-2-n-pentyl-5,6,7,8-tetrahydro-1H-1,3,4a,8a-tetraza-cyclopentanaphthalene-8-carboxylic acid,
123) 1-[(4-carboxyphenyl)methyl]-4,9-dioxo-8-methyl-2-n-propyl-5,6,7,8-tetrahydro-1H-1,3,4a,8a-tetraza-cyclopentanaphthalene-5-carboxylic acid,
124) 2-n-butyl-1-[(4-carboxyphenyl)methyl]-4,9-dioxo-8-methyl-5,6,7,8-tetrahydro-1H-1,3,4a,8a-tetraza-cyclopentanaphthalene-5-carboxylic acid,
125) 1-[(4-carboxyphenyl)methyl]-4,9-dioxo-8-methyl-2-n-pentyl-5,6,7,8-tetrahydro-1H-1,3,4a,8a-tetraza-cyclopentanaphthalene-5-carboxylic acid,
126) 1-[(4-carboxyphenyl)methyl]-5,8-dihydro-4,9-dioxo-5-methyl-2-n-propyl-1H-1,3,4a,8a-tetraza-cyclopentanaphthalene-8-carboxylic acid,
127) 2-n-butyl-1-[(4-carboxyphenyl)methyl]-5,8-dihydro-4,9-dioxo-5-methyl-1H-1,3,4a,8a-tetraza-cyclopentanaphthalene-8-carboxylic acid,
128) 1-[(4-carboxyphenyl)methyl]-5,8-dihydro-4,9-dioxo-5-methyl-2-n-pentyl-1H-1,3,4a,8a-tetraza-cyclopentanaphthalene-8-carboxylic acid,
129) 1-[(4-carboxyphenyl)methyl]-5,8-dihydro-4,9-dioxo-8-methyl-2-n-propyl-1H-1,3,4a,8a-tetraza-cyclopentanaphthalene-5-carboxylic acid,
130) 2-n-butyl-1-[(4-carboxyphenyl)methyl]-5,8-dihydro-4,9-dioxo-8-methyl-1H-1,3,4a,8a-tetraza-cyclopentanaphthalene-5-carboxylic acid,
131) 1-[(4-carboxyphenyl)methyl]-5,8-dihydro-4,9-dioxo-8-methyl-2-n-pentyl-1H-1,3,4a,8a-tetraza-cyclopentanaphthalene-5-carboxylic acid,
132) 1-[(4-carboxyphenyl)methyl]-4,9-dioxo-5-methyl-2-n-propyl-1H-1,3,4a,8a-tetraza-cyclopentanaphthalene-8-carboxylic acid,
133) 2-n-butyl-1-[(4-carboxyphenyl)methyl]-4,9-dioxo-5-methyl-1H-1,3,4a,8a-tetraza-cyclopentanaphthalene-8-carboxylic acid,
134) 1-[(4-carboxyphenyl)methyl]-4,9-dioxo-5-methyl-2-n-pentyl-1H-1,3,4a,8a-tetraza-cyclopentanaphthalene-8-carboxylic acid,
135) 1-[(4-carboxyphenyl)methyl]-4,9-dioxo-8-methyl-2-n-propyl-1H-1,3,4a,8a-tetraza-cyclopentanaphthalene-5-carboxylic acid,
136) 2-n-butyl-1-[(4-carboxyphenyl)methyl]-4,9-dioxo-8-methyl-1H-1,3,4a,8a-tetraza-cyclopentanaphthalene-5-carboxylic acid, 137) 1-[(4-carboxyphenyl)methyl]-4,9-dioxo-8-methyl-2-n-pentyl-1H-1,3,4a,8a-tetraza-cyclopentanaphthalene-5-carboxylic acid,
138) ethyl 4,9-dioxo-5-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-8-carboxylate,
139) ethyl 4,9-dioxo-8-methyl-2-n-propyl-5,6,7,8-tetrahydro-1-[(2'-(1H-tetrazol-5yl)biphenyl-4-yl)methyl]-1H-1,3,4a,8a-tetraza-cyclopentanaphthalene-5-carboxylate,
140) ethyl 5,8-dihydro-4,9-dioxo-5-methyl-2-n-propyl-1H-1,3,4a,8a-tetraza-cyclopentanaphthalene-8-carboxylate,
141) ethyl 2-n-butyl-5,8-dihydro-4,9-dioxo-5-methyl-1H-1,3,4a,8a-tetraza-cyclopentanaphthalene-8-carboxylate,
142) ethyl 5,8-dihydro-4,9-dioxo-5-methyl-2-n-pentyl-1H-1,3,4a,8a-tetraza-cyclopentanaphthalene-8-carboxylate,
143) 5,8-dihydro-5,8-ethano-2-n-propyl-1H-1,3,4a,8a-tetraza-cyclopentanaphthalene-4,9-dione,
144) 2-n-butyl-5,8-dihydro-5,8-ethano-1H-1,3,4a,8a-tetraza-cyclopentanaphthalene-4,9-dione,
145) 5,8-dihydro-5,8-ethano-2-n-pentyl-1H-1,3,4a,8a-tetraza-cyclopentanaphthalene-4,9-dione,
146) 5,8-ethano-2-n-propyl-5,6,7,8-tetrahydro-1H-1,3,4a,8a-tetraza-cyclopentanaphthalene-4,9-dione,
147) 2-n-butyl-5,8-ethano-5,6,7,8-tetrahydro-1H-1,3,4a,8a-tetraza-cyclopentanaphthalene-4,9-dione,
148) 5,8-ethano-2-n-pentyl-5,6,7,8-tetrahydro-1H-1,3,4a,8a-tetraza-cyclopentanaphthalene-4,9-dione,
149) methyl 5,8-dihydro-5,8-ethano4,9-dioxo-2-n-propyl-1H-1,3,4a,8a-tetraza-cyclopentanaphthalene-8-carboxylate,
150) methyl 2-n-butyl-5,8-dihydro-5,8-ethano4,9-dioxo-1H-1,3,4a,8a-tetraza-cyclopentanaphthalene-8-carboxylate,
151) methyl 5,8-dihydro-5,8-ethano4,9-dioxo-2-n-pentyl-1H-1,3,4a,8a-tetraza-cyclopentanaphthalene-8-carboxylate,
152) methyl 5,8-ethano4,9-dioxo-2-n-propyl-5,6,7,8-tetrahydro-1H-1,3,4a,8a-tetraza-cyclopentanaphthalene-8-carboxylate,
153) methyl 2-n-butyl-5,8-ethano-4,9-dioxo-5,6,7,8-tetrahydro-1H-1,3,4a,8a-tetraza-cyclopentanaphthalene-8-carboxylate,
154) methyl 5,8-ethano4,9-dioxo-2-n-pentyl-5,6,7,8-tetrahydro-1H-1,3,4a,8a-tetraza-cyclopentanaphthalene-8-carboxylate,
155) methyl 5,8-ethano-4,9-dioxo-2-n-propyl-5,6,7,8-tetrahydro-1-[{2'-(5-yl)biphenyl-4-yl}methyl]-1H-1,3,4a,8a-tetraza-cyclopentanaphthalene-8-carboxylate,
156) methyl 2-n-butyl-5,8-ethano-4,9-dioxo-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate,
157) methyl 5,8-ethano-4,9-dioxo-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate,
158) methyl 5,8-ethano-4,9-dioxo-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
159) methyl 2-n-butyl-5,8-ethano-4,9-dioxo-5,6,7,8-tetrahydro-1-[{2'-(1H-tetrazol-5-yl)biphenyl 4-yl}methyl]-1H-1,3,4a,8a-tetraza-cyclopentanaphthalene-5-carboxylate,
160) methyl 5,8-ethano4,9-dioxo-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
161) 5,8-ethano4,9-dioxo-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylic acid, 162) 2-n-butyl-5,8-ethano-4,9-dioxo-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylic acid,
163) 5,8-ethano4,9-dioxo-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylic acid,
164) 5,8-ethano4,9-dioxo-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylic acid,
165) 2-n-butyl-5,8-ethano4,9-dioxo-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylic acid,
166) 5,8-ethano4,9-dioxo-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylic acid,
167) ethyl 2-n-butyl-4,9-dioxo-5-methyl-5,6,7,8-tetrahydro-1-[{2'-(1H-tetrazol-5yl)biphenyl-4-yl}methyl]-1H-1,3,4a,8a-tetraza-cyclopentanaphthalene-8-carboxylate,
168) ethyl 4,9-dioxo-5-methyl-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate,
169) ethyl 2-n-butyl-4,9-dioxo-8-methyl-5,6,7,8-tetrahydro-1-[{2'-(1H-tetrazol-5yl)biphenyl-4-yl}methyl]-1H-1,3,4a,8a-tetraza-cyclopentanaphthalene-5-carboxylate,
170) ethyl 4,9-dioxo-8-methyl-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
171) ethyl 4,9-dioxo-5,8-ethano-2-n-propyl-5,6,7,8-tetrahydro-1H-1,3,4a,8a-tetraza-cyclopentanaphthalene-5-carboxylate,
172) ethyl 2-n-butyl-4,9-dioxo-5,8-ethano-5,6,7,8-tetrahydro-1H-1,3,4a,8a-tetraza-cyclopentanaphthalene-5-carboxylate,
173) 5-hydroxymethyl-8-methyl-2-n-propyl-5,6,7,8-tetrahydro-1H-1,3,4a,8a-tetraza-cyclopentanaphthalene-4,9-dione,
174) 2-n-butyl-5-hydroxymethyl-8-methyl-5,6,7,8-tetrahydro-1H-1,3,4a,8a-tetraza-cyclopentanaphthalene-4,9-dione,
175) 4,9-dioxo-8-methyl-2-n-propyl-5,6,7,8-tetrahydro-1H-1,3,4a,8a-tetraza-cyclopentanaphthalene-5-carboxy-N,N-diethylamide,
176) 2-n-butyl-4,9-dioxo-8-methyl-5,6,7,8-tetrahydro-1H-1,3,4a,8a-tetraza-cyclopentanaphthalene-5-carboxy-N,N-diethylamide,
177) 4,9-dioxo-8-methyl-2-n-propyl-5,6,7,8-tetrahydro-1H-1,3,4a,8a-tetraza-cyclopentanaphthalene-5-carboxy-N-t-butylamide,
178) 2-n-butyl-4,9-dioxo-8-methyl-5,6,7,8-tetrahydro-1H-1,3,4a,8a-tetraza-cyclopentanaphthalene-5-carboxy-N-t-butylamide,
179) 4,9-dioxo-8-methyl-2-n-propyl-5,6,7,8-tetrahydro-1H-1,3,4a,8a-tetraza-cyclopentanaphthalene-5-carboxy-N,N-bis(2-hydroxyethyl)amide,
180) 2-n-butyl-4,9-dioxo-8-methyl-5,6,7,8-tetrahydro-1H-1,3,4a,8a-tetraza-cyclopentanaphthalene-5-carboxy-N,N-bis(2-hydroxyethyl)amide,
181) 5-acetyl-8-methyl-2-n-propyl-5,6,7,8-tetrahydro-1H-1,3,4a,8a-tetraza-cyclopentanaphthalene-4,9-dione,
182) 2-n-butyl-5-acetyl-8-methyl-5,6,7, 8-tetrahydro-1H-1,3,4a,8a-tetraza-cyclopentanaphthalene-4,9-dione,
183) 5,8-ethano-5-hydroxymethyl-2-n-propyl-5,6,7,8-tetrahydro-1H-1,3,4a,8a-tetraza-cyclopentanaphthalene-4,9-dione,
184) 2-n-butyl-5,8-ethano-5-hydroxymethyl-5,6,7, 8-tetrahydro-1H-1,3,4a,8a-tetraza-cyclopentanaphthalene-4,9-dione,
185) 5-t-butoxycarbonylmethoxymethyl-5,8-ethano-2-n-propyl-5,6,7,8-tetrahydro-1H-1,3,4a,8a-tetraza-cyclopentanaphthalene-4,9-dione,
186) 5-t-butoxycarbonylmethoxymethyl-2-n-butyl-5,8-ethano-5,6,7,8-tetrahydro-1H-1,3,4a,8a-tetraza-cyclopentanaphthalene-4,9-dione,
187) 5,8-ethano-5-(2-hydroxypropyl)methoxymethyl-2-n-propyl-5,6,7,8-tetrahydro-1H-1,3,4a,8a-tetraza-cyclopentanaphthalene-4,9-dione,
188) 2-n-butyl-5,8-ethano-5-(2-hydroxypropyl)methoxymethyl-5,6,7,8-tetrahydro-1H-1,3,4a,8a-tetraza-cyclopentanaphthalene-4,9-dione,
189) 4,9-dioxo-5,8-ethano-2-n-propyl-5,6,7,8-tetrahydro-1H-1,3,4a,8a-tetraza-cyclopentanaphthalene-5-carboxy-N,N-diethylamide,
190) 2-n-butyl-4,9-dioxo-5,8-ethano-5,6,7,8-tetrahydro-1H-1,3,4a,8a-tetraza-cyclopentanaphthalene-5-carboxy-N,N-diethylamide,
191) 4,9-dioxo-5,8-ethano-2-n-propyl-5,6,7, 8-tetrahydro-1H-1,3,4a,8a-tetraza-cyclopentanaphthalene-5-carboxy-N-t-butylamide,
192) 2-n-butyl-4,9-dioxo-5,8-ethano-5,6,7,8-tetrahydro-1H-1,3,4a,8a-tetraza-cyclopentanaphthalene-5-carboxy-N-t-butylamide,
193) 4,9-dioxo-5,8-ethano-2-n-propyl-5,6,7,8-tetrahydro-1H-1,3,4a,8a-tetraza-cyclopentanaphthalene-5-carboxy-N,N-bis(2-hydroxyethyl)amide,
194) 2-n-butyl-4,9-dioxo-5,8-ethano-5,6,7,8-tetrahydro-1H-1,3,4a,8a-tetraza-cyclopentanaphthalene-5-carboxy-N,N-bis(2-hydroxyethyl)amide,
195) ethyl 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
196) ethyl 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
197) ethyl 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate,
198) ethyl 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate
199) 5-hydroxymethyl-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
200) 2-n-butyl-5-hydroxymethyl-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
201) 8-hydroxymethyl-5-methyl-2-n-propyl-5,6,7,8-tetrahydro-1-[{2'-(1H-tetrazol-5-yl)biphenyl-4- yl}methyl]-1H-1,3,4a,8a-tetraza-cyclopentanaphthalene-4,9-dione,
202) 2-n-butyl-8-hydroxymethyl-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
203) 4,9-dioxo-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide,
204) 2-n-butyl-4,9-dioxo-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide,
205) 4,9-dioxo-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-diethylamide,
206) 2-n-butyl-4,9-dioxo-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-diethylamide,
207) 4,9-dioxo-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N-t-butylamide,
208) 2-n-butyl-4,9-dioxo-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N-t-butylamide,
209) 4,9-dioxo-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N-t-butylamide,
210) 2-n-butyl 4,9-dioxo-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N-t-butylamide,
211) 4,9-dioxo-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-bis(2-hydroxyethyl)amide,
212) 2-n-butyl-4,9-dioxo-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-bis(2-hydroxyethyl)amide,
213) 4,9-dioxo-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-bis(2-hydroxyethyl)amide,
214) 2-n-butyl-4,9-dioxo-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-bis(2-hydroxyethyl)amide,
215) 5-acetyl-8-methyl-2-n-propyl-5,6, 7,8-tetrahydro-1-[{2'-(1H-tetrazol-5-yl)biphenyl-4-yl}methyl]-1H-1,3,4a,8a-tetraza-cyclopentanaphthalene-4,9-dione,
216) 5-acetyl-2-n-butyl-8-methyl-5,6,7, 8-tetrahydro-1-[{2'-(1H-tetrazol-5-yl)biphenyl-4-yl }methyl]-1H-1,3,4a,8a-tetraza-cyclopentanaphthalene-4,9-dione,
217) 8-acetyl-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
218) 8-acetyl-2-n-butyl-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
219) 5,8-ethano-5-hydroxymethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
219) 5,8-ethano-5-hydroxymethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
220) 2-n-butyl-5,8-ethano-5-hydroxymethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
221) 5,8-ethano-8-hydroxymethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
222) 2-n-butyl-5,8-ethano-8-hydroxymethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
223) 5-t-butoxycarboxylmethoxymethyl-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
224) 5-t-butoxycarboxylmethoxymethyl-2-n-butyl-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
225) 8-t-butoxycarboxylmethoxymethyl-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
226) 8-t-butoxycarbonylmethoxymethyl-2-n-butyl-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
227) 5,8-ethano-5-(2-hydroxypropyl)methoxymethyl-2-n-propyl-5,6,7,8-tetrahydro-1-[{2'-(1H-tetrazol-5-yl)biphenyl-4-yl }methyl]-1H-1,3,4a,8a-tetraza-cyclopentanaphthalene-4,9-dione, dione,
228) 2-n-butyl-5,8-ethano-5-(2-hydroxypropyl)methoxymethyl-5,6,7,8-tetrahydro-1-[{2'-(1H-tetrazol-5-yl)biphenyl-4-yl }methyl]-1H-1,3,4a,8a-tetraza-cyclopentanaphthalene-4,9-dione,
229) 5,8-ethano-8-(2-hydroxypropyl)methoxymethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
230) 2-n-butyl-5,8-ethano-8-(2-hydroxypropyl)methoxymethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
231) 4,9-dioxo-5,8-ethano-2-n-propyl-5,6,7,8-tetrahydro-1-[{2'-(1H-tetrazol-5-yl)biphenyl 4-yl}methyl]-1H-1,3,4a,8a-tetraza-cyclopentanaphthalene-5-carboxy-N,N-diethylamide,
232) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide,
233) 4,9-dioxo-5,8-ethano-2-n-propyl-5,6,7, 8-tetrahydro-1-[{2'-(1H-tetrazol-5-yl)biphenyl-4-yl}methyl]-1H-1,3,4a,8a-tetraza-cyclopentanaphthalene-8-carboxy-N,N-diethylamide,
234) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-diethylamide, 235) 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N-t-butylamide, 236) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N-t-butylamide, 237) 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N-t-butylamide, 238) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N-t-butylamide, 239) 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-bis(2-hydroxyethyl)amide, 240) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-bis(2-hydroxyethyl)amide, 241) 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-bis(2-hydroxyethyl)amide, 242) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-bis(2-hydroxyethyl)amide, 243) 5,8-dihydro-5-hydroxymethyl-8-methyl-2-n-propyl-1-[{2'-(1H-tetrazol-5-yl)biphenyl 4-yl}methyl]-1H-1,3,4a,8a-tetraza-cyclopentanaphthalene-4,9-dione, 244) 2-n-butyl-5,8-dihydro-5-hydroxymethyl-8-methyl-1-[{2'-(1H-tetrazol-5-yl)biphenyl-4-yl}methyl]-1H-1,3,4a,8a-tetraza-cyclopentanaphthalene-4,9-dione, 245) 5,8-dihydro-8-hydroxymethyl-5-methyl-2-n-propyl-1-[{2'-(1H-tetrazol-5-yl)biphenyl-4-yl}methyl]-1H-1,3,4a,8a-tetraza-cyclopentanaphthalene-4,9-dione, 246) 2-n-butyl-5,8-dihydro-8-hydroxymethyl-5-methyl-1-[{2'-(1H-tetrazol-5-yl)biphenyl-4-yl}methyl]-1H-1,3,4a,8a-tetraza-cyclopentanaphthalene-4,9-dione, 247) 5,8-dihydro-5,8-ethano-5-hydroxymethyl-2-n-propyl-1-[{2'-(1H-tetrazol-5-yl)biphenyl-4-yl}methyl]-1H-1,3,4a,8a-tetraza-cyclopentanaphthalene-4,9-dione, 248) 2-n-butyl-5,8-dihydro-5,8-ethano-5-hydroxymethyl-1-[{2'-(1H-tetrazol-5-yl)biphenyl-4-yl}methyl]-1H-1,3,4a,8a-tetraza-cyclopentanaphthalene-4,9-dione, 249) 5,8-dihydro-5,8-ethano-8-hydroxymethyl-2-n-propyl-1-[{2'-(1H-tetrazol-5yl)biphenyl-4-yl}methyl]-1H-1,3,4a,8a-tetraza-cyclopentanaphthalene-4,9-dione, 250) 2-n-butyl-5,8-dihydro-5,8-ethano-8-hydroxymethyl-1-[{2'-(1H-tetrazol-5-yl)biphenyl-4-yl}methyl]-1H-1,3,4a,8a-tetraza-cyclopentanaphthalene-4,9-dione, 251) 5,8-dihydro-8-hydroxymethyl-5-methyl-2-n-propyl-1-[{2'-(1H-tetrazol-5-yl)biphenyl-4-yl}methyl]-1H-1,3,4a,8a-tetraza-cyclopentanaphthalene-4,9-dione, 252) 2-n-butyl-5,8-dihydro-8-hydroxymethyl-5-methyl-1-[{2'-(1H-tetrazol-5-yl)biphenyl-4-yl}methyl]-1H-1,3,4a,8a-tetraza-cyclopentanaphthalene-4,9-dione, 253) 4,9-dioxo-5,8-ethano-2-n-propyl-5,6,7, 8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide, 254) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide, 255) 6,7-diethyl-5,8-dihydro-2-ethyl-1H-1,3,4a,8a-tetraza-cyclopentanaphthalene-4,9-dione, 256) 6,7-diethyl-5,8-dihydro-2-n-propyl-1H-1,3,4a,8a-tetraza-cyclopentanaphthalene-4,9-dione, 257) 2-n-butyl-6,7-diethyl-5,8-dihydro-1H-1,3,4a,8a-tetraza-cyclopentanaphthalene-4,9-dione, 258) 6,7-diethyl-5,8-dihydro-2-n-pentyl-1H-1,3,4a,8a-tetraza-cyclopentanaphthalene-4,9-dione, 259) 6,7-bis(2,2,2-trifluoroethyl)-5,8-dihydro-2-ethyl-1H-1,3,4a,8a-tetraza-cyclopentanaphthalene-4,9-dione, 260) 6,7-bis(2,2,2-trifluoroethyl)-5,8-dihydro-2-n-propyl-1H-1,3,4a,8a-tetraza-cyclopentanaphthalene-4,9-dione, 261) 6,7-bis(2,2,2-trifluoroethyl)-2-n-butyl-5,8-dihydro-1H-1,3,4a,8a-tetraza-cyclopentanaphthalene-4,9-dione, 262) 6,7-bis(2,2,2-trifluoroethyl)-5,8-dihydro-2-n-pentyl-1H-1,3,4a,8a-tetraza-cyclopentanaphthalene-4,9-dione, 263) 2-ethyl-6-phenyl-5,6,7,8-tetrahydro-1H-1,3,4a,8a-tetraza-cyclopentanaphthalene-4,9-dione, 264) 6-phenyl-2-n-propyl-5,6,7,8-tetrahydro-1H-1,3,4a,8a-tetraza-cyclopentanaphthalene-4,9-dione, 265) 2-n-butyl-6-phenyl-5,6,7,8-tetrahydro-1H-1,3,4a,8a-tetraza-cyclopentanaphthalene-4,9-dione, 266) 2-n-pentyl-6-phenyl-5,6,7,8-tetrahydro-1H-1,3,4a,8a-tetraza-cyclopentanaphthalene-4,9-dione, 267) 5,8-dihydro-2-ethyl-6-phenyl-1H-1,3,4a,8a-tetraza-cyclopentanaphthalene-4,9-dione, 268) 5,8-dihydro-6-phenyl-2-n-propyl-1H-1,3,4a,8a-tetraza-cyclopentanaphthalene-4,9-dione, 269) 2-n-butyl-5,8-dihydro-6-phenyl-1H-1,3,4a,8a-tetraza-cyclopentanaphthalene-4,9-dione, 270) 5,8-dihydro-2-n-pentyl-6-phenyl-1H-1,3,4a,8a-tetraza-cyclopentanaphthalene-4,9-dione, 271) 5,8-dihydro-2-ethyl-6-methyl-1H-1,3,4a,8a-tetraza-cyclopentanaphthalene-4,9-dione, 272) 5,8-dihydro-6-methyl-2-n-propyl-1H-1,3,4a,8a-tetraza-cyclopentanaphthalene-4,9-dione, 273) 2-n-butyl-5,8-dihydro-6-methyl-1H-1,3,4a,8a-tetraza-cyclopentanaphthalene-4,9-dione, 274) 5,8-dihydro-6-methyl-2-n-pentyl-1H-1,3,4a,8a-tetraza-cyclopentanaphthalene-4,9-dione, 275) 2-ethyl-5-methyl-5,6,7,8-tetrahydro-1H-1,3,4a,8a-tetraza-cyclopentanaphthalene-4,9-dione, 276) 5-methyl-2-n-propyl-5,6,7,8-tetrahydro-1H-1,3,4a,8a-tetraza-cyclopentanaphthalene-4,9-dione, 277) 2-n-butyl-5-methyl-5,6,7,8-tetrahydro-1H-1,3,4a,8a-tetraza-cyclopentanaphthalene-4,9-dione, 278) 5-methyl-2-n-pentyl-5,6,7,8-tetrahydro-1H-1,3,4a,8a-tetraza-cyclopentanaphthalene-4,9-dione, 279) 5,8-dimethyl-2-ethyl-5,6,7,8-tetrahydro-1H-1,3,4a,8a-tetraza-cyclopentanaphthalene-4,9-dione, 280) 5,8-dimethyl-2-n-propyl-5,6,7,8-tetrahydro-1H-1,3,4a,8a-tetraza-cyclopentanaphthalene-4,9-dione, 281) 2-n-butyl-5,8-dimethyl-5,6,7,8-tetrahydro-1H-1,3,4a,8a-tetraza-cyclopentanaphthalene-4,9-dione,
282) 5,8-dimethyl-2-n-pentyl-5,6,7,8-tetrahydro-1H-1,3,4a,8a-tetraza-cyclopentanaphthalene-4,9-dione,
283) 5,8-dimethyl-2-ethyl-1H-1,3,4a,8a-tetraza-cyclopentanaphthalene-4,9-dione,
284) 5,8-dimethyl-2-n-propyl-1H-1,3,4a,8a-tetraza-cyclopentanaphthalene-4,9-dione,
285) 2-n-butyl-5,8-dimethyl-1H-1,3,4a,8a-tetraza-cyclopentanaphthalene-4,9-dione,
286) 5,8-dimethyl-2-n-pentyl-1H-1,3,4a,8a-tetraza-cyclopentanaphthalene-4,9-dione,
287) 5,8-ethano-2-ethyl-5-methyl-5,6,7,8-tetrahydro-1H-1,3,4a,8a-tetraza-cyclopentanaphthalene-4,9-dione,
288) 5,8-ethano-5-methyl-2-n-propyl-5,6,7,8-tetrahydro-1H-1,3,4a,8a-tetraza-cyclopentanaphthalene-4,9-dione,
289) 2-n-butyl-5,8-ethano-5-methyl-5,6,7,8-tetrahydro-1H-1,3,4a,8a-tetraza-cyclopentanaphthalene-4,9-dione,
290) 5,8-ethano-5-methyl-2-n-pentyl-5,6,7,8-tetrahydro-1H-1,3,4a,8a-tetraza-cyclopentanaphthalene-4,9-dione,
291) 5,8-dimethyl-5,8-ethano-2-ethyl-5,6,7,8-tetrahydro-1H-1,3,4a,8a-tetraza-cyclopentanaphthalene-4,9-dione,
292) 5,8-dimethyl-5,8-ethano-2-n-propyl-5,6,7,8-tetrahydro-1H-1,3,4a,8a-tetraza-cyclopentanaphthalene-4,9-dione,
293) 2-n-butyl-5,8-dimethyl-5,8-ethano-5,6,7,8-tetrahydro-1H-1,3,4a,8a-tetraza-cyclopentanaphthalene-4,9-dione,
294) 5,8-dimethyl-5,8-ethano-2-n-pentyl-5,6,7,8-tetrahydro-1H-1,3,4a,8a-tetraza-cyclopentanaphthalene-4,9-dione,
295) 5,8-diethyl-5,8-ethano-2-ethyl-5,6,7,8-tetrahydro-1H-1,3,4a,8a-tetraza-cyclopentanaphthalene-4,9-dione,
296) 5,8-diethyl-5,8-ethano-2-n-propyl-5,6,7,8-tetrahydro-1H-1,3,4a,8a-tetraza-cyclopentanaphthalene-4,9-dione,
297) 2-n-butyl-5,8-diethyl-5,8-ethano-5,6,7,8-tetrahydro-1H-1,3,4a,8a-tetraza-cyclopentanaphthalene-4,9-dione,
298) 5,8-diethyl-5,8-ethano-2-n-pentyl-5,6,7,8-tetrahydro-1H-1,3,4a,8a-tetraza-cyclopentanaphthalene-4,9-dione,
299) 2-ethyl-5-(2-pyridyl)-5,6,7,8-tetrahydro-1H-1,3,4a,8a-tetraza-cyclopentanaphthalene-4,9-dione,
300) 2-n-propyl-5-(2-pyridyl)-5,6,7,8-tetrahydro-1H-1,3,4a,8a-tetraza-cyclopentanaphthalene-4,9-dione,
301) 2-n-butyl-5-(2-pyridyl)-5,6,7,8-tetrahydro-1H-1,3,4a,8a-tetraza-cyclopentanaphthalene-4,9-dione,
302) 2-n-pentyl-5-(2-pyridyl)-5,6,7,8-tetrahydro-1H-1,3,4a,8a-tetraza-cyclopentanaphthalene-4,9-dione,
303) 2-ethyl-5,6,7,8-tetrahydro-5-trifluoromethyl-1H-1,3,4a,8a-tetraza-cyclopentanaphthalene-4,9-dione,
304) 2-n-propyl-5,6,7,8-tetrahydro-5-trifluoromethyl-1H-1,3,4a,8a-tetraza-cyclopentanaphthalene-4,9-dione,
305) 2-n-butyl-5,6,7,8-tetrahydro-5-trifluoromethyl-1H-1,3,4a,8a-tetraza-cyclopentanaphthalene-4,9-dione,
306) 2-n-pentyl-5,6,7,8-tetrahydro-5-trifluoromethyl-1H-1,3,4a,8a-tetraza-cyclopentanaphthalene-4,9-dione,
307) 2-ethyl-5,6,7,8-tetrahydro-5-(2,2,2-trifluoroethyl)-1H-1,3,4a,8a-tetraza-cyclopentanaphthalene-4,9-dione,
308) 2-n-propyl-5,6,7,8-tetrahydro-5-(2,2,2-trifluoroethyl)-1H-1,3,4a,8a-tetraza-cyclopentanaphthalene-4,9-dione,
309) 2-n-butyl-5,6,7,8-tetrahydro-5-(2,2,2-trifluoroethyl)-1H-1,3,4a,8a-tetraza-cyclopentanaphthalene-4,9-dione,
310) 2-pentyl-5,6,7,8-tetrahydro-5-(2,2,2-trifluoroethyl)-1H-1,3,4a,8a-tetraza-cyclopentanaphthalene-4,9-dione,
311) 5,8-dihydro-2-ethyl-6-trifluoromethyl-1H-1,3,4a,8a-tetraza-cyclopentanaphthalene-4,9-dione,
312) 5,8-dihydro-2-n-propyl-6-trifluoromethyl-1H-1,3,4a,8a-tetraza-cyclopentanaphthalene-4,9-dione,
313) 2-n-butyl-5,8-dihydro-6-trifluoromethyl-1H-1,3,4a,8a-tetraza-cyclopentanaphthalene-4,9-dione,
314) 5,8-dihydro-2-n-pentyl-6-trifluoromethyl-1H-1,3,4a,8a-tetraza-cyclopentanaphthalene-4,9-dione,
315) 5,8-ethano-2-ethyl-5-isopropyl-8-methyl-5,6,7,8-tetrahydro-1H-1,3,4a,8a-tetraza-cyclopentanaphthalene-4,9-dione,
316) 5,8-ethano-5-isopropyl-8-methyl-2-n-propyl-5,6,7,8-tetrahydro-1H-1,3,4a,8a-tetraza-cyclopentanaphthalene-4,9-dione,
317) 2-n-butyl-5,8-ethano-5-isopropyl-8-methyl-5,6,7,8-tetrahydro-1H-1,3,4a,8a-tetraza-cyclopentanaphthalene-4,9-dione,
318) 5,8-ethano-5-isopropyl-8-methyl-2-n-pentyl-5,6,7,8-tetrahydro-1H-1,3,4a,8a-tetraza-cyclopentanaphthalene-4,9-dione,
319) 5-phenyl-2-n-propyl-5,6,7,8-tetrahydro-1H-1,3,4a,8a-tetraza-cyclopentanaphthalene-4,9-dione,
320) 2-n-butyl-5-phenyl-5,6,7,8-tetrahydro-1H-1,3,4a,8a-tetraza-cyclopentanaphthalene-4,9-dione,
321) 8-methyl-5-(3-methyloxadiazol-5-yl)-2-n-propyl-5,6,7,8-tetrahydro-1H-1,3,4a,8a-tetraza-cyclopentanaphthalene-4,9-dione,
322) 2-n-butyl-8-methyl-5-(3-methyloxadiazol-5-yl)-5,6,7,8-tetrahydro-1H-1,3,4a,8-a-tetraza-cyclopentanaphthalene-4,9-dione,
323) 5,8-ethano-5-(1-hydroxy-1-methylethyl)-2-n-propyl-5,6,7,8-tetrahydro-1H-1,3,4a,8a-tetraza-cyclopentanaphthalene-4,9-dione,
324) 2-n-butyl-5,8-ethano-5-(1-hydroxy-1-methylethyl)-5,6,7,8-tetrahydro-1H-1,3,4a,8a-tetraza-cyclopentanaphthalene-4,9-dione,
325) 5-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
326) 2-n-butyl-5-phenyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
327) 8-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
328) 2-n-butyl-8-phenyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
329) 8-methyl-5-(3-methyloxadiazol-5-yl)-2-n-propyl-5,6,7,8-tetrahydro-1-[{2'-(1-tetrazol-5-yl)biphenyl-4-yl}methyl]-1H-1,3,4a,8a-tetraza-cyclopentanaphthalene-4,9-dione,
330) 2-n-butyl-8-methyl-5-(3-methyloxadiazol-5-yl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 331) 5-methyl-8-(3-methyloxadiazol-5-yl)-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 332) 2-n-butyl-5-methyl-8-(3-methyloxadiazol-5-yl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 333) 5,8-ethano-5-(1-hydroxy-1-methylethyl)-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 334) 2-n-butyl-5,8-ethano-5-(1-hydroxy-1-methylethyl)-5,6,7,8-tetrahydro-1-[{240 -(1H-tetrazol-5-yl)biphenyl-4-yl}methyl]-1H-1,3,4a,8a-tetraza-cyclopentanaphthalene-4,9-dione, 335) 5,8-ethano-8-(1-hydroxy-1-methylethyl)-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 336) 2-n-butyl-5,8-ethano-8-(1-hydroxy-1-methylethyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 337) 5,8-dimethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 338) 2-n-butyl-5,8-dimethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 339) 2-n-propyl-5-(2-pyridyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 340) 2-n-butyl-5-(2-pyridyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 341) 2-n-propyl-8-(2-pyridyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 342) 2-n-butyl-8-(2-pyridyl)-5,6,7, 8-tetrahydro-1-[{2'-(1H-tetrazol-5-yl)biphenyl-4-yl}methyl]-1H-1,3,4a,8a-tetraza-cyclopentanaphthalene-4,9-dione, 343) 5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 344) 2-n-butyl-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 345) 8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 346) 2-n-butyl-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 347) 6-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 348) 2-n-butyl-6-phenyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 349) 7-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 350) 2-n-butyl-7-phenyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 351) 5,8-dihydro-6-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 352) 2-n-butyl-5,8-dihydro-6-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 353) 5,8-dihydro-7-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 354) 2-n-butyl-5,8-dihydro-7-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 355) 5,8-diethyl-5,8-ethano-2-ethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 356) 5,8-diethyl-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 357) 2-n-butyl-5,8-diethyl-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 358) 5,8-diethyl-5,8-ethano-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 359) 6,7-diethyl-5,8-dihydro-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 360) 2-n-butyl-6,7-diethyl-5,8-dihydro-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 361) 5,8-dimethyl-5,8-ethano-2-ethyl-5,6,7,8-tetrahydro-1-[{2'-(1H-tetrazol-5-yl)biphenyl 4-yl}methyl]-1H-1,3,4a,8a-tetraza-cyclopentanaphthalene-4,9-dione, 362) 5,8-dimethyl-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 363) 2-n-butyl-5,8-dimethyl-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 364) 5,8-dimethyl-5,8-ethano-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 365) 2-ethyl-5,6,7,8-tetrahydro-1-[{2'-(1H-tetrazol-5-yl)biphenyl-4-yl}methyl]-1H-1,3,4a,8a-tetraza-cyclopentanaphthalene-9-one, 366) 2-n-propyl-5,6,7,8-tetrahydro-1-[{2'-(1H-tetrazol-5-yl)biphenyl-4-yl}methyl]-1H-4H, 1,3,4a,8a-tetraza-cyclopentanaphthalene-9-one, 367) 2-n-butyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 368) 2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 369) 5,8-dihydro-2-ethyl-1-[{2'-(1H-tetrazol-5-yl)biphenyl-4-yl}methyl]-1H,4H-1,3,4a,8a-tetraza-cyclopentanaphthalene-9-one, 370) 5,8-dihydro-2-n-propyl-1-[{2'-(1H-tetrazol-5-yl)biphenyl-4-yl}methyl]-1H,4H-1,3,4a,8a-tetraza-cyclopentanaphthalene-9-one, 371) 2-n-butyl-5,8-dihydro-1-[{2'-(1H-tetrazol-5-yl)biphenyl-4-yl}methyl]-1H,4H-1,3,4a,8a-tetraza-cyclopentanaphthalene-9-one, 372) 5,8-dihydro-2-n-pentyl-1-[{2'-(1H-tetrazol-5-yl)biphenyl-4-yl}methyl]-1H,4H-1,3,4a,8a-tetraza-cyclopentanaphthalene-9-one, 373) 2-ethyl-1-[{2'-(1H-tetrazol-5-yl)biphenyl-4-yl}methyl]-1H,4H-1,3,4a,8a-tetraza-cyclopentanaphthalene-9-one, 374) 2-n-propyl-1-[{2'-(1H-tetrazol-5-yl)biphenyl-4-yl}methyl]-1H,4H-1,3,4a,8a-tetraza-cyclopentanaphthalene-9-one, 375) 2-n-butyl-1-[{2'-(1H-tetrazol-5-yl)biphenyl-4-yl}methyl]-1H,4H-1,3,4a,8a-tetraza-cyclopentanaphthalene-9-one, 376) 2-n-pentyl-1-[{2'-(1H-tetrazol-5-yl)biphenyl-4-yl}methyl]-1H,4H-1,3,4a,8a-tetraza-cyclopentanaphthalene-9-one, 377) 6,7-dimethyl-2-ethyl-5,6,7,8-tetrahydro-1-[{2'-(1H-tetrazol-5-yl)biphenyl-4-yl}methyl]-1H,4-1,3,4a,8a-tetraza-cyclopentanaphthalene-9-one, 378) 6,7-dimethyl-2-n-propyl-5,6,7,8-tetrahydro-1-[{2'-(1H-tetrazol-5-yl)biphenyl-4-yl }methyl]-1H,4H-1,3,4a,8a-tetraza-cyclopentanaphthalene-9-one, 379) 2-n-butyl-6,7-dimethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 380) 6,7-dimethyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 381) 5,8-dihydro-6,7-dimethyl-2-ethyl-1-[{2'-(1H-tetrazol-5-yl)biphenyl-4-yl}methyl]-1H,4H-1,3,4a,8a-tetraza-cyclopentanaphthalene-9-one, 382) 5,8-dihydro-6,7-dimethyl-2-n-propyl-1-[{2'-(1H-tetrazol-5-yl)biphenyl-4-yl}methyl]-1H,4H-1,3,4a,8a-tetraza-cyclopentanaphthalene-9-one, 383) 2-n-butyl-5,8-dihydro-6,7-dimethyl-1-[{2'-(1H-tetrazol-5-yl)biphenyl-4-yl}methyl]-1H,4H-1,3,4a,8a-tetraza-cyclopentanaphthalene-9-one, 384) 5,8-dihydro-6,7-dimethyl-2-n-pentyl-1-[{2'-(1H-tetrazol-5-yl)biphenyl-4-yl}methyl]-1H,4H-1,3,4a,8a-tetraza-cyclopentanaphthalene-9-one, 385) 6,7-dimethyl-2-ethyl-1-[{2'-(1H-tetrazol-5-yl)biphenyl-4-yl}methyl]-1H,4H-1,3,4a,8a-tetraza-cyclopentanaphthalene-9-one, 386) 6,7-dimethyl-2-n-propyl-1-[{2'-(1H-tetrazol-5-yl)biphenyl-4-yl}methyl]-1H,4H-1,3,4a,8a-tetraza-cyclopentanaphthalene-9-one, 387) 2-n-butyl-6,7-dimethyl-1-[{2'-(1H-tetrazol-5-yl)biphenyl-4-yl}methyl]-1H,4-1,3,4a,8a-tetraza-cyclopentanaphthalene-9-one, 388) 6,7-dimethyl-2-n-pentyl-1-[{2'-(1H-tetrazol-5-yl)biphenyl-4-yl}methyl]-1H,1H-1,3,4a,8a-tetraza-cyclopentanaphthalene-9-one, 389) 6,7-diethyl-5,8-dihydro-2-ethyl-1-[{2'-(1H-tetrazol-5-yl)biphenyl-4-yl}methyl]-1H,4H-1,3,4a,8a-tetraza-cyclopentanaphthalene-9-one, 390) 6,7-diethyl-5,8-dihydro-2-n-propyl-1-[{2'-(1H-tetrazol-5-yl)biphenyl-4-yl}methyl]-1H,4H-1,3,4a,8a-tetraza-cyclopentanaphthalene-9-one, 391) 2-n-butyl-6,7-diethyl-5,8-dihydro-1-[{2'-(1H-tetrazol-5-yl)biphenyl-4-yl}methyl]-1H,4H-1,3,4a,8a-tetraza-cyclopentanaphthalene-9-one, 392) 6,7-diethyl-5,8-dihydro-2-n-pentyl-1-[{2'-(1H-tetrazol-5-yl)biphenyl-4-yl}methyl]-1H,4H-1,3,4a,8a-tetraza-cyclopentanaphthalene-9-one, 393) 6,7-bis(2,2,2-trifluoroethyl)-5,8-dihydro-2-ethyl-1-[{2'-(1H-tetrazol-5-yl)biphenyl-4-yl}methyl]-1H,4H-1,3,4a,8a-tetraza-cyclopentanaphthalene-9-one, 394) 6,7-bis(2,2,2-trifluoroethyl)-5,8-dihydro-2-n-propyl-1-[{2'-(1H-tetrazol-5-yl)biphenyl-4-yl}methyl]-1H,4H-1,3,4a,8a-tetraza-cyclopentanaphthalene-9-one, 395) 6,7-bis(2,2,2-trifluoroethyl)-2-n-butyl-5,8-dihydro-1-[{2'-(1H-tetrazol-5-yl)biphenyl-4-yl}methyl]-1H,4H-1,3,4a,8a-tetraza-cyclopentanaphthalene-9-one, 396) 6,7-bis(2,2,2-trifluoroethyl)-5,8-dihydro-2-n-pentyl-1-[{2'-(1H-tetrazol-5-yl)biphenyl-4-yl}methyl]-1H,4-1,3,4a,8a-tetraza-cyclopentanaphthalene-9-one, 397) 2-ethyl-6-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 398) 6-phenyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 399) 2-n-butyl-6-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 400) 2-n-pentyl-6-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 401) 2-ethyl-7-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 402) 7-phenyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 403) 2-n-butyl-7-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 404) 2-n-pentyl-7-phenyl-5,6,7,8-tetrahydro-1-[{2'-(1H-tetrazol-5-yl)biphenyl-4-y}methyl]-1H ,4H-1,3,4a,8a-tetraza-cyclopentanaphthalene-9-one, 405) 5,8-dihydro-2-ethyl-6-phenyl-1-[{2'-(1H-tetrazol-5-yl)biphenyl-4-yl}methyl]-1H,4H-1,3,4a,8a-tetraza-cyclopentanaphthalene-9-one, 406) 5,8-dihydro-6-phenyl-2-n-propyl-1-[{2'-(1H-tetrazol-5-yl)biphenyl-4-yl}methyl]-1H,4H-1,3,4a,8a-tetraza-cyclopentanaphthalene-9-one, 407) 2-n-butyl-5,8-dihydro-6-phenyl-1-[{2'-(1H-tetrazol-5-yl)biphenyl-4-yl}methyl]-1H,4H-1,3,4a,8a-tetraza-cyclopentanaphthalene-9-one, 408) 5,8-dihydro-2-n-pentyl-6-phenyl-1-[{2'-(1H-tetrazol-5-yl)biphenyl-4-yl}methyl]-1H,4H-1,3,4a,8a-tetraza-cyclopentanaphthalene-9-one, 409) 5,8-dihydro-2-ethyl-7-phenyl-1-[{2'-(1H-tetrazol-5-yl)biphenyl-4-yl }methyl]-1H,4H-1,3,4a,8a-tetraza-cyclopentanaphthalene-9-one, 410) 5,8-dihydro-7-phenyl-2-n-propyl-1-[{2'-(1H-tetrazol-5-yl)biphenyl-4-yl}methyl]-1H,4H-1,3,4a,8a-tetraza-cyclopentanaphthalene-9-one, 411) 2-n-butyl-5,8-dihydro-7-phenyl-1-[{2'-(1H-tetrazol-5-yl)biphenyl-4-yl}methyl]-1H,4H-1,3,4a,8a-tetraza-cyclopentanaphthalene-9-one, 412) 5,8-dihydro-2-n-pentyl-7-phenyl-1-[{2'-(1H-tetrazol-5-yl)biphenyl-4-yl}methyl]-1H,4H-1,3,4a,8a-tetraza-cyclopentanaphthalene-9-one,
413) 5,8-dihydro-2-ethyl-6-methyl-1-[{2'-(1H-tetrazol-5-yl)biphenyl-4-yl}methyl]-1H,4H-1,3,4a,8a-tetraza-cyclopentanaphthalene-9-one,
414) 5,8-dihydro-6-methyl-2-n-propyl-1-[{2'-(1H-tetrazol-5-yl)biphenyl-4-yl}methyl]-1H,4H-1,3,4a,8a-tetraza-cyclopentanaphthalene-9-one,
415) 2-n-butyl-5,8-dihydro-6-methyl-1-[{2'-(1H-tetrazol-5-yl)biphenyl-4-yl}methyl]-1H,4H-1,3,4a,8a-tetraza-cyclopentanaphthalene-9-one,
416) 5,8-dihydro-6-methyl-2-n-pentyl-1-[{2'-(1H-tetrazol-5-yl)biphenyl-4-yl}methyl]-1H,4H-1,3,4a,8a-tetraza-cyclopentanaphthalene-9-one,
417) 5,8-dihydro-2-ethyl-7-methyl-1-[{2'-(1H-tetrazol-5-yl)biphenyl-4-yl}methyl]-1H,4H-1,3,4a,8a-tetraza-cyclopentanaphthalene-9-one,
418) 5,8-dihydro-7-methyl-2-n-propyl-1-[{2'-(1H-tetrazol-5-yl)biphenyl-4-yl}methyl]-1H,4H-1,3,4a,8a-tetraza-cyclopentanaphthalene-9-one,
419) 2-n-butyl-5,8-dihydro-7-methyl-1-[{2'-(1H-tetrazol-5-yl)biphenyl-4-yl}methyl]-1H,4H-1,3,4a,8a-tetraza-cyclopentanaphthalene-9-one,
420) 5,8-dihydro-7-methyl-2-n-pentyl-1-[{2'-(1H-tetrazol-5-yl)biphenyl-4-yl}methyl]-1H,4H-1,3,4a,8a-tetraza-cyclopentanaphthalene-9-one,
421) 2-ethyl-5-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
422) 5-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
423) 2-n-butyl-5-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
424) 5-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
425) 2-ethyl-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
426) 8-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
427) 2-n-butyl-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
428) 8-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
429) 5,8-dimethyl-2-ethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
430) 5,8-dimethyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
431) 2-n-butyl-5,8-dimethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
432) 5,8-dimethyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
433) 5,8-dimethyl-2-ethyl-1-[{2'-(1H-tetrazol-5-yl)biphenyl-4-yl}methyl]-1H,4H-1,3,4a,8a-tetraza-cyclopentanaphthalene-9-one,
434) 5,8-dimethyl-2-n-propyl-1-[{2'-(1H-tetrazol-5-yl)biphenyl-4-yl}methyl]-1H,4H-1,3,4a,8a-tetraza-cyclopentanaphthalene-9-one,
435) 2-n-butyl-5,8-dimethyl-1-[{2'-(1H-tetrazol-5-yl)biphenyl-4-yl}methyl]-1H,4H-1,3,4a,8a-tetraza-cyclopentanaphthalene-9-one,
436) 5,8-dimethyl-2-n-pentyl-1-[{2'-(1H-tetrazol-5-yl)biphenyl-4-yl}methyl]-1H,4H-1,3,4a,8a-tetraza-cyclopentanaphthalene-9-one,
437) 5,8-ethano-2-ethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
438) 5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
439) 2-n-butyl-5,8-ethano-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
440) 5,8-ethano-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
441) 5-8-ethano-2-ethyl-5-methyl-5,6,7,8,tetrahydro-1-[{2'-(1H-tetrazol-5-yl)biphenyl-4yl}methyl]-1H,4H-1,3,4a,8a-tetraza-cyclopentanaphthalene-9-one,
442) 5,8-ethano-5-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
443) 2-n-butyl-5,8-ethano-5-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
444) 5,8-ethano-5-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
445) 5,8-ethano-2-ethyl-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
446) 5,8-ethano-8-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
447) 2-n-butyl-5,8-ethano-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
448) 5,8-ethano-8-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
449) 5,8-dimethyl-5,8-ethano-2-ethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
450) 5,8-dimethyl-5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
451) 2-n-butyl-5,8-dimethyl-5,8-ethano-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
452) 5,8-dimethyl-5,8-ethano-2-n-pentyl-5,6,7,8-tetrahydro-1-[{2'-(1H-tetrazol-5-yl)biphenyl-4-yl}me- 453) 5,8-diethyl-5,8-ethano-2-ethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 454) 5,8-diethyl-5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 455) 2-n-butyl-5,8-diethyl-5,8-ethano-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 456) 5,8-diethyl-5,8-ethano-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 457) 5,8-di-n-propyl-5,8-ethano-2-ethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 458) 5,8-di-n-propyl-5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 459) 2-n-butyl-5,8-di-n-propyl-5,8-ethano-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 460) 5,8-di-n-propyl-5,8-ethano-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 461) 5,8-diisopropyl-5,8-ethano-2-ethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 62) 5,8-diisopropyl-5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 463) 2-n-butyl-5,8-diisopropyl-5,8-ethano-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 464) 5,8-diisopropyl-5,8-ethano-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 465) 2-ethyl-5-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 466) 5-phenyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 467) 2-n-butyl-5-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 468) 2-n-pentyl-5-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 469) 2-ethyl-8-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 470) 8-phenyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 471) 2-n-butyl-8-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 472) 2-n-pentyl-8-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 473) 2-ethyl-5-(2-pyridyl)-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 474) 2-n-propyl-5-(2-pyridyl)-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 475) 2-n-butyl-5-(2-pyridyl)-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 476) 2-n-pentyl-5-(2-pyridyl)-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 477) 2-ethyl-8-(2-pyridyl)-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 478) 2-n-propyl-8-(2-pyridyl)-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 479) 2-n-butyl-8-(2-pyridyl)-5,6,7,8-tetrahydro-1-[{2'-(1H-tetrazol-5-yl)biphenyl-4-}methyl]-1H,4H-1,3,4a,8a-tetraza-cyclopentanaphthalene-9-one, 480) 2-n-pentyl-8-(2-pyridyl)-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 481) 2-ethyl-5,6,7,8-tetrahydro-5-trifluoromethyl-1-[{2'-(1H-tetrazol-5-yl)biphenyl-4-yl}methyl]-1H,4H-1,3,4a,8a-tetraza-cyclopentanaphthalene-9-one, 482) 2-n-propyl-5,6,7,8-tetrahydro-5-trifluoromethyl-1-[{2'-(1H-tetrazol-5-yl)biphenyl-4-yl}methyl]-1H,4H-1,3,4a,8a-tetraza-cyclopentanaphthalene-9-one, 483) 2-n-butyl-5,6,7,8-tetrahydro-5-trifluoromethyl-1-[{2'-(1H-tetrazol-5-yl)biphenyl-4-yl}methyl]-1H,4H-1,3,4a,8a-tetraza-cyclopentanaphthalene-9-one, 484) 2-n-pentyl-5,6,7,8-tetrahydro-5-trifluoromethyl-1-[{2'-(1H-tetrazol-5-yl)biphenyl-4-yl}methyl]-1H,4H-1,3,4a,8a-tetraza-cyclopentanaphthalene-9-one, 485) 2-ethyl-5,6,7,8-tetrahydro-8-trifluoromethyl-1-[{2'-(1H-tetrazol-5-yl)biphenyl-4-yl}methyl]-1H,4H-1,3,4a,8a-tetraza-cyclopentanaphthalene-9-one, 486) 2-n-propyl-5,6,7,8-tetrahydro-8-trifluoromethyl-1-[{2'-(1H-tetrazol-5-yl)biphenyl-4-yl}methyl]-1H,4H-1,3,4a,8a-tetraza-cyclopentanaphthalene-9-one, 487) 2-n-butyl-5,6,7,8-tetrahydro-8-trifluoromethyl-1-[{2'-(1H-tetrazol-5-yl)biphenyl-4-yl}methyl]-1H,4H-1,3,4a,8a-tetraza-cyclopentanaphthalene-9-one, 488) 2-n-pentyl-5,6,7,8-tetrahydro-8-trifluoromethyl-1-[{2'-(1H-tetrazol-5-yl)biphenyl-4-yl}methyl]-1H,4H-1,3,4a,8a-tetraza-cyclopentanaphthalene-9-one, 489) 2-ethyl-5,6,7,8-tetrahydro-5-(2,2,2-trifluoroethyl)-1-[{2'-(1H-tetrazol-5-yl)biphenyl-4-yl}methyl]-1H,4H-1,3,4a,8a-tetraza-cyclopentanaphthalene-9-one, 490) 2-n-propyl-5,6,7,8-tetrahydro-5-(2,2,2-trifluoroethyl)-1-[{2'-(1H-tetrazol-5-yl)biphenyl-4-yl}methyl]-1H,4H-1,3,4a,8a-tetraza-cyclopentanaphthalene-9-one, 491) 2-n-butyl-5,6,7,8-tetrahydro-5-(2,2,2-trifluoroethyl)-1-[{2'-(1H-tetrazol-5-yl)biphenyl-4-yl}methyl]-1H,4H-1,3,4a,8a-tetraza-cyclopentanaphthalene-9-one, 492) 2-n-pentyl-5,6,7,8-tetrahydro-5-(2,2,2-trifluoroethyl)-1-[{2'-(1H-tetrazol-5-yl)biphenyl-4-yl}methyl]-1H,4H-1,3,4a,8a-tetraza-cyclopentanaphthalene-9-one, 493) 2-ethyl-5,6,7,8-tetrahydro-8-(2,2,2-trifluoroethyl)-1-[{2'-(1H-tetrazol-5-yl)biphenyl-4-yl}methyl]-1H,4H-1,3,4a,8a-tetraza-cyclopentanaphthalene-9-one, 494) 2-n-propyl-5,6,7,8-tetrahydro-8-(2,2,2-trifluoroethyl)-1-[{2'-(1H-tetrazol-5-yl)biphenyl-4-yl}methyl]-1H,4H-1,3,4a,8a-tetraza-cyclopentanaphthalene-9-one, 495) 2-n-butyl-5,6,7,8-tetrahydro-8-(2,2,2-trifluoroethyl)-1-[{2'-(1H-tetrazol-5-yl)biphenyl-4-yl}methyl]-1H,4H-1,3,4a,8a-tetraza-cyclopentanaphthalene-9-one, 496) 2-n-pentyl-5,6,7,8-tetrahydro-8-(2,2,2-trifluoroethyl)-1-[{2'-(1H-tetrazol-5-yl)biphenyl-4-yl}methyl]-1H,4H-1,3,4a,8a-tetraza-cyclopentanaphthalene-9,-one, 497) 5,8-dihydro-2-ethyl-6-trifluoromethyl-1-[{2'-(1H-tetrazol-5-yl)biphenyl-4-yl}methyl]-1H,4H-1,3,4a,8a-tetraza-cyclopentanaphthalene-9-one, 498) 5,8-dihydro-2-n-propyl-6-trifluoromethyl-1-[{2'-(1H-tetrazol-5-yl)biphenyl-4-yl}methyl]-1H,4H-1,3,4a,8a-tetraza-cyclopentanaphthalene-9-one, 499) 2-n-butyl-5,8-dihydro-6-trifluoromethyl-1-[{2'-(1H-tetrazol-5-yl)biphenyl-4-yl}methyl]-1H,4H-1,3,4a,8a-tetraza-cyclopentanaphthalene-9-one, 500) 5,8-dihydro-2-n-pentyl-6-trifluoromethyl-1-[{2'-(1H-tetrazol-5-yl)biphenyl-4-yl}methyl]-1H,4H-1,3,4a,8a-tetraza-cyclopentanaphthalene-9-one, 501) 5,8-dihydro-2-ethyl-7-trifluoromethyl-1-[{2'-(1H-tetrazol-5-yl)biphenyl-4-yl}methyl]-1H,4H-1,3,4a,8a-tetraza-cyclopentanaphthalene-9-one, 502) 5,8-dihydro-2-n-propyl-7-trifluoromethyl-1-[{2'-(1H-tetrazol-5-yl)biphenyl-4-yl}methyl]-1H,4H-1,3,4a,8a-tetraza-cyclopentanaphthalene-9-one, 503) 2-n-butyl-5,8-dihydro-7-trifluoromethyl-1-[{2'-(1H-tetrazol-5-yl)biphenyl-4-yl}methyl]-1H,4H-1,3,4a,8a-tetraza-cyclopentanaphthalene-9-one, 504) 5,8-dihydro-2-n-pentyl-7-trifluoromethyl-1-[{2'-(1H-tetrazol-5-yl)biphenyl-4-yl}methyl]-1H,4H-1,3,4a,8a-tetraza-cyclopentanaphthalene-9-one, 505) 2-ethyl-5-hydroxymethyl-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 506) 5-hydroxymethyl-8-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 507) 2-n-butyl-5-hydroxymethyl-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 508) 5-hydroxymethyl-8-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 509) 2-ethyl-8-hydroxymethyl-5-methyl-5,6,7,8-tetrahydro-1-[{2'-(1H-tetrazol-5-yl)biphenyl-4-yl}methyl]-1H ,4H-1,3,4a,8a-tetraza-cyclopentanaphthalene -9-one, 510) 8-hydroxymethyl-5-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 511) 2-n-butyl-8-hydroxymethyl-5-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 512) 8-hydroxymethyl-5-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 513) 5,8-ethano-2-ethyl-5-hydroxymethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 514) 5,8-ethano-5-hydroxymethyl-2-n-propyl-5,6,7,8-tetrahydro-1-[{2'-(1H-tetrazol-5yl)biphenyl-4-yl}methyl]-1H,4H-1,3,4a,8a-tetraza-cyclopentanaphthalene-9-one, 515) 2-n-butyl-5,8-ethano-5-hydroxymethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 516) 5,8-ethano-5-hydroxymethyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 517) 5,8-ethano-2-ethyl-8-hydroxymethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 518) 5,8-ethano-8-hydroxymethyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 519) 2-n-butyl-5,8-ethano-8-hydroxymethyl-5,6,7,8-tetrahydro-1-[{2'-(1H-tetrazol-5-yl)biphenyl-4-yl}methyl]-1H,4H-1-,3,4a,8a-tetraza-cyclopentanaphthalene-9one, 520) 5,8-ethano-8-hydroxymethyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 521) 5,8-diethyl-5,8-ethano-2-(1-E-propenyl)-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 522) 2-(1E-butenyl)-5,8-diethyl-5,8,ethano-5,6,7,8-tetrahydro-1-[{2-(1H-tetrazol-5-yl)biphenyl-4-yl}methyl]-1H,4H-1,3,4a-tetraza-cyclopentanaphthalene-9-one, 523) 5,8-ethano-4,5,6,7,8,9-hexahydro-2-n-propyl-1-[{2'-tetrazol-5-yl)biphenyl-4-4-yl}methyl]-1H-1,3,4a,8a-tetraza-cyclopentanaphthalene, 524) 2-n-butyl-5,8-ethano-4,5,6,7,8,9-hexahydro-1-[{2'-tetrazol-5-yl)biphenyl-4-yl}methyl 1-1H-1,3,4a,8a-tetraza-cyclopentanaphthalene, 525) 4-methyl-2-n-propyl-5,6,7,8-tetrahydro-1-[{2'-tetrazol-5-yl)biphenyl-4-yl}methyl]-1H,4H-1,3,4a,-8a-tetraza-cyclopentanaphthalene-9-one, 526) 2-n-butyl-1-methyl-5,6,7,8-tetrahydro-1-[{2'-tetrazol-5-yl)biphenyl-4-yl}methyl]-1-H,4H-1,3,4a,8a-tetraza-cyclopentanaphthalene-9-one, 527) 4,4-dimethyl-2-n-propyl-5,6,7,8-tetrahydro-1-[{2'-tetrazol-5-yl)biphenyl-4-yl}methyl]-1H,4H-1,3,4a,8a-tetraza-cyclopentanaphthalene-9-one, 528) 2-n-butyl-4,4-dimethyl-5,6,7,8-tetrahydro-1-[{2'-tetrazol-5-yl)biphenyl-4-yl}methyl]-1H,4H-1,3,4a,8a-tetraza-cyclopentanaphthalene-9-one, 529) 5,8-ethano-4-methyl-2-n-propyl-5,6,7,8-tetrahydro-1-[{2'-tetrazol-5-yl)biphenyl-4-yl}methyl]-1H,4H-1,3,4a,8a-tetraza-cyclopentanaphthalene-9-one, 530) 2-n-butyl-5,8-ethano-4-methyl-5,6,7,8-tetrahydro-1-[{2'-tetrazol-5-yl)biphenyl-4-yl}methyl]-1H,4H-1,3,4a,8a-tetraza-cyclopentanaphthalene-9-one, 531) 4,4-dimethyl-5,8-ethano-2-n-propyl-5,6,7,8-tetrahydro-1-[{2'-tetrazol-5-yl)biphenyl-4-yl}methyl]-1H,4H-1,3,4a,8a-tetraza-cyclopentanaphthalene-9-one, 532) 2-n-butyl-1,4-dimethyl-5,8-ethano-5,6,7,8-tetrahydro-1-[{2'-tetrazol-5-yl)biphenyl-4-yl}methyl]-1H,4H-1,3,4a,8a-tetraza-cyclopentanaphthalene-9-one, 533) 5,8-ethano-2-n-propyl-5,6,7,8-tetrahydro-4,5,8-trimethyl-1-[{2'-tetrazol-5-yl)biphenyl-4-yl}methyl]-1H,4H-1,3,4a,8a-tetraza-cyclopentanaphthalene-9-one, 534) 2-n-butyl-5,8-ethano-5,6,7,8-tetrahydro4,5,8-trimethyl-1-[{2'-tetrazol-5-yl)biphenyl-4-yl}methyl]-1H,4H-1,3,4a,8a-tetraza-cyclopentanaphthalene-9-one, 535) 5,8-ethano-2-n-propyl-5,6,7,8-tetrahydro-4,4,5,8-tetramethyl-1-[{2'-tetrazol-5-yl)biphenyl-4-yl}methyl]-1H,4H-1,3,4a,8a-tetraza-cyclopentanaphthalene-9-one, 536) 2-n-butyl-5,8-ethano-5,6,7,8-tetrahydro4,4,5,8-tetramethyl-1-[{2'-tetrazol-5-yl)biphenyl-4-yl}methyl]-1H,4H-1,3,4a,8a-tetraza-cyclopentanaphthalene-9-one, 537) 5-hydroxymethyl-8-methyl-2-n-propyl-5,6,7,8-tetrahydro-1-[{2'-tetrazol-5-yl)biphenyl-4-yl}methyl]-1H,9H-1,3,4a,8a-tetraza-cyclopentanaphthalene-4-one, 538) 2-n-butyl-5-hydroxymethyl-8-methyl-5,6,7,8-tetrahydro-1-[{2'-tetrazol-5-yl)biphenyl-4-yl}methyl]-1H,9H-1,3,4a,8a-tetraza-cyclopentanaphthalene-4-one, 539) 8-hydroxymethyl-5-methyl-2-n-propyl-5,6,7,8-tetrahydro-1-[{2'-tetrazol-5-yl)biphenyl-4-yl}methyl]-1H,9H-1,3,4a,8a-tetraza-cyclopentanaphthalene-4-one, 540) 2-n-butyl-8-hydroxymethyl-5-methyl-5,6,7,8-tetrahydro-1-[{2'-tetrazol-5-yl)biphenyl-4-yl}methyl]-1H,9H-1,3,4a,8a-tetraza-cyclopentanaphthalene-4-one, 541) 2-n-butyl-5-hydroxymethyl-8-methyl-5,6,7,8-tetrahydro-1H,4H-1,3,4a,8a-tetraza-cyclopentanaphthalene-9-one, 542) 2-n-butyl-8-hydroxymethyl-5-methyl-5,6,7,8-tetrahydro-1H,4H-1,3,4a,8a-tetraza-cyclopentanaphthalene-9-one, 543) 5,8-ethano-2-ethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 544) 2-n-butyl-1-[(4-carboxyphenyl)methyl]-5,8-ethano-5,6,7,8-tetrahydro-1H-1,3,4a,8a-tetraza-cyclopentanaphthalene 4,9-dione, 545) 5,8-dihydro-5,8-dimethyl-5,8-ethano-2-n-propyl-1H-1,3,4a,8a-tetraza-cyclopentanaphthalene-4,9-dione, and 546) 2-n-butyl-5,8-dihydro-5,8-dimethyl-5,8-ethano-1H-1,3,4a,8a-tetraza-cyclopentanaphthalene-4,9-dione, 547) 2-n-butyl-5,8-diethyl-5,8-ethano-5,6,7,8-tetrahydro-1-[(2'-cyanobiphenyl-4-yl)methyl]-1H,4H-1,3,4a,8a-tetraza-cyclopentanaphthalene-9-one, 548) 2-n-butyl-5,8-di-n-propyl-5,8-ethano-5,6,7,8-tetrahydro-1H-1,3,4a,8a-tetraza-cyclopentanaphthalene-4,9-dione, 549) 2-n-butyl-5,8-diisopropyl-5,8-ethano-5,6,7,8-tetrahydro-1H-1,3,4a,8a-tetraza-cyclopentanaphthalene-4,9-dione, The imidazole derivatives of the present invention represented by the general formula [I] wherein $R^2$ and $R^3$, or $R^4$ and $R^5$ are taken together to form =O bond can be prepared, for example, according to the following reaction scheme.

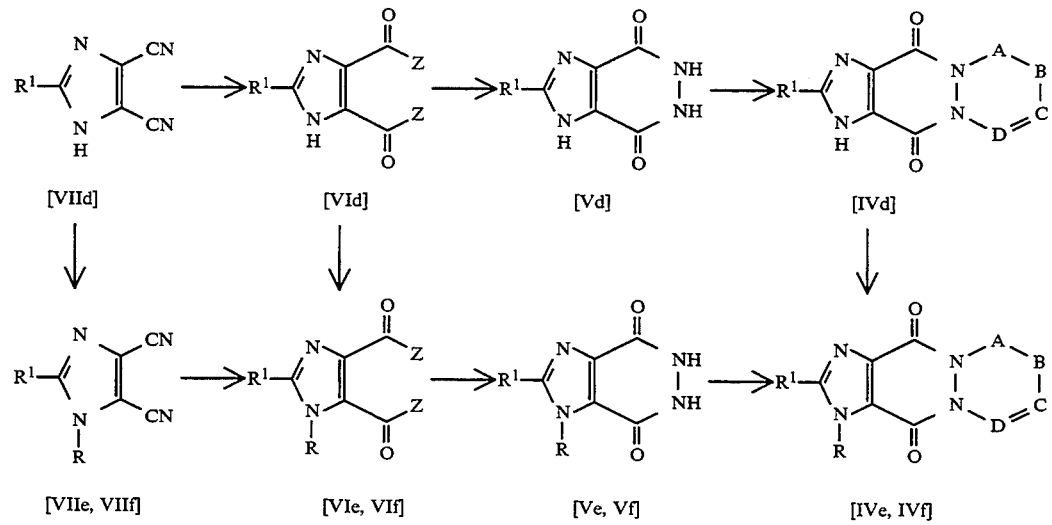

wherein d, e and f mean that the nitrogen atom of the imidazole ring binds to a hydrogen atom, substituted or unsubstituted phenylmethyl group or biphenylmethyl group, respectively, and Z is —OH group or a lower alkoxy group.

The imidazole derivative [VIIb] which can be readily obtained from an diaminomaleonitrile and various orthoesters can be converted into an imidazole derivative [VIIe] or [VIIf] by alkylation under basic conditions using substituted or unsubstituted phenylmethyl or biphenylmethyl group according to conventional methods. As examples of a base which can be used for the basic conditions, there are metal hydrides such as lithium hydride, sodium hydride, potassium hydride and the like, an organometallic lithium compound such as n-butyl lithium, phenyl lithium and the like, sodium carbonate, potassium carbonate, sodium methoxide, sodium ethoxide, potassium t-butoxide, or organic amines such as triethylamine, 1,5-diazabicyclo[4.3.0.]-5-nonene, 1,8-diazabicyclo[5.4.0]-7-undecene and the like. The reaction solvent varies depending upon the kind of the base, reaction conditions and the like, but it can be appropriately selected from ether solvents such as diethyl ether, diisopropyl ether, tetrahydrofuran and the like, alcohol solvents such as methanol, ethanol, propanol, isopropanol, butanol, t-butanol and the like, amido solvents such as dimethylformamide, diethylformamide, N-methylpyrrolidone, pyrrolidone and the like, or dimethyl sulfoxide and the like. The reaction temperature varies depending upon the kind of base or solvent. For example, when sodium hydride is used as the base and dimethylformamide is used as the solvent, a temperature in a range of from −30° C. to 50° C. is suitable, and when potassium carbonate is used as the base and a mixed solution of tetrahydrofuran and dimethylformamide is used as the solvent, a range of from room temperature to 80° C. is suitable.

A method for converting the nitrile group of [VIId,e,f] into a corresponding carboxylic acid (Z=OH) and alkoxycarbonyl group is known. For example, conversion into the end product [IIIa,b,c] can be carried out in high yield by heating in water or an alcohol, respectively, using sulfuric acid as a catalyst when acidic conditions are used.

Conversion of the compound [VId] into the compound [Vd] by heating with hydrazine is described in EP-A 400974 (JP-A 3-95181), and the compound [Ve] wherein the nitrogen atom in the imidazole ring in [Vd] is bound to a substituted phenylmethyl group is described in WO-91/11999.

On the other hand, conversion of —NH—NH— linkage in [Vd], [Ve] into —N=N— linkage by an oxidative reaction is also described in the above-described EP-A 400974 and WO-91/11999. However, as also described in J.Am.Chem.Soc., Vol. 84, 966(1962), a compound having a —N=N— linkage becomes unstable. In fact, since an imidazole derivative bonded to

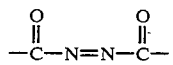

group which is shown in EP-A 400974, WO91/11999 degrades rapidly at room temperature, it can not be used as a drug. The stability of an imidazole derivative bonded to

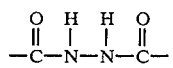

group is improved in comparison with that of

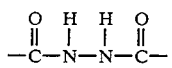

but the stability thereof in air is not necessarily sufficient because of conversion into

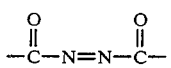

in the oxidative conditions.

On the other hand, since the synthesis where R is substituted by lower alkyl group in

has not been reported, the comparison with such the case can not be made. However, it has been found that an imidazole derivative bonded to

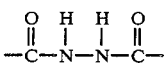

has high in vitro receptor binding activity and the activity when intravenously administered and, however, the water absorption is low such that the activity when orally administered is far from the practical level and the action lasting time is extremely short as 2 to 3 hours.

From this point of view, the present inventors studied ways to improve the physiological activity of imidazole derivatives represented by [Vd], [Ve], and at the same time to inhibit the lowering of the stability which is caused by the oxidizing reaction of —NH—NH— linkage, and finally to prolong the action lasting time of a drug. As a result, it has been found that a compound obtained by subjecting a compound having a —N=H— linkage and various dienes to Diels Alder reaction, and a compound obtained by subjecting this to hydrogenating or dehydrogenating reaction, or a compound obtained by subjecting —NH—NH— linkage to cyclizing alkylation reaction have a bridge structure as shown below and becomes metabolically stable due to steric hindrance and can maintain high activity for a long period of time.

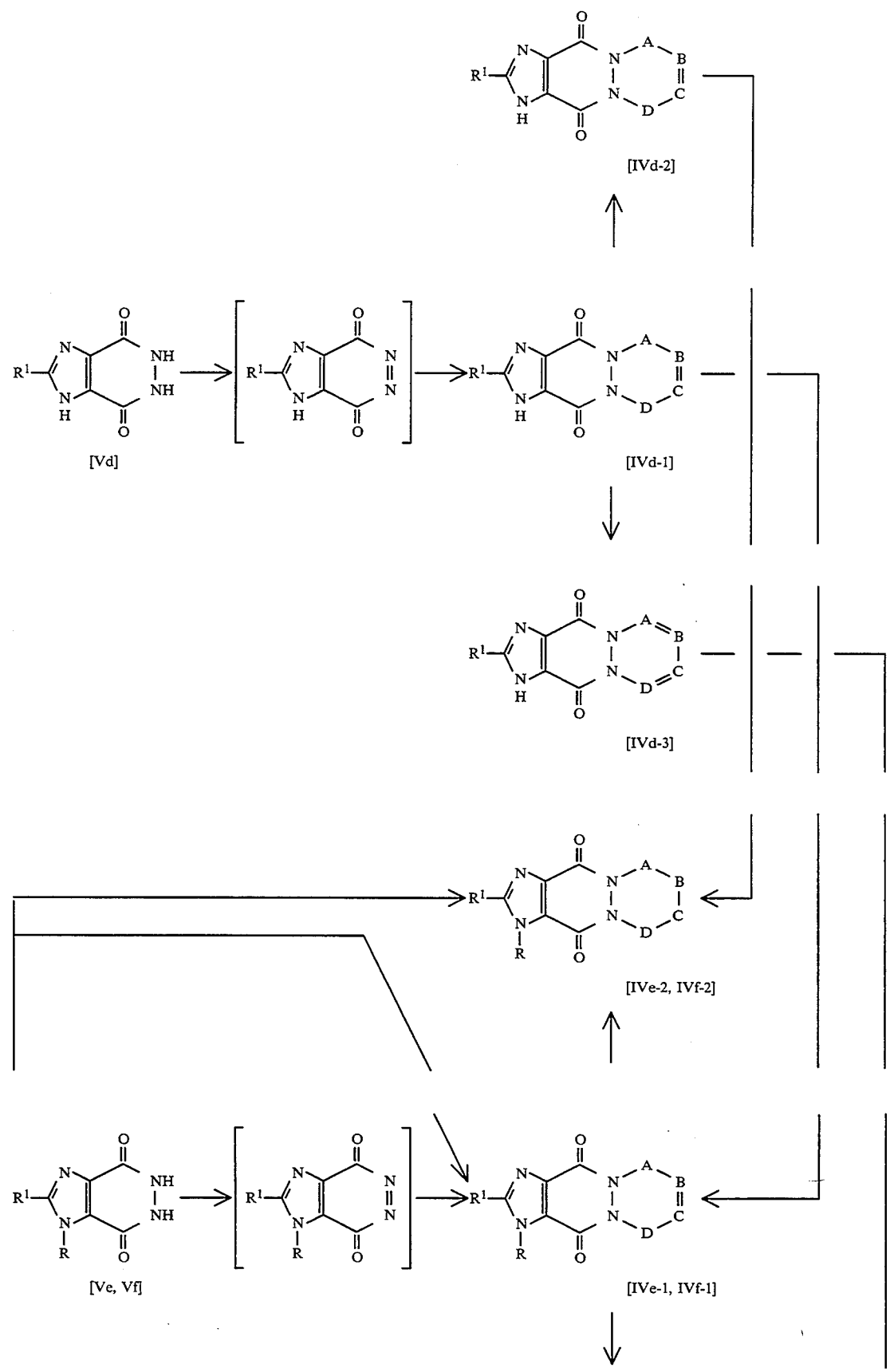

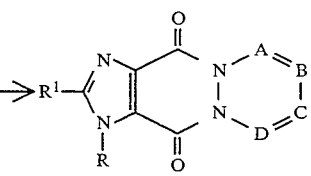

[IVe-3, IVf-3]

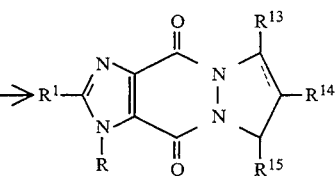

[IVe-4, IVf-4]

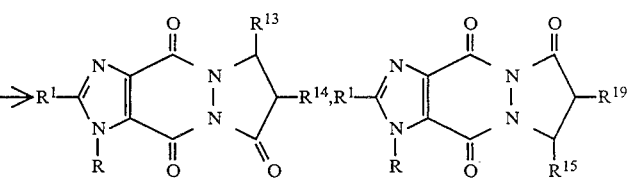

[IVe-5, IVf-5]

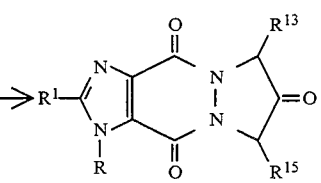

[IVe-6, IVf-6]

A compound having the hydrazine bridge structure is only known in the significantly restricted number of medicines and candidates therefor.

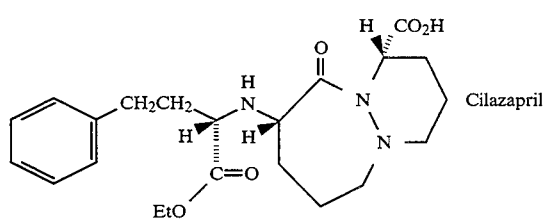

Cilazapril

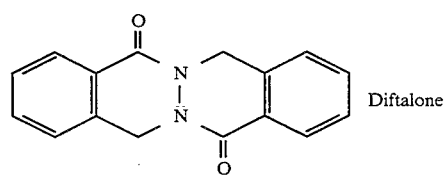

Diftalone

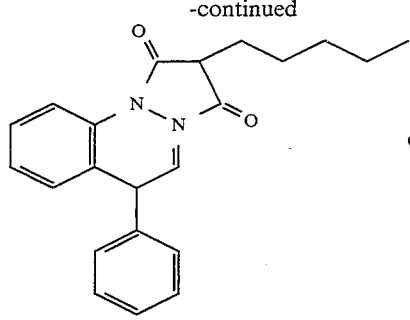

Cintazone

That is, there are cilazapril as an angiotensin convening enzyme inhibitor used for hypertension, diftalone and cintazone used for an anti-inflammatory agent and the like, the structures of which am shown above. However, an antagonist to angiotensin (ID receptor is not known.

By treating [Vd], [Ve], [Vf] with an oxidizing agent such as lead tetraacetate, N-bromosuccinimide, or t-butyl hypochlorite at a low temperature according to the methods which are known in the literature [see, for example, J.Am.Chem.Soc., 101, 7347 (1979); Angew. Chem., 78, 376(1966)], a

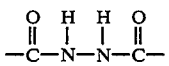

group is converted into a

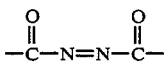

group, and since this group

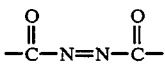

is unstable also at a low temperature as described in J. Am. Chem. Soc., 84, 966(1962), conversion into [IVd-1], [IVe-1], [IVf-1] can be carried out by forming

and at the same time performing Diels Alder reaction in the presence of the various dienes. As usual reaction operations, the following operations can be employed. A diene in an amount of from equal mole to 5 times moles relative to [Vd-Vf] is mixed with a halogenated hydrocarbon solvent such as dichloromethane, dichloroethane and the like, and an oxidizing agent such as lead tetraacetate, N-bromosuccinimide, t-butyl hypochlorite and the like in an amount of from equal mole to 5 times moles is added thereto at a temperature of $-78°$ C. to room temperature. Although varies in the kind of substituents, even at $-30°$ C. to room temperature, since degradation proceeds in case of —N=N— linkage as described in J. Am. Chem. Soc., 84 966(1962), reaction operations are carried out preferably at a temperature as low as possible in view of the reaction rate.

In the [IVd-1], [Ive-1] or [IVf-1], the double bond between B and C of A—B=C—D— can be converted into a saturated bond by hydrogenating reaction in the presence of a catalyst such as palladium-carbon, palladium hydroxide and the like to obtain [IVd-2], [IVe-2] or [IVf-2] as described in J. Am. Chem. Soc., 101, 7347(1979). However, when R is a substituted or unsubstituted phenylmethyl or biphenylmethyl group and the reaction is carried out at a temperature of not lower than 50° C., the reaction causes reductive elimination of R, and as a result, only [IVd-2] is obtained in some cases. Therefore, the reaction for obtaining [IVe-2][IVf-2] must be carried out under mild conditions at a temperature of not higher than room temperature.

On the other hand, when A—B—C—D is —C($R^{13}$)($R^{16}$)—C($R^{14}$)=C($R^{15}$)—C($R^{17}$)($R^{18}$) and both of $R^{16}$ and $R^{18}$ are hydrogen in the general formula [IVd-1], [Ive-1], [IVf-1], a carbon atom to which $R^{13}$ or $R^{17}$ is bonded is brominated by the bromination reaction using an equal molar amount of N-bromosuccinimide by a method according to that in J. Org. Chem., 51, 3123(1986), and the relevant compound can be beat-treated to be converted into a corresponding diene [IVd-3], [IVe-3], [IVf-3] as shown in the reaction scheme below.

Alternatively, there may be used the method such as epoxidation of a double bond by metachloroperbenzoic acid, followed by ring cleavage of epoxy ring and dehydration by conc. sulfuric acid [J. Org. Chem., 50, 5604 (1985)], or addition of bromine to a double bond, followed by de-hydrogen bromide by a base [J. Heterocyclic Chem., 22, 273 (1985)]. As the base usually used, there are sodium carbonate, potassium carbonate, sodium methoxide, sodium ethoxide, potassium t-butoxide or organic amines such as triethylamine, diisopropylethylamine, 1,5-diazabicyclo[4.3.0]-5-nonene, 1,8-diazabicyclo[5.4,0,]-7-undecene and the like. Further, alternatively, a diol can be obtained by the reaction using a stoichiometric amount of osmium tetroxide, or using a catalytic amount of osmium tetroxide in the presence of triethylamine N-oxide, morpholine N-oxide and the like, and the diol can be converted into diene [IVd-3], [IVe-3], [IVf-3] by treating with sulfuric acid, polyphosphoric acid and the like at room temperature or under heating.

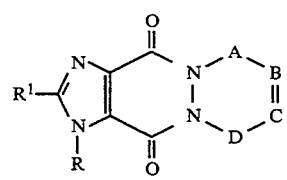

[IVd-1, IVe-1, IVf-1]

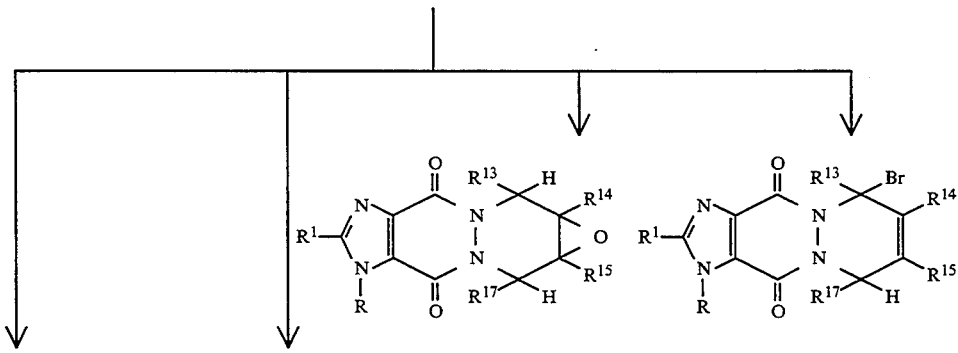

-continued

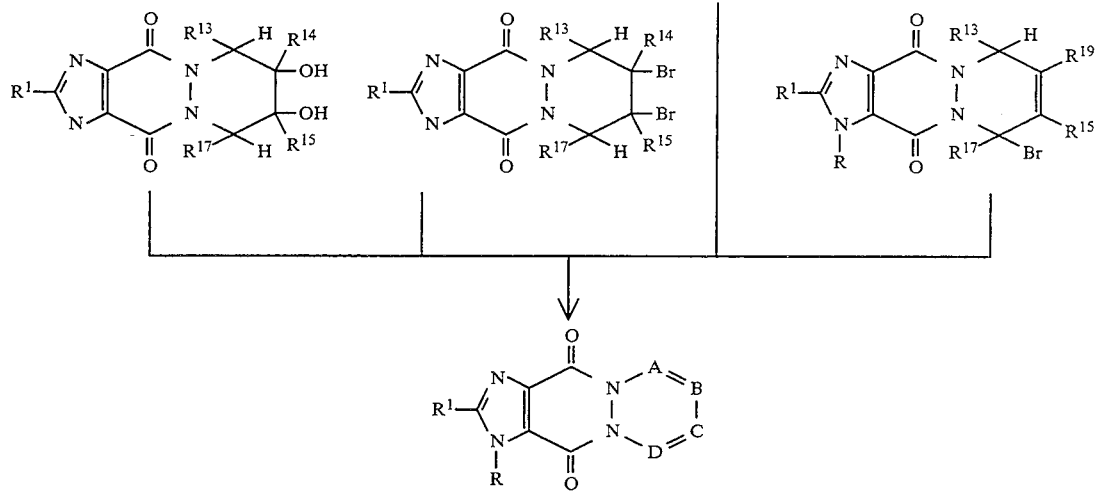

[IVd-3, IVe-3, IVf-3]

And, [IVe-4,IVf-4], [IVe-1,IVf-1], [IVe-2,IVf-2] or [IVe-3,IVf-3] can be synthesized respectively, by reacting substituted or unsubstituted 1,3-dibromopropane (or 1,3-dichloropropane), 1,4-dibromo-2-butene (or 1,4-dichloro-2-butene), 1,4-dibromobutane (or 1,4-dichlorobutane) or 2,5-dimethoxy-2,5-dihydrofuran (or 2,5-dibromo-2,5-dihydrofuran) in an amount of from equal mole to 1.5 times moles with [Ve] or [Vf] using a basic compound, for example, sodium carbonate, potassium carbonate, n-butyl lithium, phenyl lithium, lithium hydride, sodium hydride, potassium hydride, sodium methoxide, potassium methoxide, potassium t-butoxide and the like in an amount of 2 to 4 times moles relative to [Ve] or [Vf] in an ether solvent such as diethyl ether, diisopropyl ether, tetrahydrofuran and the like, or an amido solvent such as dimethylformamide, diethylformamide and the like preferably at a temperature in the range of 0° C. to 80° C. under the reaction conditions which are usually used for alkylation reaction of amides.

On the other hand, by reacting substituted or unsubstituted acrylic chloride, acrylic ester and the like with [Ve] or [Vf] under the presence of the above-described basic compound, it can be derived into [IVe-5,IVf-5] via the known Michael addition reaction. Similarly, [IVe-6,IVf-6] can be obtained by hydrolysis after reaction with 2,2-dimethoxy-1,3-dibromopropane.

When $R^2$ and $R^3$ are both hydrogen or lower alkyl group and $R^4$ and $R^5$ are taken together to form $=O$ bond, or $R^2$ and $R^3$ are taken together to from $=O$ bond and $R^4$ and $R^5$ are both hydrogen or lower alkyl group, or $R^2$, $R^3$, $R^4$ and $R^5$ are hydrogen or lower alkyl group in the general formula [I], then the imidazole derivative of the present invention can be prepared, for example, by the following reaction scheme.

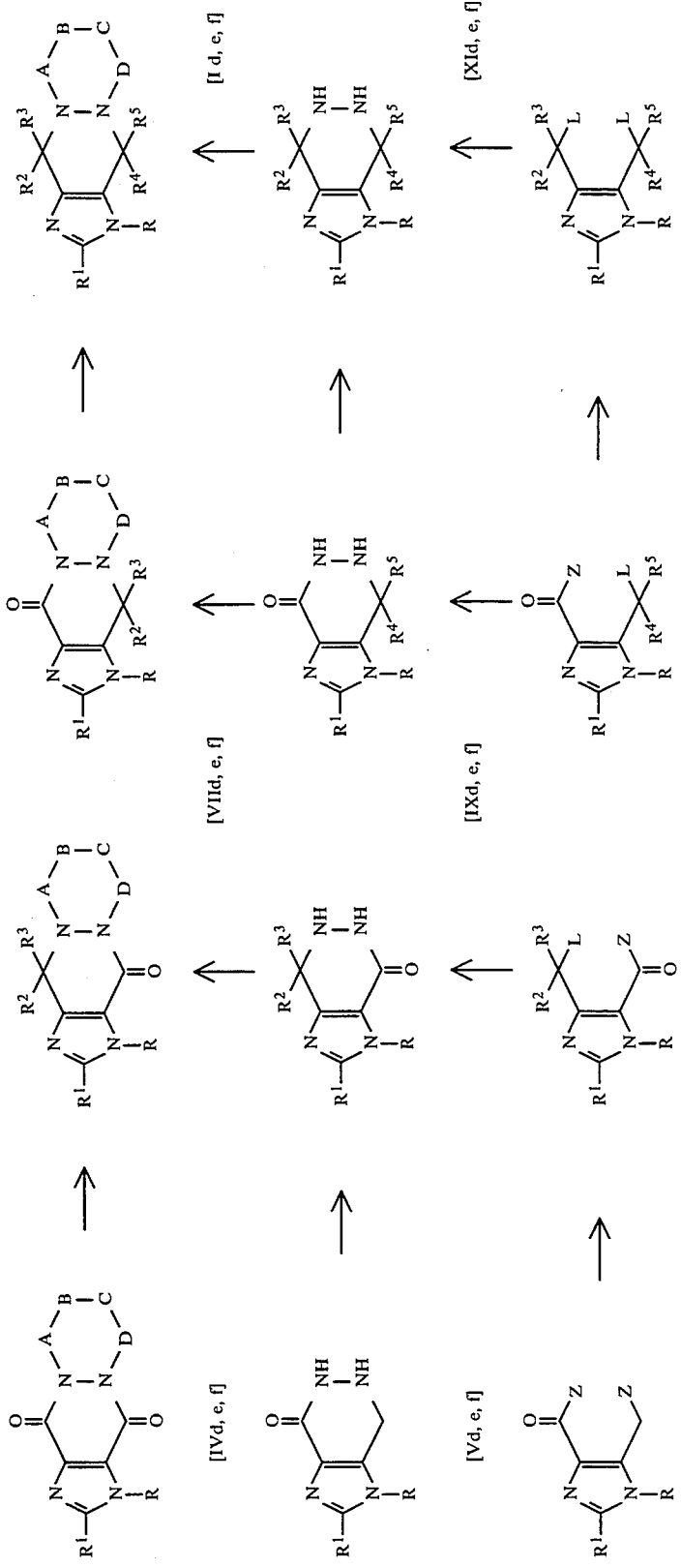

wherein d, e or f means that the nitrogen atom in the imidazole ring bonds to hydrogen atom, substituted or unsubstituted phenylmethyl group or biphenylmethyl group, Z is hydroxy group or lower alkoxy group, and L is hydroxy group, halogen, or hydroxy group activated by p-toluenesulfonyl group, methanesulfonyl group and the like.

An imidazole derivative represented by [IVd,e,f], [Vd,e,f] or [VId,e,f] can be convened into [VIIId,e,f], [IXd,e,f] or [Xd,e,f], respectively, wherein $R^2$, $R^3$, $R^4$ and $R^5$ are hydrogen by reducing one of amidocarbonyl groups using metal hydrides such as lithium aluminum hydride, diisobutylaluminum hydride, lithium tri-t-butoxyaluminum, borane, tributyltin hydride and the like, or into [Id,e,f], [XId,e,f] or[XIId,e,f], respectively, wherein both amidocarbonyl groups are reduced by using an excess amount of the above reducing agent or rising the reaction temperature according to the conventional methods. As the reaction solvent, there can be used ether, tetrahydrofuran, dimethoxyethane, toluene, dichloromethane and the like. The reaction temperature of $-78°$ C. to room temperature is suitable, but a low temperature is desirable in order to obtain selectively [VIIId,e,f], [IXd,e,f] or [Xd,e,f], respectively.

One ester group of 4,5-diester of [VId] can be reduced into hydroxymethyl group in a good selectivity using lithium triethylborohydride under ice-cooling in tetrahydrofuran, for example, according to the method described in WO91/19715. And when R is trityl group in [VI], a compound [XI] wherein L is hydroxy group and Z is methoxy group can be obtained preferentially according to the method described in Can. J. Chem., 60, 723 (1982). On the other hand, when $R^2$, $R^3$, $R^4$ and $R^5$ are lower alkyl group or allyl group, [VIIId,e,f], [IXd,e,f] or [Xd,e,f] can be obtained by reacting [IVd,e,f], [Vd,e,f] or [VId,e,f] with an organometallic compound such as lower alkyl lithium, lower alkyl Grignard reagent, alkyltrimethylsilane and the like. [Xd,e,f] or [XIId,e,f] can be derived into [IXd,e,f] or [XId,e,f] by the reaction with hydrazine according to the method for converting [VII into IV]. And, the ring closure from [IXd,e,f] to [VIIId,e,f], or from [XId,e,f] to [Id,e,f] can be carried out according to the above method for synthesizing the various cyclized derivatives from [IV].

When A or D is absent in A—B—C—D in the general formula [I], [Id-4,Ie-4,If-4], [Id-5,Ie-5,If-5] or [Id-6,Ie-6,If-5] can be obtained using the above method of conversion from [IVe-4,5,6] to [VIIId,e,f], or from [Id-,e,f] or [Ve,f] to [IVe-4,5,6] according to the following reaction scheme.

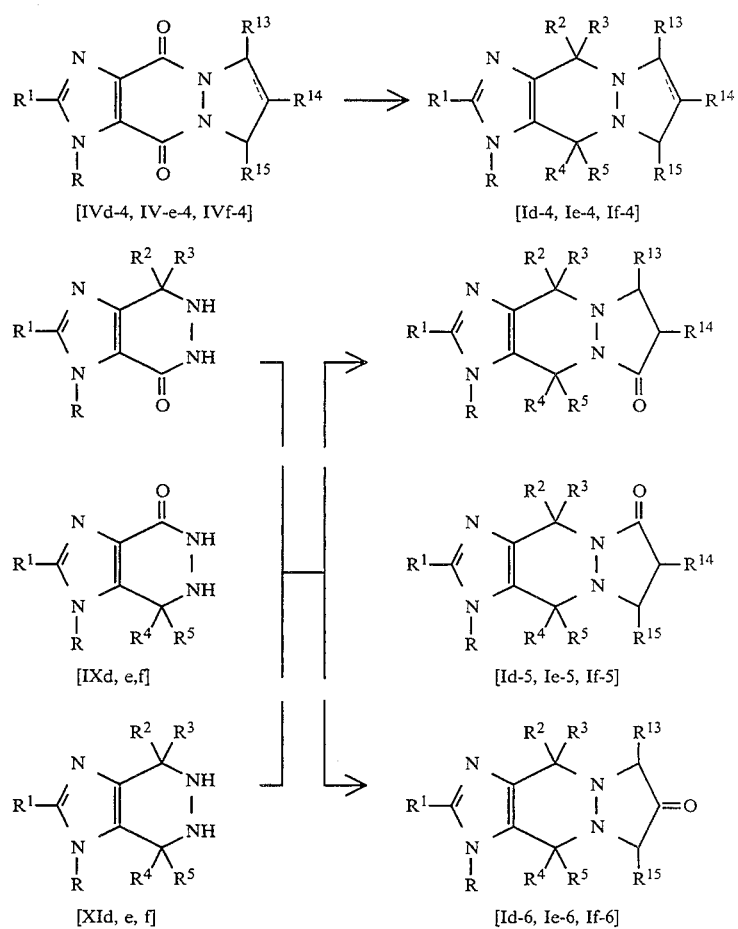

When A—B—C—D is —C($R^{13}$)($R^{1-6}$)—C($R^{14}$)=C($R^{15}$)—C($R^{17}$)($R^{18}$)—and $R^{14}$ and $R^{15}$ are both hydrogen atom in the general formula [Ib], an alcohol derivative [XIIId,e,f] can be obtained by the hydroboration reaction using the various boron hydride compounds, followed by the reaction with hydrogen peroxide as shown in the reaction scheme below. As the boron hydride compound, there are diborane, borane-tetrahydrofuran, borane-dimethylsulfide, 9-BBN, dicyamylborane, thexylborane and the like. Usually, as the solvent, there are used ether, tetrahydrofuran, dimethoxyethane, diglyme and the like. The reaction temperature of −20° C. to room temperature is suitable. The reaction with hydrogen peroxide is usually carried out at 0° C. to room temperature in methanol or ethanol. In addition, [XIIId,e,f] can be convened into ketone [XIVd,e,f] by oxidation using a metal oxide such as manganese dioxide, chromium trioxide and the like.

[see Gunther, S., Gimbrone, M. A. and Alexander, R. W., Circ. Res., 17:278-286, 1980].

2) In vitro adrenal cortex angiotensin II receptor binding assay

According to the method by Capponi et al. (1), angiotensin II receptor binding assay was carried out by preparing a membrane fraction from an adrenal cortex

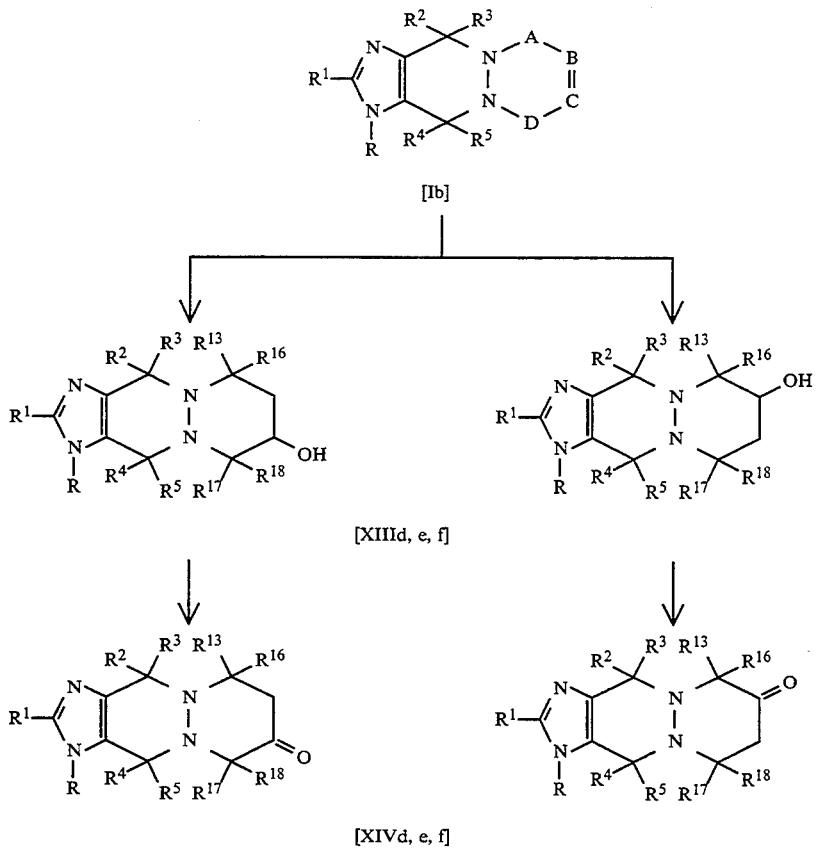

Pharmacological Activity

The pharmacological activity of the compounds of the invention is shown by the following tests.

1) In vitro angiotensin II mesenteric artery receptor binding assay

According to the method (1) by Gunther et al., a membrane fraction was prepared from mesenteric artery of male rat 50 μm protein equivalent of it and 0.2 nM $^{125}$I-Ang II as well as various concentrations of test compounds were incubated at 22° C. for 90 minutes in an incubation buffer (50 mM Tris-HCl, 120 mM NaCl, 5 mM MgCl$_2$, 0.25% bovine serum albumin, pH 7.2) (reaction volume; 200 μl). The incubated was cooled, and the reaction was stopped by addition of ice-cooled phosphate buffer (10 mM phosphate, 140 mM NaCl, pH 7.4, hereinafter referred to as PBS), and then the reaction solution was filtered through a glass fiber filter (Whatman CF/B), the filter was washed, dried, and then the radioactivity of captured $^{125}$I-angiotensin II which bound to the receptor was measured by a γ-counter. Non-specific bound amount was obtained from the reaction in the presence of 1 μM of unlabeled angiotensin II. The test compounds were tested at the concentration of 0.01 to 1 μM, and the compounds that inhibited not less than 50% of total specific bound amount at 1 μM were determined as an active compound to obtain 50% inhibiting concentration (IC$_{50}$)

of a male rat and using this as a receptor material in the same manner as that described in the above pharmacological test 1) [see Capponi, A. M. and Cart, K., J. Biol. Chem. 254:5120-5127(1979)].

3) Antagonism to angiotensin II constriction in an isolated rabbit thoracic aorta A rectangular strip-like sample of thoracic aorta isolated from an anaesthetized rabbit was prepared, and the sample was suspended at 2.0 g of loaded tension in a Magnus tube filled with Krebs-Henseleitoid nutrition solution which was well aerated with 95% O$_2$-5% CO$_2$, and the constriction tension was measured using an isometric transducer. After the tension of the sample at rest became stable, accumulative administration of angiotensin II was carried out to obtain a concentration-action curve. Thereafter, the sample was washed with the same nutrition solution, then treated with test compound (10$^{-6}$ M) for 20 minutes to obtain again a concentration-action curve of angiotensin II. The results were obtained as followed: generated maximum tension at the first accumulative administration of angiotensin II was regarded as 100 %, and the 50% effective concentration (ED$_{50}$) was obtained in the presence or absence of the test compound, and pA$_2$ value was calculated according to the following equations:

$pA_2 = -\log K_B$ $K_B = C/\{(A'/A) - 1\}$

C; concentration of the test compound (M)
A '; $ED_{50}$ in the presence of test compound (M)
A; $ED_{50}$ in the absence of the test compound (M)

4) Antagonism to blood pressure increasing by angiotensin II in a spine destroyed rat Wistar rat anaesthetized with pentobarbital was fixed at dorsal position, and a cannula for measuring blood pressure was inserted into sinister arteria carotis communis, and a cannula for administration of the test compound into dexter external jugular vein and a cannula for administration of angiotensin II into sinister external jugular vein, ambilateral nervus vagus was cut, and artificial respiration was carried out. A thin bar made of metal was stabbed into spinal column through sinister orbita to destroy spine. Blood pressure was recorded on polygraph via pressure transducer from an arterial cannula. After blood pressure was stable for more than 30 min., 3 μg/kg of angiotensin II was administered intravenously four times every 15 min., and every 5 min. before the administration of angiotensin II from the second administration onward, a solvent, a lower dose of the test compound, and a higher dose of the test compound were administered intravenously in this order to observe the blood pressure increasing response by angiotensin II. $ED_{50}$ values were calculated from the inhibiting rate when the first blood pressure increase by angiotensin II was regarded as 100%.

In above tests, the compounds of the present invention showed high activity. In particular, the Compound No. 450 (U-96849), No. 451 (U-97018), No. 454 (U-96934) and No. 455 (U-97030) showed $ED_{50}$ value of 0.95, 0.84, 1.28 and 0.81 mg/kg, respectively, and all of them showed the action lasting time of not less than 5 hours at 3, 1, 3 and 1 mg/kg, respectively, in blood pressure increase by angiotensin II-inhibiting test (intraduodenal administration) of angiotensin II using an anesthetized normotensive rat In hypertensive rat model (SHR), the compound No. 451 (U-97018) was confirmed to have the significant vasodepressor activity over 24 hours in 10 mg/kg oral administration test in hypertensive rat model (SHR).

The results of the above tests on the main compounds of the present invention are shown in Table 1.

TABLE 1

| Compound No. | Angiotensin II receptor binding $IC_{50}$ (nM) (test 1) | Inhibiton of rabbit aorta constriction $pA_2$ (test 3) | Inhibition of blood pressure increase by angiotensin II in pithed rat $ED_{50}$ (mg/kg) (test 4) |
| --- | --- | --- | --- |
| 46 | 3.3 | 8.95 | |
| 47 | 5.3 | | |
| 50 | 5.3 | | 0.2 |
| 51 | 4.6 | 9.04 | 0.65 |
| 56 | >30 | | |
| 67 | 14 | | |
| 68 | 8.1 | | 0.56 |
| 71 | 7.0 | 9.09 | |
| 105 | 1.5 | 9.42 | 0.10 |
| 106 | 3.8 | 9.2 | |
| 108 | 1.9 | 9.53 | 0.069 |
| 109 | 2.8 | 9.49 | 0.21 |
| 111 | 21 | 9.01 | 0.51 |
| 121 | >100 | | |
| 124 | >100 | | |
| 138 | 4.0 | | 0.096 |
| 139 | 1.9 | 10.63 | 0.038 |
| 156 | 69 | | |
| 159 | 5.1 | | |
| 167 | 3.2 | | |
| 169 | 1.3 | 10.19 | |
| 196 | 4.6 | | 0.23 |
| 198 | >100 | | |
| 199 + 210 | 3.0 | 9.83 | 0.065 |
| 200 + 202 | 3.4 | 9.85 | 0.2 |
| 203 | 1.9 | 10.0 | |
| 205 | 47 | | |
| 207 | 3.9 | 10.1 | 0.033 |
| 208 | 8.2 | | 0.12 |
| 209 | 58 | | |
| 210 | 29 | | |
| 211 + 213 | 4.2 | | |
| 215 + 217 | 2.2 | 9.58 | |
| 219 + 221 | 3.5 | 9.28 | 0.26 |
| 220 | 2.6 | 9.93 | 0.27 |
| 222 | 3.0 | | 0.56 |
| 223 | 9.8 | 9.68 | 0.10 |
| 225 | 66 | | |
| 227 | 38 | | |
| 229 | 8.7 | | |
| 231 | 9.8 | | 0.074 |
| 233 | >100 | | |
| 235 | 21 | 9.62 | 0.07 |
| 236 | 32 | | 0.11 |
| 238 | >100 | | |
| 239 | >100 | | |
| 241 | 25 | | |

TABLE 1-continued

| Compound No. | Angiotensin II receptor binding $IC_{50}$ (nM) (test 1) | Inhibiton of rabbit aorta constriction $pA_2$ (test 3) | Inhibition of blood pressure increase by angiotensin II in pithed rat $ED_{50}$ (mg/kg) (test 4) |
|---|---|---|---|
| 243 + 245 | 3.7 | 9.56 | |
| 248 + 250 | 3.0 | | |
| 280 | 4.6 | | |
| 323 | >100 | | |
| 325 + 327 | 8.3 | 10.05 | 0.33 |
| 329 | 65 | | |
| 331 | 3.9 | | |
| 333 + 335 | >100 | | |
| 337 | 4.6 | | |
| 339 + 341 | 1.6 | | |
| 343 + 345 | 2.7 | | |
| 347 + 349 | 8.1 | | |
| 351 + 353 | 6.2 | | |
| 355 | >100 | | |
| 359 | 35 | | |
| 361 | 55 | | |
| 366 | 32 | 9.32 | |
| 378 | 4.6 | | |
| 382 | 26 | | |
| 390 | 35 | | |
| 398 + 402 | 49 | | |
| 414 + 418 | 29 | | |
| 430 | 3.9 | 10.04 | |
| 438 | 7.5 | 8.57 | 0.37 |
| 443 | 1.3 | | |
| 447 | 2.5 | | |
| 450 | 1.7 | 9.92 | 0.32 |
| 451 | 1.9 | 10.04 | 0.63 |
| 453 | >100 | | |
| 454 | 3.5 | 10.34 | 0.34 |
| 455 | 3.3 | 8.82 | 0.64 |
| 470 | 20 | | |
| 474 + 478 | 18 | | |
| 507 + 511 | 6.6 | | |
| 514 + 518 | >100 | | |
| 521 | 9.1 | | |
| 523 | >100 | | |
| 538 | >100 | | |
| 540 | 34 | | |
| 541 | >100 | | |
| 542 | 34 | | |
| 543 | 26 | | |
| 544 | >100 | | |

As seen by the foregoing, the compounds of the present invention are useful whenever it is medically necessary or desirable to inhibit the renin-angiotensin-aldosterone system. The angiotensin II receptor antagonist compounds of the present invention are thus administered to humans to treat or prevent a variety of cardiovascular disorders related to the improper functioning of the renin-angiotensin-aldosterone system including hypertension, congestive heart failure, renal failure, glucoma, or hyperuricemia. Such conditions are readily apparent to an ordinarily skilled physician.

The imidazole derivatives or pharmacologically acceptable esters or salts thereof are administered orally, parenterally by insufflation, rectally, locally. Parenteral administration includes subcutaneous, intravenous, intramuscular, intranasal administration or injection. Dose to be administered to an adult is in a range of 1to 50 mg/day. The exact dose can be selected from the above range, taking the age of patient, weight, condition and route of administration into consideration. The frequency of administration is usually one to four times a day.

Additionally, no toxicity of the compound of the present invention or pharmacologically acceptable esters or salts thereof was observed in the above-described dose range.

The imidazole derivatives or pharmacologically acceptable esters or salts thereof of the present invention can be formulated, by a conventional method, into a dosage unit form such as tablets, capsules, pills, powders, granules, powder packet, cachets, sterile parenteral solutions or suspensions, eyedrops, solutions or suspensions, elixirs, suppositories, aerosols and emulsions which contains them in a predetermined amount.

For oral administration, solid or fluid unit dosage form can be prepared. For preparing solid composition, the active compound is mixed with an excipient or a carrier such as magnesium stearate, dicalcium phosphate, magnesium aluminum silicate, calcium sulphate, starch, lactose, acacia, methyl cellulose and the like. A capsule agent is prepared by mixing the compound of the present invention with an inert pharmaceutical excipient, filling the mixture into a hard gelatin capsule having suitable size. A soft gelatin capsule is prepared by machine capsulation of slurry composed of the compound, suitable vegetable oil, light petrolatum or other inert oil.

For preparing a fluid composition, the compound of the present invention is dissolved in aqueous vehicle together with sugar, aromatic flavor and preservative to obtain a syrup. Elixirs are prepared using an alcoholic vehicle such as ethanol, a sweetener such as sugar and saccharin as well as a flavor. Suspensions am prepared using a suspending agent such as acacia, tragacanth or methyl cellulose and an aqueous vehicle.

For parenteral administration, a fluid unit dosage form is prepared using the compound of the present invention and a sterile vehicle. Depending upon a vehicle such as water, Ringer's solution, isotonic sodium chloride solution and the concentration to be used, the compound is suspended or dissolved in the vehicle. For preparing solutions, the compound is dissolved in water for injection, and this is sterile filtered, filled into a vial or an ampoule, and sealed. Advantageously, an adjuvant such as local anaesthetic, preservative and buffer is dissolved in vehicle. Alternatively, a lyophilized powder having good shelf stability can be prepared, In the case of this formulation, the powder is reconstituted upon use. Parenteral suspensions can be similarly prepared using the compound of the present invention. In the case of this formulation, the compound of the present invention can be sterilized by exposure to ethylene oxide before suspended in a sterile vehicle. Advantageously, a surfactant or a wetting agent is added to facilitate dispersion of the compound.

Alternatively, the compound of the present invention can be formulated into a local dosage form in combination with a suitable carrier for local administration. Examples of a carrier to be used are cream, ointment, lotion, paste, jelly, spray, aerosol and the like. Further, when other form can not be administered, suppositories can be prepared. Examples of a base are cacao butter, polyethylene glycol, polyethylene sorbitan monostearate and the like.

EXAMPLES

The following Examples further illustrate the present invention in detail but are not to be construed to limit the scope thereof.

Example 1

Preparation of 2-n-butyl-6,7-dimethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (compound No. 51)

1-Benzyl-2-n-butylimidazo[4,5-d]pyridazine-4(5H),7(6H)-dione (564 mg, 1.89 mmol which was synthesized according to the known method in the reference [J. Am. Chem. Soc., 78, 159(1956), 80, 6083(1958)] was suspended in 15 ml of dry methylene chloride, and the suspension was cooled to −78 °C. in a dry ice-acetone bath. Lead tetraacetate (1.4 g, 2.84 mmol) and of 2,3-dimethyl-1,3-butadiene (235 mg, 2.86 mmol) were added thereto, and the mixture was stirred for 7 hours while allowing to rise the temperature to room temperature. The reaction solution was poured into water, extracted with methylene chloride, washed with water and dried over magnesium sulfate. The solvent was distilled off under reduced pressure and the residue was purified by silica gel column chromatography to obtain 1-benzyl-2-n-butyl-5,8-dihydro-6,7-dimethyl-1H-1,3,4a,8a-tetraza-cyclopentanaphthalene-4,9-dione (532 mg, 74.4%) as pale yellow oily material. This compound has the following NMR spectrum:

$^1$H-NMR(CDCl$_3$) δ(ppm): 0.87 (3H, t, J = 7 Hz), 1.34 (2H, sextet, J = 7 Hz), 1.70 (2H, quintet, J = 8 Hz), 1.80 (6H, s), 2.73 (2H, t, J = 8 Hz), 4.43 (2H, bs), 4.52 (2H, bs), 572 (2H, s), 7.11 (2H, dd, J = 8 Hz,2 Hz), 7.25–7.39 (3H, m)

The above compound (521 mg, 1.38 mmol) was dissolved in methanol (100 ml), 20% palladium hydroxide on carbon (100 mg) was suspended therein and the suspension was reacted for four hours under hydrogen atmosphere using an ambient pressure catalytic reduction apparatus. The catalyst was filtered and the solvent was distilled off under reduced pressure to obtain 2-n-butyl-6,7-dimethyl-5,6,7,8-tetrahydro-1H-1,3,4a,8a-tetraza-cyclopentanaphthalene-4,9-dione (compound No. 4) (364 mg, 91.0%) as pale yellow oily material. This compound has the following NMR spectrum:

$^1$H-NMR (CDCl$_3$) δ(ppm): 097 (3H, t, J = 7 Hz), 103 (6H, d, J = 6 Hz), 127-150 (2H, m), 1.71–1.89 (2H, m), 2.11–2.27 (2H, m), 2.89 (2H, t, J = 8 Hz), 3.87 (2H, dd, J = 13 Hz, 7 Hz), 4.09 (2H, dd, J = 13 Hz, 4 Hz)

The above compound (165 mg, 0.569 mmol) was dissolved in dimethylformamide (3 ml) and 60% sodium hydride (27 mg, 0.675 mmol) was added thereto. The mixture was reacted at room temperature for 20 minutes, a solution of {2'-(1-triphenylmethyltetrazol-5-yl)biphenyl-4-yl}methyl bromide (380 mg, 0.682 mmol) in dimethylformamide (3 ml) was added thereto and the mixture was reacted for 14 hours. The reaction mixture was poured in water, extracted with ethyl acetate, washed with water and dried over anhydrous sodium sulfate. The solvent was distilled off under reduced pressure and the residue was purified by silica gel column chromatography to obtain 2-n-butyl-6,7-dimethyl-5,6,7,8-tetrahydro-1-[{2'-(triphenylmethyltetrazol-5-yl)biphenyl-4-yl}methyl]-1H-1,3,4a,8a-tetraza-cyclopentanaphthalene-4,5-dione (322 mg, 73.9%) as colorless oily material. This compound has the following NMR spectrum:

$^1$H-NMR (CDCl$_3$) δ(ppm): 0.85 (3H, d J = 7 Hz), 1.02 (3H, t, J = 6 Hz), 1.03 (3H, d, J = 6 Hz), 1.29 (2H, sextet, J = 8 Hz), 1.70 (2H, quintet, J = 8 Hz), 2.12–2.19 (2H, m)264 (2H, t, J = 7 Hz), 3.06 (0.33H, m), 3.77–3.89 (1.67H, m), 3.99–4.18 (1.67H, m), 4.62–4.84 (0.33H, m), 5.51–5.74 (2H, m), 6.93 (8H, m), 7.12 (2H, d, J = 8 Hz), 7.19–7.36 (10H, m,), 741–751 (2H, m), 7.90–7.93 (1H, m)

The compound (314 mg, 0.409 mmol) was dissolved in acetone (6 ml), 10% hydrochloric acid (0.5 ml) was added and the solution was stirred at room temperature for 3.5 hours. The reaction mixture was concentrated, diluted with methylene chloride and the dilution was neutralized by a saturated ammonium chloride solution containing sodium bicarbonate. The separated methylene chloride layer was washed with water and dried over anhydrous sodium sulfate. The solvent was distilled off under reduced pressure and the residue was purified by silica gel column chromatography to obtain 2-n-butyl-6,7-dimethyl-5,6,7,8-tetrahydro-1-[{2'-(1H-tetrazol-5-yl)biphenyl-4-yl}methyl]-1H-1,3,4a,8a-tetraza-cyclopentanaphthalene-4,5-dione (187 mg, 87.0%) as a colorless oily material. This compound has the following NMR spectrum:

$^1$H-NMR (CDCl$_3$) δ(ppm): 0.83 (3H, t, J = 8 Hz), 1.01 (6H, d, J = 6 Hz), 1.30 (2H, sextet, J = 8 Hz), 1.66 (2H, quintet, J = 8 Hz), 2.16 (2H, broad), 2.69 (2H, t, J = 8 Hz), 3.07–326 (0.33H, m), 3.69–3.84 (1.67H, m), 3.99–4.14 (1.67H, m), 456–4.74 (0.33H, m), 5.54–5.77 (2H, m), 703 (2H, d, J = 8 Hz), 7.12 (2H, d, J = 8 Hz), 7.38 (1H, d, J = 7 Hz), 7.40–7.65 (2H, m), 7.92 (1H, d, J = 8 Hz)

Example 2

Preparation of 6,7-dimethyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione (compound No. 50)

According to the same procedures as those in Example 1 except that 1-benzyl-2-n-propyl-imidazo[4,5-d]pyridazine-4(5),7(6H)-dione was used as a starting material, there was obtained the titled compound via 2-n-propyl-6,7-dimethyl-5,6,7,8-tetrahydro-1H-1,3,4a,-8a-tetraaza-cyclopentanaphthalene-4,9-dione (compound No. 3). These compounds have the following NMR spectrum:

Compound No. 50: $^1$H-NMR(CDCl$_3$) δ(ppm): 0.88 (3H, t, J=7 Hz), 0.99–1.06 (6H, m), 1.65–1.74 (2H, m), 2.66 (2H, t, J=7 Hz), 3.08–3.27 (0.5H, m), 3.73–3.84 (1.5H, m), 3.99–4.12 (1.5H, m), 4.55–4.74 (0.5H, m), 5.53–5.76 (2H, m), 7.02 (2H, d, J=8 Hz), 7.12 (2H, d, J=8 Hz), 7.39 (1H, dd, J=2 Hz, 8 Hz), 7.44–7.58 (2H, m), 7.89 (1H, dd, J=2 Hz, 8 Hz)

Compound No. 3: $^1$H-NMR(CDCl$_3$) δ(ppm): 0.96–1.00 (3H, m), 1.23–1.30 (3H, m), 1.31–1.39 (3H, m), 1.77–2.00 (3H, m), 2.03–2.52 (3H, m), 2.89–3.08 (2H, m), 4.18–4.32 (2H, m), 5.15 (1H, m), 5.39 (1H, m)

Example 3

Preparation of 2-n-butyl-5,8-dihydro-6,7-dimethyl-1-[{2'-(1H-tetrazol-5-yl)biphenyl-4-yl}methyl]-1H-1,3,4a,8a-tetraaza-cyclopentanaphthalene-4,9-dione (compound No. 68)

2-n-Butylimidazo[4,5-d]pyridazine4(5H),7(6H)-dione (1.50 g, 7.20 mmol) was suspended in dry methylene chloride (150 ml) and the suspension was cooled to −78° C. in a dry ice-acetone bath. Lead tetraacetate (5.3 g, 10.8 mmol) and 2,3-dimethyl-1,3-butadiene (5.9 g, 71.8 mmol) were added thereto and the mixture was stirred for 24 hours while allowing to rise the temperature to room temperature. The reaction mixture was poured in water, extracted with methylene chloride, washed with water and dried over magnesium sulfate. The solvent was distilled off under reduced pressure and the residue was re, crystallized from ethyl acetate to obtain 2-n-butyl-5,8-dihydro-6,7-dimethyl-1H-1,3,4a,8a-tetraaza-cyclopentanaphthalene-4,9-dione (compound No. 10) (824 mg, 39.6%) as white powders. This compound has the following NMR spectrum: $^1$H-NMR(CDCl$_3$) δ(ppm): 0.96 (3H, t, J=7 Hz), 1.43 (2H, sextet, J=7 Hz), 1.84 (6H, s), 1.88 (2H, m), 2.97 (2H, t, J=8 Hz), 4.54 (4H, bs)

The above compound (52 mg, 0.180 mmol) was dissolved in dimethylformamide (1 ml), 60% sodium hydride (9 mg, 0.225 mmol) was added thereto. The mixture was reacted at more temperature for one hour and {2'-(1-triphenylmethyltetrazol-5-yl)biphenyl-4-yl}methyl bromide (120 mg, 0.215 mmol) was added thereto to react for 11 hours. The reaction mixture was poured in water, extracted with ethyl acetate, washed with water and dried over anhydrous sodium sulfate. The solvent was distilled off under reduced pressure and the residue was purified by silica gel preparative thin layer chromatography to obtain 2-n-butyl-5,8-dihydro-6,7-dimethyl-1-[{2'-(triphenylmethyltetrazol-5-yl)biphenyl-4-yl}methyl]-1H-1,3,4a,8a-tetraza-cyclopentanaphthalene-4,9-dione (68 mg, 49.3%) as a colorless oily material. This compound has the following NMR spectrum:

$^1$-NMR(CDCl-$_3$) δ(ppm): 0.86 (3H, t, J=8 Hz), 1.30 (2H, sextet, J=8 Hz), 1.72 (2H, quintet, J=8 Hz), 1.80 (6H, s), 2.65 (2H, t, J=8 Hz), 4.14 (2H, bs), 4.50 (2H, bs),5.62(2H, s), 6.92 (8H, m), 7.08 (2H, d, J=9 Hz), 7.17–7.36 (10H, m), 7.41–7.52 (2H, m), 7.90–793 (1H, m)

The compound (68 mg, 0.089 mmol) was dissolved in acetone (2 ml) and 10% hydrochloric acid (0.2 ml) was added thereto. The solution was stirred at room temperature for 3.5 hours. The reaction mixture was concentrated and diluted with methylene chloride. The dilution was neutralized with a saturated ammonium chloride aqueous solution containing sodium bicarbonate. The separated methylene chloride layer was washed with water and dried over anhydrous sodium sulfate. The solvent was distilled off under reduced pressure and the residue was purified by silica gel preparative thin layer chromatography to obtain 2-n-butyl-5,8-dihydro-6,7-dimethyl-1-[{2'-(1H-tetrazol-5-yl)biphenyl-4-yl}methyl]-1H-1,3,4a,8a-tetraza-cyclopentanaphthalene-4,9-dione (30 mg, 65.2%) as a colorless oily material. This compound has the following NMR spectrum:

$^1$H-NMR(CDCl$_3$) δ(ppm): 0.86 (3H, t, J=8 Hz), 1.34 (2H, sextet, J=8 Hz), 1.72 (2H, quintet, J=7 Hz), 1.80 (6H, s), 2.73 (2H, t, J=7 Hz), 4.43 (2H, bs), 4.50 (2H, bs), 5.66 (2H, s), 7.02 (2H, d, J=8 Hz), 7.09 (2H, d, J=8 Hz), 7.37 (1H, dd, J=8 Hz, 1z), 7.46–7.58(2H, m), 796 (1H, d, J=8 Hz)

Alternatively, the titled compound can be synthesized according to the following steps: 2-n-Butyl-imidazol-4,5-dicarboxylate (1 g, 4.2 mmol) was dissolved in THF (15 ml)-DMF (15 ml) and the solution was ice-cooled. Sodium hydride (176 mg, 4.4 mmol, 60% in oil) was added thereto and the mixture was stirred for 10 minutes. 2'-(N-Triphenylmethyl-tetrazol-5-yl)biphenyl-4-ylmethyl bromide (2.95 g, 5.3 mmol) was further added thereto and the mixture was stirred for a while and stirred at room temperature overnight An aqueous saturated ammonium chloride solution was added to the reaction mixture. The mixture was extracted with ethyl acetate, the combined ethyl acetate layer was further washed with water and dried over anhydrous sodium sulfate. The solvent was distilled off and the residue was separated and purified by silica gel column chromatography (ethyl acetate:hexane=1-:2–2:3) to obtain 2-n-butyl-1-{(2'-tetrazol-5-yl)biphenyl-4-yl)methyl]imidazol-4,5-dicarboxylate (2.32 g, 78%). This compound has the following NMR spectrum:

$^1$H-NMR (CDCl$_3$) δ(ppm): 0.85 (3H, t, J=7 Hz), 1.29 (2H, sextet, J=7 Hz), 1.63 (2H, quintet, J=7 Hz), 2.59 (2H, t, J=7 Hz), 3.75 (3H, s), 3.92 (3H, s), 5.30 (2H, s), 6.78 (2H, d, J=8 Hz), 6.9–7.0 (6H, m), 7.10 (2H, d, J=8 Hz), 7.2–7.4 (10H, m), 7.4–7.55 (2H, m), 7.9 (1H, m)

The above compound (1.12 g, 1.56 mmol) and hydrazine monohydrate (1 ml) were refluxed to heat in isopropanol (20 ml) for 15.5 hours. The reaction mixture was concentrated to dryness. The residue was washed a few times with isopropyl ether and dried under reduced pressure to obtain white solid (839 mg) which was found, from proton nuclear magnetic resonance spectrum, to be a 4:1 mixture of the desired ring-closed 2-n-butyl-4,5,6,7-tetrahydro-1-[(2'-tetrazol-5-yl)biphenyl-4-yl)methyl]imidazo[4,5d]pyridazine-4(5H),7(6H)-dione and non-ring-closed dihydrazide. The desired pure product has the following NMR spectrum:

¹H-NMR (DMSO-d₆) δ(ppm): 0.84 (3H, t, J=7 Hz), 1.30 (2H, sextet, J=7 Hz), 1.61 (2H, quintet, J=7 Hz), 2.71 (2H, t, J=7 Hz), 5.70 (2H, s), 6.9–7.6 (8H, m)

The above compound (739 mg) was dissolved in dimethylformamide (10 ml) and the solution was cooled to −10° C. Into the solution was added 2,3-dimethyl-1,3-butadiene (0.69 g, 8.4 mmol), followed by lead tetraacetate (1.70 g, 3.5 mmol). The mixture was stirred at −10° C. to −5° C. for 35 minutes. Lead tetraacetate (0.77 g, 1.8 mmol) and 2,3-dimethyl-1,3-butadiene (0.69 g, 8.4 mmol) were further added at −5° C. and the mixture was stirred at −5° C. to room temperature for 3 hours. Ethyl acetate was added to the reaction mixture and the mixture was washed with an aqueous saturated ammonium chloride solution and water and dried over anhydrous sodium sulfate. The solvent was distilled off under reduced pressure and the residue was separated and purified by silica gel column chromatography to obtain 2-n-butyl-5,8-dihydro-6,7-dimethyl-1-[(2'-(1H-tetrazol-5-yl)biphenyl-4-yl)methyl]-1H-1,3,4a,8a-tetraza-cyclopentanaphthalene-4,9-dione (233 mg, yield 43% in two steps). The NMR spectrum of this material was consistent with that obtained by the above-described procedures in Example 3.

Example 4

Preparation of 2-n-butyl-5,6,7,8-tetrahydro-1-[{2'-(1H-tetrazol-5-yl)biphenyl-4-yl}methyl-1H-1,3,4a,8a-tetrazol-cyclopentanaphthalene-4,9-dione (compound No. 47)

1-Benzyl-2-n-butylimidazo[4,5-d]pyridazine-4(5H),7(6H)-dione (1 g, 3.35 mmol) was suspended in dry methylene chloride (30 ml) and the suspension was cooled to −40° C. in a dry ice-acetone bath. To the suspension were added butadiene (1.2 ml) which had been collected under cooling and lead tetraacetate (3.30 g, 6.7 mmol) and the mixture was stirred for 7 hours while allowing to rise the reaction temperature to room temperature. The reaction mixture was poured in water, extracted with methylene chloride, washed with water and dried over sodium sulfate. The solvent was distilled off under reduced pressure and the residue was purified by silica gel column chromatography (ethyl acetate) to obtain 1-benzyl-2-n-butyl-5,8-dihydro-1H-1,3,4a,8a-tetraza-cyclopentanaphthalene-4,9-dione (0.75 g, 64%) as pale yellow oily material.

The above compound was debenzylated and hydrogenated by the same procedures as in Example 1 to obtain the titled compound via 2-n-butyl-5,6,7,8-tetrahydro-1H-1,3,4a,8a-tetraza-cyclopentanaphthalene-4,9-dione (compound No. 15). These compounds have the following NMR spectrum.

Compound No. 15: ¹H-NMR (CDCl₃) δ(ppm): 0.94 (3H, t, J=7 Hz), 1.40 (2H, sextet, J=7 Hz), 1.86 (quintet, J=7 Hz), 2.0 (4H, m), 2.96 (2H, t, J=7 Hz), 4.30 (4H, bs), 12.87 (1H, bs)

Compound No. 47: ¹H-NMR (CDCl₃) δ(ppm): 0.82 (3H, t, J=7 Hz), 1.29 (2H, sextet, J=7 Hz), 1.65 (2H, quintet, J=7 Hz), 1.93 (4H, bs), 2.67 (2H, t, J=7 Hz), 4.08 (4H, m), 5.65 (2H, s), 7.01 (2H, d, J=Hz), 7.10 (2H, d, J=8 Hz), 7.3–7.6 (3H, m), 7.89 (1H, d, J=7 Hz)

Example 5

Preparation of 2-n-butyl-5,8-dihydro-1-[{2'-(1H-tetrazol-5-yl)biphenyl-4-yl}methyl]-1H-1,3,4a,8a-tetraza-cyclopentanaphthalene-4,9-dione (compound No. 71)

Starting from 2-n-butyl-4,5,6,7-tetrahydro-1-[{2'-(1H-tetrazol-5-yl}methyl]imidazo[4,5-d]pyridazine-4(5H),7(6H)-dione and using the same procedures as those in Example 3 except that butadiene was used and the reaction temperature was −40° C. to room temperature, there was obtained the titled compound. This compound has the following NMR spectrum.

Compound No. 71: ¹H-NMR (CDCl₃) δ(ppm): 0.83 (3H, t, J=7Hz), 1.28 (2H, sextet, J=7 Hz), 1.67 (2H, quintet, J=7 Hz), 2.69 (2H, t, J=7 Hz), 4.54 (2H, s), 4.58 (2H, s), 5.62 (2H, s), 6.03 (2H, s), 6.9–7.6 (7H, m), 7.87 (1H, d, J=7 Hz)

Example 6

Preparation of 2-n-butyl-5,8-ethano-5,6,7,8-tetrahydro-1-[(2'-(1H-tetrazol-5-yl)biphenyl-4-yl}methyl]-1H-1,3,4a,8a-tetraza-cyclopentanaphthalene-4,9-dione (compound No. 109)

1-Benzyl-2-n-butylimidazo[4,5-d]pyridazine-4(5H),7(6H)-dione (500 mg, 1.68 mmol) was suspended in dry methylene chloride (20 ml) and of 1,3-cyclohexadiene (405 mg, 5 mmol) was added to the suspension. The mixture was ice-cooled. To the mixture was added lead tetraacetate (1.25 g, 2.5 mmol) and the mixture was stirred for 3.5 hours while allowing to rise the reaction temperature to more temperature. The solvent was distilled off under reduced pressure and the residue was purified by silica gel column chromatography to obtain 1-benzyl-2-n-butyl-5,8-dihydro-5,8-ethano-1H-1,3,4a,8a-tetraza-cyclopentanaphthalene-4,9-dione (0.59 g, 93%) as pale yellow oily material.

The compound was debenzylated and hydrogenated according to the same procedures as those in Example 1 to obtain the titled compound via 2-n-butyl-5,8-ethano-5,6,7,8-tetrahydro-1H-1,3,4a,8a-tetraza-cyclopentanaphthalene-4,9-dione (compound No. 147). These compounds have the following NMR spectrum.

Compound No. 147: ¹H-NMR (CDCl₃) δ(ppm): 0.99 (3H, t, J=7 Hz), 1.40 (2H, sextet, J=7 Hz), 1.80 (2H, quintet, J=7 Hz), 1.9–2.15 (8H, m), 2.93 (2H, t, J=7 Hz), 5.30 (2H, s)

Compound No. 109: ¹H-NMR (CDCl₃) δ(ppm): 0.85 (3H, t, J=7 Hz), 1.32 (2H, sextet, J=7 Hz), 1.72 (2H, quintet, J=7 Hz), 1.9–2.1 (8H, m), 2.72 (2H, t, J=7 Hz), 5.27 (1H, s), 5.42 (1H, s) 5.70 (2H, s), 7.04 (2H, d, J=8 Hz), 7.14 (2H, d, J=8 Hz), 7.3–7.6 (3H, m), 7.96 (1H, dd, J=8 Hz, 1 Hz), Example 7

Preparation of 5,8-dihydro-5,8-ethano-2-n-propyl-1-[{2'-(1H-tetrazol-5-yl)biphenyl-4-yl}methyl]-1H-1,3,4a,8a-tetraza-cyclopentanaphthalene-4,9-dione (compound No. 105)

2-n-Propylimidazo[4,5-d]pyridazine4(5H),7(6H)-dione (870 mg, 4.48 mmol) and 1,3-cyclohexadiene (538 mg, 6.72 mmol) were suspended in dry methylene chloride and the suspension was cooled to −10° C. Lead tetraacetate was added thereto and the mixture was stirred for two days while allowing to rise the reaction temperature to room temperature. Precipitates were filtered. The filtrate was washed with an aqueous saturated sodium bicarbonate solution and saturated brine and dried by anhydrous sodium sulfate. The solvent was distilled off and the residue was purified by silica gel column chromatography (chloroform:methanol=10-0:-100:5) to obtain 5,8-dihydro-5,8-ethano-2-n-propyl-1H-1,3,4a,8a-tetraza-cyclopentanaphthalene-4,9-dione (compound No. 143) (511 mg, 41.9%) as white powders. This compound has the following NMR spectrum.

Compound No. 143: $^1$H-NMR (CDCl$_3$) δ(ppm): 1.01 (3H, t, J=8 Hz), 1.73-1.81 (2H, m), 1.83-1.99 (2H, m), 2.04-2.18 (2H, m), 2.39 (1H, bs), 2.96 (2H, t, J=8 Hz), 6.00 (1H, brd, J=5 Hz), 6.17 (1H, brd, J=4 Hz), 6.65-6.80 (2H, m)

Using the compound (150 mg, 0.55 mmol) and the same procedures as those in Example 1, there was obtained 5,8-dihydro-5,8-ethano-2-n-propyl-1-[{2'-(1H-tetrazol-5-yl)biphenyl-4-yl}methyl]-1H-1,3,4a,8a-tetraza-cyclopentanaphthalene-4,9-dione (compound No. 105) (225 mg, 81.3%). This compound has the following NMR spectrum.

Compound No. 105: $^1$H-NMR (CDCl$_3$) δ(ppm): 0.84 (3H, t, J=7 Hz), 1.58-1.72 (4H, m), 2.00-2.10 (2H, m), 2.61 (2H, t, J=7 Hz), 5.59 (1H, d, J=16 Hz), 5.71 (1H, d, J=16 Hz), 5.92 (1H, bs), 601 (1H, bs), 6.61-6.70 (2H, m), 6.98 (2H, d, J=8 Hz), 7.08 (2H, d, J=8 Hz), 7.32-7.42 (1H, m), 7.45 (1H, d, J=7 Hz), 7.50-7.57 (1H, m), 7.82 (1H, d, J=8 Hz)

Example 8

Preparation of ethyl 2-n-butyl-4,9-dioxo-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate (compound No. 167) and ethyl 2-n-butyl-4,9-dioxo-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate (compound No. 169)

2-n-Butyl-imidazo[4,5-d]pyridazine-4(5H),7(6H)-dione (1.0 g, 4.80 mmol) was suspended in dry methylene chloride (30 ml) and the suspension was cooled to −78° C. in a dry ice-acetone bath. Lead tetraacetate (content 91%) (3.5 g, 7.18 mmol) and ethyl sorbate (1.0 g, 7.13 mmol) were added thereto and the mixture was stirred for 24 hours while allowing to rise the reaction temperature to room temperature. The reaction mixture was poured into water, extracted with methylene chloride, washed with an aqueous saturated ammonium chloride solution and saturated brine and dried over magnesium sulfate. The solvent was distilled off under reduced pressure and the residue was purified by silica gel column chromatography (chloroform-methanol 50:1-5:1) to obtain ethyl 2-n-butyl-5,8-dihydro-4,9-dioxo-5-methyl-1H-1,3,4a,8a-tetraza-cyclopentanaphthalene-8-carboxylate (897 mg, 53.9%) as colorless oily material. This compound has the following NMR spectrum.

$^1$H-NMR (CDCl$_3$) δ(ppm): 0.95 (3H, t, J=7 Hz), 1.31 (3H, t, J=7 Hz), 1.41 (2H, m), 1.51 (3H, d, J=7 Hz), 1.86 (2H, quintet, J=8 Hz), 2.97 (2H, t, J=7 Hz), 4.26 (2H, q, J=7 Hz), 5.57-5.64 (2H, m), 6.14 (1H, dd, J=10 Hz, 5 Hz), 6.29 (1H, dd, J=10 Hz,5 Hz)

The above compound (861 mg, 2.49 mmol) was dissolved in methanol (100 ml) and 10% palladium carbon (100 mg) was suspended therein. The atmospheric catalytic reduction was carried out under hydrogen atmosphere for 4.5 hours. The catalyst was filtered and the solvent was distilled off under reduced pressure to obtain ethyl 2-n-butyl-4,9-dioxo-5-methyl-5,6,7,8-tetrahydro-1H-1,3,4a,8a-tetraza-cyclopentanaphthalene-8-carboxylate (compound No. 28) (809 mg, 93.4%) as colorless oily material. This compound has the following NMR spectrum.

$^1$H-NMR (CDCl$_3$) δ(ppm): 0.94 (3H, t, J=8 Hz), 1.25 (3H, t, J=7 Hz), 1.30-1.49 (2H, m), 1.38 (3H, d, J=8 Hz), 1.71-1.91 (4H, m), 2.12-2.54 (2H, m), 2.51 (2H, t, J=8 Hz), 4.25 (2H, q, J=7 Hz), 5.13-5.20 (1H, m), 5.42-5.45 (1H, m)

The above compound (320 mg, 0.918 mmol) was dissolved in dimethylformamide (5 ml) and 60% sodium hydride (40 mg, 1.0 mmol) was added thereto. The mixture was reacted at room temperature for 45 minutes and {2'-(1-triphenylmethyltetrazol-5-yl)biphenyl-4-yl}methyl bromide (615 mg, 1.10 mmol) was added thereto to react for 14 hours. The reaction mixture was poured into an aqueous saturated ammonium chloride solution, extracted with ethyl acetate, washed with water and dried over anhydrous sodium sulfate. The solvent was distilled off under reduced pressure and the residue was purified by silica gel column chromatography (hexane:ethyl acetate=1:1-1:4) to obtain less polar isomer ethyl 2-n-butyl-4,9-dioxo-5-methyl-5,6,7,8-tetrahydro-1-[{2'-(triphenylmethyltetrazol-5-yl)biphenyl-4-yl}methyl]-1H-1,3,4a, 8a-tetraza-cyclopentanaphthalene-8-carboxylate (131 mg, 17.3%) and more polar isomer ethyl 2-n-butyl-4,9-dioxo-8-methyl-5,6,7,8-tetrahydro-1-[{2'-(triphenylmethyltetrazol-5-yl)biphenyl-4-yl}methyl]-1H-1,3,4a,8a-tetraza-cyclopentanaphthalene-5-carboxylate (122 mg, 16.1%), as colorless oily material, respectively. These compounds have the following NMR spectrum. Less polar isomer (Rf=0.41, silica gel TLC plate, ethyl acetate: hexane-4:1)

$^1$H-NMR (CDCl$_3$) δ(ppm): 0.85 (3H, t, J=7 Hz), 1.19-2.0 (12H, m), 2.0-2.5 (2H, m), 2.62 (2H, t, J=8 Hz), 4.20-4.27 (2H, m), 4.9-5.15 (1H, m), 5.4-5.5 (1H, m), 5.50 (1H, d, J=15 Hz), 5.70 (1H, d, J=15 Hz), 6.87-6.94 (8H, m), 7.18 (2H, m), 7.23-7.36 (10H, m), 7.44-7.49 (2H, m), 7.89-7.93 (1H, m) More polar isomer (Rf=0.28, silica gel TLC plate, ethyl acetate:hexane=4:1)

$^1$H-NMR (CDCl$_3$) δ(ppm): 0.85 (3H, t, J=7 Hz), 1.22-1.32 (5H, m), 1.38 (3h, d, J=7 Hz), 1.60-1.90 (4H, m), 2.05-2.50 (2H, m), 2.62 (2H, t, J=7 Hz), 4.24 (2H, q, J=7 Hz), 5.1-5.26 (2H, m), 5.50 (1H, d, J=16 Hz), 5.66 (1H, d, J=16 Hz), 6.90-6-93 (8H, m), 7.10 (2H, d, J=8 Hz), 7.22-7.36 (10H, m), 7.44-7.49 (2H, m), 7.89-7.93 (1H, m)

The less polar isomer (131 mg, 0.159 mmol) was dissolved in acetone (2 ml), 10% hydrochloric acid (0.2 ml) was added and the solution was stirred at room temperature for 3 hours. The reaction mixture was concentrated and diluted with methylene chloride. The dilution was neutralized with an aqueous saturated ammonium chloride solution containing sodium bicarbonate. The separated methylene chloride layer was washed with water and dried over anhydrous sodium sulfate. The solvent was distilled off under reduced pressure and the residue was purified by silica gel column chromatography (chloroform:methanol=10:1) to obtain ethyl 2-n-butyl-4,9-dioxo-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate (compound No. 167) (92 mg, 98.9%) as colorless oily material. This compound has the following NMR spectrum.

¹H-NMR (CDCl₃) δ(ppm): 0.86 (3H, t, J=8 Hz), 1.25 (3H, t, J=7 Hz), 1.34 (3H, d, J=7 Hz), 1.18–1.41 (2H, m), 1.66–1.79 (4H, m), 2.06–2.42 (2H, m), 2.73 (2H, t, J=8 Hz), 4.16–4.29 (2H, m), 4.97–5.04 (1H, m), 5.38–5.43 (1H, m), 5.59 (1H, d, J=16 Hz), 5.78 (1H, d, J=16 Hz), 7.06 (2H, d, J=8 Hz), 7.15 (2H, d, J=8 Hz), 7.38–7.42 (1H, m), 7.48–7.61 (2H, m), 7.99 (1H, d, J=8 Hz)

The more polar isomer (122 mg, 0.148 mmol) was dissolved in acetone (2 ml) and 10% hydrochloric acid (2 ml) was added thereto. The solution was stirred at room temperature for 5 hours. The reaction mixture was concentrated and diluted with methylene chloride. The dilution was neutralized with an aqueous saturated ammonium chloride solution containing sodium bicarbonate. The separated methylene chloride layer was washed with water and dried over anhydrous sodium sulfate. The solvent was distilled off under reduced pressure and the residue was purified by silica gel column chromatography (chloroform:methanol=20:1–10:1) to obtain ethyl 2-n-butyl-4,9-dioxo-8-methyl-5,6,7,8-tetrahydro-1-[{2'-(1H-tetrazol-5-yl diphenyl-4-yl}methyl]-1H-1,3,4a,8a-tetraaza-cyclopentanaphthalene-5-carboxylate (compound No. 169) (23 mg, 26.7%) as white solid. This compound has the following NMR spectrum.

¹H-NMR (CDCl₃) δ(ppm): 0.87 (3H, t, J=8 Hz), 1.26 (3H, t, J=7 Hz), 1.34 (3H,d, J=7 Hz), 1.23–1.49 (2H, m), 1.64–1.84 (4H, m), 2.04–2.43 (2H, m), 2.74 (2H, t, J=7 Hz), 422 (2H, q, J=7 Hz), 5.12–5.24 (2H, m), 5.57 (1H, d, J=16 Hz), 5.71 (1H, d, J=16 Hz), 7.04 (2H, d, J=8 Hz), 7.15 (2H, d, J=8 Hz), 7.38–7.41 (1H, m), 7.48–7.65 (2H, m), 8.01 (1H, dd, J=8 Hz,2 Hz)

Example 9

Preparation of ethyl 4,9-dioxo-5-methyl-2-n-propyl-5,6,7,8-tetrahydro-1-[(2'-(1H-tetrazol-5-yl)biphenyl-4-yl)methyl]-1H-1,3,4a,8a-tetraaza-cyclopentanaphthalene-8-carboxylate (compound No. 138) and 4,9-dioxo-8-methyl-2-n-propyl-5,6,7,8-tetrahydro-1-[(2'-(1H-tetrazol-5-yl)biphenyl-4-yl)methyl]-1H-1,3,4a,8a-tetraaza-cyclopentanaphthalene-5-carboxylate (compound No. 139)

Using the same procedures as those in Example 8 and 2-n-propylimidazo[4,5-d]pyridazine4(5H),7(6H)-dione as a starting material, there was obtained ethyl 5,8-dihydro-4,9-dioxo-5-methyl-2-n-propyl-1H-1,3,4a,8a-tetraaza-cyclopentanaphthalene-8-carboxylate (compound No. 140) as white powders. This compound has the following NMR spectrum.

¹H-NMR (CDCl₃) δ(ppm): 1.01 (3H, t, J=7 Hz), 1.32 (3H, t, J=7 Hz), 1.49 (1.5H, d, J=7 Hz), 1.55 (1.5H, d, J=7 Hz), 1.82–2.00 (2H, m), 2.94 (2H, t, J=8 Hz), 4.21–435 (2H, m), 546–5.50 (1H, m), 5.63–5.74 (1H, m), 6.07–6.21 (1H, m), 6.25–6.36 (1H, m)

The above compound (1.59 g, 4.78 mmol) was dissolved in methanol (50 ml) and 5% palladium-carbon (150 mg) was added thereto. The solution was stirred at room temperature for 21 hours under hydrogen atmosphere. The resulting filtrate was concentrated and dried to obtain ethyl 4,9-dioxo-5-methyl-2-n-propyl-5,6,7,8-tetrahydro-1H-1,3,4a,8a-tetraaza-cyclopentanaphthalene-8-carboxylate (compound No. 28) (1.50 g, 94.3%) as slightly tan powders. This compound has the following NMR spectrum.

Compound No. 28: ¹H-NMR (CDCl₃) δ(ppm): 1.00 (3H, t, J=8 Hz), 1.28 (3H, t, J=7 Hz), 1.40 (3H, d, J=6 Hz), 1.65–1.88 (1H, m), 1.82–1.98 (2H, m), 2.12.2.24 (1H, m), 2.24–2.50 (2H, m), 2.93 (2H, t, J=8 Hz), 4.24 (2H, q, J=7 Hz), 5.05–5.12 (1H, m), 5.19–5.25 (1H, m)

Using the same procedures as those in Example 8 and the above compound (1083 mg, 3.24 mmol), there were obtained two positional isomers as less polar material and more polar material. Respective isomers were deprotected by the same procedures as those in Example 8 to obtain ethyl 4,9-dioxo-5-methyl-2-n-propyl-5,6,7,8-tetrahydro-1-[(2'-(1H-tetrazol-5yl)biphenyl-4-yl)methyl]-1H-1,3,4a,8a-tetraaza-cyclopentanaphthalene-8-carboxylate (compound No. 138) (493 mg, 27.1%) as less polar material and ethyl 4,9-dioxo-8-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-5-carboxylate (compound No. 139) (469 mg, 25.9%) as more polar material, as white powders, respectively. Retention values thereof by thin layer chromatography (chloroform:methanol=10:1) and NMR spectrum are as follows.

Compound No. 138 (less polar material): Retention value=0.22 ¹H-NMR (CDCl₃) δ(ppm): 0.92 (3H, t, J=7 Hz), 1.25 (3H, t, J=7 Hz), 1.32 (3H, d, J=6 Hz), 1.67–1.78 (3H, m), 2.12–2.20 (1H, m), 2.24–2.42 (2H, m), 2.70 (2H, t, J=7 Hz), 4.15–4.28 (2H, m), 4.96–5.06 (1H, m), 4.39 (1H, dd, J=4,8 Hz), 5.59 (1H, d, J=16 Hz), 5.77 (1H, d, J=16 Hz), 7.05 (2H, d, J=8 Hz), 7.15 (2H, d, J=8 Hz), 7.40 (1H, dd, J=2,7 Hz),7.46–7.60 (2H, m), 7.96 (1H, J=1 Hz,7 Hz)

Compound No. 139 (more polar material): Retention value=0.18 ¹H-NMR (CDCl₃) δ(ppm): 0.92 (3H, t, J=7 Hz), 1.25 (3H, t, 7 Hz), 1.33 (3H, d, J=7 Hz), 1.62–1.82 (3H, m), 2.13–2.42 (3H, m), 2.69 (2H, t, J=7 Hz), 4.22 (2H, q, J=7 Hz), 5.08–5.20 (1H, m), 5.22 (1H, dd, J=4,8 Hz), 5.57 (1H, d, J=16 Hz), 5.70 (1H, d, J=16 Hz), 7.02 (2H, d, J=8 Hz), 7.13 (2H, d, J=8 Hz), 7.40 (1H, dd, J=2,7 Hz), 7.46–7.60 (2H, m), 7.96 (1H, dd, J=1,7 Hz)

Example 10

Preparation of 4,9-dioxo-5-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-8-carboxylate (compound No. 56)

Ethyl 4,9-dioxo-5-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-8-carboxylate (compound No. 138) (200 mg) was dissolved in acetone (5 ml) and 6N aqueous sodium hydroxide solution (5 ml) was added thereto. The solution was stirred at 50° C. for 1 hour. PH was adjusted to 2 using 2N hydrochloric acid. The resulting precipitates were filtered and purified by reverse phase high performance liquid chromatography to obtain 4,9-dioxo-5-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-8-carboxylic acid (compound No. 56) (42 mg, 22.1%) as white powders. This compound has the following NMR spectrum.

¹H-NMR (CD₃OD) δ(ppm): 0.96 (3H, t, J=7 Hz), 1.16 (3H, d, J=7 Hz), 1.50–1.80 (6H, m), 2.66 (2H, t, J=7 Hz), 5.20–5.30 (2H, m), 5.66 (1H, d, J=16 Hz), 5.75 (1H, d, J=16 Hz), 6.96–7.16 (4H, m), 7.52–7.60 (2H, m), 7.63–7.70 (2H, m)

Example 11

Preparation of 4,9-dioxo-8-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-5-carboxylic acid (compound No. 111)

Using the same procedures as those in Example 10 and ethyl 4,9-dioxo-8-methyl-2-n-propyl-5,6,7,8-tetrahydro-1-[(2'-2(1H-tetrazol-5-yl)biphenyl-4-yl)methyl]-1H-1,3,4a,8a-tetraza-cyclopentanaphthalene-5-carboxylate (compound No. 139), there was obtained 4,9-dioxo-8-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-5-carboxylic acid (compound No. 111) (93 mg, 49.0%) as white powders. This compound has the following NMR spectrum.

Compound No. 111: $^1$H-NMR (CD$_3$OD) δ(ppm): 0.93 (3H, t, J=7 Hz), 1.33 (3H, t, J=7 Hz), 1.50–2.12 (6H, m), 2.64 (2H, t, J=7 Hz), 5.23 (1H, m), 5.70 (2H, s), 6.94 (1H, d, J=8 Hz), 7.00–7.18 (3H, m), 7.50–7.60 (2H, m), 7.60–7.70 (2H, m)

Example 12

Preparation of methyl 2-n-butyl-5,8-ethano-4,9-dioxo-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate (compound No. 156) and methyl 2-n-butyl-5,8-ethano-4,9-dioxo-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate (compound No. 159)

1-Benzyl-2-n-butylimidazo[4,5-d]pyridazine-4-(5H),7(6H)-dione (300 mg, 1 mmol) was suspended in dry methylene chloride (10 ml) and methyl 1,3-cyclohexadiene-1-carboxylate (230 mg, 1.7 mmol) synthesized according to the known method [Chem. Ber. Chem., 90, 238(1957), J. Org. Chem., 53, 3262(1988)] was added. The mixture was cooled to −12° C. in an ice-acetone bath. To the mixture was added lead tetraacetate (0.74 g, 1.5 mmol) and the mixture was stirred for 2 hours while allowing to rise the reaction temperature to 10° C. The reaction mixture was poured in water, extracted with methylene chloride, washed with water and dried over sodium sulfate. The solvent was distilled off under reduced pressure and the residue was dissolved in methanol (20 ml) without purification. 20% Palladium hydroxide (50 mg) was added thereto and the mixture was stirred at room temperature for 24 hours under hydrogen atmosphere. The catalyst was removed by filtration, the resulting filtrate was concentrated under reduced pressure and the residue was purified by silica gel column chromatography (chloroform:methanol=40:1) to obtain methyl 2-n-butyl-5,8-ethano-4,9-dioxo-5,6,7,8-tetrahydro-1H-1,3,4a,8a-tetraza-cyclopentanaphthalene-8-carboxylate (compound No. 153) (370 mg, >100%). This compound has the following NMR spectrum.

$^1$H-NMR (CDCl$_3$)δ(ppm): 0.93 (3H, t, J=7 Hz), 1.42 (2H, sextet, J=7 Hz), 1.85 (2H, quintet, J=7 Hz), 1.5–2.8 (8H, m), 2.96 (2H, t, J=7 Hz), 3.78,3.85 (3H, two s), 5.35, 547 (1H, two bs), 12.95, 13.05 (1H, two bs)

The above compound was alkylated according to the same procedures as those in Example 8 to obtain two isomers of less polar one (Rf=0.37, silica gel TLC plate, ethyl acetate:hexane=3:1) and more polar one (Rf=0.23, silica gel TLC plate, ethyl acetate:hexane=3:1) in an amount of 261 mg (31%) and 247 mg (30%), respectively. The isomers were further detritylated, respectively, to obtain methyl 2-n-butyl-5,8-ethano-4,9-dioxo-5,6,7,8-tetrahydro-1-[{2'-(1H-tetrazol-5-yl)biphenyl}methyl]-1H-1,3,4a,8a-tetraza-cyclopentanaphthalene-8-carboxylate (compound No. 156) from the less polar isomer, and methyl 2-n-butyl-5,8-ethano-4,9-dioxo-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate (compound No. 159) from the more polar isomer. These compounds have the following NMR spectrum.

Compound No. 156: $^1$H-NMR (CDCl$_3$)δ(ppm): 0.84 (3H, t, J=7 Hz), 1.32 (2H, sextet, J=7 Hz), 1.69 (2H, quintet, J=7 Hz), 1.8–2.7 (8H, m), 2.71 (2H, t. J=7 Hz), 3.77 (3H, t), 5.23 (1H,bs), 5.64 (1H, d, J=16 Hz), 5.67 (1H, d, J=16 Hz), 7.05 (2H, d, J=8 Hz), 7.15 (2H, d, J=8 Hz), 7.3–7.6 (3H, m), 7.96 (1H, d, J=8 Hz, 2 Hz)

Compound No. 159: $^1$H-NMR (CDCl$_3$)δ(ppm): 0.85 (3H, t, J=7 Hz), 1.33 (2H, sextet, J=7 Hz), 1.70 (2H, quintet, J=7 Hz), 1.8–2.7 (8H, m), 2.73 (2H, t, J=7 Hz), 3.75 (3H, s), 5.38 (1H, bs), 5.61 (1H, s), 7.01 (2H, d, J=8 Hz), 7.13 (2H, d, J=8 Hz), 7.3–7.6 (3H, m), 7.93 (1H, dd, J=8 Hz, 2 Hz)

Example 13

Preparation of ethyl 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate (Compound No. 196) and ethyl 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate (Compound No. 198)

Using the same procedures as those in Example 8 except that ethyl 1,3-cyclohexadiene-1-carboxylate synthesized by the known method in the literature [Helv. Chim. Acta, 4, 1191 (1958)] was used, there was obtained the titled compound via Compound No. 172. These compounds have the following NMR spectrum.

Compound No. 196 $^1$H-NMR (CDCl$_3$) δ(ppm): 0.86 (3H, t, J=7 Hz), 1.22 (3H, t, J=7 Hz), 1.33 (2H, sextet, J=7 Hz), 1.71 (2H, quintet, J=7 Hz), 1.8–2.6 (8H, m), 2.73 (2H, t, J=7 Hz), 4.23 (2H, m), 5.38 (1H, s), 5.61 (2H, s), 6.99 (2H, d, J=9 Hz), 7.13 (2H, d, J=9 Hz), 7.40 (1H, dd, J=7 Hz, 1 Hz), 7.45–7.6 (2H, m), 7.95 (1H, dd, J=7 Hz, 1 Hz)

Compound No. 198 $^1$H-NMR (CDCl$_3$) δ(ppm): 0.85 (3H, t, J=7 Hz), 1.27 (3H, t, J=7 Hz), 1.2–1.4 (2H, m), 1.70 (2H, quintet, J=7 Hz), 1.8–2.2 (6H, m), 2.4–2.7 (2H, m), 2.72 (2H, t, J=7 Hz, 4.26 (2H, m), 5.23 (1H, s), 5.66 (2H, s), 7.07 (2H, d, J=8 Hz), 7.15 (2H, d, J=8 Hz), 7.41 (1H, d, J=8 Hz), 7.45–7.6 (2H, m), 7.96 (1H, d, J=8 Hz)

Example 14

Preparation of 5
hydroxymethyl-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 199) and
8-hydroxymethyl-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 201)

Using the same procedures as those in Example 1 as well as 1-benzyl-2-n-propylimidazo[4,5-d]pyridazine-4(5H),7(6H)-dione and 2,4-hexadiene-1-ol as a starting material, there was obtained an intermediate 5-hydroxymethyl-8-methyl-2-n-propyl-5,6,7,8-tetrahydro-1H-1,3,4a,8a-tetraza-cyclopentanaphthalene-4,9-dione (Compound No. 173). This compound has the following NMR spectrum.

$^1$H-NMR (CDCl$_3$) δ(ppm): 0.98 (3H, t, J=7 Hz), 1.50 (3H, d, J=6 Hz), 1.78–1.87 (3H, m), 2.12 (3H, m), 2.85 (2H, t, J=7 Hz), 3.35 (1H, s), 3.78 (2H, d, J=7 Hz), 4.9 (1H, m), 5.10 (1H, m)

Starting from the above intermediate and using the same procedures as those in Example 1, there were obtained 5-hydroxymethyl-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 199) and 8-hydroxymethyl-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 201) as white powders. These compounds have the following NMR spectrum.

$^1$H-NMR (CDCl$_3$) δ(ppm): 0.85 (3H, t, J=7 Hz), 1.38 (3H, d, J=7 Hz), 1.60–1.80 (3H, m), 1.90–2.20 (3H, m), 2.62 (2H, t, J=8 Hz), 3.70–3.90 (2H, m), 4.96 (2H, m), 5.58 (1H, d, J=16 Hz), 5.67 (1H, d, J=16 Hz), 6.92–7.05 (4H, m), 7.36 (1H, d, J=7 Hz), 7.42–7.57 (2H, m), 7.82 (1H, d, J=8 Hz)

Example 15

Preparation of
2-n-butyl-5-hydroxymethyl-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 200) and
2-n-butyl-8-hydroxymethyl-5-methyl-5,6,7,8-tetrahydro-1-[{2'-(1H-tetrazol-5-yl)biphenyl-4-yl}]-1H-1,3,4a,-8a-tetraza-cyclopentanaphthalene-4,9-dione (Compound No. 202)

Using the same procedures as those in Example 1 as well as 1-benzyl-2-n-butylimidazo[4,5-d]pyridazine-4(5H),7(6H)-dione and 2,4-hexadiene-1-ol as a starting material, there was obtained an intermediate 2-n-butyl-5-hydroxymethyl-8-methyl-5,6,7,8-tetrahydro-1H-1,3,4a,8a-tetraza-cyclopentanaphthalene-4,9-dione (Compound No. 174). This compound has the following NMR spectrum.

Compound No. 173: $^1$NMR (CDCl$_3$) δ(ppm): 1.14 (3H, t, J=7 Hz), 1.57 (2H, m), 1.69 (3H, d, J=6 Hz), 1.90–2.04 (3H, m), 2.31 (3H, m), 3.05 (2H, t, J=7 Hz), 3.96 (2H, d, J=7 Hz), 5.09 (1H, m), 5.28 (1H, m)

Starting from the above intermediate and the same procedures as those in Example 1, there was obtained a mixture of 2-n-butyl-5-hydroxymethyl-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 200) and 2-n-butyl-8-hydroxymethyl-5-methyl-5,6,7,8-tetrahydro-1-[{2'-(1H-tetrazol-5-yl)biphenyl-4-yl]1H-1,3,4a-8a-tetraza-cyclopentanaphthalene-4,9-dione (Compound No. 202) as white powders. These compounds have the following NMR spectrum.

$^1$H-NMR (CDCl$_3$) δ(ppm): 0.81–0.89 (3H, m), 1.26–1.39 (2H, m), 1.39–1.42 (3H, m), 1.60–1.70 (3H, m), 1.86–2.16 (3H, m), 2.65–2.78 (2H, m), 3.71–3.96 (3H, m), 4.95–5.10 (2H, m), 5.50–5.71 (2H, m), 6.90–7.10 (4H, m), 7.27–7.59 (3H, m), 7.88–7.92 (1H, m)

Example 16

Preparation of
4,9-dioxo-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide (Compound No. 203) and
4,9-dioxo-5-methyl-2-n-propyl-5,6,7,8-tetrahydro-1-[{2'-(1 h-tetrazol-5-yl)biphenyl-4-yl}methyl]-1H-1,3,4a,8a-tetraza-cyclopentanaphthalene-8-carboxy-N,N-diethylamide (Compound No. 205)

Sorbic acid (5.01 g, 44.7 mmol) and diethylamine (3.59 g, 49 mmol) were dissolved in dimethylformamide (100 ml) and the solution was stirred under ice-cooling. To the solution was added diphenylphosphoryl azide (15.0 g, 54.5 mmol) and the mixture was stirred for 20 hours while allowing to rise the temperature to room temperature. The reaction mixture was diluted with ethyl acetate and washed with an aqueous saturated sodium chloride solution. The ethyl acetate layer was washed with an aqueous saturated sodium carbonate and aqueous saturated sodium chloride solution and dried over anhydrous sodium sulfate. The solvent was distilled off under reduced pressure and the residue was purified by silica gel column chromatography (chloroform:methanol=200:1–50:1) to obtain sorbic acid N,N-diethylamide (7.40 g, 99.9%) as pale yellow solid. This compound has the following NMR spectrum.

$^1$H-NMR (CDCl$_3$) δ(ppm): 1.17 (6H, t, J=7 Hz), 1.83 (3H, d, J=6 Hz), 3.41 (4H, quartet, J=7 Hz), 5.92–6.32 (3H, m), 7.15–7.35 (1H, m)

Starting from the above compound and using the same procedures as those in Example 2, there was obtained 4,9-dioxo-8-methyl-2-n-propyl-5,6,7,8-tetrahydro-1H-1,3,4a,8a-tetraza-cyclopentanaphthalene-5-carboxy-N,N-diethylamide (Compound No. 175) as colorless oily material. This compound has the following NMR spectrum.

$^1$H-NMR (CD$_3$OD) δ(ppm): 1.31 (3H, t, J=7 Hz), 1.43 (3H, t, J=7 Hz), 1.66 (3H, t, J=7 Hz), 1.73 (3H, d, J=6 Hz), 2.05–2.25 (2H, m), 2.2–2.55 (3H, m), 2.7–2.9 (1H, m), 3.1–3.25 (2H, t, J=7 Hz), 3.4–3.65 (2H, m), 3.654.0 (2H, m), 5.15–5.4 (1H, m), 5.85–6.0 (1H, m)

Starting from the above compound and using the same procedures as those in Example 8, there were obtained 4,9-dioxo-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide (Compound No. 203) and 4,9-dioxo-5-methyl-2-n-propyl-5,6,7,8-tetrahydro-1-[{2'-(1H-tetrazol-5-yl)biphenyl-4-yl}methyl]-1H-1,3,4a,8a-tetrazacyclopentanaphthalene-8-carboxy-N,N-diethylamide (Compound No. 205) as colorless oily material. These compounds have the following NMR spectrum.

Compound No. 203: $^1$H-NMR (CDCl$_3$) δ(ppm): 0.90 (3H, t, J=7 Hz), 1.10 (3H, t, J=8 Hz), 1.33 (3H, t, J=7 Hz), 1.41 (3H, d, J=6 Hz), 1.68-1.92 (1H, m), 1.73 (2H, m), 1.95-2.40 (3H, m), 2.66 (2H, t, J=7 Hz), 3.05-3.3 (1H, m), 3.3-3.64 (1H, m), 3.43 (2H, quartet, J=7 Hz), 5.0-5.2 (1H, m), 5.2-5.4 (1H, m), 5.50 (1H, d, J=16 Hz), 5.61 (1H, d, J=16 Hz), 6.92 (2H, d, J=7 Hz), 7.02 (2H, d, J=7 Hz), 7.2-7.6 (3H, m), 7.81 (1H, d, J=7 Hz)

Compound No. 205: $^1$H-NMR (CDCl$_3$) δ(ppm): 0.93 (3H, t, J=7 Hz), 1.09 (3H, t, J=7 Hz), 1.34 (3H, t, J=7 Hz), 1.43 (3H, d, J=6 Hz), 1.80 (2H, m), 1.8-2.0 (1H, m), 2.0-2.2 (2.45 (1H, m), 2.71 (2H, t, J=7 Hz), 3.1-3.3 (1H, m), 3.3-3.6 (3H, m), 4.8-5.0 (1H, m), 5.60 (2H, s) 5.5-5.75 (1H, m), 7.05 (4H, s), 7.3-7.65 (3H, m), 7.86 (1H, d, J=7 Hz)

Example 17

Preparation of 4,9-dioxo-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N-t-butylamide (Compound No. 207) and 4,9-dioxo-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N-t-butylamide (Compound No. 209)

Sorbic acid (5.01 g, 44.7 mmol) and t-butylamide (3.59 g, 49 mmol) were dissolved in dimethylformamide (150 ml) and the solution was stirred under ice-cooling. To the solution was added diphenylphosphoryl azide (14.8 g, 53.8 mmol) and triethylamine (9.95 g, 98.3 mmol) was added thereto. The mixture was stirred for 18 hours while allowing to rise the temperature to room temperature. The reaction mixture was diluted with ethyl acetate and the dilution was washed with an aqueous saturated sodium chloride solution. The ethyl acetate layer was washed with an aqueous saturated sodium carbonate solution and an aqueous saturated sodium chloride solution and dried over anhydrous sodium sulfate. The solvent was distilled off and the residue was purified by silica gel column chromatography (hexane:ethyl acetate=20:1–5:1) to obtain sorbic acid N-t-butylamide as (2.82 g, 37.6%) pale yellow solid. This compound has the following NMR spectrum.

$^1$-NMR (CDCl$_3$) δ(ppm): 1.39 (9H, s), 1.82 (3H, d, J=6 Hz), 5.30 (1H, bs), 5.67 (1H, d, J=15 Hz), 5.95-6.22 (2H, m), 7.13 (1H, dd, J=1 1 Hz, 15 Hz)

Starting from the above compound and using the same procedures as those in Example 8, there was obtained the titled compound via 4,9-dioxo-8-methyl-2-n-propyl-5,6,7,8-tetrahydro-1H-1,3,4a,8a-tetraaza-cyclopentanaphthalene-5-carboxy-N-t-butylamide (Compound No. 177). These compounds have the following NMR spectrum.

Compound No. 177: $^1$-NMR (CD$_3$OD) δ(ppm): 0.99 (3H, t, J=7 Hz), 1.36 (9H, s), 1.41 (3H, d, J=8 Hz), 1.72-1.92 (2H, m), 2.05-2.35 (4H, m), 2.87 (2H, t, J=7 Hz), 4.85-5.03 (2H, m)

Compound 207: $^1$H-NMR (CDCl$_3$) δ(ppm): 0.89 (3H, t, J=7 Hz), 1.32 (12H, s), 1.6-1.8 (2H, m), 1.8-2.25 (3H, m), 2.25-2.45 (1H, m), 2.67 (2H, t, J=7 Hz), 4.9-5.0 (1H, m), 5.15-5.35 (1H, m). 5.68 (1H, d, J=16 Hz), 5.78 (1H, d, J=16 Hz), 6.48 (1H, s), 6.97 (2H, d, J=8 Hz), 7.05 (2H, d, J=8 Hz), 7.36 (1H, d, J=7 Hz), 7.4-7.65 (2H, m), 7.84 (1H, d, J=7 Hz)

Compound 209: $^1$H-NMR (CDCl$_3$) δ(ppm): 0.92 (3H, t, J=7 Hz), 1.31 (12H, s), 1.65-1.85 (2H, m), 1.85-2.05 (2H, m), 2.05-2.30 (1H, m), 2.30-2.50 (1H, m), 2.70 (3H, t, J=7 Hz), 5.1-5.18 (1H, m), 5.18-5.3 (1H, m), 5.55 (1H, d, J=16 Hz), 5.79 (1H, d, J=16 Hz), 6.84 (1H, s), 7.05 (2H, d, J=8 Hz), 7.11 (2H, d, J=8 Hz), 7.39 (1H, d, J=8 Hz), 7.42-7.65 (2H, m), 7.85-7.95 (1H, m)

Example 18

Preparation of 2-n-butyl-4,9-dioxo-8-methyl-5,6,7,8-tetrahydro-1-[{2'-(1H-tetrazol-5-yl)biphenyl-4-yl}methyl]-1H-1,3,4a,8a-tetraaza-cyclopentanaphthalene-5-carboxy-N-t-butylamide (Compound No. 208) and 2-n-butyl-4,9-dioxo-5-methyl-5,6,7,8-tetrahydro-1-[{2'-(1H-tetrazol-5-yl)biphenyl-4-yl}methyl]-1H-1,3,4a,8a-tetraaza-cyclopentanaphthalene-8-carboxy-N-t-butyl amide (Compound No. 210)

Starting from the sorbic acid N-t-butylamide synthesized according to the method described in Example 8 and using the same procedures as those in Example 12, there was obtained the titled compound via 2-n-butyl-4,9-dioxo-8-methyl-5,6,7,8-tetrahydro-1H-1,3,4a,8a-tetraaza-cyclopentanaphthalene-5-carboxy-N-t-butylamide (Compound No. 178). These compounds have the following NMR spectrum.

Compound 178: $^1$H-NMR (CD$_3$OD)δ(ppm): 1.07 (3H, t, J=7 Hz), 1.45 (9H, s), 1.51 (3H, d, j=6 Hz), 1.80-2.0 (4H, m), 2.15-2.50 (4H, m), 3.10 (2H, t, J=8 Hz), 5.05-5.30 (2H, m)

Compound No. 208 $^1$H-NMR (CDCl$_3$) δ(ppm): 0.82 (3H, t, J=7 Hz), 1.15-1.45 (14H, m), 1.5-1.75 (2H, m), 1.75-1.95 (1H, m), 1.95-2.25 (2H, m), 2.25-2.42 (1H, m), 2.69 (2H, t J=7 Hz), 4.90-5.05 (1H, m), 5.15-5.35 (1H, m), 5.49 (1H, d, J=16 Hz), 5.68 (1H, d, J=16 Hz), 6.53 (1H, s), 6.96 (2H, d, J=8 Hz), 7.04 (2H, d, J=8 Hz), 7.35 (1H, d, J=7 Hz), 7.38-7.60 (2H, m), 7.83 (1H, d, J=7 Hz)

Compound No. 210: $^1$H-NMR (CDCl$_3$) δ(ppm): 0.85 (3H, t, J=7 Hz), 1.2-1.45 (14H, m), 1.70 (2H, m), 1.82-2.06 (1H, m), 2.06-2.30 (1H, m), 2.30-2.55 (2H, m), 2.72 (2H, t, J=8 Hz), 5.08-5.18 (1H, m), 5.18-5.32 (1H, m), 5.54 (1H, d, J=16 Hz), 5.78 (1H, d, J=16 Hz), 6.85 (1H, s), 7.04 (2H, d, J=8 Hz), 7.11 (2H, d, J=8 Hz), 7.39 (1H, d, J=7 Hz), 7.42-7.62 (2H, m), 7.87 (1H, d, J=7 Hz)

Example 19

Preparation of 4,9-dioxo-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-dihydroxyethylamide (Compound No. 211) and 4,9-dioxo-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-dihydroxyethylamide (Compound No. 213)

Starting from sorbic acid (1 g, 8.9 mmol) and ethanolamine (0.86 g, 8.2 mmol) and using diphenylphosphoryl azide (2.30 g, 8.4 mmol) and triethylamine (17 mmol) as well as the same procedures as those in Example 16, there was obtained sorbic acid N,N-dihydroxyethylamide (994 mg, 56%). This compound has the following NMR spectrum.

$^1$H-NMR (CDCl$_3$) δ(ppm): 1.85 (3H, d, J=9 Hz), 3.57 (2H, t, J=5 Hz), 3.63 (2H, t J=5 Hz), 3.81 (2H, t, J=5 Hz), 3.86 (2H, t, J=5 Hz), 6.0-6.4 (3H, m), 7.25 (1H, t, J=10 Hz)

Using the same procedures as those in Example 8 as well as the above compound and 1-benzyl-2-n-butylimidazo[4,5-d]pyridazine-4(5H),7(6h0-dione as a starting material, there was obtained a mixture of the titled compounds via an intermediate (Compound No. 179). These compounds have the following NMR spectrum.

Compound No. 179: $^1$H-NMR (CDCl$_3$) δ(ppm): 0.99 (3H, t, J=7 Hz), 1.48 (3H, d, J=6.5 Hz), 1.85 (2H, m), 2.15 (bs), 2.89 (2H, t, J=7 Hz), 3.4–4.0 (m)

Mixture of Compound Nos. 211 and 213 $^1$H-NMR (CDCl$_3$) δ(ppm): 0.95,1.00 (3H, two t, J=7 Hz), 1.43, 1,46 (3H, two d, J=7 Hz), 1.6–2.5 (m), 2.74,2.85 (2H, two t, J=7 Hz), 3.2–4.0 (m), 5.0–5.7 (m), 5.23,5.67(2H, two s), 6,7–8.0 (8H, m)

Example 20

Preparation of 5-acetyl-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 215) and 8-acetyl-5-methyl-2-n-propyl-5,6,7,8-tetrahydro-1-[{2'-(1H-tetrazol-5-yl}biphenyl-4-yl}methyl]-1H-1,3,4a,8a-tetraza-cyclopentanaphthalene-4,9-dione (Compound No. 217)

Using 1-benzyl-2-n-propylimidazo[4,5-d]pyridazine-4(5H),7(6H)-dione and 2,4-heptadiene-6-one as a starting material as well as the same procedures as those in Example 1, there was obtained an intermediate 5-acetyl-8-methyl-2-n-propyl-5,6,7,8-tetrahydro-1H-1,3,4a,8a-tetraza-cyclopentanaphthalene-4,9-dione (Compound No. 181). This compound has the following NMR spectrum.

$^1$H-NMR (CDCl$_3$) δ(ppm): 1.01 (3H, t, J=7 Hz), 1.25 (2H, m), 1.33 (3H, d, J=3 Hz, d, J=7 Hz), 1.8–2.3 (6H, m), 3.14 (2H, m), 5.11 (2H, m)

Starting from the above intermediate and using the same procedures as those in Example 1, there was obtained a mixture of 5-acetyl-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 2 15) and 8-acetyl-5-methyl-2-n-propyl-5,6,7,8-tetrahydro-t -[{2'-(1H-tetrazol-5-yl)biphenyl-4-yl}methyl]-1H-1,3,4a,8a-tetraza-cyclopentanaphthalene-4,9-dione (Compound No. 217) as white powders. This mixture has the following NMR spectrum.

Mixture of Compounds Nos. 215 and 217: $^1$H-NMR (CDCl$_3$) δ(ppm): 0.87–0.93 (3H, m), 1.30 (3H, d, J=7 Hz), 1.73 (3H, m), 2.06–2.27 (3H, m), 2.27 (3H, m), 2.68 (2H, m), 4.98–5.09 (2H, m), 5.55–5.80 (2H, m), 6.98–7.13 (4H, m), 7.27–7.60 (3H, m), 7.92 (1H, m)

Example 21

Preparation of 5,8-ethano-5-hydroxymethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 219) and 5,8-ethano-8-hydroxymethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 221)

1,3Cyclohexadiene-1-carboxyaldehyde (8.02 g, 0.617 mol) synthesized according to the known method [Chem.Ber.,90, 238 (1957)] was dissolved in methanol (100 ml) and sodium borohydride was added thereto in small portions while stirring under ice-cooling. Consumption of the starting material was confirmed by thin layer chromatography (ethyl acetate:hexane=1:10), the reaction mixture was concentrated under reduced pressure and the residue was distilled under the reduced pressure to obtain 1,3-cyclohexadiene-1-methanol (9.89 g, 54%), b.p. 73°–83° C./5 mmHg. This compound has the following NMR spectrum.

$^1$H-NMR (CDCl$_3$) δ(ppm): 2.1–2.3 (4H, m), 4.12 (2H, s), 5.7–6.0 (3H, m)

Using the above diene compound and 1-benzyl-2-n-propylimidazo[4,5-d]pyridazine-4(5H),7(6H)-dione as a starting material as well as the same procedures as those in Example 1, there were obtained the titled compounds as a mixture. This mixture has the following NMR spectrum.

Mixture of Compound Nos. 219 and 221 $^1$H-NMR (CDCl$_3$) δppm): 0.92,0.93 (3H, two t, J=7 Hz), 1.75 (2H, sextet, J=7 Hz), 1.7–2.3 (8H, m), 2.67 (2H, t, J=7 Hz), 3.95 (2H, bs), 5.41, 5.52 (1H, two broad s), 5.63, 5.68 (2H, two s), 7.0–7.2 (4H, m), 7.35–7.65 (3H, m), 7.95 (1H, two d, J=8 Hz)

Example 22

Preparation of 2-n-butyl-5,8-ethano-5-hydroxymethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 220) and 2-n-butyl-5,8-ethano-8-hydroxymethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 222)

Using 1-benzyl-2-n-butylimidazo[4,5-d]pyridazine-4(5H),7(6H)-dione and 1,3-cyclohexadiene-1-methanol synthesized according to the method described in Example 21 as well as the same procedures as those in Example 1, there were obtained the titled compounds as a mixture. This mixture has the following NMR spectrum.

Mixture of Compound Nos. 220 and 222 $^1$H-NMR (CDCl$_3$) δ(ppm): 0.85, 0.87 (3H, two t, J=7 Hz), 1.2–1.45 (2H, m), 1.6–1.8 (4H, m), 1.8–2.3 (6H, m), 2.69, 2.72 (2H, two t, J=7 Hz), 3.96 (2H, bs), 4.95 (1H, bs), 5.39,5.52 (1H, two bs), 5.62, 5.68 (2H, two s), 7.0–7.2 (4H, m), 7.35–7.65 (3H, m), 7.84 (1H, d, J=6.5 Hz)

Example 23

Preparation of 5-t-butoxycarbonylmethoxymethyl-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 223) and 5-t-butoxy-carbonylmethoxymethyl-2-n-butyl-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 225)

1,3-Cyclohexadiene-1-methanol (3 g, 0.027 tool) synthesized according to the method described in Example 21 was dissolved in DMF (15 ml) and 60% sodium hydride (1.1 g, 0.027 mol) was added thereto under ice-cooling. The mixture was stirred for 15 minutes, t-butyl ester of bromoacetate (6 g, 0.031 mol) was added dropwise and the mixture was stirred at room temperature for 30 minutes. The reaction mixture was poured in an aqueous saturated ammonium chloride solution, extracted with ethyl acetate, the combined ethyl acetate layer was washed with water and dried over anhydrous sodium sulfate. The solvent was distilled off and the residue was separated and purified by silica gel column chromatography (ethyl acetate:hexane=1:10) to obtain t-butyl-1,3-cyclohexadiene-1-methoxyacetate (0.90 g, 15%). This compound has the following NMR spectrum.

$^1$H-NMR (CDCl$_3$) δ(ppm): 1.48 (9H, s), 2.20 (4H, s), 3.95 (2H, s), 4.08 (2H, s), 5.7–6.0 (3H, m), Using the above diene compound and 1-benzyl-2-n-propylimidazo[4,5-d]pyridazine-4(5H),7(6H)-dione as a starting material as well as the same procedures as those in Example 8, there were obtained the titled compounds. These compounds have the following NMR spectrum.

Compound No. 223: $^1$H-NMR (CDCl$_3$) δ(ppm): 0.90 (3H, t, J=7 Hz), 1.42 (9H, s), 1.73 (2H, sextet, J=7 Hz), 1.8–2.2 (8H, m), 2.68 (2H, t, J=7 Hz), 4.00 (2H, s), 4.37 (2H, s), 5.43 (1H, bs), 5.67 (2H, s), 6.99 (2H, d, J=8 Hz), 7.15 (2H, d, J=8 Hz), 7.4–7.6 (3H, m), 7.95 (1H, dd, J=8 Hz, 1 Hz)

Compound No. 225 $^1$H-NMR (CDCl$_3$) δ(ppm): 0.89 (3H, t, J=7 Hz), 1.46 (9H, s), 1.71 (2H, sextet, J=7 Hz), 1.89–2.2 (8H, m), 2.65 (2H, t, J=7 Hz), 4.07 (2H, s), 4.41 (2H, s), 5.26 (1H, bs), 5.63 (2H, s), 7.03 (2H, d, J=8 Hz), 7.12 (2H, d, J=8 Hz), 7.39 (1H, dd, J=8 Hz, 1 Hz), 7.45–7.6 (2H, m), 7.93 (1H, dd, J=8 Hz, 1 Hz)

Example 24

Preparation of
5,8-ethano-5-(2-hydroxypropyl)methoxymethyl-2-n-propyl-5,6,7,8-tetrahydro-1-[{2'-(1H-tetrazol-5-yl)biphenyl-4-yl}methyl]-1H-1,3,4a,8a-tetraaza-cyclopentanaphthalene-4,9-dione (Compound No. 227) and
5,8-ethano-8-(2-hydroxypropoxy)methyl-2-n-propyl-5,6,7,8-tetrahydro-1-[{1'-(1H-tetrazol-5-yl)biphenyl-4-yl)methyl]-1H-1,3,4a,8a-tetraaza-cyclopentanaphthalene-4,9-dione (Compound No. 229) 1,3-Cyclohexadiene-1-methanol (2 g, 0.0182 mol) synthesized in Example 21 was dissolved in DMF (10 ml) and 60% sodium hydride (775 mg, 0.0194 mol) was added at 0° C. The mixture was stirred for 10 minutes and a solution of epibromohydrin (3 g, 0.022 mol) in DMF (3 ml) was added dropwise. The mixture was stirred at room temperature for 1 hour and at 40° C. for 1 hour and the reaction mixture was poured in water, extracted with ethyl acetate and the combined ethyl acetate layer was washed with water, dried over sodium sulfate and the solvent was distilled off. The residue was separated and purified by silica gel column chromatography (silica gel 60 g, ethyl acetate:hexane=1:10) to obtain 1-(2,3-epoxypropoxymethyl)-cyclohexa-1,3-diene (2.31 g, 76%). This compound has the following NMR spectrum.

$^1$H-NMR (CDCl$_3$) δ(ppm): 2.20 (4H, m), 2.62 (1H, m), 2.81 (1H, m), 3.18 (1H, m), 3.40 (1H, dd, J=12 Hz, 6 Hz), 3.71 (1H, dd, J=12 Hz, 3 Hz), 4.04 (2H, m), 5.7–60 (3H, m)

Using the above diene compound and 1-benzyl-2-n-propylimidazo[4,5-d]pyridazine-4(5H),7(6H)-dione as a starting material as well as the same procedures as those in Example 8, there were obtained the titled compounds. These compounds have the following NMR spectrum.

Compound No. 227: $^1$H-NMR (CDCl$_3$) δ(ppm): 0.89 (3H, t, J=7 Hz), 1.08 (3H, d, J=6.5 Hz), 1.69 (1H, sextet, J=7 Hz), 1.8–2.3 (8H, m), 2.66 (2H, t, J=7 Hz), 3.35 (1H, t, J=8 Hz), 3.53 (1H, dd, J=10 Hz, 3 Hz) 4.00 (1H, m), 4.18 (1H, d, J=10 Hz), 4.38 (1H, d, J=10 Hz), 5.30 (1H, bs), 5.64 (2H, s), 7.04 (2H, d, J=8 Hz), 7.11 (2H, d, J=8 Hz), 7.38–7.60 (3H, m), 7.90 (1H, dd, J=7 Hz, 1 Hz)

Compound No. 229 $^1$H-NMR (CDCl$_3$) δ(ppm): 0.83 (3H, d, J=6.5 Hz), 0.96 (3H, t, J=7 Hz), 1.7–2.2 (10H, m), 2.78 (2H, t, J=7 Hz), 3.3–3.45 (2H, m), 3.75 (1H, d, J=9 Hz), 3.95 (1H, m), 4.40 (1H, d, J=9 Hz), 5.50 (1H, bs), 5.57 (1H, d, J=17 Hz), 5.76 (1H, d, J=17 Hz), 6.93 (2H, d, J=8 Hz), 7.16 (2H, d, J=8 Hz), 7.45–7.64 (3H, m), 8.08 (1H, dd, J=8 Hz, 1 Hz)

Example 25

Preparation of
4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide (Compound No. 231) and
4,9-dioxo-5,8-ethano-2-n-propyl-5,6,7,8-tetrahydro-1-[{2'-(1H-tetrazol-5-yl)biphenyl-4-yl]methyl]-1H-1,3,4a,8a-tetraza-cyclopentanaphthalene-8-carboxy-N,N-diethylamide (Compound Methyl 1,3-cyclohexadiene-1-carboxylate (914 mg, 6.62 mmol) was dissolved in methanol (10 ml) and a 2N aqueous sodium hydroxide solution (4 ml) was added thereto and the solution was stirred at room temperature for 1 hour. The reaction mixture was concentrated, made acidic with hydrochloric acid and extracted with ethyl acetate. The ethyl acetate layer was washed with an aqueous saturated sodium chloride solution and dried over anhydrous sodium sulfate. The solvent was distilled off under reduced pressure to obtain 1,3-cyclohexadiene-1-carboxylic acid (761 mg, 92.7%) as white solid. This compound has the following NMR spectrum.

$^1$H-NMR (CDCl$_3$) δ(ppm): 2.15–2.40 (2H, m), 2.40–2.56 (2H, m), 6.0–6.15 (1H, m), 6.15–6.30 (1H, m), 7.14 (1H, d, J=8 Hz)

The above compound (535 mg, 4.31 mmol) and diethylamine (350 mg, 4.79 mmol) were dissolved in dimethylformamide (2 ml) and the solution was stirred under ice-cooling. Diphenylphosphoryl azide (1.42 g, 5.16 mmol) was added thereto, followed by triethylamine (960 mg, 9.49 mmol), and the mixture was stirred for 1 hour under ice-cooling and stirred at room temperature for 1 hour. The reaction mixture was diluted with ethyl acetate and washed with an aqueous saturated sodium chloride solution. The ethyl acetate layer was washed with an aqueous saturated sodium carbonate solution and aqueous saturated sodium chloride solution and dried over anhydrous sodium sulfate. The solvent was distilled off under reduced pressure and the residue was purified by silica gel column chromatography (chloroform:methanol=50:1) to obtain 1,3-cyclohexadiene-1-carboxylic acid N,N-diethylamide (763 mg, 98.7%) as pale yellow liquid. This compound has the following NMR spectrum.

$^1$H-NMR (CDCl$_3$) δ(ppm): 1.19 (6H, t, J=7 Hz), 2.15–2.45 (4H, m), 3.25–3.50 (4H, m), 5.80–6.05 (2H, m), 7.26 (1H, d, J=7 Hz)

Starting from the above compound and using the same procedures as those in Example 8, there were obtained the titled compounds via 4,9-dioxo-5,8-ethano- 2-n-propyl-5,6,7,8-tetrahydro-1H-1,3,4a,8a-tetraaza-cyclopentanaphthalene-5-carboxy-N,N-diethylamide (Compound No. 189). These compounds have the following NMR spectrum.

Compound No. 189: ¹H-NMR (CD₃OD) δ(ppm): 1.13 (3H, t, J=7 Hz), 1.20–1.40 (6H, m), 1.8–2.05 (2H, m), 2.05–2.80 (8H, m), 2.98 (2H, t, J=7 Hz), 3.2–3.75 (4H, m), 5.25–5.4 (1H, m)

Compound No. 231: ¹H-NMR (CDCl₃) δ(ppm): 0.99 (3H, t, J=7 Hz), 1.02–1.14 (6H, m), 1.70–1.9 (4H, m), 1.9–2.2 (2H, m), 2.2–2.4 (2H, m), 2.5–2.7 (1H, m), 2.79 (2H, t, J=7 Hz), 2.7–2.95 (1H, m), 3.21–3.44 (4H, m), 5.3 (1H, s), 5.55 (2H, s), 6.91 (2H, d, J=8 Hz), 7.10 (2H, d, J=8 Hz), 7.39 (1H, d, J=8 Hz), 7.47–7.65 (2H, m), 7.89 (1H, d, J=8 Hz)

Compound No. 233: ¹H-NMR (CDCl₃) δ(ppm): 0.92 (3H, t, J=8 Hz), 1.05–1.20 (6H, m), 1.65–1.85 (4H, m), 1.85–2.45 (5H, m), 2.5–2.7 (1H, m), 2.71 (2H, t, J=7 Hz), 3.0–3.6 (4H, m), 5.21 (1H, m), 5.64 (1H, d, J=16 Hz), 5.71 (1H, d, J=16 Hz), 7.11 (2H, d, J=8 Hz), 7.18 (2H, d, J=8 Hz), 7.42 (1H, d, J=8 Hz), 7.48–7.65 (2H, m), 7.96 (1H, d, J=8 Hz)

Example 26

Preparation of
4,9-dioxo-5,8-ethano-2-n-propyl-5,6,7,8-tetrahydro-1-
[{2'-(1H-tetrazol-5-yl)biphenyl-4-yl}methyl]-1H-
1,3,4a,8a-tetraaza-cyclopentanaphthalene-5-carboxy-N-t-butylamide (Compound No. 235) and
4,9-dioxo-5,8-ethano-2-n-propyl-5,6,7,8-tetrahydro-1-
[{2'-(1H-tetrazol-5-yl)biphenyl-4-yl}methyl]-1H-
1,3,4a,8a-tetraaza-cyclopentanaphthalene-8-carboxy-N-t-butylamide (Compound No. 237)

t-Butylamine (2.38 g, 0.033 mmol) was dissolved in THF (20 ml), 1.6M solution of n-butyl lithium in hexane (20 ml, 0.032 mol) was added thereto at 0° C. and the mixture was stirred as it was for 40 minutes. A solution of methyl 1,3-cyclohexadiene-1-carboxylate (3 g, 0.0217 mol) synthesized in Example 12 in THF (3 ml) was added dropwise and the solution was further stirred for 30 minutes. The reaction mixture was poured in water, extracted with methylene chloride and dried over anhydrous sodium sulfate. The solvent was distilled off under reduced pressure and the residue was purified by silica gel column chromatography (silica gel 60 g, ethyl acetate:hexane=1:5) to obtain 1,3-cyclohexadiene-1-carboxylic acid t-butylamide (1.98 g, 5 1%). This compound has the following NMR spectrum.

¹H-NMR (CDCl₃) δppm): 1.40 (9H, s), 2.2–2.45 (4H, m), 6.02 (1H, m), 6.55 (1H, m), 7.44 (1H, m), 7.72 (1H, dd, J=8 Hz, 1 Hz)

Using the above diene compound and 1-benzyl-2-n-propylimidazo[4,5-d]pyridazine-4(5H),7(6H)-dione as a starting material as well as the same procedures as those in Example 8, there were obtained the titled compounds via an intermediate (Compound No. 191). These compounds have the following NMR spectrum.

Compound No. 191: ¹H-NMR (CDCl₃) δ(ppm): 0.96 (3H, t, J=7 Hz), 1.41 (9H, s), 1.75–2.2 (8H, m), 2.56 (2H, m), 2.89 (2H, t, J=7 Hz), 5.22 (1H, bs), 5.46 (1H, s)

Compound No. 235: ¹H-NMR (CDCl₃+CD₃OD) δ(ppm): 0.10 (3H, t, J=7Hz), 1.34 (9H, s), 1.8–2.2 (8H, m), 2.4–2.55 (2H, m), 2.80 (2H, t, J=7 Hz), 5.31 (1H, bs), 5.53 (1H, s), 5.56 (2H, s), 698 (2H, d, J=8 Hz), 7.11 (2H, d, J=8 Hz), 7.44–7.62 (3H, m), 7.91 (1H, dd, J=8 Hz) 1 Hz)

Example 27

Preparation of
2-n-butyl-4,9-dioxo-5,8-ethano-5,6,7,8-tetrahydro-1-
[{2'-(1H-tetrazol-5-yl)biphenyl-4-yl}methyl]-1H-
1,3,4a,8a-tetraza-cyclopentanaphthalene-5-carboxy-N-t-butylamide (Compound No. 236) and
2-n-butyl-4,9-dioxo-5,8-ethano-
5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N-t-butylamide (Compound No. 238)

Using the same procedures as those in Example 26 except that 1-benzyl-2-n-butylimidazo[4,5-d]pyridazine4(5H),7(6H)-dione was used as a starting material, there were obtained the titled compounds. These compounds have the following NMR spectrum.

Compound NO. 236: ¹H-NMR (CDCl₃+CD₃OD) δ(ppm): 0.91 (3H, t, J=7 Hz), 1.33 (9H, s), 1.40 (1H, m), 1.7–2.15 (8H, m), 2.4–2.55 (2H, m), 2.81 (2H, t, J=7 Hz), 5.30 (1H, bs), 5.57 (2H, s), 5.58 (1H, s), 6.99 (2H, d, J=8 Hz), 7.11 (2H, d, J=8 Hz), 7.43–7.63 (3H, m), 7.89 (1H, dd, J=8 Hz, 1 Hz) Compound No. 238 ¹H-NMR (CDCl₃+CD₃OD) δ(ppm): 0.84 (3H, t, J=7 Hz), 1.2–1.4 (2H, m), 1.36 (9H, s), 1.66 (2H, sextet, J=7 Hz), 1.8–2.15 (6H, m), 2.4–2.55 (2H, m), 2.70 (2H, t, J=7 Hz, 5.15 (1H, bs), 5.60,5.59 (3H, two s), 7.03 (4H, s), 7.37 (1H, dd, J=7 Hz, 1s), 7.45–7.6 (1H, dd, J=7 Hz, 1 Hz)

Example 28

Preparation of
4,9-dioxo-5,8-ethano-2-n-propyl-5,6,7,8-tetrahydro-1-
[{2'-(1H-tetrazol-5-yl)biphenyl-4-yl}methyl]-1H-
1,3,4a,8a-tetraza-cyclopentanaphthalene-5-carboxy-N,N-bis(2-hydroxyethyl)amide (Compound No. 239)
and
4,9-dioxo-5,8-ethano-2-n-propyl-5,6,7,8-tetrahydro-1-
[{2'-(1H-tetrazol-5-yl)biphenyl-4-yl}methyl]-1H-
1,3,4a,8a-tetraza-cyclopentanaphthalene-8-carboxy-N,N-bis(2-hydroxyethyl)amide (Compound No. 241)

Using the same procedures as those in Example 5 as well as 1,3-cyclohexadiene-1-carboxylic acid and diethanolamine as a starting material, there was obtained 1,3-cyclohexadiene-1-carboxylic acid N,N-bis (2-hydroxyethyl)amide.

Using the above diene compound and 1-benzyl-2-n-propylimidazo[4,5-d]pyridazine-4,7-dione as a starting material as well as the same procedures as those in Example 8, there were obtained the titled compounds via an intermediate (Compound No. 193).

Compound No. 239 ¹H-NMR (CDCl₃) δ(ppm): 1.00 (3H, t, J=7 Hz), 1.7–2.4 (m), 2.81 (2H, t, J=7 Hz), 324 (1H, m), 3.4–3.85 (m), 4.08 (1H, m), 4.94 (1H, b s), 5.16 (1H, b s), 5.54 (1H, d, J=16 Hz), 5.70 (1H, d, J=16 Hz), 7.02 (2H, d, J=8 Hz), 7.12 (2H, d, J=8 Hz), 7.49–7.65 (3H, m), 4.83 (1H, m)

Compound No. 241: ¹H-NMR (CDCl₃) δ(ppm): 0.98 (3H, t, J=7 Hz), 1.7–2.4 (m), 2.61 (2H, m), 2.74 (2H, t, J=7 Hz), 3.25–3.85 (m), 4.25 (1H, m), 5.30 (1H, t, J=16 Hz), 5.33 (1H, s), 6.01 (1H, d, J=16 Hz), 6.93 (2H, d, J=8 Hz), 7.18 (2H, d, J=8 Hz), 7.45–7.65 (3H, m), 8.04 (1H, d, J=8 Hz)

Example 29

Preparation of
5,8-dihydro-5-hydroxymethyl-8-methyl-2-n-propyl-1-[{2'-(2'-(1H-tetrazol-5-yl)biphenyl-4-yl}methyl]-1H-1,3,4a,8a-tetraaza-cyclopentanaphthalene-4,9-dione (Compound No. 243) and
5,8-dihydro-8-hydroxymethyl-5-methyl-2-n-propyl-1-[{2'-(1H-tetrazol-5-yl)biphenyl-4-yl}methyl]-1H-1,3,4a,8a-tetraaza-cyclopentanaphthalene-4,9-dione (Compound No. 245)

Using 1-benzyl-2-n-propylimidazo[4,5-d]pyridazine-4(5H),7(6H)-dione and 2,4-hexadiene-1-ol as a starting material and the same procedures as those in Example 1, there was obtained an intermediate 5,8-dihydro-5-hydroxymethyl-8-methyl-2-n-propyl-1H-1,3,4a,8a-tetraza-cyclopentanaphthalene-4,9-dione (Compound No. 25 1). This compound has the following NMR spectrum.

$^1$H-NMR (CD$_3$OD) δ(ppm): 1.17 (3H, t, J=7 Hz), 1.77 (3H, d, J=6 Hz), 2.0 (2H, m), 3.03 (2H, t, J=7 Hz), 4.02 (1H, dd, J=11, 5 Hz), 4.16 (1H, dd, J=11, 5 Hz), 5.42–5.54 (2H, m), 6.30 (1H, dd, J=11, 5 Hz), 6.43 (1H, dd, J=1 1, 5 Hz), 8.08 (1H, s)

Starting from the intermediate and using the same procedures as those in Example 1, there was obtained a mixture of 5,8-dihydro-5-hydroxymethyl-8-methyl-2-n-propyl-1-[{2'-(1H-tetrazol-5-yl)biphenyl-4-yl}methyl]-1H-1,3,4a,8a-tetraaza-cyclopentanaphthalene-4,9-dione (Compound No. 243) and 5,8-dihydro-8-hydroxymethyl-5-methyl-2-n-propyl-1-[{2'-(1H-tetrazol-5yl)biphenyl-4yl}methyl]-1H-1,3,4a-8a-tetraaza-cyclopentanaphthalene-4,9-dione (Compound No. 245) as white powders. This mixture has the following NMR spectrum.

Mixture of Compound Nos. 243 and 245 $^1$H-NMR (CDCl$_3$) δ(ppm): 0.87 (3H, m), 1.45 (3H, m), 1.60–1.80 (2H, m), 2.60–2.71 (2H, m), 3.80–3.95 (2H, m), 5.30–5.45 (2H, m), 5.58–5.74 (2H, m), 5.97 (1H, m), 6.12 (1H, m), 6.92–7.07 (4H, m), 7.35–7.57 (3H, m), 7.81 (1H, d, J=8 Hz)

Example 30

Preparation of
5,8-dihydro-6-methyl-2-n-propyl-1-[{2'-(1H-tetrazol-5-yl)biphenyl-4-yl}methyl]-1H-1,3,4a,8a-tetraaza-cyclopentanaphthalene-4,9-dione (Compound No. 35 1) and 5,8-dihydro-7-methyl-2-n-propyl-1-[{2'-(1H-tetrazol-5-yl)biphenyl-4-yl}methyl]-1H-1,3,4a,8a-tetraza-cyclopentanaphthalene-4,9-dione (Compound No. 353)

Starting from isoprene and using the same procedures as those in Example 8, there was obtained the titled compounds as a mixture via 5,8-dihydro-6-methyl-2-n-propyl-1H-1,3,4a,8a-tetraza-cyclopentanaphthalene-4,9-dione (Compound No. 272). These compounds have the following NMR spectrum.

Compound No. 272: $^1$H-NMR (CDCl$_3$) δ(ppm): 1.00 (3H, t, J=7 Hz), 1.65–2.2 (2H, m), 1.96 (3H, s), 2.96 (2H, t, J=7 Hz), 4.55 (2H, s), 4.63 (2H, d, J=2 Hz), 5.79 (1H, d, J=2 Hz)

Mixture of Compound No. 35 1 and 353: $^1$H-NMR (CDCl$_3$) δ(ppm): 0.86 (3H, t, J=7 Hz), 1.66 (2H, m), 1.86 (3H, s), 2.64 (2H, t, J=7 Hz), 4.3–3.6 (4H, m), 5.64 (2H, s), 5.71 (1H, s), 7.00, 7.06 (each 2H, b), 7.3–7.6 (3H, m), 7.81 (1H, broad)

Example 31

Preparation of
8-methyl-5-(3-methyloxadiazol-5-yl)-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 329) and
5-methyl-8-(3-methyloxadiazol-5-yl)-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 331)

Acetamidoxime (640 mg, 8.64 mmol) was dissolved in tetrahydrofuran (10 ml), 60% sodium hydride (345 mg, 8.63 mmol) was added thereto, 10 particles of molecular sieve and ethyl sorbate (1.1 g, 7.85 mmol) were added thereto, and the mixture was stirred under heating at reflux for 8 hours. The reaction mixture was diluted with ethyl acetate, and an aqueous saturated solution of ammonium chloride was added thereto to stop the reaction. The ethyl acetate layer was separated, washed with an aqueous saturated solution of sodium chloride and dried over anhydrous sodium sulfate. The solvent was distilled off under reduced pressure, the residue was purified by silica gel column chromatography (hexane-ethyl acetate 50:1–10:1–5:1) to obtain methyloxadiazolyl-1,3-pentadiene (546 mg, 46.3%) as white solid. This compound has the following NMR spectrum.

$^1$H-NMR (CDCl$_3$) δ(ppm): 1.89 (3H, d, J=6 Hz), 2.39 (3H, s), 6.1–6.4 (3H, m), 7.36 (1H, dd, J=16 Hz, 10 Hz)

Starting from the above compound and using the same procedures as those in Example 8, there was synthesized the titled compound via 8-methyl-(3-methyloxadiazol-5-yl)-2-n-propyl-5,6,7,8-tetrahydro-1H-1,3,4a,-8a-tetraza-cyclopentanaphthalene-4,9-dione (Compound No. XXX). These compounds have the following NMR spectrum.

Compound No. 321: $^1$H-NMR (CDCl$_3$) δ(ppm): 0.97 (3H, t, J=7 Hz), 1.37 (3H, d, J=6 Hz), 1.7–1.95 (2H, m), 2.05–2.45 (4H, m), 2.26 (3H, s), 2.85 (2H, t, J=7 Hz), 5.0–5.2 (1H, m), Compound No. 329: $^1$H-NMR (CD$_3$OD) δ(ppm): 0.84 (3H, t, J=7 Hz), 1.30 (3H, d, J=8 Hz), 1.45–1.85 (2H, m), 2.07 (3H, s), 2.3–2.8 (6H, m), 4.4–4.6 (1H, m), 5.38, 5.96 (each 1H, d, J=16 Hz), 7.0–7.25 (4H, m), 7.45–7.8 (4H, m)

Compound No. 331: $^1$H-NMR (CD$_3$OD) δ(ppm): 0.90 (3H, t, J=7 Hz), 1.37 (3H, d, J=7 Hz), 1.5–2.6 (6H, m), 2.19 (3H, s), 2.71 (2H, t, J:7 Hz), 4.95–5.5 (1H, m), 5.6–6.0 (1H, m), 5.71 (2H, s), 6.95–7.2 (4H, m), 7.35–7.8 (4H, m)

Example 32

Preparation of
5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene -9-one (Compound No. 438)

5,8-Ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 108) (300 mg, 0.59 mmol) was dissolved in dry tetrahydrofuran (30 ml) and the solution was cooled to −10° C. A 1.5M solution (1.97 ml) of diisobutylaluminum hydride in toluene was slowly added dropwise thereto while stirring, the mixture was reacted for 30 minutes, water (2 ml) was added thereto and the mixture was stirred at 0° C. for 10 minutes. The reaction mixture was concentrated under reduced pressure, dilute hydrochloric acid was added to adjust pH to 3, the mixture was extracted with chloroform, washed with water, and dried over sodium sulfate. After filtration, the filtrate was concentrated under reduced pressure, the resulting white residue was subjected to silica gel column chromatography to obtain the titled compound (Compound No. 438) (107 mg, 36.8%) as colorless oily material from the fraction which eluted at chloroform-methanol (100:1). This compound has the following NMR spectrum.

$^1$H-NMR (CDCl$_3$) δ(ppm): 0.85 (3H, t, J=7 Hz), 1.50-1.78 (6H, m), 1.80-2.00 (2H, m), 2.02-2.20 (2H, m), 2.44 (2H, t, J=7 Hz), 2.85 (1H, s), 3.66 (2H, s), 4.46 (1H, s), 541 (2H, s), 6.90-7.05 (4H, m), 7.43-7.60 (3H, m), 7.76 (1H, d, J=7 Hz)

Example 33

Preparation of 5,8-ethano-2-n-propyl-4,5,6,7,8,9-hexahydro-1-[{2'-(1H-tetrazol-5-yl)biphenyl-4-yl}methyl]-1H-1,3,4a,8a-tetraza-cyclopentanaphthalene (Compound No. 523)

5,8-Ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 108) (1.77 g, 3.48 mmol) was dissolved in dry tetrahydrofuran (80 ml) and the solution was cooled to −10° C.c. A 1.5M solution (14 ml) of diisobutylaluminum hydride in toluene was slowly added dropwise thereto while stirring, the mixture was reacted for 1 hour, water (5 ml) was added thereto and the mixture was stirred at 0° C. for 10 minutes. The reaction mixture was concentrated under reduced pressure, dilute hydrochloric acid was added to adjust pH to 3, the mixture was extracted with chloroform, washed with water, and dried over sodium sulfate. After filtration, the filtrate was concentrated under reduced pressure, the resulting white residue was subjected to silica gel column chromatography to obtain the titled compound (Compound No. 523) (220 mg, 13.2%) as pale yellow oily material and 5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 438) (108 mg, 6.3%) from the fraction which eluted at chloroform-methanol (50:1 20:1 10:1 5:1). Starting material was recovered in an mount of 514 mg (29.0%). The titled compound has the following NMR spectrum.

Compound No. 523:

$^1$H-NMR (CDCl$_3$) δ(ppm): 0.90 (3H, t, J=7 Hz), 1.4-2.35 (10H, m), 2.47 (2H, t, J=7 Hz), 2.72 (1H, bs), 2.80 (1H, bs), 3.3-3.8 (4H), 4.85 (2H, s), 6.70, 6.92 (each 2H, d, J=8 Hz), 7.35-7.55 (3H, m), 7.69 (1H, d, J=7 Hz)

Example 34

Preparation of 2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 366)

Starting from 2-n-propyl-5,6,7,8-tetrahydro-1H-1,3,4a,8a-tetraza-cyclopentanaphthalene-4,9-dione (Compound No. 14) synthesized according to the same manner as that in Example 4 and using the same procedures as those in Example 32, there was obtained the titled compound (yield 58.6%) via 2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No.46). These compounds have the following NMR spectrum.

Compound No. 14: $^1$H-NMR (CD$_3$OD) δ(ppm): 1.12 (3H, t, J=8 Hz), 1.99 (2H, sextet, J=8 Hz), 3.06 (2H, sextet, J=8 Hz), 4.26 (4H, t, J=6 Hz), 5.01 (4H, s)

Compound No. 46: $^1$-NMR (CDCl$_3$) δ(ppm): 0.87 (3H, t, J=7 Hz), 1.68 (2H, sextet, J=7 Hz), 1.93 (4H, bs), 2.65 (2H, t, J=7 Hz), 3.95-4.2 (4H, m), 5.64 (2H, s), 7.00, 7.10 (each 2H, d, J'8 Hz), 7.3-7.65 (3H, m), 7.86 (1H, d, J=8 Hz)

Compound No. 366: $^1$H-NMR (CDCl$_3$) δ(ppm): 0.93 (3H, t, J=7 Hz), 1.4-1.55 (2H, m), 1.66 (2H, quintet, J=7 Hz), 1.75-1.9 (2H, m), 2.54 (2H, t, J=7 Hz), 2.76 (2H, t, J=6 Hz), 3.55-3.7 (2H, m), 4.00 (2H, s), 5.47 (2H, s), 6.93, 7.10 (each 2H, d, J=9 Hz), 7.46 (1H, d, J=8 Hz), 7.5-7.7 (2H, m), 7.97 (1H, d, J=8 Hz).

Example 35

Preparation of 5,8-dihydro-6,7-dimethyl-2-n-propyl-1-[{2'-(1H-tetrazol-5-yl)biphenyl-4-yl}methyl]-1H,4H-1,3,4a,8a-tetraaza-cyclopentanaphthalene-9-one (Compound No. 382)

Starting from 5,8-dihydro-6,7-dimethyl-2-n-propyl-1H-1,3,4a,8a-tetraaza-cyclopentanaphthalene-4,9-dione (Compound No. 9) synthesized as the same manner as that in Example 3 and using the same procedures as those in Example 32, there was synthesized the titled compound (yield 76.6%) via 5,8-dihydro-6,7-dimethyl-2-n-propyl-1-[{2'-(1H-tetrazol-5-yl)biphenyl-4-yl}methyl]-1H-1,3,4a,8a-tetraaza-cyclopentanaphthalene-4,9-dione (Compound No.67). These compounds have the following NMR spectrum.

Compound No. 9: $^1$-NMR (CDCl$_3$) δ(ppm): 1.02 (3H, t, J=7 Hz), 1.84 (6H, s), 1.8-2.05 (2H, m), 2.95 (2H, t, J=7 Hz), 4.54 (4H, s)

Compound No. 67: $^1$H-NMR (CDCl$_3$) δ(ppm): 0.94 (3H, t, J=7 Hz), 1.7-1.8 (2H, m), 1.77 (6H, s), 2.73 (2H, t, J=7 Hz), 4.42 (2H, s), 4.50 (2H, s), 5.69 (2H, s), 7.06, 7.17 (each 2H, d, J=8 Hz), 7.40 (1H, d, J=8 Hz), 7.45-7.75 (2H, m), 8.03 (1H, d, J=8 Hz)

Compound No. 382: $^1$H-NMR (CDCl$_3$) δ(ppm): 0.91 (3H, t, J=7 Hz), 1.55, 1.61 (each 3H, s), 1.5-1.75 (2H, m), 2.46 (2H, t, J=7 Hz), 3.14 (2H, s), 3.94, 4.00 (each 2H, s), 5.47 (2H, s), 6.90, 707 (each 2H, d, J=7 Hz), 7.45 (1H, d, J=7 Hz), 7.5-7.7 (2H, m), 7.94 (1H, d, J=7 Hz)

Example 36

Preparation of 2-n-butyl-5,8-dihydro-6,7-dimethyl-1-[{2'-(1H-tetrazol-5-yl)biphenyl-4-yl}methyl]-1H,4H-1,3,4a,8a-tetraaza-cyclopentanaphthalene-9-one (Compound No. 383)

2-n-Butyl-5,8-dihydro-6,7-dimethyl-1-[{2'-(triphenyl-methyltetrazol-5-yl)biphenyl-4-yl}methyl]-1H-1,3,4a,-8a-tetraza-cyclopentanaphthalene-4,9-dione (504 mg, 0.659 mmol) synthesized according to the same manner as that in Example 3 was dissolved in dry tetrahydrofuran (10 ml) and the solution was cooled to −10° C. A 1.5M solution (1.76 ml) of diisobutylaluminum hydride in toluene was slowly added dropwise thereto while stirring, the mixture was reacted for 30 minutes, diluted with methylene chloride, water (2 ml) was added, and the mixture was stirred at 0° C. for 10 minutes. The insoluble was filtered, the filtrate was extracted with methylene chloride, washed with water and dried over sodium sulfate. After filtration, the filtrate was concentrated under reduced pressure to obtain 2-n-butyl-5,8-dihydro-6,7-dimethyl-1-[{2'-(triphenylmethyltetrazol-5-yl)biphenyl-4-yl}methyl]-1H,1,3,4a,8-a-tetraaza-cyclopentanaphthalene-9-one (426 mg, 86.1%) as pale yellow oily material.

Starting from the above compound and using the same manner as that in Example 32, there was synthesized the titled compound (yield 49.1%). This compound has the following NMR spectrum.

Compound No. 383: $^1$-NMR (CDCl$_3$) δ(ppm): 0.88 (3H, t, J=7 Hz), 1.33 (2H, sextet, J=7 Hz), 1.5–1.75 (2H, m), 1.55 (3H, s), 1.64 (3H, s), 2.54 (2H, t, J=7 Hz), 3.17 (2H, s), 4.01 (3H,s), 4.04 (2H, s), 5.47 (2H, s), 6.95, 7.10 (each 2H, d, J=7 Hz), 7.29 (1H, d, J=7 Hz), 7.5–7.7 (2H, m), 8.01 (1H, d, J=7 Hz)

Example 37

Preparation of
6,7-dimethyl-2-n-propyl-5,6,7,8-tetrahydro-1-[{2'-(1H-tetrazol-5-yl)biphenyl-4-yl}methyl]-1H , 4H-1,3,4a,8a-tetraza-cyclopentanaphthalene-9-one (Compound No. 378)

Starting from 6,7-dimethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 50) and using the same manner as that in Example 32, there was synthesized the titled compound (yield 67.9%). This compound has the following NMR spectrum.

Compound No. 378: $^1$H-NMR (CDCl$_3$) δ(ppm): 0.72 (d, J=7 Hz), 0.75–1.05 (m) total 9H, 1.45–1.85 (3H, m), 1.85–2.0 (1H, m), 2.35–2.65 (4H, m), 2.65–2.85 (1H, m), 3.2–2.45 (1H, m), 3.55–4.3 (2H, m), 5.40, 5.48 (each 1H, d, J=16 Hz), 6.88, 7.04 (each 2H, d, J=7 Hz), 7.41 (1H, d, J=7 Hz), 7.45–7.65 (2H, m), 7.87 (1H, b)

Example 38

Preparation of
5,8-dihydro-6-methyl-2-n-propyl-1-[{2'-(1H-tetrazol-5-yl)biphenyl-4-yl}methyl]-1H,4H-1,3,4a,8a-tetraza-cyclopentanaphthalene-9-one (Compound No. 414) and 5,8-dihydro-7-methyl-2-n-propyl-1-[{2'-(1H-tetrazol-5-yl)biphenyl-4-yl}methyl]-1H,4H-1,3,4a,8a-tetraza-cyclopentanaphthalene-9-one (Compound No. 418)

Starting from a mixture of 5,8-dihydro-6-methyl-2-n-propyl-1-[{2'-(1H-tetrazol-5-yl)biphenyl-4-yl}methyl]-1H-1,3,4a,8a-tetraza-cyclopentanaphthalene-4,9-dione (Compound No. 351) and 5,8-dihydro-7-methyl-2-n-propyl-1-[{2'-(1H-tetrazol-5-yl)biphenyl-4-yl}nethyl]-1H-1,3,4a,8a-tetraza-cyclopentanaphthalene-4,9-dione (Compound No. 353) and using the same manner as that in Example 32, there was obtained the titled compound (yield 69.7%) as a mixture. This compound has the following NMR spectrum.

Mixture of Compound Nos. 414 and 418: $^1$H-NMR (CDCl$_3$) δ(ppm): 0.92 (3H, t, J=7 Hz), 1.5–1.8 (2H, m), 1.62 (s, 1H), 1.68 (s, 2H), 2.49 (2H, m), 3.19 (0.7H, s), 3.27 (1.3H, s), 3.8–4.2 (4H, m ), 5.49 (2H, s), 6.93, 7.09 (each 2H, d, J=8 Hz), 7.45 (1H, d, J=7 Hz), 7.5–7.7 (2H, m), 7.98 (1H, d, J=7 Hz)

Example 39

Preparation of
2-n-butyl-8-hydroxymethyl-5-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 511) and 2-n-butyl-5-hydroxymethyl-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 507)

Starting from (2E,4E)-2,4-hexadienol and using the same manner as that in Example 1, there were synthesized 1-benzyl-2-n-butyl-2,8-dihydro-5-hydroxymethyl-8-methyl-1H-1,3,4a,8a-tetraza-cyclopentanaphthalene-4,9-dione and 1-benzyl-2-n-butyl-5,8-dihydro-8-hydroxymethyl-5-methyl-1H-1,3,4a,8a-tetraza-cyclopentanaphthalene-4,9-dione. Starting from these compounds and using the same manner as that in Example 32, them were synthesized 1-benzyl-2-n-butyl-2,8-dihydro-5-hydroxymethyl-8-methyl-1H,4H-1,3,4a,8a-tetraza-cyclopentanaphthalene-4-one and 1-benzyl-2-n-butyl-5,8-dihydro-8-hydroxymethyl-5-methyl-1H,4H-1,3,4a,8a-tetraza-cyclopentanaphthalene-9-one. This compound has the following NMR spectrum.

$^1$H-NMR (CDCl$_3$) δ(ppm): 0.86, 0.87 (3H, t and t, J=7 Hz, 7 Hz), 1.16, 1.40 (3H, d and d, J=7 Hz, 7 Hz), 1.26–1.41 (2H, m), 1.57–1.71 (2H, m), 2.56–2.63 (2H, m), 3.54–3.98, 4.32–4.32–4.53 (4H, m and m), 5.10–5.20, 5.53–6.01 (4H, m and m), 7.06–7.35 (5H, m)

1-Benzyl-2-n-butyl-2,8-dihydro-5-hydroxymethyl-8-methyl-1H,4H-1,3,4a,8a-tetraz-cyclopentanaphthalene-4,9-dione and 1-benzyl-2-n-butyl-5,8-dihydro-8-hydroxymethyl-5-methyl-1H,4H-1,3,4a,8a-tetraza-cyclopentanaphthalene-9-one which were obtained in the above reaction were subjected to debenzylation, reduction of double bond, alkylation and detritylation using the same manner as that in Example 1 to obtain the titled compound via a mixture of 2-n-butyl-5-hydroxymethyl-8-methyl-1H,4H-1,3,4a,8a-tetraza-cyclopentanaphthalene-9-one (Compound No. 541) and 2-n-butyl-8-hydroxymethyl-5-methyl-1H,4H-1,3,4a,8a-tetraza-cyclopentanaphthalene-9-one (Compound No. 542). These compounds have the following NMR spectrum.

Mixture of Compound Nos. 541 and 542:
$^1$H-NMR (CDCl$_3$) δ(ppm): 0.92, 0.93 (3H, t and t, J=7 Hz, 7 Hz), 1.04, 1.36 (3H, d and d, J=6 Hz, 7 Hz), 1.22–1.89 (8H, m), 2.75–2.83 (2H, m), 3.08–3.11 (1H, m), 4.11 (2H, m), 4.17–4.52 (2H, m), 4.72–4.86 (1H, m), 5.10 (1H, brs)

Mixture of Compound Nos. 507 and 511:
1-NMR (CDCl$_3$) δ(ppm): 0.76–0.84 (3H, m), 0.98–1.71 (12H, m), 2.46–2.61 (2H, m), 2.88–2.96 (1H, m), 3.56–4.42 (5H, m), 4.60–4.65 (1H, m), 5.16–5.76 (2H, m) 6.87–7.09 (4H, m), 7.41–7.61 (3H, m), 7.90–7.95 (1H, m)

Example 40

Preparation of
2-n-butyl-8-hydroxymethyl-5-methyl-5,6,7,8-tetrahydro-1-[{2'-(1H-tetrazol-5-yl)biphenyl-4-yl}methyl]-1H,9H-1,3,4a,8a-tetraza-cyclopentanaphthalene-4-one (Compound No. 540)

Starting from (2E,4E)-2,4-hexadienol and using the same manner as that in Example 32, there was synthesized the titled compound via 2-n-butyl-5-hydroxymethyl-8-methyl-1H,4-1,3,4a,8a-tetraza-cyclopentanaphthalene-4-one (Compound No. 541). This compound has the following NMR spectrum.

Compound No. 540:

$^1$-NMR (CDCl$_3$) δ(ppm): 0.85 (3H, t, J=7 Hz), 1.24 (3H, d, J=4 Hz), 1.27-1.73 (9H, m), 2.68-2.87 (3H, m), 3.33-3.46 (2H, m), 4.12 (1H, d, J=17 Hz), 4.41 (1H, d, J=17 Hz), 4.76 (1H, brs), 4.87 (1H, d, J=17 Hz), 5.19 (1H, d, J=17 Hz), 6.97 (2H, d, J=8 Hz), 7.11 (2H, d, J=8 Hz), 7.39-7.57 (3H, m), 7.88 (1H, d, J=7 Hz)

Example 41

Preparation of 2-n-butyl-5-hydroxymethyl-8-methyl-5,6,7,8-tetrahydro-1-[{2'-(1H-tetrazol-5-yl)biphenyl-4-yl}methyl]-1H,9H-1,3,4a,8a-tetraza-cyclopentanaphthalene-4-one (Compound No. 538)

Starting from (2E,4E)-2,4-hexadienol and using the same manner as that in Example 39, there was synthesized the titled compound via 2-n-butyl-8-hydroxymethyl-5-methyl-1H,4H-1,3,4a,8a-tetraza-cyclopentanaphthalene-4-one (Compound No. 542). This compound has the following NMR spectrum.

Compound No. 538:

$^1$H-NMR (CDCl$_3$) δ(ppm): 0.87 (3H, d, J=7 Hz), 0.92 (3H, t, 7 Hz), 1.25-2.10 (11H, m), 2.78 (2H, t, J=8 Hz), 3.02 (1H, brs), 3.72-3.79 (3H, m), 4.08-4.15 (1H, m), 4.76 (1H, brs), 4.85 (1H, d, J=16 Hz), 5.26 (1H, d, J=17 Hz), 7.02 (2H, d, J=8Hz), 7.21 (2H, d, J=8 Hz), 7.39-7.56 (3H, m), 7.97 (1H, d, J=8 Hz)

Example 42

Preparation of 5,8-ethano-5-hydroxymethyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 514) and 5,8-ethano-8-hydroxymethyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 518)

Starting from 1-hydroxymethyl-1,3-cyclohexadiene and using the same manner as that in Examples 1 and 36, there was synthesized the titled compound via 5,8-ethano-5-hydroxymethyl-2-n-propyl-1H-1,3,4a,8a-tetraza-cyclopentanaphthalene-4,9-dione (Compound No. 183). These compounds have the following NMR spectrum.

Compound No. 514:

$^1$H-NMR (CDCl$_3$+CD$_3$OD) δ(ppm): 0.97-1.04 (3H, m), 1.62-2.29 (11H, m), 2.82-2.90 (2H, m), 4.02 (2H, s), 4.92 (1H, brs), 5.48 (1H, brs)

Compound No. 518:

$^1$H-NMR (CDCl$_3$) δ(ppm): 0.87 (3H, t, J=7 Hz), 1.59-1.84 (4H, m), 1.97-2.15 (2H, m), 2.37-2.48 (6H, m), 3.41, 3.59 (2H, s and s), 3.65, 4.64 (2H, s and s), 3.76 (1H, brs), 5.07, 5.55 (2H, s and s), 6.70-7.52 (7H, m), 7.82-7.95 (1H, m)

Example 43

Preparation of 5,8-ethano-5-(1-hydroxy-1-methylethyl)-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 333) and 5,8-ethano-8-(1-hydroxy-1-methylethyl)-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 335)

Methyl (1,3-cyclohexadiene)carboxylate (1.20 g, 9.82 mmol) was dissolved in tetrahydrofuran (20 ml) under nitrogen atmosphere, a methyl lithium-ether solution (1.4M, 18.0 ml, 25.2 mmol) was added dropwise thereto under ice-cooling, and the mixture was stirred at room temperature for 2 hours. An aqueous saturated solution of ammonium chloride was added thereto under ice-cooling, the mixture was extracted with ethyl acetate, the organic layer was washed with an aqueous saturated solution of sodium chloride and dried over sodium sulfate. The solvent was distilled off under reduced pressure, the residue was purified by silica gel column chromatography (ethyl acetate-hexane 1:5) to obtain 1-(1-hydroxy-1-methylethyl)-1,3-cyclohexadiene (1.16 g) as colorless oily material. This compound has the following NMR spectrum.

$^1$H-NMR (CDCl$_3$) δ(ppm): 1.36 (6H, s), 2.19 (4H, m), 5.70-5.96 (3H, m)

Starting from 1-(1-hydroxy-1-methylethyl)-1,3-cyclohexadiene and using the same manner as that in Example 1, there was obtained the titled compound via 5,8-ethano-5-(1-hydroxy-1-methylethyl)-2-n-propyl-1H-1,3,4a,8a-tetraza-cyclopentanaphthalene-4,9-dione (Compound No. 323). These compounds have the following NMR spectrum.

Compound No. 323:

$^1$H-NMR (CDCl$_3$+CD$_3$OD) δ(ppm): 0.94-1.05 (3H, m), 1.16-1.44 (4H, m), 1.26 (6H, s), 1.59-2.19 (7H, m), 2.91 (2H, t, J=8 Hz), 4.90 (1H, brs), 5.12-5.14 (1H, m )

Mixture of Compound Nos. 323 and 353:

$^1$H-NMR (CDCl$_3$) δ(ppm): 1.00 (3H, t, J=7 Hz), 1.11-1.36 (4H, m), 1.18 (6H, s), 1.62-1.98 (4H, m), 2.27-2.32 (2H, m), 2.92-2.97 (11/5H, m), 5.08 (6/5H, brs), 5.23 (8/5H, brs), 6.91-7.11 (4H, m), 7.40-7.61 (3H, m), 7.83-7.93 (1H, m)

Example 44

Preparation of 5,8-ethano-5,8-dimethyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 450)

Starting from 1,4-dimethyl-1,3-cyclohexadiene synthesized according to the method of W. T. Brady, et al. (Synthesis, 1985, 704) and using the same manner as that in Examples 1 and 36, there was synthesized the titled compound via 5,8-ethano-5,8-dimethyl-2-n-propyl-1H-1,3,4a,8a-tetraza-cyclopentanaphthalene-4,9-dione (Compound No. 292). These compounds have the following NMR spectrum.

Compound No. 292:

$^1$H-NMR (CDCl$_3$) δ(ppm): 1.01 (3H, t, J=7 Hz), 1.75-1.95 (6H, m), 1.86 (6H, s 2.10-2.25 (4H, m), 3.10 (2H, t, J=7 Hz)

Compound No. 450:

¹H-NMR (CDCl₃) δ(ppm): 0.90 (3H, t, J=7 Hz), 1.02 (3H, s), 1.59 (3H, s), 1.59–1.65 (6H, m), 1.90–2.07 (4H, m), 2.42 (2H, t, J=6 Hz), 3.64 (2H, brs), 5.44 (2H, d, J=8 Hz), 7.08 (2H, d, J=8 Hz), 7.45–7.65 (3H, m), 7.92 (1H, brs)

Example 45

Preparation of 5,8-dimethyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 430)

Starting from (2E,4Z)-2,4-hexadiene and using the same manner as that in Examples 1 and 36, there was synthesized the titled compound via 5,8-dimethyl-2-n-propyl-1H-1,3,4a,8a-tetraza-cyclopentanaphthalene-4,9-dione (Compound No. 280). These compounds have the following NMR spectrum.

Compound No. 280:
¹H-NMR (CDCl₃) δ(ppm): 1.02 (3H, t, J=7 Hz), 1.22 (6H, d, J=7 Hz), 1.65–1.76 (2H, m), 1.86–2.00 (2H, m), 2.26–2.40 (2H, m), 2.95 (2H, t, J=7 Hz), 5.36–5.38 (2H, m)

Compound No. 430:
¹H-NMR (CDCl₃) δ(ppm): 0.70 (3H, d, J=7 Hz), 0.90 (3H, t, J=7 Hz), 1.21–1.36 (2H, m), 1.27 (3H, d, J=6 Hz), 1.61–1.69 (2H, m), 1.71–1.83 (1H, m), 2.05–2.15 (1H, m), 2.50 (2H, t, J=8 Hz), 2.98–3.00 (1H, m), 3.77 (1H, d, J=17 Hz), 4.32 (1H, d, J=17 Hz), 4.74–4.52 (1H, m), 5.37 (1H, d, J=16 Hz), 5.58 (1H, d, J=16 Hz), 6.90 (2H, d, J=8 Hz), 7.09 (2H, d, J=8 Hz), 7.45–7.65 (3H, m), 7.92 (1H, d, J=8 Hz)

Example 46

Preparation of 5,8-dimethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 362)

Starting from (2E,4Z)-24,-hexadiene and using the same manner as that in Examples 1 and 36, them was synthesized the titled compound via 5,8-dimethyl-2-n-propyl-1H-1,3,4a,8a-tetraza-cyclopentanaphthalene-4,9-dione (Compound No. 280). This compound has the following NMR spectrum.

Compound No. 362:
¹H-NMR (CDCl₃) δ(ppm): 0.94 (3H, t, J=7 Hz), 1.16 (3H, d, J=6 Hz), 1.62–1.66 (2H, m), 1.72–1.80 (2H, m), 2.26–2.29 (2H, m), 2.70 (2H, t, J=7 Hz), 5.21 (1H, brs), 5.58 (1H, d, J=16 Hz), 5.78 (1H, d, J=16 Hz), 7.06 (2H, d, J=7 Hz), 7.18 (2H, d, J=7Hz), 7.39–7.61 (3H, m), 8.02 (1H, brs)

Example 47

Preparation of 2-n-butyl-5,8-ethano-5,8-diethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 455)

1,4-Diethyl-1,3-cyclohexadiene was synthesized using the same method for synthesizing 1,4-dimethyl-1,3-cyclohexadiene. This compound has the following NMR spectrum.

¹H-NMR (CDCl₃) δ(ppm): 1.03 (6H, t, J=7 Hz), 2.07 (4H, q, J=7 Hz), 2.11 (4H, s), 5.61 (2H, s)

Starting from 1,4-diethyl-1,3-cyclohexadiene and using the same manner as that in Examples 1 and 36, there was synthesized the titled compound via 2-n-butyl-5,8-ethano-5,8-diethyl-1H-1,3,4a,8a-tetraza-cyclopentanaphthalene-4,9-dione (Compound No. 297). This compound has the following NMR spectrum.

Compound No. 297: ¹H-NMR (CD₃OD) δ(ppm): 0.75 (6H,t,J=7.8 Hz), 0.99 (3H,t,J=7.8Hz), 1.42 (2H, s, J=7.8 Hz), 1.84 (6H, m), 2.18 (4H, m) 2.36 (4H, q, J=7.8 Hz), 3.06 (2H, t, J=7.8 Hz)

Compound No. 455: ¹-NMR (CDCl₃) δ(ppm): 0.77–0.87 (9H, m), 1.23–1.40 (4H, m), 1.52– 1.66 (6H, m), 1.75–2.09 (6H, m), 2.43 (2H, t, J=8 Hz), 3.59 (2H, s), 5.44 (2H, s), 6.91 (2H, d, J=8 Hz), 7.06 (2H, d, J=8 Hz), 7.43–7.63 (3H, m), 7.93 (1H, d, J=7 Hz)

Example 48

Preparation of 2-n-butyl-5,8-ethano-5-methyl-5,6,7,8-tetrahydro-1-[{2'-(1H-tetrazol-5-yl)biphenyl-4-yl}methyl]-1H,4H-1,3,4a,-8a-tetraaza-cyclopentanaphthalene-9-one (Compound No. 443)

1-Methyl-1,3-cyclohexadiene was synthesized according to the method described by A. J. Birch, et al. (Aust. J. Chem.,23, 1641 (1970) and L. A. Paquette, et al. (Tetrahedron Lett., 1977, 159).

Starting from 1-methyl-1,3-cyclohexadiene and using the same manner as that in Examples 1 and 36, there was synthesized the titled compound via 2-n-butyl-5,8-ethano-5-methyl-1H-1,3,4a,8a-tetraaza-cyclopentanaphthalene-4,9-dione (Compound No. 289). This compound has the following NMR spectrum.

Compound No. 289: ¹H-NMR (CDCl₃+CD₃OD) δ(ppm): 0.93 (3H, t, J=7 Hz), 1.32–1.48 (2H, m), 1.55–2.20 (10H, m), 2.00 (3H, s), 2.99 (2H, t, J=8 Hz), 5.43 (1H, brs)

Compound No. 443: ¹-NMR (CDCl₃) δ(ppm): 0.82 (3H, t, J=7 Hz), 1.00 (3H, s), 1.23–1.32 (2H, m), 1.46–1.67 (6H, m), 1.87–1.95 (4H, m), 2.46 (2H, t, J=8 Hz), 3.66 (2H, s), 4.46 (1H, br s), 5.37 (2H, s), 6.96 (2H, d, J=8 Hz), 7.02 (2H, d, J=8 Hz), 7.44–7.62 (3H, m), 7.77 (1H, d, J=8 Hz)

Example 49

Preparation of 2-n-butyl-5,8-ethano-8-methyl-5,6,7,8-tetrahydro-1-[{2'-(1H-tetrazol-5-yl)biphenyl-4-yl}methyl]-1H,4H-1,3,4a,-8a-tetraaza-cyclopentanaphthalene-9-one (Compound No. 447)

Starting from 1-methyl-1,3-cyclohexadiene and using the same manner as that in Examples 1 and 36, there was synthesized the titled compound via 2-n-butyl-5,8-ethano-5-methyl-1H-1,3,4a,8a-tetraaza-cyclopentanaphthalene-4,9-dione (Compound No. 289). This compound has the following NMR spectrum.

1-NMR (CDCl₃) δ(ppm): 0.83 (3H, t, J=7 Hz), 1.21–1.34 (4H, m), 1.48–1.74 (4H, m), 1.54 (3H, s), 2.00–2.19 (4H, m), 2.41 (2H, t, J=8 Hz), 2.89 (1H, brs), 3.57 (2H, s), 5.44 (2H, s), 6.89 (2H, d, J=8 Hz), 7.05 (2H, d, J=8 Hz), 7.45–7.62 (3H, m), 7.81 (1H, d, J=7 Hz)

Example 50

Preparation of
6-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 347)
and
7-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 349)

A 1.0M solution (75 ml) of trimethylsilylmethyl magnesium chloride in diethyl ether was diluted with dry diethyl ether (50 ml). After the interior of an reaction vessel was replaced by nitrogen, a solution (50 ml) of benzaldehyde (5.3 g) in dry diethyl ether was slowly added dropwise to the solution in the reaction vessel while stirring. The reaction mixture was stirred at 40° C. for 2 hours under nitrogen atmosphere and cooled in an ice bath. A 25% aqueous solution (100 ml) of ammonium chloride was added dropwise thereto, the mixture was extracted with diethyl ether, washed with water and dried over sodium sulfate. After filtration, the filtrate was concentrated under reduced pressure to obtain 1-trimethylsilyl-2-hydroxy-2-phenylethane (13.1 g) as pale yellow oily material.

While ice-cooling, this trimethylsilyl derivative (5.0 g) was added dropwise to Collins reagent which had been prepared separately by stirring dry pyridine (41 g) and chromic anhydride (26 g) for 40 minutes in dichloromethane (300 ml) under nitrogen atmosphere. The mixture was stirred at room temperature for 1 minute, diethyl ether (500 ml) was poured in the reaction solution, the mixture was filtered, the filtrate was dried over sodium sulfate. After filtration, the filtrate was concentrated under reduced pressure to obtain trimethylsilylmethylphenyl ketone (2.8 g).

The above phenylketone (2.6 g) was dissolved in dry tetrahydrofuran (50 ml), and this solution was slowly added dropwise to a 1.0M solution (22 ml) of vinyl magnesium bromide in tetrahydrofuran while stirring. The reaction mixture was stirred under heating at 40° C. for 2 hours under nitrogen atmosphere and cooled in an ice bath. A 25% aqueous solution (100 ml) of ammonium chloride was added thereto, the mixture was extracted with diethyl ether, washed with water and dried over sodium sulfate. After filtration, the filtrate was concentrated under reduced pressure, the resulting orange oily material was subjected to silica gel column chromatography to obtain 1-trimethylsilyl-2-hydroxy-2-phenyl-3-butene (1.2 g) as pale yellow oily material from a fraction which eluted at hexane-ethyl acetate (1:1).

This butene derivative (1.1 g) was dissolved in acetic acid (2 ml) saturated with sodium acetate, and the solution was stirred at 60° C. for 1hour under nitrogen atmosphere. The reaction mixture was cooled to room temperature, diluted with water (400 ml), and extracted with diethyl ether. The extract solution was washed with an aqueous saturated solution of sodium bicarbonate and aqueous saturated solution of sodium chloride, and dried over sodium sulfate. After filtration, the filtrate was concentrated under reduced pressure to obtain 2-phenyl-1,3-butadiene (670 mg) as pale yellow oily material. Staring from this diene and using the same manner as that in Example 1, the titled compound was synthesized via 6-phenyl-2-n-propyl-5,6,7,8-tetrahydro-1H-1,3,4a,8a-tetraza-cyclopentanaphthalene-4,9-dione (Compound No. 264). These compounds have the following NMR spectrum.

$^1$H-NMR (CDCl$_3$) δ(ppm): 0.94 (3H, t, J=7 Hz), 1.88 (2H, m), 2.14 (1H, m), 2.34(1H, m), 2.93 (2H, t, 7 Hz), 3.22 (1H, m), 3.59 (1H, m), 3.75 (1H, m), 4.98 (2H, brs), 7.30 (5H, m)

Mixture of Compound Nos. 347 and 349: $^1$H-NMR (CDCl$_3$) δ(ppm): 0.88 (3H, t, J=7 Hz), 1.71 (2H, m), 2.11 (1H, m), 2.27 (1h, m), 2.67 (2H, t, J=7 Hz), 3.15 (1H, m), 3.44 (1H, m), 3.62 (1H, m), 4.654.96 (2H, m) 5.54 (1H, dd, J=7 and 15 Hz), 5.70 (1H, d, J=15 Hz), 7.00, 7.09 (each 2H, m), 7.25–7.57 (3H, m), 7.87 (1H, d, J=8 Hz)

Example 51

Preparation of
6,7-diethyl-5,8-dihydro-2-n-propyl-1-[{2'-(1H-tetrazol-5-yl)biphenyl-4-yl}methyl]-1H-1,3,4a,8a-tetraza-cyclopentanaphthalene-4,9-dione (Compound No. 359)

2,3-Dimethyl-1,3-butadiene (9,6 g) was dissolved in dry pentane (50 ml), and potassium t-butoxide (26 g) was slowly added dropwise thereto under nitrogen atmosphere while stirring. A 15% solution (100 ml) of n-butyl lithium in hexane was slowly added thereto, and the mixture was stirred at room temperature for 10 minutes. Then, methyl iodide (35 g) was slowly added over 30 minutes, the mixture was stirred for 30 minutes and cooled in an ice bath. An aqueous saturated solution of ammonium chloride was then poured therein, the separated organic layer was washed with an aqueous solution of sodium chloride and dried over magnesium sulfate. After filtration, the filtrate was distilled under atmospheric pressure, the factions having the boiling point of 50°–80° C. were collected. The solvent was distilled off by standing the fractionated solution at room temperature overnight to obtain 2,3-diethyl-1,3-butadiene (3.3 g) as colorless oily material.

Starting from this diethylbutadiene and using the same manner as that in Example 3, there was synthesized the titled compound via 5,8-dihydro-6,7-diethyl-2-n-propyl-1H-1,3,4a,8a-tetraza-cyclopentanaphthalene-4,9-dione (Compound No. 256). These compounds have the following NMR spectrum.

Compound No. 256: $^1$H-NMR (CDCl$_3$) δ(ppm): 0.85 (3H, t, J=7 Hz), 1.01 (6H, t, J=7 Hz), 1.66 (2H, m), 2.19 (4H, q, J=7 Hz), 2.64 (2H, t, J=7 Hz), 4.50 (2H, s), 4.54 (2H, s), 4.89 (1H,brs)

Compound No. 359: $^1$H-NMR (CDCl$_3$) δ(ppm): 0.85 (3H, t, J=7 Hz), 1.02 (6H, t, J=7 Hz), 1.66 (2H, m), 2.19 (4H, q, J=7 Hz), 2.64 (2H, t, J=7 Hz), 4.50 (2H, s), 4.54 (2H, s), 5.65 (2H, s), 6.97 (2H, d, J=8 Hz), 7.06 (2H, d, J=8 Hz), 7.36–7.56 (3H, m), 7.79 (1H, d, J=7 Hz)

Example 52

Preparation of
6-phenyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 398)
and
7-phenyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 402)

A mixture of 6-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene:4,9-dione and 7-phenyl-2-n-propyl- 5,6,7,8-tetrahydro-1-[{2'-(1H-tetrazol-5-yl)biphenyl-4-yl}methyl]-1H-1,3,4a, 8a-tetrazacyclopentanaphthalene-4,9-dione (Compound Nos. 347 and 349) (100 mg, 0.18 mmol) was dissolved in dry tetrahydrofuran (3 ml), and the solution was cooled to −10° C. To this solution was added a 1.5M solution (0.36 ml) of diisobutylaluminum hydride in toluene, and the mixture was stirred for 30 minutes. Methanol (5 ml) was then added thereto, the mixture was stirred at room temperature for 30 minutes, and the precipitate was filtered. The filtrate was concentrated under reduced pressure, the resulting white residue was subjected to silica gel column chromatography to obtain the titled compound (59 mg, 67%) as pale yellow oily material from a fraction which eluted at chloroform-methanol (9:1). This compound has the following NMR spectrum.

Compound No. 402 $^1$-NMR (CDCl$_3$) δ(ppm): 0.95 (3H, t, J=7 Hz), 1.82 (2H, m), 2.15 (1H, m), 2.28 (1H, 2.73 (2H, t, J=7 Hz), 3.06 (2H, s), 3.17 (1H, m), 3.38–3.65 (3H, m), 4.70–5.05 (3H, m), 5.59 (1H, dd, J=7 and 15 Hz), 5.80 (1H, dd, 7, 15 Hz), 7.08, 7.16 (each 2H, m), 7.26–7.52 (3H, m), 7.89 (1H, d, J=8 Hz)

Example 53

Preparation of 6,7-diethyl-5,8-dihydro-2-n-propyl-1-[{2'-(1H-tetrazol-5-yl)biphenyl-4-yl}methyl]-1H,4H-1,3,4a,8a-tetrazacyclopentanaphthalene-9-one (Compound No. 390)

Starting from 5,8-dihydro-6,7-diethyl-2-n-propyl-1-[{2'-(1H-tetrazol-5-yl)biphenyl-4-yl}methyl]-1H-1,3,4a,8a-tetraza-cyclopentanaphthalene-4,9-dione (Compound No. 359) and the same manner as that in Example 52, there was synthesized the titled compound (yield 53%). This compound has the following NMR spectrum.

Compound No. 359: $^1$H-NMR (CDCl$_3$) δ(ppm): 0.92 (9H, t, J=7 Hz), 1.60 (2H, m), 1.94 (2H, q, J=7 Hz). 1.99 (2H, q, J=7 Hz), 2.41 (2H, s), 5.46 (2H, s), 6.85 (2H, d, J=8 Hz), 7.02 (2H, d, J=8 Hz), 7.42–7.62 (3H, m), 7.87 (1H, d, J=7 Hz)

Example 54

Preparation of 5,8-diethyl-5,8-ethano-2-ethyl-5,6,7,8-tetrahydro-1-[{2'-(1H-tetrazol-5-yl)biphenyl-4-yl}methyl]-1H,4H-1,3,4a,-8a-tetraza-cyclopentanaphthalene-9-one (Compound No. 453)

Starting from 1-benzyl-2-ethylimidazo[4,5-d]pyridazine-4(5H),7(6H)-dione and 1,4-diethyl-1,3-cyclohexadiene and using the same manner as that in Examples 1 and 36, there was synthesized the titled compound via 5,8-diethyl-5,8-ethano-2-ethyl-5,6,7,8-tetrahydro-1H-1,3,4a,8a-tetraza-cyclopentanaphthalene-4,9-dione (Compound No. 295). These compounds have the following NMR spectrum.

Compound No. 295: $^1$-NMR (CDCl$_3$) δ(ppm): 0.87 (6H, t, J=7 Hz), 1.43 (3H, t, J=7 Hz), 1.72 (4H, m), 2.18 (4H, m), 2.42 (4H, q, J=7 Hz), 2.95 (2H, q, J=7 Hz)

Compound No. 453:
$^1$H-NMR (CDCl$_3$) δ(ppm): 0.77 (3H, t, J=7 Hz), 0.80 (3H, t, J=7 Hz), 1.05 (3H, t, J=7 Hz), 1.29 (2H, q, J=7 Hz), 1.5–1.7 (4H, m), 1.78 (2H, t, J=7 Hz), 2.06 (2H, q, J=7 Hz), 2.42 (2H, q, J=7 Hz), 3.42 (2H, s), 5.44 (2H, s), 6.86 (2H, d, J=8 Hz), 7.03 (2H, d, J=8 Hz), 7.4–7.65 (3H, m), 7.89 (1H, dd, J=8and 1 Hz)

Example 55

Preparation of 5,8-diethyl-5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 454)

Starting from 1-benzyl-2-n-propylimidazo[4,5-d]pyridazine-4(5H),7(6H)-dione and 1,4-diethyl-1,3-cyclohexadiene and using the same manner as that in Examples 1 and 36, there was synthesized the title compound via 5,8-diethyl-5,8-ethano-2-n-propyl-5,6,7,8-tetrahydro-1H-1,3,4a,8a-tetraza-cyclopentanaphthalene-4,9-dione (Compound No. 296). These compounds have the following NMR spectrum.

Compound No. 296:
$^1$H-NMR (CDCl-$_3$) δ(ppm): 0.8–0.95 (6H, m), 1.01 (3H, t, J=7 Hz), 1.6–1.8 (4H, m), 190 (2H, sextet, J=7 Hz), 2.1–2.3 (4H, m), 2.44 (4H, q, J=7 Hz), 2.90 (2H, t, J=7 Hz),13.0 (1H, broad)

Compound No. 454:
$^1$-NMR (CDCl$_3$) δ(ppm): 0.75–0.9 (9H, three t), 1.32 (2H, sextet, J=7 Hz), 1.5–2.15 (12H, m), 2.37 (2H, t, J=7 Hz), 3.52 (2H, s), 5.43 (2H, s), 6.87 (2H, d, J=8 Hz), 7.02 (2H, d, J=8 Hz), 7.4–7.65 (3H, m), 7.83 (1H, d, J=8 Hz)

Example 56

Preparation of 5-phenyl-2-n-propyl-5,6,7,8-tetrahydro-1-[{2'-(1H-tetrazol-5-yl)biphenyl-4-yl}methyl]-1H-1,3,4a,8a-tetrazacyclopentanaphthalene-4,9-dione (Compound No. 325) and 8-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 327)

Starting from 1-benzyl-2-n-propylimidazo[4,5-d]pyridazine-4(5H),7(6H)-dione and 1-phenyl-1,3-butadiene and using the same manner as that in Example 1, there was synthesized the titled compound via 5-phenyl-2-n-propyl-5,6,7,8-tetrahydro-1H-1,3,4a,8a-tetraza-cyclopentanaphthalene-4,9-dione (Compound No. 319). These compounds have the following NMR spectrum.

Compound No. 319:
$^1$H-NMR (CDCl$_3$) δ(ppm): 1.00 (3H, t, J=7.3 Hz), 1.76–1.91 (4H), 2.30–2.40 (2H), 2.85 (2H, t, J=7.3 Hz), 3.61 (1H, m), 4.64 (1H, m), 6.29 (1H, m), 7.09 (2H, d, J=6.8 Hz), 7.20–7.32 (3H)

Mixture of Compound Nos. 325 and 327: $^1$H-NMR (CDCl$_3$) δ(ppm): 0.83, 0.86 (3H, t, J=7.3Hz), 1.56–1.74 (2H, m), 1.81 (2H, m), 2.15–2.40 (2H), 2.61, 2.64 (2H, t, J=7.3Hz), 3.45, 3.62 (1H, m), 4.49, 4.75 (1H, m), 5.55, 5.65 (2H, two d, J=15.7 Hz), 6.20, 6.31 (1H, m), 6.88–7.50 (12H), 7.78 (1H, d, J=7.3 Hz)

Example 57

Preparation of 8-phenyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 470)

Starting from a mixture of the compound obtained in Example 56 and a precursor for Compound 327 and using the same manner as that in Example 36, there can be synthesized the titled compound. This compound has the following NMR spectrum.

Compound No. 470:

¹-NMR (CDCl₃) δ(ppm): 0.93 (3H, t, J=7 Hz), 1.5–2.2 (4H, m), 1.69 (2H, sextet, J=7 Hz), 2.55 (2H, t, J=7 Hz), 2.6 (1, m), 3.06 (1H, m), 3.71 (1H, d, J=17 Hz), 4.34 (1H, d, J=17 Hz), 5.54 (2H, s), 5.70 (1H, broad s), 6.98 (2H, d, J=8 Hz), 7.11 (2H, d, J=8 Hz),7.2–7.6 (8H, m), 7.94 (1H, d, J=8 and 1 Hz)

Example 58

Preparation of 2-n-propyl-5-(2-pyridyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 339) and 2-n-propyl-8-(2-pyridyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione (Compound No. 34 1)

Starting from 2-n-propylimidazo[4,5-d]pyridazine-4(5H),7(6H)-dione and 1-(2-pyridyl)-1,3-butadiene and using the same manner as that in Example 3, there was obtained 5,8-dihydro-2-n-propyl-5-(2-pyridyl)-1H-1,3,4a,8a-tetraza-cyclopentanaphthalene-4,9-dione (Compound No. 300). This compound has the following NMR spectrum.

Compound No. 300:

¹-NMR (CDCl₃) δ(ppm): 0.93 (3H, t, J=7.4 Hz), 1.85 (2H, sextet, J=7.4 Hz), 2.83 (2H, t, J=7.4 Hz), 9.16 (1H, broad d, J=18.4 Hz), 4.94 (1H, broad d, J=18.4 Hz), 6.18 (1H, m), 6.33 (1H, m), 6.62 (1H, broad s), 7.15 (1H, m), 7.60 (1H, m), 8.46 (1H, d, J=4.3 Hz)

The above compound was reacted with 4-bromomethyl-2'-(1-triphenylmethyl-1H-tetrazol-5-yl)biphenyl using the same manner as that in Example 3 to obtain an alkylated compound which was subjected to catalytic hydrogenation using 10% palladium-carbon as a catalyst in methanol, which resulted in reduction of a double bond and detritylation to obtain the rifled compound. This compound has the following NMR spectrum.

Mixture of Compound Nos. 339 and 341:

¹H-NMR (CDCl₃) δ(ppm): 0.86, 0.87 (3H, t, J=7.6 Hz), 1.50–1.90 (4H, m), 2.23 (1H, m), 2.64 (2H, t, J=7.6 Hz), 2.65 (1H, m), 3.42–3.70 (1), 4.46, 4.69 (1H, m), 5.44–5.68 (2H), 6.27, 6.35 (1H, m), 6.75–7.60 (10H), 7.74 (1H, m), 8.38 (1H, m)

Example 59

Preparation of 5-methyl-2-n-propyl-5,6,7,8-tetrahydro-1-[{2'-(1H-tetrazol-5-yl)biphenyl-4-yl}methyl]-1H-1,3,4a,8a-tetra-cyclopentanaphthalene-4,9-dione (Compound No. 343) and 8-methyl-2-n-propyl-5,6,7,8-tetrahydro-1-[{2'-(1H-tetrazol-5yl)biphenyl-4-yl}methyl]-1H-1,3,4a,8a-tetraza-cyclopentanaphthalene-4,9-dione (Compound No. 345)

Starting from 1-benzyl-2-n-propylimidazo[4,5-d]pyridazine-4(5H),7(6H)-dione and piperylene and using the same manner as that in Example 1, there was synthesized the titled compound via 5-methyl-2-n-propyl-5,6,7,8-tetrahydro-1H-1,3,4a,8a-tetraza-cyclopentanaphthalene-4,9-dione (Compound No. 276). This compound has the following NMR spectrum.

Mixture of Compound Nos. 343 and 345:

¹H-NMR (CDCl₃) δ(ppm): 0.95 (3H, t, J=7.4 Hz), 1.23, 1.24 (3H, d, J=6.8 Hz), 1.79 (2H, sextet, J=7.4 Hz), 1.6–2.20 (3H, 2.30 (1H, m), 2.73, 2.74 (2H, t, J=7.4 Hz), 3.52 (1H, m), 4.72, 4.87 (1H, m), 5.12, 5.27 (1H, m), 5.68, 5.69, 5.69 (2H, two d, J=16.2 Hz and s), 7.07–7.65 (7H), 8.05 (1H, m)

Example 60

Preparation of 2-n-butyl-5,8-dimethyl-5,8-ethano-5,6,7,8-tetrahydro-1-[{2'-(1H-tetrazol-5-yl)biphenyl-4-yl}methyl]-1H,4H-1,3,4a,8a-tetraza-cyclopentanaphthalene-9one (Compound No. 451)

Starting from 1-benzyl-2-n-butylimidazo[4,5-d]pyridazine-4(5),7(6H)-dione and 1,4-dimethyl-1,3-cyclohexadiene and using the same manner as that in Example 1 and 36, there was synthesized the titled compound via 2-n-butyl-5,8-ethano-5,6,7,8-tetrahydro-1H-1,3,4a,8a-tetraza-cyclopentanaphthalene-4,9-dione (Compound No, 2.93). These compounds have the following NMR spectrum.

Compound No. 293:

¹H-NMR (CDCl₃+CD₃OD) δ(ppm): 0.97 (3H, t J=7 Hz), 1.43 (2H, sextet, J=7 Hz), 1.86 (6H, s), 2.16 (2H, m), 3.13 (2H, t, J=7 Hz)

Compound No. 451:

¹H-NMR (CDCl₃+CD₃OD) δ(ppm): 0.87 (3H, t, J=7.3 Hz), 1.17 (3H, s), 1.65 (3H, s), 2.61 (2H, t, J=7.8 Hz), 3.98 (2H, s), 5.56 (2H, s), 7.11 (4H, s), 7.48–7.66 (4H, m), 2.16 (2H, m), 3.13 (2H, t, J=7 Hz)

Alternatively, the titled compound can be synthesized according to the following steps.

Starting from 2-n-butylimidazo[4,5-]pyridazine-4(5H),7(6H)-dione and 1,4-dimethyl-1,3-cyclohexadiene and using the same manner as that in Example 3, there is obtained 2-n-butyl-5,8-dimethyl-5,8-ethano-5,8-dihydro-1H-1,3,4a,8a-tetraza-cyclopentanaphthalene-4,9-dione (Compound No. 546). This compound has the following NMR spectrum.

Compound No. 546:

¹H-NMR (CDCl₃) δ(ppm): 0.92 (3H, t, J=7.3 Hz), 1.38 (2H, m), 1.68 (2H, m), 1.81 (2H, m), 2.24 (6H, s), 2.32 (2H, m), 2.90 (2H, t, J=7.8 Hz), 6.37 (1H, s), 6.41 (1H, s)

The above compound is reacted with 4-bromomethyl-2'-(1-triphenylmethyl-1H-tetrazol-5-yl)biphenyl according to the same manner as that in Example 3 to obtain 2-n-butyl-5,8-dimethyl-5,8-ethano-5,8-dihydro-1-[{2'-(1-triphenylmethyl-1H-tetrazol-5-yl)biphenyl-4-yl}methyl]-1H-1,3,4a,8a-tetraza-cyclopentanaphthalene-4,9-dione, This compound has the following NMR spectrum.

¹H-NMR (CDCl₃) δ(ppm): 0.82 (3H, t, J=7.3 Hz), 1.23 (2H, m), 1.54–1.71 (4H), 2.14 (3H, s), 2.22 (3H, s), 2.27 (2H, m), 2.54 (2H, t, J=7.3 Hz), 5.57 (2H, AB, J$_{AB}$=15.9 Hz), 6.36 (2H, AB, J$_{AB}$=8.1 Hz), 6.85–7.50 (22H), 7.90 (1H, m)

The above compound (408 mg) is dissolved in tetrahydrofuran (4 ml), the solution is cooled to −10° C. 1.5M Solution (0.86 ml) of diisobutylaluminum hydride in toluene is added dropwise thereto and the mixture is reacted at −10° C. for 30 minutes. Methanol (0.2 ml) is added thereto to degrade the excess reagent, the reaction solution is diluted with dichloromethane and dried over sodium sulfate. The solvent is distilled off under reduced pressure, the residue is dissolved in methanol (50 ml), 10% palladium-carbon (95 mg) is added, and the mixture is subjected to catalytic hydrogenation at atmospheric pressure. After reaction, the catalyst is filtered, and the filtrate is concentrated under reduced pressure. The residue is purified by silica gel column chromatography (chloroform:methanol 20:1) to obtain the titled compound (162 mg, 58.5%).

Example 61

Preparation of 5,8-dimethyl-5,8-ethano-2-ethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one (Compound No. 449)

Starting from 1-benzyl-2-ethylimidazo[4,5-d]pyridazine-4(5H),7(6H)-dione and 1,4-dimethyl-1,3-cyclohexadiene and using the same manner as that in Examples 1 and 36, there was synthesized the titled compound via 5,8-dimethyl-5,8-ethano-2-ethyl-5,6,7,8-tetrahydro-1H-1,3,4a,8a-tetraza-cyclopentanaphthalene-4,9-dione (Compound No. 291). These compounds have the following NMR spectrum.

Compound No. 291:
$^1$H-NMR (CD$_3$OD) δ(ppm): 1.52 (3H, t, J=7.6 Hz), 1.87 (6H, s), 1.94 (4H, m), 2.18 (4H, m), 3.29 (2H, q, J=7.6 Hz)

Compound No. 449:
$^1$H-NMR (CDCl$_3$) δ(ppm): 0.98 (3H, s), 1.07 (3H, t, J=7.5 Hz), 1.59 (3H, s), 1.62 (4H, m), 1.94 (4H, m), 2.43 (2H, q, J=7.5 Hz), 3.50 (2H, s), 5.44 (2H, s), 6.88 (2H, d, J=8 Hz), 7.05 (2H, d, J=8.1 Hz), 7.48–7.64 (3H), 7.87 (1H, m)

Example 62

2-{(E)-1-Butenyl}-5,8-diethyl-5,8-ethano-5,6,7,8-tetrahydro-1-[{2'-(1H-tetrazol-5-yl)biphenyl-4-yl}methyl]-1H,4H-1,3,4a,8a-tetraaza-cyclopentanaphthalene-9-one (compound 522)

To a solution of 2-n-butyl-5,8-diethyl-5,8-ethano-5,6,7,8-tetrahydro-1-[{2'-(1-triphenylmethyl-1H-tetrazol-5-yl)biphenyl-4yl}methyl]-1H-1,3,4a,8a-tetraaza-cyclopentanaphthalene-4,9-dione (500 mg, 0.61 mmol) in carbon tetrachloride (10 mL) was added N-bromosuccinimide (195 mg, 1.10 mmol) and benzoyl peroxide (15 mg, 0.06 mmol) at room temperature, and the mixture was heated at reflux. After 2 hours, the reaction mixture was cooled to room temperature, and purified by silica gel chromatography (acetone/hexane;1/3) to give 2-(1-bromobutyl)-5,8-diethyl-5,8-ethano-5,6,7,8-tetrahydro-1-[{2'-(1-triphenylmethyl-1H-tetrazol-5-yl)biphenyl-4-yl}methyl]-1H-1,3,4a,8a-tetraaza-cyclopentanaphthalene-4,9-dione (147 mg, 27%) as a colorless solid.

The compound 2-(1-bromobutyl)-5,8-diethyl-5,8-ethano-5,6,7,8-tetrahydro-1-[{2'-(1-triphenylmethyl-1H-tetrazol-5-yl)biphenyl-4-yl}methyl]-1H,4H-1,3,4a,8a-tetraaza-cyclopentanaphthlene-9-one was prepared from 2-(1-bromobutyl)-5,8-diethyl-5,8-ethano-5,6,7,8-tetrahydro-1-[{2'-(1-triphenylmethyl-1H-tetrazol-5-yl)biphenyl-4-yl}methyl]-1H-1,3,4a,8a-tetraaza-cyclopentanaphthalene-4,9-dione according to the procedure described in Example 32.

To a solution of 2-(1-bromobutyl)-5,8-diethyl-5,8-ethano-5,6,7,8-tetrahydro-1-[{2'-(1-triphenylmethyl-1H-tetrazol-5-yl)biphenyl-4-yl}methyl]-1H,4H-1,3,4a,8a-tetraaza-cyclopentanaphthalene-9-one (4.73 mg, 0.053 mmol) in tetrahydrofuran (1.0 mL) was added 1,8-diazabicyclo[5,4,0]undec-7-ene (0.02 mL, 0.13 mmol) at room temperature, and the mixture was stirred at same temperature. After 14 hours, water and ethyl acetate were added, and organic layer was separated and washed with water and brine, dried (Na$_2$SO$_4$), and concentrated. The residue was purified by silica gel chromatography (acetone/hexane;1/4) to give 2-{(E)-1-butenyl}-5,8-diethyl-5,8-ethano-5,6,7,8-tetrahydro-1-[{2'-(1-triphenylmethyl-1H-tetrazol-5-yl)biphenyl-4-yl}methyl]-1H,4H-1,3,4a,8a-tetraaza-cyclopentanaphthalene-9-one (24.8 m g, 58%) a colorless solid.

The title compound was prepared from 2-{(E)-1-butenyl}-5,8-diethyl-5,8-ethano-5,6,7,8-tetrahydro-1-[{2'-(1-triphenylmethyl-1H-tetrazol-5-yl)biphenyl-4-yl}methyl]-1H,4H-1,3,4a,8a-tetraaza-cyclopentanaphthalen-9-one according to the procedure described in Example 1.

Compound No. 522: $^1$H-NMR (CDCl$_3$) δppm: 0.79 (3H, t, J=7.3 Hz), 0.80 (3H, t, J=7.3 Hz), 0.98 (3H, t, J=7.4 Hz), 1.23–1.43 (3H, m), 1.54–1.67 (3H, m), 1.83–1.90 (2H, m), 1.97–2.09 (4H, m), 2.13–2.23 (2H, m), 3.73 (2H, s), 5.48 (2H, s), 6.13 (1H, d, J=15.9 Hz), 6.73 (1H, dt, J=1.59, 6.2 Hz), 7.02 (2H, d, J=8.6 Hz), 7.08 (2H, d, J=8.6 Hz), 7.42–7.62 (3H, m), 7.96 (1H, dd, J=1.2,7.7 Hz)

Example 63

Preparation of 5,8-dimethyl-5,8-ethano-2-n-pentyl-5,6,7,8-tetrahydro-1-[{2'-(1H-tetrazol-5-yl)biphenyl-4-yl}methyl]-1H,4H-1,3,4a,8a-tetraaza-cyclopentanaphthalen- 9-one (Compound No. 452)

The title compound was prepared starting from 1,4-dimethyl-1,3-cyclohexadiene and 1-benzyl-2-n-pentylimidazo[4,5-d]-pyridizine-4(5H),7(6H)-dione according to the procedure described in Example 1 and 36 through 5,8-ethano-5,8-dimethyl-2-n-pentyl-5,6,7,8-tetrahydro-1H-1,3,4a,8a-tetraaza-cyclopentanaphthalene-4,9-dione (Compound No. 294).

Compound No. 294: $^1$H-NMR (CDCl$_3$) δppm: 0.90 (3H, t, J=6.5 Hz), 1.32–1.40 (4H, m), 1.79–1.91 (6H, m), 1.86 (6H, s), 2.14–2.21 (4H, m), 3.17 (2H, t, J=7.4 Hz)

Compound No. 452: $^1$H-NMR (CDCl$_3$) δppm: 0.84 (3H, t, J=7.0 Hz), 1.00 (3H, s), 1.21–1.29 (4H, m), 1.55–1.69 (6H, m), 1.61 (3H, s), 1.88–2.05 (4H, m), 2.39 (2H, t, J=7.7 Hz), 3.59 (2H, s), 5.43 (2H, s), 6.90 (2H, d, J=8.1 Hz), 7.05 (2H, d, J=8.1 Hz), 7.44–7.65 (3H, m), 7.88 (1H, d, J=7.6 Hz),

Example 64

Preparation of 2-n-butyl-5,8-diethyl-5,8-ethano-5,6,7,8-tetrahydro-1-[{2'-(1H-tetrazol-5-yl)biphenyl-4-yl}methyl]-1H,4H-1,3,4a,8a-tetraaza-cyclopentanaphthalen-9-one (compound 455)

Using the procedure of Example 39, 2-n-butyl-5,8-diethyl-5,8-ethano-5,6,7,8-tetrahydro-1H,4H-1,3,4a,8a-tetraaza-cyclopentanaphthalene-9-one was prepared from 1,4-diethyl-1,3-cyclohexadiene via 1-benzyl-2-n-butyl-5,8-diethyl-5,8-ethano-5,6,7,8-tetrahydro-1H-1,3,4a,8a-tetraaza-cyclopentanaphthalen-4,9-dione. The NMR spectrometric data of this compound was shown below.

$^1$H-NMR (CDCl$_3$) δppm: 0.75–1.0 (9H, m), 1.25–1.55 (4H, m), 1.55–1.85 (6H, m), 1.85–2.15 (4H, m), 2.15–2.35 (2H, m), 2.79 (2H, t, 8 Hz), 3.88 (2H, s)

To a solution of this product (187 mg, 0.566 mmol) in dimethylformamide (7 ml) was added 60% sodium hydride (30 mg, 0.750 mmol). After the resulting mixture was stirred for 15 min. at room temperature, (2'-cyanobiphenyl-4-yl)methyl bromide (230 mg, 0.845 mmmol) was added. Then the resultant solution was stirred for 3 hrs. Ethyl acetate and purified water were added and the organic phase was washed with saturated brine. The organic layer was dried over anhyd. sodium sulfate and concentrated and the crude product chromatographed to separate the two regioisomers in 50:1chloroform/methanol over silica gel. 2-n-butyl-5,8-diethyl-5,8-ethano-5,6,7,8-tetrahydro-1-[(2'-cyanobiphenyl-4-yl)methyl]-1H,4H-1,3,4a,8a-tetraaza-cyclopentanaphthalen-9-one (compound 547) was obtained as the faster moving isomer (92 mg 31.2% colorless oil). The NMR spectrometric data of this compound was shown below.

$^1$H-NMR (CDCl$_3$) δppm: 0.75-0.95 (9H, m), 1.2-1.4 (2H, m), 1.4-1.55 (2H, m), 1.55-1.8 (6H, m), 1.85-2.25 (6H, m), 2.57 (2H, t, J=8 Hz), 3.93 (2H, s), 5.62 (2H, s), 7.15-7.25 (2H, m), 7.4-7.55 (4H, m), 7.6 (1H, d, J=8 Hz), 7.75 (1H, d, J=8 Hz)

This compound (92 mg, 0. 176 mmol), sodium azide (100 mg, 1.54 mmol) and ammonium chloride (85 mg, 1.59 mmol) were mixed and stirred in dimethylformamide (5 ml) under nitrogen atmosphere. After that, the reaction temperature was raised to 100° C. through 120° C. and the mixture was stirred for 4 days. After the reaction mixture was cooled and the inorganic material was filtered off, the filtrate was concentrated. The residue was purified on preparative silica gel thin layer chromatography to afford the title compound as a white solid (27 mg 27%).

Example 65

Preparation of 2-n-butyl-5,8-diisopropyl-5,8-ethano-5,6,7,8-tetrahydro-1-[{2'-(2'-(1H-tetrazol-5-yl)biphenyl-4-yl}methyl]-1H,4H-1,3,4a,8a-tetraaza-cyclopentanaphthalene-9-one (Compound No. 463)

The title compound was prepared starting from 1,4-diisopropyl-1,3-cyclopentadiene according to the procedure described in the examples 1 and 36 through 2-n-butyl-5,8-diisopropyl-5,8-ethano-5,6,7,8-tetrahydro-1H-1,3,4a,8a-tetraaza-cyclopentanaphthalene-4,9-dione (Compound No. 549).

Compound No. 463: $^1$H-NMR (CDCl$_3$) δppm: 0.75 (12H, d, J=7.6 Hz), 0.88 (3H, t, J=7.6 Hz), 1.27 (2H, m), 1.55 (2H, m), 1.57-1.75 (9H, m), 2.39 (2H, t, J=7.6 Hz), 3.28 (1H, m), 3.49 (2H, s), 5.44 (2H, s), 6.85 (2H, d, J=7.8 Hz), 7.01 (2H, d, J=7.8 Hz), 7.43 (1H, dd, J=1.4 and 7.8 Hz), 7.55 (2H, m), 7.89 (1H, d, 6.5 Hz)

Compound No. 549: $^1$H-NMR (CDCl$_3$) δppm: 0.86 (15H, m), 1.43 (2H, m), 1.80-2.00 (10H, m), 3.06 (2H, t, J=7.6 Hz), 3.82 (2H, m)

Example 66

Preparation of 2-n-butyl-5,8-di-n-propyl-5,8-ethano-5,6,7,8-tetrahydro-1-[{2'-(1H-tetrazol-5-yl)biphenyl-4-yl56 methyl]-1H,4H-1,3,4a,8a-tetraaza-cyclopentanaphthalene-9-one (Compound No. 459)

The title compound was prepared starting from 1,4-di-n-propyl-1,3-cyclopentadiene according to the procedure described in the examples 1 and 36 through 2-n-butyl-5,8-di-n-propyl-5,8-ethano-5,6,7,8-tetrahydro-1H-1,3,4a,8a-tetraaza-cyclopentanaphthalene-4,9-dione (Compound No. 548).

Compound No. 459: $^1$H-NMR (CDCl$_3$) δppm: 0.82 (3H, t, J=7.6 Hz), 0.86 (6H, t, J=7.6 Hz), 1.24 (8H, m), 1.63 (6H, m), 1.83 (2H, m), 1.95 (4H, m), 2.46 (2H, t, J=7.6 Hz), 3.60 (2H, br, s), 5.42 (2H, s), 6.94 (2H, d, J=7.8 Hz), 7.04 (2H, d, J=7.8 Hz), 7.43-7.60 (3H, m), 7.90 (1H, d, J=7.3 Hz)

Compound No. 548 $^1$H-NMR (DMSO-d$_6$) δppm: 0.82 (6H, s, J=7.3 Hz), 0.89 (3H, t, J=7.3 Hz), 1.14 (4H, m), 1.29 (4H, m), 1.70 (6H, m), 1.98 (2H, m), 2.20 (4H, m), 2.76 (2H, t, J=7.3 Hz)

We claim:

1. An imidazole derivative represented by the general formula I:

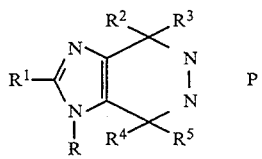

wherein
R$^1$ is
  (a) hydrogen atom,
  (b) C$_1$-C$_8$ alkyl group,
  (c) C$_1$-C$_8$ alkoxy group,
  (d) C$_1$-C$_8$ alkylthio group,
  (e) C$_1$-C$_8$ alkylamino group,
  (f) alkenyl of up to 8 C atoms,
  (g) alkynyl of up to 8 C atoms,
  (h) —CF$_3$ group,
  (i) C$_6$-C$_{10}$ aryl group, or
  (j) C$_6$-C$_{10}$ aralkyl group;
R is
  (a) hydrogen atom, or
  (b) a group selected from the following groups;

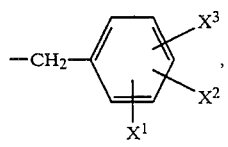

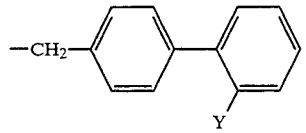

wherein
each occurrence of X$^1$, X$^2$ and X$^3$ is independently selected from
  (a) hydrogen atom,
  (b) halogen atom,
  (c) C$_1$-C$_8$ alkyl group,
  (d) C$_1$-C$_8$ alkoxy group,
  (e) nitro group,
  (f) cyano group,
  (g) 1H-tetrazol-5-yl group or an alkali metal salt thereof,
  (h) —CO$_2$R$^7$ group,
  (i) —CONR'R" group,
  (j) —CONHSO$_2$R$^8$ group,
  (k) an amino group,
  (l) —NHSO$_2$CF$_3$ group
  (m) —SO$_3$H group, or
  (n) a moiety selected from the following:

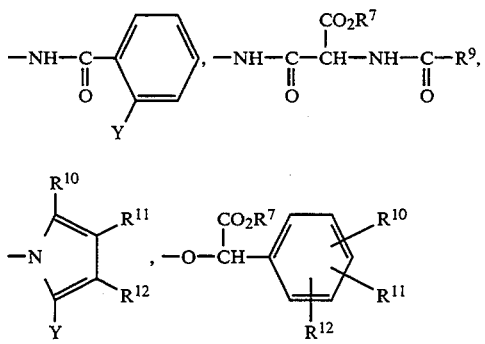

wherein
Y is
(a) cyano group,
(b) 1H-tetrazol-5-yl group or alkali metal salt thereof,
(c) —$CO_2R^7$ group,
(d) —CONR'R" group,
(e) —$CONHSO_2R^8$ group,
(f) an amino group,
(g) —$NHSO_2CF_3$ group or,
(h) —$SO_3H$ group;
wherein
each occurrence of $R^2$, $R^3$, $R^4$ and $R^5$ is independently selected from
(a) hydrogen atom, or
(b) $C_1$-$C_8$ alkyl group, or
(c) $R^2$ and $R^3$, or $R^4$ and $R^5$ taken together form a =O bond;
(a) hydrogen atom,
(b) alkali metal atom, or
(c) $C_1$-$C_8$ alkyl group;
wherein
each occurrence of R' and R" is independently
(a) hydrogen atom, or
(b) $C_1$-$C_8$ alkyl group, or
(c) R' and R" are taken together to form an alicyclic structure;
$R^8$ is
(a) $C_1$-$C_8$ alkyl group,
(b) $C_6$-$C_{10}$cycloalkyl group or
(c) $C_6$-$C_{10}$ aryl group;
$R^9$ is
(a) $C_1$-$C_8$ alkyl group,
(b) $C_1$-$C_8$ alkoxy group,
(c) $C_6$-$C_{10}$ cycloalkyl group,
(d) $C_6$-$C_{10}$ cycloalkoxy group,
(e) $C_6$-$C_{10}$ aryl group, or
(f) $C_6$-$C_{10}$ aryloxy group;
$R^{10}$, $R^{11}$ and $R^{12}$ are independently
(a) hydrogen atom,
(b) halogen atom,
(c) $C_1$-$C_8$ alkyl group,
(d) $C_1$-$C_8$ alkoxy group,
(e) nitro group,
(f) cyano group,
(g) —$CO_2R^7$ group, or
(h) —CONR'R" group;
—P— is
(a) A—B—C—D—,
(b) A—B=C—D, or
(c) A=B—C=D; wherein A or D may be absent or present and wherein
A—B—C—D, A—B=C—D or A=B—C=D represents, when A or D is not present, B—C—D, B=C—D, B—C=D, A—B—C, A—B=C or A=B—C, wherein these moieties are:
(a) —$CH(R^{13})$—$CH(R^{14})$—$CH(R^{15})$—,
(b) —$C(R^{13})$=$C(R^{14})$—$C(R^{15})$—,
(c) —$CH(R^{13})$—$C(R^{14})$=$C(R^{15})$—,
(d) —$CH(R^{13})$—$CH(R^{14})$—C(=O)—,
(e) —C(=O)—$CH(R^{14})$—$CH(R^{15})$—, or
(f) —$CH(R^{13})$—C(=O)—$CH(R^{15})$—, or
represents, when A and D are present, as A—B—C—D—, A—B=C—D or A=B—C=D, wherein these moieties are:
(a) —$C(R^{13})(R^{16})$—$CH(R^{14})$—$CH(R^{15})$—$C(R^{17})(R^{18})$—,
(b) —$C(R^{13})(R^{16})$—$C(R^{14})$=$C(R^{15})$—$C(R^{17})(R^{18})$—,
(c) —$C(R^{13})$=$C(R^{14})$—$CH(R^{15})$=$C(R^{17})$—,
(d) —C(=O)—$CH(R^{14})$—$CH(R^{15})$—$C(R^{17})(R^{18})$—,
(e) —$C(R^{13})(R^{16})$—C(=O)—$CH(R^{15})$—$C(R^{17})(R^{18})$—,
(f) —$C(R^{13})(R^{16})$—$CH(R^{14})$—C(=O)—$C(R^{17})(R^{18})$—, or
(g) —$C(R^{13})(R^{16})$—$CH(R^{14})$—$CH(R^{15})$—C(=O)—;
wherein
each occurrence of $R^{13}$, $R^{14}$, $R^{15}$, $R^{16}$, $R^{17}$ and $R^{18}$ is independently
(a) hydrogen atom,
(b) $C_1$-$C_8$ alkyl group,
(c) $C_1$-$C_8$ fluoroalkyl
(d) —C(R')(R")—$OR^{19}$ group,
(e) —$(CH_2)_j$—$CO_2R^7$ group,
(g) —$(CH_2)_j$—C(=O)R' group,
(h) —$(CH_2)_j$CONR'R" group, or,
(i) —$(CH_2)_j$—Aryl group wherein j is 0, 1 or 2, or
(j) wherein $R^{16}$ and $R^{18}$ may be taken together to form —$(CH_2)_i$—group, wherein i is 1,2 or 3;
wherein Aryl is
(a) phenyl group,
(b) pyridyl group,
(c) pyrimidinyl,
(d) pyridazinyl group,
(e) furyl group,
(f) thienyl group,
(g) pyrazolinyl group,
(h) oxazolyl group,
(i) thiazolyl group,
(j) oxadiazolyl group, or
(k) isoxazolyl group, or
(i) any of the foregoing groups substituted with
 (i) halogen atom,
 (ii) $C_1$-$C_8$ alkyl group,
 (iii) hydroxy group,
 (iv) $C_1$-$C_8$ alkoxy group,
 (v) nitro group, or
 (vi) cyano group;
wherein
$R^{19}$ is
(a) hydrogen atom, or
(b) $C_1$-$C_8$ alkyl group optionally substituted with hydroxy group or ether group; or a pharmacologically acceptable ester or salt thereof.

2. The imidazole derivative according to claim 1, represented by the general formula

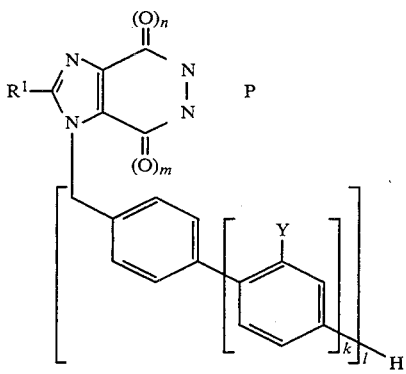

wherein

R¹, Y and P are as defined in claim 1, k, l, m and n are, independently, 0 or 1, or a pharmacologically acceptable ester or salt thereof.

3. The imidazole derivative according to claim 1, represented by the general formula:

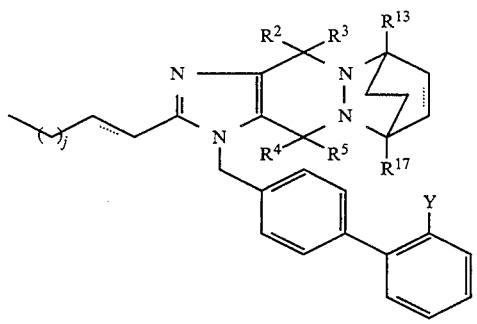

wherein

Y is cyano group, 1H-tetrazol-5-yl group or alkali metal salt thereof, or —$CO_2R^7$ group;

is single bond or double bond;

and $R^2$, $R^3$, $R^4$, $R^5$, $R^7$, $R^{13}$, $R^{17}$ and j are as defined in claim 1.

4. The imidazole derivative according to claim 1, represented by the general formula:

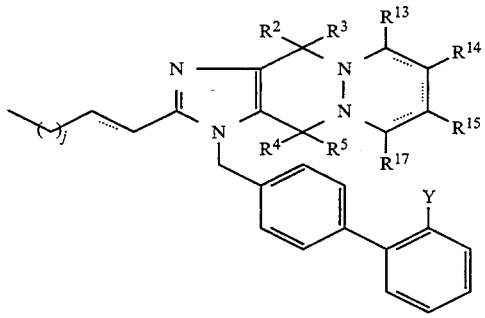

wherein

Y is cyano group, 1H-tetrazol-5-yl group or alkali metal salt thereof, or $CO_2R^7$ group;

is single bond or double bond;

$C(R^{13})$  $C(R^{14})$—  $C(R^{15})$  $C(R^{17})$ is single bond, double bond or diene bond;

and $R^2$, $R^3$, $R^4$, $R^5$, $R^7$, $R^{13}$, $R^{17}$ and j are defined in claim 1, or a pharmacologically acceptable ester or salt thereof.

5. The compound according to claim 1, which is selected from the group consisting of:

1) 2-methyl-6,7-dimethyl-5,6,7,8-tetrahydro-1H-1,3,4a,8a-tetraza-cyclopentanaphthalene-4,9-dione, 2) 2-ethyl-6,7-dimethyl-5,6,7,8-tetrahydro-1H-1,3,4a,-8a-tetraza-cyclopentanaphthalene-4,9-dione, 3) 2-n-propyl-6,7-dimethyl-5,6,7,8-tetrahydro-1H-1,3,4a,8a-tetraza-cyclopentanaphthalene-4,9-dione, 4) 2-n-butyl-6,7-dimethyl-5,6,7,8-tetrahydro-1H-1,3,4a,8a-tetraza-cyclopentanaphthalene-4,9-dione, 5) 2-n-pentyl-6,7-dimethyl-5,6,7,8-tetrahydro-1H-1,3,4a,8a-tetraza-cyclopentanaphthalene-4,9-dione, 6) 2-n-hexyl-6,7-dimethyl-5,6,7,8-tetrahydro-1H-1,3,4a,8a-tetraza-cyclopentanaphthalene-4,9-dione, 7) 2-methyl-5,8-dihydro-6,7-dimethyl-1H-1,3,4a,8a-tetraza-cyclopentanaphthalene-4,9-dione, 8) 2-ethyl-5,8-dihydro-6,7-dimethyl-1H-1,3,4a,8a-tetraza-cyclopentanaphthalene-4,9-dione, 9) 2-n-propyl-5,8-dihydro-6,7-dimethyl-1H-1,3,4a,8a-tetraza-cyclopentanaphthalene-4,9-dione, 10) 2-n-butyl-5,8-dihydro-6,7-dimethyl-1H-1,3,4a,8a-tetraza-cyclopentanaphthalene-4,9-dione, 11) 5,8-dihydro-6,7-dimethyl-2-n-pentyl-1H-1,3,4a,-8a-tetraza-cyclopentanaphthalene-4,9-dione 12) 5,8-dihydro-6,7-dimethyl-2-n-hexyl-1H-1,3,4a,8a-tetraza-cyclopentanaphthalene-4,9-dione 13) 2-ethyl-5,4,7,8-tetrahydro-1H-1,3,4a,8a-tetraza-cyclopentanaphthalene-4,9-dione, 14) 2-n-propyl-5,6,7,8-tetrahydro-1H-1,3,4a,8a-tetraza-cyclopentanaphthalene-4,9-dione, 15) 2-n-butyl-5,6,7,8-tetrahydro-1H-1,3,4a,8a-tetraza-cyclopentanaphthalene -4,9-dione, 16) 2-n-pentyl-5,6,7,8-tetrahydro-1H-1,3,4a,8a-tetraza-cyclopentanaphthalene-4,9-dione, 17) 5,8-dihydro-2-ethyl-1H-1,3,4a,8a-tetraza-cyclopentanaphthalene-4,9-dione, 18) 5,8-dihydro-2-n-propyl-1H-1,3,4a,8a-tetraza-cyclopentanaphthalene-4,9-dione, 19) 2-n-butyl-5,8-dihydro-1H-1,3,4a,8a-tetraza-cyclopentanaphthalene-4,9-dione, 20) 5,8-dihydro-2-n-pentyl-1H-1,3,4a,8a-tetraza-cyclopentanaphthalene-4,9-dione, 27) ethyl 4,9-dioxo-2-ethyl-5-methyl-5,6,7,8-tetrahydro-1H-1,3,4a,8a-tetraza-cyclopentanaphthalene-8-carboxylate, 28) ethyl 4,9-dioxo-5-methyl-2-n-propyl-5,6,7,8-tetrahydro-1H-1,3,4a,8a-tetraza-cyclopentanaphthalene-8-carboxylate, 29) ethyl 2-n-butyl-4,9-dioxo-5-methyl-5,6,7,8-tetrahydro-1H-1,3,4a,8a-tetraza-cyclopentanaphthalene-8-carboxylate, 44) 2-methyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 45) 2-ethyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 46) 2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 47) 2-n-butyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 48) 2-n-pentyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 49) 6,7-dimethyl-2-ethyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 50) 6,7-dimethyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 51) 2-n-butyl-6,7-dimethyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 55) 4,9-dioxo-2-ethyl-5-methyl-5,6,7,8-tetrahydro-1-[(2'-(1H-tetrazol-5-yl)biphenyl-4-yl)methyl]-1H-1,3,4a,8a-tetraza-cyclopentanaphthalene-8-carboxylic acid, 56) 4,9-dioxo-5-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-8-carboxylic acid, 57) 2-n-butyl-4,9-dioxo-5-methyl-5,6,7,8-tetrahydro-1-[(2'-(1H-tetrazol-5-yl)biphenyl-4-yl)methyl]-1H-1,3,4a,8a-tetraza-cyclopentanaphthalene-8-carboxylic acid, 58) 4,9-dioxo-5-methyl-2-n-pentyl-5,6,7,8-tetrahydro-1-[(2'-(1H-tetrazol-5-yl)diphenyl-4-yl)methyl]-1H-1,3,4a,8a-tetraza-cyclopentanaphthalene-8-carboxylic acid, 59) 5,8-dihydro-4,9-dioxo-2-ethyl-5-methyl-1-[(2'-(1H-tetrazol-5-yl)biphenyl-4-yl)methyl]-1H-1,3,4a,8a-tetraza-cyclopentanaphthalene-8-carboxylic acid, 60) 5,8-dihydro-4,9-dioxo-5-methyl-2-n-propyl-1-[(2'-(1H-tetrazol-5-yl)biphenyl-4-yl)methyl-1H-1,3,4a,8a-tetraza-cyclopentanaphthalene-8-carboxylic acid, 61) 2-n-butyl-5,8-dihydro-4,9-dioxo-5-methyl-1-[(2'-(1H-tetrazol-5-yl)biphenyl-4-yl)methyl]-1H-1,3,4a,8a-tetraza-cyclopentanaphthalene-8-carboxylic acid, 62) 5,8-dihydro-4,9-dioxo-5-methyl-2-n-pentyl-1-[(2'-(1H-tetrazol-5-yl)biphenyl-4-yl)methyl]-1H-1,3,4a,8a-tetraza-cyclopentanaphthalene-8-carboxylic acid, 66) 5,8-dihydro-6,7-dimethyl-2-ethyl-1-[(2'-(1H-tetrazol-5-yl)biphenyl-4-yl)methyl]-1H-1,3,4a,8a-tetraza-cyclopentanaphthalene-4,9-dione, 67) 5,8-dihydro-6,7-dimethyl-2-n-propyl-1-[(2'-(1H-tetrazol-5-yl)biphenyl-4-yl)methyl]-1H-1,3,4a,8a-tetraza-cyclopentanaphthalene-4,9-dione, 68) 2-n-butyl-5,8-dihydro-6,7-dimethyl-1-[(2'-(1H-tetrazol-5-yl)biphenyl-4-yl)methyl]-1H-1,3,4a,8a-tetraza-cyclopentanaphthalene-4,9-dione, 69) 5,8-dihydro-6,7-dimethyl-2-n-pentyl-1-[(2'-(1H-tetrazol-5-yl)biphenyl-4-yl)methyl]-1H-1,3,4a,8a-tetraza-cyclopentanaphthalene-4,9-dione, 70) 5,8-dihydro-2-n-propyl-1-[(2'-(1H-tetrazol-5-yl)biphenyl-4-yl)methyl]-1H-1,3,4a,8a-tetraza-cyclopentanaphthalene-4,9-dione, 71) 2-n-butyl-5,8-dihydro-1-[(2'-(1H-tetrazol-5-yl)biphenyl-4-yl)methyl]-1H-1,3,4a,8a-tetraza-cyclopentanaphthalene-4,9-dione, 72) 5,8-dihydro-2-n-pentyl-1-[(2'-(1H-tetrazol-5-yl)biphenyl-4-yl)methyl]-1H-1,3,4a,8a-tetraza-cyclopentanaphthalene-4,9-dione, 105) 5,8-dihydro-5,8-ethano-2-n-propyl-1-[(2'-(1H-tetrazol-5-yl)biphenyl-4-yl)methyl]-1H-1,3,4a,8a-tetraza-cyclopentanaphthalene-4,9-dione, 106) 2-n-butyl-5,8-dihydro-5,8-ethano-1-[(2'-(1H-tetrazol-5-yl)biphenyl-4-yl)methyl]-1H-1,3,4a,8a-tetraza-cyclopentanaphthalene-4,9-dione, 107) 5,8-dihydro-5,8-ethano-2-n-pentyl-1-[(2'-(1H-tetrazol-5-yl)biphenyl-4-yl)methyl]-1H-1,3,4a,8a-tetraza-cyclopentanaphthalene-4,9-dione, 108) 5,8-ethano-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 109) 2-n-butyl-5,8-ethano-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 110) 5,8-ethano-2-n-pentyl-5,6,7,8-tetrahydro-1-[(2'-(1H-tetrazol-5-yl)biphenyl-4-yl)methyl]-1H-1,3,4a,8a-tetraza-cyclopentanaphthalene-4,9-dione, 111) 4,9-dioxo-8-methyl-2-n-propyl-5,6,7,8-tetrahydro-1-[(2'-(1H-tetrazol-5-yl)biphenyl-4-yl)methyl]-1H-1,3,4a-8a,-tetraza-cyclopentanaphthalene-5-carboxylic acid, 112) 2-n-butyl-4,9-dioxo-8-methyl-5,6,7,8-tetrahydro-1-[(2'-(1H-tetrazol-5-yl)biphenyl-4-yl)methyl]-1H-1,3,4a,8a-tetraza-cyclopentanaphthalene-5-carboxylic acid, 113) 4,9-dioxo-8-methyl-2-n-pentyl-5,6,7,8-tetrahydro-1-[(2'-(1H-tetrazol-5-yl)biphenyl-4-yl)methyl]-1H-1,3,4a,8a-tetraza-cyclopentanaphthalene-5-carboxylic acid, 114) 5,8-dihydro-4,9-dioxo-8-methyl-2-n-propyl-1-[(2'-(1H-tetrazol-5-yl)biphenyl-4-yl)methyl]-1H-1,3,4a,8a-tetraza-cyclopentanaphthalene-5-carboxylic acid, 115) 2-n-butyl-5,8-dihydro-4,9-dioxo-8-methyl-1-[(2'-(1H-tetrazol-5-yl)biphenyl-4-yl)methyl]-1H-1,3,4a,8a-tetraza-cyclopentanaphthalene-5-carboxylic acid, 116) 5,8-dihydro-4,9-dioxo-8-methyl-2-n-pentyl-1-[(2'-(1H-tetrazol-5-yl)biphenyl-4-yl)methyl]-1H-1,3,4a,8a-tetraza-cyclopentanaphthalene-5-carboxylic acid, 120) 1-[(4-carboxyphenyl)methyl]-4,9-dioxo-5-methyl-2-n-propyl-5,6,7,8-tetrahydro-1H-1,3,4a,8a-tetraza-cyclopentanaphthalene-8-carboxylic acid, 121) 2-n-butyl-1-[(4-carboxyphenyl)methyl]-4,9-dioxo-5-methyl-5,6,7,8-tetrahydro-1H-1,3,4a,8a-tetraza-cyclopentanaphthalene-8-carboxylic acid, 122) 1-[(4-carboxyphenyl)methyl]-4,9-dioxo-5-methyl-2-n-pentyl-5,6,7,8-tetrahydro-1H-1,3,4a,8a-tetraza-cyclopentanaphthalene-8-carboxylic acid, 123) 1-[(4-carboxyphenyl)methyl]-4,9-dioxo-8-methyl-2-n-propyl-5,6,7,8-tetrahydro-1H-1,3,4a,8a-tetraza-cyclopentanaphthalene-5-carboxylic acid, 124) 2-n-butyl-1-[(4-carboxyphenyl)methyl]-4,9-dioxo-8-methyl-5,6,7,8-tetrahydro-1H-1,3,4a,8a-tetraza-cyclopentanaphthalene-5-carboxylic acid, 125) 1-[(4-carboxyphenyl)methyl]-4,9-dioxo-8-methyl-2-n-pentyl-5,6,7,8-tetrahydro-1,3,4a,8a-tetraza-cyclopentanaphthalene-5-carboxylic acid, 126) 1-[(4-carboxyphenyl)methyl]-5,8-dihydro-4,9-dioxo-5-methyl-2-n-propyl-1H-1,3,4a,8a-tetraza-cyclopentanaphthalene-8-carboxylic acid, 127) 2-n-butyl-1-[(4-carboxyphenyl)methyl]-5,8-dihydro-4,9-dioxo-5-methyl-1H-1,3,4a,8a-tetraza-cyclopentanaphthalene-8-carboxylic acid, 128) 1-[(4-carboxyphenyl)methyl]-5,8-dihydro-4,9-dioxo-5-methyl-2-n-pentyl-1H-1,3,4a,8a-tetraza-cyclopentanaphthalene-8-carboxylic acid, 129) 1-[(4-carboxyphenyl)methyl]-5,8-dihydro-4,9-dioxo-8-methyl-2-n-propyl-1H-1,3,4a,8a-tetraza-cyclopentanaphthalene-5-carboxylic acid,
130) 2-n-butyl-1-[(4-carboxyphenyl)methyl]-5,8-dihydro-4,9-dioxo-8-methyl-1H-1,3,4a,8a-tetraza-cyclopentanaphthalene-5-carboxylic acid,
131) 1-[(4-carboxyphenyl)methyl]-5,8-dihydro-4,9-dioxo-8-methyl-2-n-pentyl-1H-1,3,4a,8a-tetraza-cyclopentanaphthalene-5-carboxylic acid,
138) ethyl 4,9-dioxo-5-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-8-carboxylate,
139) ethyl 4,9-dioxo-8-methyl-2-n-propyl-5,6,7,8-tetrahydro-1-[(2'-(1H-tetrazol-5-yl)biphenyl-4-yl)methyl]-1H-1,3,4a,8a-tetraza-cyclopentanaphthalene-5-carboxylate,
140) ethyl 5,8-dihydro-4,9-dioxo-5-methyl-2-n-propyl-1H-1,3,4a,8a-tetraza-cyclopentanaphthalene-8-carboxylate,
141) ethyl 2-n-butyl-5,8-dihydro-4,9-dioxo-5-methyl-1H-1,3,4a,8a-tetraza-cyclopentanaphthalene-8-carboxylate,
142) ethyl 5,8-dihydro-4,9-dioxo-5-methyl-2-n-pentyl-1H-1,3,4a,8a-tetraza-cyclopentanaphthalene-8-carboxylate,
143) 5,8-dihydro-5,8-ethano-2-n-propyl-1H-1,3,4a,8a-tetraza-cyclopentanaphthalene-4,9-dione,
144) 2-n-butyl-5,8-dihydro-5,8-ethano-1H-1,3,4a,8a-tetraza-cyclopentanaphthalene-4,9-dione,
145) 5,8-dihydro-5,8-ethano-2-n-pentyl-1H-1,3,4a,8a-tetraza-cyclopentanaphthalene-4,9-dione,
146) 5,8-ethano-2-n-propyl-5,6,7,8-tetrahydro-1H-1,3,4a,8a-tetraza-cyclopentanaphthalene-4,9-dione,
147) 2-n-butyl-5,8-ethano-5,6,7,8-tetrahydro-1H-1,3,4a,8a-tetraza-cyclopentanaphthalene-4,9-dione,
148) 5,8-ethano-2-n-pentyl-5,6,7,8-tetrahydro-1H-1,3,4a,8a-tetraza-cyclopentanaphthalene-4,9-dione,
152) methyl 5,8-ethano-4,9-dioxo-2-n-propyl-5,6,7,8-tetrahydro-1H-1,3,4a,8a-tetraza-cyclopentanaphthalene-8-carboxylate,
153) methyl 2-n-butyl-5,8-ethano-4,9-dioxo-5,6,7,8-tetrahydro-1H-1,3,4a,8a-tetraza-cyclopentanaphthalene-8-carboxylate,
154) methyl 5,8-ethano-4,9-dioxo-2-n-pentyl-5,6,7,8-tetrahydro-1H-1,3,4a,8a-tetraza-cyclopentanaphthalene-8-carboxylate,
155) methyl 5,8-ethano-4,9-dioxo-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate,
156) methyl 2-n-butyl-5,8-ethano-4,9-dioxo-5,6,7,8-tetrahydro-1-[{2'-(1H-tetraza-5-yl)biphenyl-4-yl}methyl]-1H-1,3,4a,8a-tetraza-cyclopentanaphthalene-8-carboxylate,
157) methyl 5,8-ethano-4,9-dioxo-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate,
158) methyl 5,8-ethano-4,9-dioxo-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
159) methyl 2-n-butyl-5,8-ethano-4,9-dioxo-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
160) methyl 5,8-ethano-4,9-dioxo-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
167) ethyl 2-n-butyl-4,9-dioxo-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate,
168) ethyl 4,9-dioxo-5-methyl-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate,
169) ethyl 2-n-butyl-4,9-dioxo-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
170) ethyl 4,9-dioxo-8-methyl-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
171) ethyl 4,9-dioxo-5,8-ethano-2-n-propyl-5,6,7,8-tetrahydro-1H-1,3,4a,8a-tetraza-cyclopentanaphthalene-5-carboxylate,
172) ethyl 2-n-butyl-4,9-dioxo-5,8-ethano-5,6,7,8-tetrahydro-1H-1,3,4a,8a-tetraza-cyclopentanaphthalene-5-carboxylate,
173) 5-hydroxymethyl-8-methyl-2-n-propyl-5,6,7,8-tetrahydro-1H-1,3,4a,8a-tetraza-cyclopentanaphthalene-4,9-dione,
174) 2-n-butyl-5-hydroxymethyl-8-methyl-5,6,7,8-tetrahydro-1H-1,3,4a,8a-tetraza-cyclopentanaphthalene-4,9-dione,
175) 4,9-dioxo-8-methyl-2-n-propyl-5,6,7,8-tetrahydro-1H-1,3,4a,8a-tetraza-cyclopentanaphthalene-5-carboxy-N,N-diethyl amide,
176) 2-n-butyl-4,9-dioxo-8-methyl-5,6,7,8-tetrahydro-1H-1,3,4a,8a-tetraza-cyclopentanaphthalene-5-carboxy-N,N-diethylamide,
177) 4,9-dioxo-8-methyl-2-n-propyl-5,6,7,8-tetrahydro-1H-1,3,4a,8a-tetraza-cyclopentanaphthalene-5-carboxy-N-t-butylamide,
178) 2-n-butyl-4,9-dioxo-8-methyl-5,6,7,8-tetrahydro-1H-1,3,4a,8a-tetraza-cyclopentanaphthalene-5-carboxy-N-t-butylamide,
179) 4,9-dioxo-8-methyl-2-n-propyl-5,6,7,8-tetrahydro-1H-1,3,4a,8a-tetraza-cyclopentanaphthalene-5-carboxy-N,N-bis(2-hydroxyethyl)amide,
180) 2-n-butyl-4,9-dioxo-8-methyl-5,6,7,8-tetrahydro-1H-1,3,4a,8a-tetraza-cyclopentanaphthalene-5-carboxy-N,N-bis(2-hydroxyethyl)amide,
181) 5-acetyl-8-methyl-2-n-propyl-5,6,7,8-tetrahydro-1H-1,3,4a,8a-tetraza-cyclopentanaphthalene-4,9-dione,
182) 2-n-butyl-5-acetyl-8-methyl-5,6,7,8-tetrahydro-1H-1,3,4a,8a-tetraza-cyclopentanaphthalene-4,9-dione,
183) 5,8-ethano-5-hydroxymethyl-2-n-propyl-5,6,7,8-tetrahydro-1H-1,3,4a,8a-tetraza-cyclopentanaphthalene-4,9-dione,
184) 2-n-butyl-5,8-ethano-5-hydroxymethyl-5,6,7,8-tetrahydro-1H-1,3,4a,8a-tetraza-cyclopentanaphthalene-4,9-dione,
185) 5-t-butoxycarbonylmethoxymethyl-5,8-ethano-2-n-propyl-5,6,7,8-tetrahydro-1H-1,3,4a,8a-tetraza-cyclopentanaphthalene-4,9-dione,
186) 5-t-butoxycarbonylmethoxymethyl-2-n-butyl-5,8-ethano-5,6,7,8-tetrahydro-1H-1,3,4a,8a-tetraza-cyclopentanaphthalene-4,9-dione, 187) 5,8-ethano-5-(2-hydroxypropyl)methoxymethyl-2-n-propyl-5,6,7,8-tetrahydro-1H-1,3,4a,8a-tetraza-cyclopentanaphthalene-4,9-dione,
188) 2-n-butyl-5,8-ethano-5-(2-hydroxypropyl)methoxymethyl-5,6,7,8-tetrahydro-1H-1,3,4a,8a-tetraza-cyclopentanaphthalene-4,9-dione,
189) 4,9-dioxo-5,8-ethano-2-n-propyl-5,6,7,8-tetrahydro-1H-1,3,4a,8a-tetraza-cyclopentanaphthalene-5-carboxy-N,N-diethylamide,
190) 2-n-butyl-4,9-dioxo-5,8-ethano-5,6,7,8-tetrahydro-1H-1,3,4a,8a-tetraza-cyclopentanaphthalene-5-carboxy-N,N-diethylamide,
191) 4,9-dioxo-5,8-ethano-2-n-propyl-5,6,7,8-tetrahydro-1H-1,3,4a,8a-tetraza-cyclopentanaphthalene-5-carboxy-N-t-butylamide,
192) 2-n-butyl-4,9-dioxo-5,8-ethano-5,6,7,8-tetrahydro-1H-1,3,4a,8a-tetraza-cyclopentanaphthalene-5-carboxy-N-t-butylamide,
193) 4,9-dioxo-5,8-ethano-2-n-propyl-5,6,7,8-tetrahydro-1H-1,3,4a,8a-tetraza-cyclopentanaphthalene-5-carboxy-N,N-bis(2-hydroxyethyl)amide,
194) 2-n-butyl-4,9-dioxo-5,8-ethano-5,6,7,8-tetrahydro-1H-1,3,4a,8a-tetraza-cyclopentanaphthalene-5-carboxy-N,N-bis(2-hydroxyethyl)amide,
195) ethyl 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
196) ethyl 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxylate,
197) ethyl 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate,
198) ethyl 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-8-carboxylate,
199) 5-hydroxymethyl-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
200) 2-n-butyl-5-hydroxymethyl-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
201) 8-hydroxymethyl-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
202) 2-n-butyl-8-hydroxymethyl-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
203) 4,9-dioxo-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide,
204) 2-n-butyl-4,9-dioxo-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide,
205) 4,9-dioxo-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-diethylamide,
206) 2-n-butyl-4,9-dioxo-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-diethylamide,
207) 4,9-dioxo-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N-t-butylamide,
208) 2-n-butyl-4,9-dioxo-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N-t-butylamide,
209) 4,9-dioxo-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N-t-butylamide,
210) 2-n-butyl-4,9-dioxo-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N-t-butylamide,
211) 4,9-dioxo-8-methyl-2-n-propyl-5,6,7, 8-tetrahydro-1-[{2'-(1H-tetrazol-5-yl)biphenyl-4-yl}methyl]-1H-1,3,4a,8a-tetraza-cyclopentanaphthalene-5-carboxy-N,N-bis(2-hydroxyethyl)amide,
212) 2-n-butyl-4,9-dioxo-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-bis(2-hydroxyethyl)amide,
213) 4,9-dioxo-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-bis(2-hydroxyethyl)amide,
214) 2-n-butyl-4,9-dioxo-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-bis(2-hydroxyethyl)amide,
215) 5-acetyl-8-methyl-2-n-propyl-5,6,7,8-tetrahydro-1-[{2'-(1H-tetrazol-5-hydroxyethyl)amide.
215) 5-acetyl-8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
216) 5-acetyl-2-n-butyl-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
217) 8-acetyl-5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
218) 8-acetyl-2-n-butyl-5-methyl-5,6,7,8-tetrahydro-1-[{2'-(1H-tetrazol-5-4-yl}methyl]-1H-1,3,4a,8a-tetraza-cyclopentanaphthalene-4,9-dione,
219) 5,8-ethano-5-hydroxymethyl-2-n-propyl-5,6,7,8-tetrahydro-1-[{2'-(1H-tetrazol-5yl)biphenyl-4-yl}methyl]-1H-1,3,4a,8a-tetraza-cyclopentanaphthalene-4,9-dione,
220) 2-n-butyl-5,8-ethano-5-hydroxymethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
221) 5,8-ethano-8-hydroxymethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
222) 2-n-butyl-5,8-ethano-8-hydroxymethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
223) 5-t-butoxycarboxylmethoxymethyl-5,8-ethano-2-n-propyl-5,6,7,8-tetrahydro-1-[{2'-(1H-tetrazol- 224) 5-t-butoxycarboxylmethoxymethyl-2-n-butyl-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
225) 8-t-butoxycarboxylmethoxymethyl-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
226) 8-t-butoxycarbonylmethoxymethyl-2-n-butyl-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
227) 5,8-ethano-5-(2-hydroxypropyl)methoxymethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
228) 2-n-butyl-5,8-ethano-5-(2-hydroxypropyl)methoxymethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
229) 5,8-ethano-8-(2-hydroxypropyl)methoxymethyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
230) 2-n-butyl-5,8-ethano-8-(2-hydroxypropyl)methoxymethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
231) 4,9-dioxo-5,8-ethano-2-n-propyl-5,6,7,8-tetrahydro-1-[{2'-(1H-tetrazol-5yl)biphenyl-4-yl}methyl]-1H-1,3,4a,8a-tetraza-cyclopentanaphthalene-5-carboxy-N,N-diethylamide,
232) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide,
233) 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-diethylamide,
234) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-diethylamide,
235) 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N-t-butylamide,
236) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N-t-butylamide,
237) 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N-t-butylamide,
238) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N-t-butylamide,
239) 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-bis(2-hydroxyethyl)amide,
240) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-bis(2-hydroxyethyl)amide,
241) 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-bis(2-hydroxyethyl)amide,
242) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-8-carboxy-N,N-bis(2-hydroxyethyl)amide,
243) 5,8-dihydro-5-hydroxymethyl-8-methyl-2-n-propyl-1-[{2'-(1H-tetrazol-5-yl)biphenyl-4-yl}methyl]-1H-1,3,4a,8a-tetraza-cyclopentanaphthalene-4,9-dione,
244) 2-n-butyl-5,8-dihydro-5-hydroxymethyl-8-methyl-1-[{2'-(1H-tetrazol-5-yl)biphenyl-4-yl}methyl]-1H-1,3,4a,8a-tetraza-cyclopentanaphthalene-4,9-dione,
245) 5,8-dihydro-8-hydroxymethyl-5-methyl-2-n-propyl-1-[{2'-(1H-tetrazol-5-yl)biphenyl-4-yl}methyl]-1H-1,3,4a,8a-tetraza-cyclopentanaphthalene-4,9-dione,
246) 2-n-butyl-5,8-dihydro-8-hydroxymethyl-5-methyl-1-[{2'-(1H-tetrazol-5-yl)biphenyl-4-yl}methyl]-1H-1,3,4a,8a-tetraza-cyclopentanaphthalene-4,9-dione,
247) 5,8-dihydro-5,8-ethano-5-hydroxymethyl-2-n-propyl-1-[{2'-(1H-tetrazol-5-yl)biphenyl-4-yl}methyl]-1H-1,3,4a,8a-tetraza-cyclopentanaphthalene-4,9-dione,
248) 2-n-butyl-5,8-dihydro-5,8-ethano-5-hydroxymethyl-1-[{2'-(1H-tetrazol-5-yl)biphenyl-4-yl}methyl]-1H-1,3,4a,8a-tetraza-cyclopentanaphthalene-4,9-dione,
249) 5,8-dihydro-5,8-ethano-8-hydroxymethyl-2-n-propyl-1-[{2'-(1H-tetrazol-5-yl)biphenyl-4-yl}methyl]-1H-1,3,4a,8a-tetraza-cyclopentanaphthalene-4,9-dione,
250) 2-n-butyl-5,8-dihydro-5,8-ethano-8-hydroxymethyl-1-[{2'-(1H-tetrazol-5-yl)biphenyl-4-yl}methyl]-1H-1,3,4a,8a-tetraza-cyclopentanaphthalene-4,9-dione,
251) 5,8-dihydro-8-hydroxymethyl-5-methyl-2-n-propyl-1-[{2'-(1H-tetrazol-5-yl)biphenyl-4-yl}methyl]-1H-1,3,4a,8a-tetraza-cyclopentanaphthalene-4,9-dione,
252) 2-n-butyl-5,8-dihydro-8-hydroxymethyl-5-methyl-1-[{2'-(1H-tetrazol-5-yl)biphenyl-4-yl}methyl]-1H-1,3,4a,8a-tetraza-cyclopentanaphthalene-4,9-dione,
253) 4,9-dioxo-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide, and
254) 2-n-butyl-4,9-dioxo-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-5-carboxy-N,N-diethylamide.
255) 6,7-diethyl-5,8-dihydro-2-ethyl-1H-1,3,4a,8a-tetraza-cyclopentanaphthalene-4,9-dione,
256) 6,7-diethyl-5,8-dihydro-2-n-propyl-1H-1,3,4a,8a-tetraza-cyclopentanaphthalene-4,9-dione,
257) 2-n-butyl-6,7-diethyl-5,8-dihydro-1H-1,3,4a,8a-tetraza-cyclopentanaphthalene-4,9-dione,
258) 6,7-diethyl-5,8-dihydro-2-n-pentyl-1H-1,3,4a,8a-tetraza-cyclopentanaphthalene-4,9-dione,
263) 2-ethyl-6-phenyl-5,6,7,8-tetrahydro-1H-1,3,4a,8a-tetraza-cyclopentanaphthalene-4,9-dione, 264) 6-phenyl-2-n-propyl-5,6,7,8-tetrahydro-1H-1,3,4a,8a-tetraza-cyclopentanaphthalene-4,9-dione,
265) 2-n-butyl-6-phenyl-5,6,7,8-tetrahydro-1H-1,3,4a,8a-tetraza-cyclopentanaphthalene-4,9-dione,
266) 2-n-pentyl-6-phenyl-5,6,7,8-tetrahydro-1H-1,3,4a,8a-tetraza-cyclopentanaphthalene-4,9-dione,
271) 5,8-dihydro-2-ethyl-6-methyl-1H-1,3,4a,8a-tetraza-cyclopentanaphthalene-4,9-dione,
272) 5,8-dihydro-6-methyl-2-n-propyl-1H-1,3,4a,8a-tetraza-cyclopentanaphthalene-4,9-dione,
273) 2-n-butyl-5,8-dihydro-6-methyl-1H-1,3,4a,8a-tetraza-cyclopentanaphthalene-4,9-dione,
274) 5,8-dihydro-6-methyl-2-n-pentyl-1H-1,3,4a,8a-tetraza-cyclopentanaphthalene-4,9-dione,
275) 2-ethyl-5-methyl-5,6,7,8-tetrahydro-1H-1,3,4a,8a-tetraza-cyclopentanaphthalene-4,9-dione,
276) 5-methyl-2-n-propyl-5,6,7,8-tetrahydro-1H-1,3,4a,8a-tetraza-cyclopentanaphthalene-4,9-dione,
277) 2-n-butyl-5-methyl-5,6,7,8-tetrahydro-1H-1,3,4a,8a-tetraza-cyclopentanaphthalene-4,9-dione,
278) 5-methyl-2-n-pentyl-5,6,7,8-tetrahydro-1H-1,3,4a,8a-tetraza-cyclopentanaphthalene-4,9-dione,
279) 5,8-dimethyl-2-ethyl-5,6,7,8-tetrahydro-1H-1,3,4a,8a-tetraza-cyclopentanaphthalene-4,9-dione,
280) 5,8-dimethyl-2-n-propyl-5,6,7,8-tetrahydro-1H-1,3,4a,8a-tetraza-cyclopentanaphthalene-4,9-dione,
281) 2-n-butyl-5,8-dimethyl-5,6,7,8-tetrahydro-1H-1,3,4a,8a-tetraza-cyclopentanaphthalene-4,9-dione,
282) 5,8-dimethyl-2-n-pentyl-5,6,7,8-tetrahydro-1H-1,3,4a,8a-tetraza-cyclopentanaphthalene-4,9-dione,
287) 5,8-ethano-2-ethyl-5-methyl-5,6,7,8-tetrahydro-1H-1,3,4a,8a-tetraza-cyclopentanaphthalene-4,9-dione,
288) 5,8-ethano-5-methyl-2-n-propyl-5,6,7,8-tetrahydro-1H-1,3,4a,8a-tetraza-cyclopentanaphthalene-4,9-dione,
289) 2-n-butyl-5,8-ethano-5-methyl-5,6,7,8-tetrahydro-1H-1,3,4a,8a-tetraza-cyclopentanaphthalene-4,9-dione,
290) 5,8-ethano-5-methyl-2-n-pentyl-5,6,7,8-tetrahydro-1H-1,3,4a,8a-tetraza-cyclopentanaphthalene-4,9-dione,
291) 5,8-dimethyl-5,8-ethano-2-ethyl-5,6,7,8-tetrahydro-1H-1,3,4a,8a-tetraza-cyclopentanaphthalene-4,9-dione,
292) 5,8-dimethyl-5,8-ethano-2-n-propyl-5,6,7,8-tetrahydro-1H-1,3,4a,8a-tetraza-cyclopentanaphthalene-4,9-dione,
293) 2-n-butyl-5,8-dimethyl-5,8-ethano-5,6,7,8-tetrahydro-1H-1,3,4a,8a-tetraza-cyclopentanaphthalene-4,9-dione,
294) 5,8-dimethyl-5,8-ethano-2-n-pentyl-5,6,7,8-tetrahydro-1H-1,3,4a,8a-tetraza-cyclopentanaphthalene-4,9-dione,
295) 5,8-diethyl-5,8-ethano-2-ethyl-5,6,7,8-tetrahydro-1H-1,3,4a,8a-tetraza-cyclopentanaphthalene-4,9-dione,
296) 5,8-diethyl-5,8-ethano-2-n-propyl-5,6,7,8-tetrahydro-1H-1,3,4a,8a-tetraza-cyclopentanaphthalene-4,9-dione,
297) 2-n-butyl-5,8-diethyl-5,8-ethano-5,6,7,8-tetrahydro-1H-1,3,4a,8a-tetraza-cyclopentanaphthalene-4,9-dione,
298) 5,8-diethyl-5,8-ethano-2-n-pentyl-5,6,7,8-tetrahydro-1H-1,3,4a,8a-tetraza-cyclopentanaphthalene-4,9-dione,
299) 2-ethyl-5-(2-pyridyl)-5,6,7,8-tetrahydro-1H-1,3,4a,8a-tetraza-cyclopentanaphthalene-4,9-dione,
300) 2-n-propyl-5-(2-pyridyl)-5,6,7,8-tetrahydro-1H-1,3,4a,8a-tetraza-cyclopentanaphthalene-4,9-dione,
301) 2-n-butyl-5-(2-pyridyl)-5,6,7,8-tetrahydro-1H-1,3,4a,8a-tetraza-cyclopentanaphthalene-4,9-dione,
302) 2-n-pentyl-5-(2-pyridyl)-5,6,7,8-tetrahydro-1H-1,3,4a,8a-tetraza-cyclopentanaphthalene-4,9-dione,
315) 5,8-ethano-2-ethyl-5-isopropyl-8-methyl-5,6,7,8-tetrahydro-1H-1,3,4a,8a-tetraza-cyclopentanaphthalene-4,9-dione,
316) 5,8-ethano-5-isopropyl-8-methyl-2-n-propyl-5,6,7,8-tetrahydro-1H-1,3,4a,8a-tetraza-cyclopentanaphthalene-4,9-dione,
317) 2-n-butyl-5,8-ethano-5-isopropyl-8-methyl-5,6,7,8-tetrahydro-1H-1,3,4a,8a-tetraza-cyclopentanaphthalene-4,9-dione,
318) 5,8-ethano-5-isopropyl-8-methyl-2-n-pentyl-5,6,7,8-tetrahydro-1H-1,3,4a,8a-tetraza-cyclopentanaphthalene-4,9-dione,
319) 5-phenyl-2-n-propyl-5,6,7,8-tetrahydro-1H-1,3,4a,8a-tetraza-cyclopentanaphthalene-4,9-dione,
320) 2-n-butyl-5-phenyl-5,6,7,8-tetrahydro-1H-1,3,4a,8a-tetraza-cyclopentanaphthalene-4,9-dione,
321) 8-methyl-5-(3-methyloxadiazol-5-yl)—2-n-propyl-5,6,7,8-tetrahydro-1H-1,3,4a-tetraza-cyclopentanaphthalene-4,9-dione,
322-n-butyl-8-methyl-5-(3-methyloxadiazol-5-yl)-5,6,7,8-tetrahydro-1H-1,3,4a,8a-tetraza-cyclopentanaphthalene-4,9-dione,
323) 5,8-ethano-5-(1-hydroxy-1-methylethyl)-2-n-propyl-5,6,7,8-tetrahydro-1H-1,3,4a,8a-tetraza-cyclopentanaphthalene-4,9-dione,
324) 2-n-butyl-5,8-ethano-5-(1-hydroxy-1-methylethyl)-5,6,7,8-tetrahydro-1H-1,3,4a,8a-tetraza-cyclopentanaphthalene -4,9-dione,
325) 5-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
326) 2-n-butyl-5-phenyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
327) 8-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
328) 2-n-butyl-8-phenyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
329) 8-methyl-5-(3-methyloxadiazol-5-yl)2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
330) 2-n-butyl-8-methyl-5-(3-methyloxadiazol-5-yl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
331) 5-methyl-8-(3-methyloxadiazol-5-yl)-2-n-propyl-5,6,7,8-tetrahydro-1-[{2'-(1-tetrazol-5-yl)biphenyl-4-yl}methyl]-1H-1,3 ,4a,8a-tetraza-cyclopentanaphthalene-4,9-dione,
332) 2-n-butyl-5-methyl-8-(3-methyloxadiazol-5-yl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
333) 5,8-ethano-5-(1-hydroxy-1-methylethyl)-2-n-propyl-5,6,7,8-tetrahydro-1-[{2'-(1H-tetrazol-5-

334) 2-n-butyl-5,8-ethano-5-(1-hydroxy-1-methylethyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 335) 5,8-ethano-8-(1-hydroxy-1-methylethyl)-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 336) 2-n-butyl-5,8-ethano-8-(1-hydroxy-1-methylethyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 337) 5,8-dimethyl-2-n-propyl-5,6,7,8-tetrahydro-1-[{2'-(1H-tetrazol-5-yl)biphenyl-4-yl}methyl]-1H-13,4a,8a-tetraza-cyclopentanaphthalene-4,9-dione, 338) 2-n-butyl-5,8a-dimethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 339) 2-n-propyl-5-(2-pyridyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 340) 2-n-butyl-5-(2-pyridyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 341) 2-n-propyl-8-(2-pyridyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 342) 2-n-butyl-8-(2-pyridyl)-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 343) 5-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 344) 2-n-butyl-5-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 345) 8-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 346) 2-n-butyl-8-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 347) 6-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 348) 2-n-butyl-6-phenyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 349) 7-phenyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 350) 2-n-butyl-7-phenyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 351) 5,8-dihydro-6-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 352) 2-n-butyl-5,8-dihydro-6-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 353) 5,8-dihydro-7-methyl-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 354) 2-n-butyl-5,8-dihydro-7-methyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 355) 5,8-diethyl-5,8-ethano-2-ethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 356) 5,8-diethyl-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 357) 2-n-butyl-5,8-diethyl-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 358) 5,8-diethyl-5,8-ethano-2-n-pentyl-5,6,7,8-tetrahydro-1-[{2'-(1H-tetrazol-5-yl)biphenyl-4-yl]methyl]-1H-1,3,4a,8a-tetraza-cyclopentanaphthalene-4,9-dione, 359) 6,7-diethyl-5,8-dihydro-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 360) 2-n-butyl-6,7-diethyl-5,8-dihydro-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 361) 5,8-dimethyl-5,8-ethano-2-ethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 362) 5,8-dimethyl-5,8-ethano-2-n-propyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 363) 2-n-butyl-5,8-dimethyl-5,8-ethano-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 364) 5,8-dimethyl-5,8-ethano-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione, 365) 2-ethyl-5,6,7,8-tetrahydro-1-[{2'-(1H-tetrazol-5-yl)biphenyl-4-yl}methyl]-1H, 1,3,4a,8a-tetraza-cyclopentanaphthalene-9-one, 366) 2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 357) 2-n-butyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 368) 2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 373) 2-ethyl-1-[{2'-(1H-tetrazol-5-yl)biphenyl-4-yl}methyl]-1H,4H-1,3,4a,8a-tetraza-cyclopentanaphthalene-9-one, 374) 2-n-propyl-1-[{2'-(1H-tetrazol-5-yl)biphenyl-4-yl}methyl]-1H,4H-1,3,4a,8a,tetraza-cyclopentanaphthalene-9-one, 375) 2-n-butyl-1-[{2'-(1H-tetrazol-5-yl)biphenyl-4-yl}methyl]-1H,4H-1,3,4a,8a-tetraza-cyclopentanaphthalene-9-one, 376) 2-n-pentyl-1-[{2'-(1H-tetrazol-5-yl)biphenyl-4-yl}methyl]-1H,4H-1,3,4a,8a-tetraza-cyclopentanaphthalene-9-one, 377) 6,7-dimethyl-2-ethyl-5,6,7,8-tetrahydro-1-[{2'-(1H-tetrazol-5-yl)biphenyl-4-yl}methyl]-1H4H-1,3,4a,8a-tetraza-cyclopentanaphthalene-9-one, 378) 6,7-dimethyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 379) 2-n-butyl-6,7-dimethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 380) 6,7-dimethyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 381) 5,8-dihydro-6,7-dimethyl-2-ethyl-1-[{2'-(1H-tetrazol-5-yl)biphenyl-4-yl}methyl]-1H,4H-1,3,4a,8a-tetraza-cyclopentanaphthalene-9-one, 382) 5,8-dihydro-6,7-dimethyl-2-n-propyl-1-[{2'-(1H-tetrazol-5-yl)biphenyl-4-yl}methyl]-1H,4H-1,3,4a,-8a-tetraza-cyclopentanaphthalene-9-one, 383) 2-n-butyl-5,8-dihydro-6,7-dimethyl-1-[{2'-(1H-tetrazol-5-yl)biphenyl-4-yl}methyl]-1H,4H-1,3,4a,-8a-tetraza-cyclopentanaphthalene-9-one, 384) 5,8-dihydro-6,7-dimethyl-2-n-pentyl-1-[{2'-(1H-tetrazol-5-yl)biphenyl-4-yl}methyl]-1H,4H-1,3,4a,-8a-tetraza-cyclopentanaphthalene-9-one, 389) 6,7-diethyl-5,8-dihydro-2-ethyl-1-[{2'-(1H-tetrazol-5-yl)biphenyl-4-yl}methyl]-1H,4H-1,3,4a,8a-tetraza-cyclopentanaphthalene-9-one, 390) 6,7-diethyl-5,8-dihydro-2-n-propyl-1-{2'-(1H-tetrazol-5-yl)biphenyl-4-yl}methyl]-1H,4H-1,3,4a,-8a-tetraza-cyclopentanaphthalene-9-one, 391) 2-n-butyl-6,7-diethyl-5,8-dihydro-1-[{2'-(1H-tetrazol-5-yl)biphenyl-4-yl}methyl]-1H,4H-1,3,4a,8a-tetraza-cyclopentanaphthalene-9-one, 392) 6,7-diethyl-5,8-dihydro-2-n-pentyl-1-[{2'-(1H-tetrazol-5-yl)biphenyl-4-yl}methyl]-1H,4H-1,3,4a,-8a-tetraza-cyclopentanaphthalene-9-one, 397) 2-ethyl-6-phenyl-5,6,7,8-tetrahydro-1-[{2'-(1H-tetrazol-5-yl)biphenyl-4-yl}methyl]-1H,4H-1,3,4a,-8a-tetraza-cyclopentanaphthalene-9-one, 398) 6-phenyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 399) 2-n-butyl-6-phenyl-5,6,7,8-tetrahydro-1-[{2'-(1H-tetrazol-5-yl)biphenyl-4yl}methyl]-1H,4H-1,3,4a,8a-tetraza-cyclopentanaphthalene-9-one, 400) 2-n-pentyl-6-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 401) 2-ethyl-7-phenyl-5,6,7,8-tetrahydro-1-[{2'-(1H-tetrazol-5-yl)biphenyl-4-yl}methyl]-1H,4H-1,3,4a,-8a-tetraza-cyclopentanaphthalene-9-one, 402) 7-phenyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 403) 2-n-butyl-7-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 404) 2-n-pentyl-7-phenyl-5,6,7,8-tetrahydro-1-[{2'-(1H-tetrazol-5-yl)biphenyl-4-yl}methyl]- 1H,4H-1,3,4a,8a-tetraza-cyclopentanaphthalene-9-one, 413) 5,8-dihydro-2-ethyl-6-methyl-1-[{2'-(1H-tetrazol-5-yl)biphenyl-4-yl}methyl]H,4H-1,3,4a,8a-tetraza-cyclopentanaphthalene-9-one, 414) 5,8-dihydro-6-methyl-2-n-propyl-1-[{2'-(1H-tetrazol-5-yl)biphenyl-4-yl}methyl]-1H,4H-1,3,4a,8a-tetraza-cyclopentanaphthalene-9-one, 415) 2-n-butyl-5,8-dihydro-6-methyl-1-[{2'-(1H-tetrazol-5-yl)biphenyl-4-yl}methyl]-1H,4H-1,3,4a,8a-tetraza-cyclopentanaphthalene-9-one, 416) 5,8-dihydro-6-methyl-2-n-pentyl-1-[{2'-(1H-tetrazol-5-yl)biphenyl-4-yl}methyl]-1H,4H-1,3,4a,8a-tetraza-cyclopentanaphthalene-9-one, 417) 5,8-dihydro-2-ethyl-7-methyl-1-[{2'-(1H-tetrazol-5-yl)biphenyl-4-yl}methyl]-1H,4H-1,3,4a,8a-tetraza-cyclopentanaphthalene-9-one, 418) 5,8-dihydro-7-methyl-2-n-propyl-1-[{2'-(1H-tetrazol-5-yl)biphenyl-4-yl}methyl]-1H,4H-1,3,4a,8a-tetraza-cyclopentanaphthalene-9-one, 419) 2-n-butyl-5,8-dihydro-7-methyl-1-[{2'-(1H-tetrazol-5-yl)biphenyl-4-yl}methyl]-1H,4H-1,3,4a,8a-tetraza-cyclopentanaphthalene-9-one, 420) 5,8-dihydro-7-methyl-2-n-pentyl-1-[{2'-(1H-tetrazol-5-yl)biphenyl-4-yl}methyl]-1H,4H-1,3,4a,8a-tetraza-cyclopentanaphthalene-9-one, 421) 2-ethyl-5-methyl-5,6,7,8-tetrahydro-1-[{2'-(1H-tetrazol-5-yl)biphenyl-4-yl}methyl]-1H,4H-1,3,4a,-8a-tetraza-cyclopentanaphthalene-9-one, 422) 5-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 423) 2-n-butyl-5-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 4240 5-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 425) 2-ethyl-8-methyl-5,6,7,8-tetrahydro-1-[{2'-(1H-tetrazol-5-yl)biphenyl-4-yl}methyl]-1H,4H-1,3,4a,-8a-tetraza-cyclopentanaphthalene-9-one, 426) 8-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 427) 2-n-butyl-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 428) 8-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 429) 5,8-dimethyl-2-ethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 430) 5,8-dimethyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 431) 2-n-butyl-5,8-dimethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 432) 5,8-dimethyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 437) 5,8-ethano-2-ethyl-5,6,7,8-tetrahydro-1-[{2'-(1H-tetrazol-5-yl)biphenyl-4-yl}methyl]-1H,4H-1,3,4a,-8a-tetraza-cyclopentanaphthalene-9-one, 438) 5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 439) 2-n-butyl-5,8-ethano-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 440) 5,8-ethano-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 441) 5,8-ethano-2-ethyl-5-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 442) 5,8-ethano-5-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 443) 2-n-butyl-5,8-ethano-5-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 444) 5,8-ethano-5-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 445) 5,8-ethano-2-ethyl-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 446) 5,8-ethano-8-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 447) 2-n-butyl-5,8-ethano-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 448) 5,8-ethano-8-methyl-2-n-pentyl-5,6,7,8-tetrahydro-1-[{2'-(1H-tetrazol-5-yl)biphenyl-4-yl}methyl]-1H-1,3,4a,8a-tetraza-cyclopentanaphthalene-9-one, 449) 5,8-dimethyl-5,8-ethano-2-ethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 450) 5,8-dimethyl-5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 451) 2-n-butyl-5,8-dimethyl-5,8-ethano-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 452) 5,8-dimethyl-5,8-ethano-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 453) 5,8-diethyl-5,8-ethano-2-ethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 454) 5,8-diethyl-5,8-ethano-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 455) 2-n-butyl-5,8-diethyl-5,8-ethano-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 456) 5,8-diethyl-5,8-ethano-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 469) 2-ethyl-8-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 470) 8-phenyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 471) 2-n-butyl-8-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 472) 2-n-pentyl-8-phenyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 505) 2-ethyl-5-hydroxymethyl-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 506) 5-hydroxymethyl-8-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 507) 2-n-butyl-5-hydroxymethyl-8-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 508) 5-hydroxymethyl-8-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 509) 2-ethyl-8-hydroxymethyl-5-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 510) 8-hydroxymethyl-5-methyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 511) 2-n-butyl-8-hydroxymethyl-5-methyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 512) 8-hydroxymethyl-5-methyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 513) 5,8-ethano-2-ethyl-5-hydroxymethyl-5,6,7,8-tetrahydro-1-[{2'-(1H-tetrazol-5yl)biphenyl-4-yl}methyl]-1H,4H-1,3,4a,8a-tetraza-cyclopentanaphthalene-9-one, 514) 5,8-ethano-5-hydroxymethyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene -9-one, 515) 2-n-butyl-5,8-ethano-5-hydroxymethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 516) 5,8-ethano-5-hydroxymethyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 517) 5,8-ethano-2-ethyl-8-hydroxymethyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 518) 5,8-ethano-8-hydroxymethyl-2-n-propyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one, 519) 2-n-butyl-5,8-ethano-8-hydroxymethyl-5,6,7,8-tetrahydro-1-[{2'-(1H-tetrazol-5-yl)biphenyl-4- yl}methyl]-1H,4H-1,3,4a,8a-tetraza-cyclopentanaphthalene-9-one,
520) 5,8-ethano-8-hydroxymethyl-2-n-pentyl-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
521) 5,8-diethyl-5,8-ethano-2-(1-E-propenyl)-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
522) 2-(1-E-butenyl)-5,8-diethyl-5,8-ethano-5,6,7,8-tetrahydro-1-[{2'-(1H-tetrazol-5-yl)biphenyl-4-yl}methyl]-1H,4H-1,3,4a,8a-tetraza-cyclopentanaphthalene-9-one,
523) 5,8-ethano-4,5,6,7,8,9-hexahydro-2-n-propyl-1-[{2'-tetrazol-5-yl)biphenyl-4-yl}methyl]-1H-1,3,4a,8a-tetraza-cyclopentanaphthalene,
524)-2-n-butyl-5,8-ethano-4,5,6,7,8,9-hexahydro-1-[{2'-tetrazol-5-yl)biphenyl-4-yl}methyl]-1H-1,3,4a,8a-tetraza-cyclopentanaphthalene,
525) 4-methyl-2-n-propyl-5,6,7,8-tetrahydro-1-[{2'-tetrazol-5-yl)biphenyl-4-yl}methyl]-1H,4H-1,3,4a,8a-tetraza-cyclopentanaphthalene-9-one,
526) 2-n-butyl-4-methyl-5,6,7,8-tetrahydro-1-[{2'-tetrazol-5-yl)biphenyl-4-yl}methyl]-1H,4H-1,3,4a,8a-tetraza-cyclopentanaphthalene-9-one,
527) 4,4-dimethyl-2-n-propyl-5,6,7,8-tetrahydro-1-[{2'-tetrazol-5-yl)biphenyl-4-yl}methyl]-1H,4H-1,3,4a,8a-tetraza-cyclopentanaphthalene-9-one,
528) 2-n-butyl-4,4-dimethyl-5,6,7,8-tetrahydro-1-[{2'-tetrazol-5-yl)biphenyl-4-yl}methyl]-1H,4H-1,3,4a,8a-tetraza-cyclopentanaphthalene-9-one,
529) 5,8-ethano-4-methyl-2-n-propyl-5,6,7,8-tetrahydro-1-[{2'-tetrazol-5-yl)biphenyl-4-yl}methyl]-1H,4H-1,3,4a,8a-tetraza-cyclopentanaphthalene-9-one,
530) 2-n-butyl-5,8-ethano-4-methyl-5,6,7,8-tetrahydro-1-[{2'-tetrazol-5-yl)biphenyl-4-yl}methyl]-1H,4H-1,3,4a,8a-tetraza-cyclopentanaphthalene-9-one,
531) 4,4-dimethyl-5,8-ethano-2-n-propyl-5,6,7,8-tetrahydro-1-[{2'-tetrazol-5-yl)biphenyl-4-yl}methyl]-1H,4H-1,3,4a,8a-tetraza-cyclopentanaphthalene-9-one,
532) 2-n-butyl-4,4-dimethyl-5,8-ethano-5,6,7,9-tetrahydro-1-[{2'-tetrazol-5-yl)biphenyl-4-yl}methyl]-1H,4H-1,3,4a,8a-tetraza-cyclopentanaphthalene-9-one,
533) 5,8-ethano-2-n-propyl-5,6,7,8-tetrahydro-4,5,8-trimethyl-1-[{2'-tetrazol-5-yl)biphenyl-4-yl}methyl]-1H,4H-1,3,4a,8a-tetraza-cyclopentanaphthalene-9-one,
534) 2-n-butyl-5,8-ethano-5,6,7,8-tetrahydro-4,5,8-trimethyl-1-[{2'-tetrazol-5-yl)biphenyl-4-yl}methyl]-1H,4H-1,3,4a,8a-tetraza-cyclopentanaphthalene-9-one,
535) 5,8-ethano-2-n-propyl-5,6,7,8-tetrahydro-4,4,5,8-tetramethyl-1-[{2'-tetrazol-5-yl)biphenyl-4-yl}methyl]-1H,4H-1,3,4a,8a-tetraza-cyclopentanaphthalene-9-one,
536) 2-n-butyl-5,8-ethano-5,6,7,8-tetrahydro-4,4,5,8-tetramethyl-1-[{2'-tetrazol-5-yl)biphenyl-4-yl}methyl]-1H,4H-1,3,4a,8a-tetraza-cyclopentanaphthalene-9-one,
537) 5-hydroxymethyl-8-methyl-2-n-propyl-5,6,7,8-tetrahydro-1-[{2'-tetrazol-5-yl)biphenyl-4-yl}methyl]-1H,9H-1,3,4a,8a-tetraza-cyclopentanaphthalene-4-one,
538) 2-n-butyl-5-hydroxymethyl-8-methyl-5,6,7,8-tetrahydro-1-[{2'-tetrazol-5-yl)biphenyl-4-yl}methyl]-1H,9H-1,3,4a,8a-tetraza-cyclopentanaphthalene-4-one,
539) 8-hydroxymethyl-5-methyl-2-n-propyl-5,6,7,8-tetrahydro-1-[{2'-tetrazol-5-yl)biphenyl-4-yl}methyl]-1H,9H-1,3,4a,8a-tetraza-cyclopentanaphthalene-4-one,
540) 2-n-butyl-8-hydroxymethyl-5-methyl-5,6,7,8-tetrahydro-1-[{2'-tetrazol-5-yl)biphenyl-4-yl}methyl]-1H,9H-1,3,4a,8a-tetraza-cyclopentanaphthalene-4-one,
541) 2-n-butyl-5-hydroxymethyl-8-methyl-5,6,7,8-tetrahydro-1H,4H-1,3,4a,8a-tetraza-cyclopentanaphthalene-9-one,
542) 2-n-butyl-8-hydroxymethyl-5-methyl-5,6,7,8-tetrahydro-1H,4H-1,3,4a,8a-tetraza-cyclopentanaphthalene-9-one,
543) 5,8-ethano-2-ethyl-5,6,7,8-tetrahydro-1-[{2'-(1H-tetrazol-5-yl)biphenyl-4-yl}methyl]-1H-1,3,4a,8a-tetraza-cyclopentanaphthalene-4,9-dione,
544) 2-n-butyl-1-[(4-carboxyphenyl)methyl]-5,8-ethano-5,6,7,8-tetrahydro-1H-1,3,4a,8a-tetraza-cyclopentanaphthalene-4,9-dione,
545) 5,8-dihydro-5,8-dimethyl-5,8-ethano-2-n-propyl-1H-1,3,4a,8a-tetraza-cyclopentanaphthalene-4,9-dione, and
546) 2-n-butyl-5,8-dihydro-5,8-dimethyl-5,8-ethano-1H-1,3,4a,8a-tetraza-cyclopentanaphthalene-4,9-dione,
547) 2-n-butyl-5,8-diethyl-5,8-ethano-5,6,7,8-tetrahydro-1-[(2'-cyanobiphenyl-1-yl)methyl]-1H,4H-1,3,4a,8a-tetraza-cyclopentanaphthalene-9-one,
548) 2-n-butyl-5,8-di-n-propyl-5,8-ethano-5,6,7,8-tetrahydro-1H-1,3,4a,8a-tetraza-cyclopentanaphthalene-4,9-dione,
549) 2-n-butyl-5,8-diisopropyl-5,8-ethano-5,6,7,8-tetrahydro-1H-1,3,4a,8a-tetraza-cyclopentanaphthalene-4,9-dione.

6. A process for preparing an imidazole derivative according to claim 1 which comprises: reacting an imidazole derivative represented by the general formula:

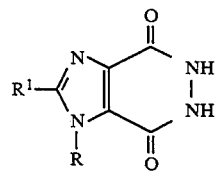

wherein
R$^1$ is hydrogen atom, C$_1$-C$_8$ alkyl group, C$_1$-C$_8$ alkoxy group, C$_1$-C$_8$ alkylthio group, C$_1$-C$_8$ alkylamino group, C$_1$-C$_8$ alkenyl group, C$_1$-C$_8$ alkynyl, —CF$_3$ group, C$_6$-C$_{10}$ aralkyl group; or C$_6$-C$_{10}$ aralkyl group;
R is hydrogen atom, or a group selected from the following groups;

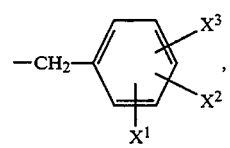

-continued

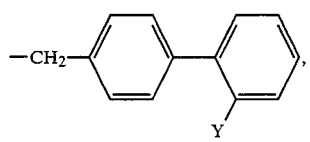

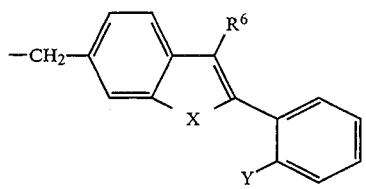

wherein
X¹, X² and X³ are, independently, hydrogen atom, halogen atom, $C_1$-$C_8$ alkyl group, $C_1$-$C_8$ alkoxy group, nitro group, cyano group, 1H-tetrazol-5-yl group or alkali metal salt thereof, —$CO_2R^7$ group, —CONR'R" group, —$CONHSO_2R^8$ group, amino group, —$NHSO_2CF_3$ group or —$SO_3$ group, or a group selected from the following groups;

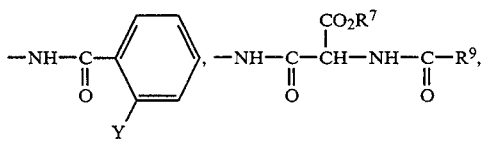

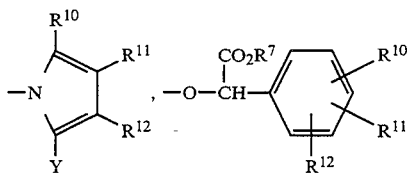

wherein
Y is cyano group, 1H-tetrazol-5-yl group or alkali metal salt thereof, —$CO_2R^7$ group, CONR'R" group, —$CONHSO_2R^8$ group, amino group, —$NHSO_2CF_3$ group or -$SO_3H$ group;

$R^6$ is hydrogen group, halogen atom, $C_1$-$C_8$ alkyl group, —$CF_3$ group or —$CF_2CF_3$ group;

$R^7$ is hydrogen atom, alkali metal atom or $C_1$-$C_8$ alkyl group;

R' and R" are, independently, hydrogen atom or $C_1$-$C_8$ alkyl group, or R" and R" are taken together to form an alicyclic structure;

$R^8$ is $C_1$-$C_8$ alkyl group, $C_6$-$C_{10}$ cycloalkyl group or $C_6$-$C_{10}$ aryl group;

$R^9$ is $C_1$-$C_8$ alkyl group, $C_1$-$C_8$ alkoxy group, $C_6$-$C_{10}$ cycloalkyl group, $C_6$'1 cycloalkoxy group or $C_6$-$C_{10}$ aryloxy group;

$R^{10}$, $R^{11}$ and $R^{12}$ are, independently, hydrogen atom, halogen atom, $C_1$-$C_8$ alkyl group, $C_1$-$C_8$ alkoxy group, nitro group, cyano group, —$CO_2R^7$ group or —CONR'R" group;

with an diene compound represented by the general formula:

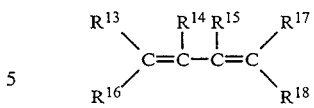

wherein
$R^{13}$, $R^{14}$, $R^{15}$, $R^{16}$, $R^{17}$ and $R^{18}$ are, independently, hydrogen atom, $C_1$-$C_8$ alkyl group, $C_1$-$C_8$ fluoroalkyl group, —C(R')(R")—$OR^{19}$ group, —($CH_2$)$_j$—$CO_2R^7$ group, —($CH_2$)$_j$—CN group, —($CH_2$)$_j$—C(=O)R' group, —($CH_2$)$_j$CONR'R" group or —($CH_2$)$_j$—Aryl group, wherein j is 0, 1 or 2, wherein $R^{16}$ and $R^{18}$ may be taken together to form —($CH_2$)$_i$— group, wherein i is 1, 2 or 3, wherein Aryl is phenyl group, pyridyl group, pyrimidinyl, pyridazinyl group, furyl group, thenyl group, pyrazolinyl group, oxazolyl group, thiazolyl group, oxadiazolyl group or isoxazolyl group which may be substituted with halogen atom, $C_1$-$C_8$ alkyl group, hydroxy group, $C_1$-$C_8$ alkoxy group, nitro group or cyano group;

$R^{19}$ is hydrogen atom, or $C_1$-$C_8$ alkyl optionally substituted with hydroxy group or ether group, after reacting the imidazole derivative with an oxidizing agent, or in the presence of an oxidizing agent, to obtain an imidazole derivative represented by the general formula:

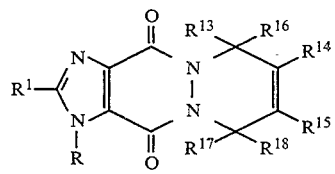

wherein
$R^1$, R, $R^{13}$, $R^{14}$, $R^{15}$, $R^{16}$, $R^{17}$ and $R^{18}$ are as defined above, then, if necessary,
i) subjecting the resulting imidazole derivative to catalytic hydrogenation reaction in the presence of palladium catalyst to obtain an imidazole derivative represented by the general formula:

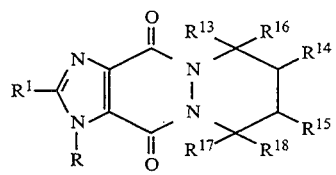

wherein
$R^1$, R, $R^{13}$, $R^{14}$, $R^{15}$, $R^{16}$, $R^{17}$ and $R^{18}$ are as defined above,
further, if necessary, reacting the resulting imidazole derivative with a metal hydride or organometallic to obtain an imidazole derivative represented by the general formula:

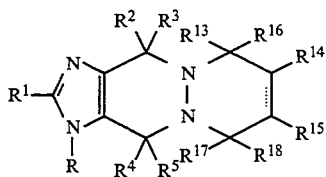

wherein
  $R^1$, $R$, $R^{13}$, $R^{14}$, $R^{15}$, $R^{16}$, $R^{17}$ and $R^{18}$ are as defined above;
  $R^2$, $R^3$, $R^4$ and $R^5$ are, independently, hydrogen atom or $C_1$–$C_8$ alkyl group, or $R^2$ and $R^3$, or $R^4$ and $R^5$ are taken together to form $=O$ bond; and
  is single bond or double bond;
  ii) subjecting the resulting imidazole derivative to the halogen addition reaction, or reacting the resulting imidazole derivative with an oxidizing agent to obtain an imidazole derivative represented by the general formula: 00

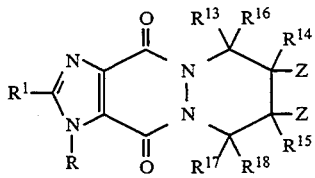

wherein
  $R^1$, $R$, $R^{13}$, $R^{14}$, $R^{15}$, $R^{16}$, $R^{17}$ and $R^{18}$ are as defined above, and Z is chlorine a bromine atom or hydroxy group, and
  when $R^{16}$ and $R^{18}$ are hydrogen atom, if necessary, subjecting the resulting imidazole derivative to remove HZ and to obtain an imidazole derivative represented by the general formula:

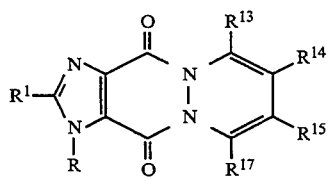

wherein
  $R^1$, $R$, $R^{13}$, $R^{14}$, $R^{15}$ and $R^{17}$ are as defined above, or
  iii) when $R^{14}$ and $R^{15}$ are hydrogen, subjecting the resulting imidazole derivative to the hydroboration reaction using a borohydride compound, then reacting with hydrogen peroxide to obtain an imidazole derivative represented by the general formula:

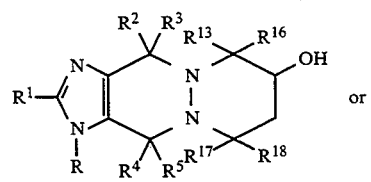

-continued

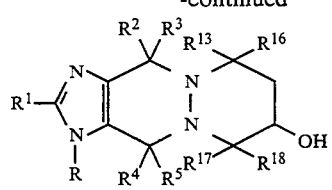

wherein
  $R^1$, $R$, $R^2$, $R^3$, $R^4$, $R^5$, $R^{13}$, $R^{16}$, $R^{17}$ and $R^{18}$ are as defined above,
  and, if necessary, reacting the resulting imidazole derivative with a metal oxide to obtain an imidazole derivative represented by the general formula:

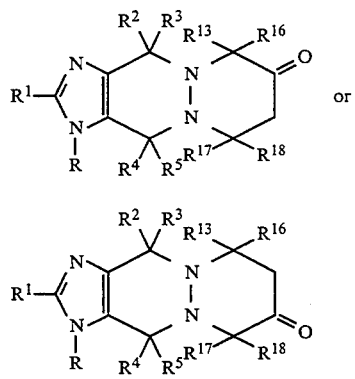

wherein
  $R^1$, $R$, $R^2$, $R^3$, $R^4$, $R^5$, $R^{13}$, $R^{16}$, $R^{17}$ and $R^{18}$ are as defined above.

7. A process for preparing an imidazole derivative represented by the general formula:

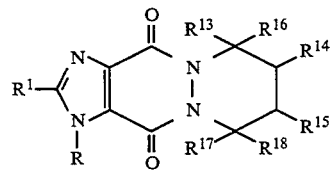

wherein
  $R^1$, $R$, $R^{13}$, $R^{14}$, $R^{15}$, $R^{16}$, $R^{17}$ and $R^{18}$ are as defined below which comprises reacting an imidazole derivative represented by the general formula:

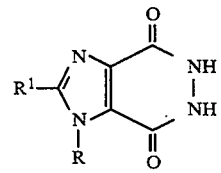

wherein
  $R^1$ is hydrogen atom, $C_1$–$C_8$ alkyl group, $C_1$–$C_8$ alkoxy group, $C_1$–$C_8$ alkylthio group, $C_1$–$C_8$ alkylamino group, $C_1$–$C_8$ alkenyl group, $C_1$–$C_8$ alkynyl, —$CF_3$ group, $C_6$–$C_{10}$ aryl group or $C_6$–$C_{10}$ aralkyl group;
  R is hydrogen atom, or a group selected from the following groups;

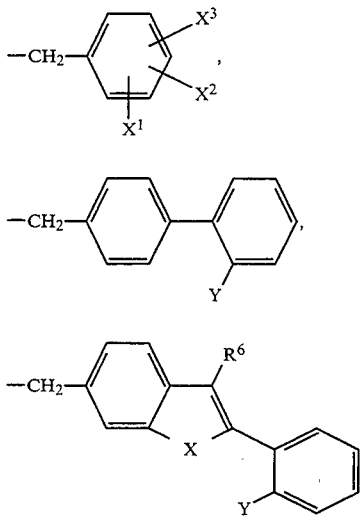

wherein
X¹, X² and X³ are, independently, hydrogen atom, halogen atom, C₁-C₈ alkyl group, C₁-C₈ alkoxy group, nitro group, cyano group, 1H-tetrazol-5-yl group or alkali metal salt thereof, —CO₂R⁷ group, —CONR'R" group, —CONHSO₂R⁸ group, amino group, —NHSO₂CF₃ group or —SO₃H group, or a group selected from the following groups;

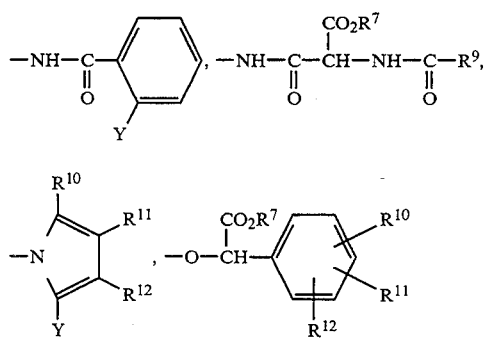

wherein
Y is cyano group, 1H-tetrazol-5-yl group or alkali metal salt thereof, —CO₂R⁷ group, —CONR'R" group, —CONHSO₂R⁸ group, amino group, —NHSO₂CF₃ group or —SO₃H group;
R⁶ is hydrogen atom, halogen atom, C₁-C₈ alkyl group, —CF₃ group or —CF2CF₃ group;
R⁷ is hydrogen atom, alkali metal atom or C₁-C₈ alkyl group;
R' and R" are, independently, hydrogen atom or C₁-C₈ alkyl group, or R' and R" are taken together to form an alicyclic structure;
R⁸ is C₁-C₈ alkyl group, cycloalkyl group or aryl group;
R⁹ is C₁-C₈ alkyl group, C₁-C₈ alkoxy group, cycloalkyl group, cycloalkoxy group, aryl group or aryloxy group;
R¹⁰, R¹¹ and R¹² are, independently, hydrogen atom, halogen atom, C₁-C₈ alkyl group, C₁-C₈ alkoxy group, nitro group, cyano group, —CO₂R⁷ group or —CONR'R" group, with a diene compound represented by the general formula:

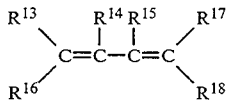

wherein
R¹³, R¹⁴, R¹⁵, R¹⁷, and R¹⁸ are, independently, hydrogen atom, C₁-C₈ alkyl group, C₁—C₈ fluoroalkyl group, —C(R')(R")—OR¹⁹ group, —(CH₂)ⱼ—CO₂R⁷ group, —(CH₂)ⱼ—CN group, —(CH₂)ⱼ—C(=O)R' group, —(CH₂)ⱼCONR'R" group or —(CH₂)ⱼ—Aryl group, wherein j is 0, 1 or 2, wherein R¹⁶ and R¹⁸ may be taken together to form —(CH₂)ᵢ—group, wherein i is 1, 2 or 3, wherein Aryl is phenyl group, pyridyl group, pyrimidinyl, pyridazinyl group, furyl group, thenyl group, pyrazolinyl group, oxazolyl group, thiazolyl group, oxadiazolyl group or isoxazolyl group which may be substituted with halogen atom, C₁-C₈ alkyl group, hydroxy group, C₁-C₈ alkoxy group, nitro group or cyano group;
R¹⁹ is hydrogen atom, or C₁-C₈ alkyl optionally substituted with hydroxy group or ether group,
by pre-treating the imidazole derivative (chemical formula 18), with an oxidizing agent.

8. A pharmaceutical composition for preventing or treating hypertension, congestive heart failure, renal failure, glaucoma or hyperuricemia which comprises as an active ingredient an imidazole derivative represented by the general formula:

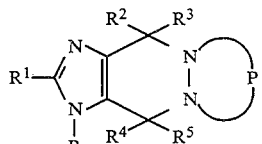

wherein
R¹ is hydrogen atom, C₁-C₈ alkyl group, C₁-C₈ alkoxy group, C₁-C₈ alkylthio group, C₁-C₈ alkylamino group, C₁-C₈ alkenyl group, C₁-C₈ alkynyl, —CF₃ group, aryl group or aralkyl group;
R is hydrogen atom, or a group selected from the following groups;

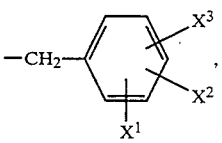

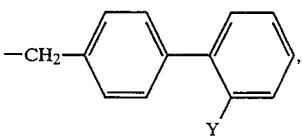

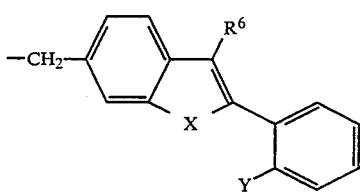

wherein
$X^1$, $X^2$ and $X^3$ are, independently, hydrogen atom, halogen atom, $C_1$-$C_8$ alkyl group, $C_1$-$C_8$ alkoxy group, nitro group, cyano group, 1H-tetrazol-5-yl group or alkali metal salt thereof, —$CO_2R^7$ group, —$CONR'R''$ group, —$CONHSO_2R^8$ group, amino group, —$NHSO_2CF_3$ group or —$SO_3H$ group, or a group selected from the following groups:

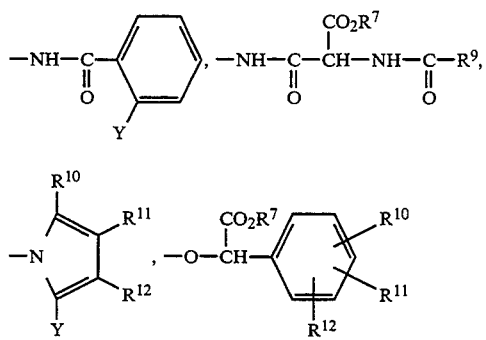

wherein
Y is cyano group, 1H-tetrazol-5-yl group or alkali metal salt thereof, —$CO_2R^7$ group, —$CONR'R''$ group, —$CONHSO_2R^8$ group, amino group, —$NHSO_2CF_3$ group or —$SO_3H$ group;

$R^2$, $R^3$, $R^4$ and $R^5$ are, independently, hydrogen atom or $C_1$-$C_8$ alkyl group, or $R^2$ and $R^3$, or $R^4$ and $R^5$ are taken together to form =O bond;

$R^6$ is hydrogen atom, halogen atom, $C_1$-$C_8$ alkyl group, —$CF_3$ group or —$CF_2CF_3$ group;

$R^7$ is hydrogen atom, alkali metal atom or $C_1$-$C_8$ alkyl group;

$R'$ and $R''$ are, independently, hydrogen atom or $C_1$-$C_8$ alkyl group, or $R'$ and $R''$ are taken together to form an alicyclic structure;

$R^8$ is $C_1$-$C_8$ alkyl group, cycloalkyl group or aryl group;

$R^9$ is $C_1$-$C_8$ alkyl group, $C_1$-$C_8$ alkoxy group, cycloalkyl group, cycloalkoxy group, aryl group or aryloxy group;

$R^{10}$, $R^{11}$ and $R^{12}$ are, independently, hydrogen atom, halogen atom, $C_1$-$C_8$ alkyl group, $C_1$-$C_8$ alkoxy group, nitro group, cyano group, —$CO_2R^7$ group or —$CONR'R''$ group;

—P— is A—B—C—D—, A—B—C=D or A=B—C=D;

wherein
A—B—C—D, A—B=C—D or A=B—C=D represents, when A or D is not present, as B—C—D, B=C—D, B—C=D, A—B—C, A—B=C or A=B—C,
—CH($R^{13}$)—CH($R^{14}$)—CH($R^{15}$)—,
—C($R^{13}$)=CH($R^{14}$)—C($R^{15}$)—,
—CH($R^{13}$)—C($R^{14}$)=C($R^{15}$)—,
—CH($R^{13}$)—CH($R^{14}$)—C(=O)—,
—C(R=O)—C($R^{14}$)—CH($R^{15}$)— or
—CH($R^{13}$)—C(=O)—CH($R^{15}$)—, or
represents, when A and D are present, as A—B—C—D—, A—B=C—D or A=B—C=D,
—C($R^{13}$)($R^{16}$)—CH($R^{14}$)—CH($R^{15}$)—C($R^{17}$)($R^{18}$)—,
—C($R^{13}$)($R^{16}$)—C($R^{14}$)=C($R^{15}$)—C($R^{17}$)($R^{18}$)—,
—C($R^{13}$)=C($R^{14}$)—CH($R^{15}$)=C($R^{17}$)—,
—C(=O)—CH($R^{14}$)—CH($R^{15}$)—C($R^{17}$)($R^{18}$)—,
—C($R^{13}$)($R^{16}$)—C(=O)—CH($R^{15}$)—C($R^{17}$)($R^{18}$)—,
—C($R^{13}$)($R^{16}$)—CH($R^{14}$)—C(=O)—C($R^{17}$)($R^{18}$)— or
—C($R^{13}$)($R^{16}$)—CH($R^{14}$)—CH($R^{15}$)—C(=O)—;

wherein
$R^{13}$, $R^{14}$, $R^{15}$, $R^{16}$, $R^{17}$ and $R^{18}$ are, independently, hydrogen atom, $C_1$-$C_8$ alkyl group, $C_1$-$C_8$ fluoroalkyl group, —C($R'$)($R''$)—$OR^{19}$ group, —($CH_2$)$_j$—$CO_2R^7$ group, —($CH_2$)$_j$—CN group, —($CH_2$)$_j$—C(=O)$R'$ group, —($CH_2$)$_j$CONR'R'' group or —($CH_2$)$_j$—Aryl group, wherein j is 0, 1 or 2, wherein $R^{16}$ and $R^{18}$ may be taken together to form —($CH_2$)$_i$—group, wherein i is 1, 2 or 3, wherein Aryl is phenyl group, pyridyl group, pyrimidinyl, pyridazinyl group, furyl group, thenyl group, pyrazolinyl group, oxazolyl group, thiazolyl group, oxadiazolyl group or isoxazolyl group which may be substituted with halogen atom, $C_1$-$C_8$ alkyl group, hydroxy group, $C_1$-$C_8$ alkoxy group, nitro group or cyano group;

$R^{19}$ is hydrogen atom, or $C_1$-$C_8$ alkyl group optionally substituted with hydroxy group or ether group, or a pharmacologically acceptable ester or salt thereof.

9. A pharmaceutical composition for preventing or treating hypertension, congestive heart failure, renal failure, glaucoma or hyperuricemia which comprises as an active ingredient an imidazole derivative represented by the general formula:

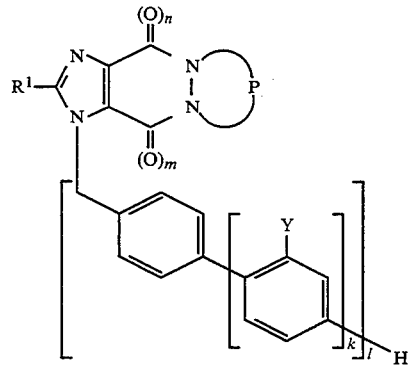

wherein
$R^1$ is hydrogen atom, $C_1$-$C_8$ alkyl group, $C_1$-$C_8$ alkoxy group, $C_1$-$C_8$ alkylthio group, $C_1$-$C_8$ alkylamino group, $C_1$-$C_8$ alkenyl group, $C_1$-$C_8$ alkynyl, -$CF_3$ group, aryl group or aralkyl group;

Y is cyano group, 1H-tetrazol-5-yl group or an alkali metal salt thereof, —$CO_2R^7$ group, —$CONR'R''$ group —$CONHSO_2R^8$ group, amino group, —$NHSO_2CF_3$ group or —$SO_3H$ group;

$R^7$ is hydrogen atom, alkali metal atom or $C_1$-$C_8$ alkyl group;

R' and R are, independently, hydrogen atom or C$_1$-C$_8$ alkyl group, or R' and R" are taken together to form an alicyclic structure;

R$^8$ is C$_1$-C$_8$ alkyl group, cycloalkyl group or aryl group;

—P— is A—B—C—D—, A—B=C—D or A=B—C—D;

wherein

A—B—C—D, A—B=C—D or A=B—C=D represents, when A or D is not present, as B—C—D, B=C—D, B—C=D, A—B—C, A—B=C or A=B—C, —CH(R$^{13}$)—CH(R$^{14}$)—CH(R$^{15}$)—,
—C(R$^{13}$)=C(R$^{14}$)—C(R$^{15}$)—,
—CH(R$^{13}$)—C(R$^{14}$)=C(R$^{15}$)—,
—CH(R$^{13}$)—CH(R$^{14}$)—C(=O)—,
—C(=O)—CH(R$^{14}$)—CH(R$^{15}$)— or
—CH(R$^{13}$)—C(=O)—CH(R$^{15}$)—, or represents, when A and D are present, as A—B—C—D—, A—B=C—D or A=B—C=D, —C(R$^{13}$)(R$^{16}$)—CH(R$^{14}$)—CH(R$^{15}$)—C(R$^{17}$)(R$^{18}$)—,
—C(R$^{13}$)(R$^{16}$)—C(R$^{14}$)=C(R$^{15}$)—C(R$^{17}$)(R$^{18}$)—,
—C(R$^{13}$)=C(R$^{14}$)—CH(R$^{15}$)=C(R$^{17}$)—,
—C(=O)—CH(R$^{14}$)—CH(R$^{15}$)—C(R$^{17}$)(R$^{18}$)—,
—C(R$^{13}$)(R$^{16}$)—C(=O)—CH(R$^{15}$)—C(R$^{17}$)(R$^{18}$)—,
—C(R$^{13}$)(R$^{16}$)—CH(R$^{14}$)—C(=O)—C(R$^{17}$)(R$^{18}$)— or
—C(R$^{13}$)(R$^{16}$)—CH(R$^{14}$)—CH(R$^{15}$)—C(=O)—;

wherein

R$^{13}$, R$^{14}$, R$^{15}$, R$^{16}$, R$^{17}$ and R$^{18}$ are, independently, hydrogen atom, C$_1$-C$_8$ alkyl group, C$_1$-C$_8$ fluoroalkyl group, —C(R')(R")—OR$^{19}$ group, —(CH$_2$)$_j$—CO$_2$R$^7$ group, —(CH$_2$)$_j$—CN group, —(CH$_2$)$_j$—C(=O)R' group, —(CH$_2$)$_j$CONR'R" group or —(CH$_2$)$_j$—Aryl group, wherein j is 0, 1 or 2, wherein R$^{16}$ and R$^{18}$ may be taken together to form —(CH$_2$)$_i$—group, wherein i is 1, 2 or 3, wherein Aryl is phenyl group, pyridyl group, pyrimidinyl, pyridazinyl group, furyl group, thenyl group, pyrazolinyl group, oxazolyl group, thiazolyl group, oxadiazolyl group or isoxazolyl group which may be substituted with halogen atom, C$_1$-C$_8$ alkyl group, hydroxy group, C$_1$-C$_8$ alkoxy group, nitro group or cyano group;

R$^{19}$ is hydrogen atom, or C$_1$-C$_8$ alkyl group optionally substituted with hydroxy group or ether group;

k, l, m and n are, independently, 0 or 1, or a pharmacologically acceptable ester or salt thereof, in an amount effective to treat or prevent said diseases.

10. A pharmaceutical composition for preventing or treating hypertension, congestive heart failure, renal failure, glaucoma or hyperuricemia which comprises as an active ingredient an imidazole derivative represented by the general formula:

wherein

Y is cyano group, 1H-tetrazol-5-yl group or alkali metal salt thereof, or —CO$_2$R$^7$ group;

R$^2$, R$^3$, R$^4$ and R$^5$ are, independently, hydrogen atom or C$_1$-C$_8$ alkyl group, or R$^2$ and R$^3$, or R$^4$ and R$^5$ are taken together to form =O bond;

is single bond or double bond;

R$^{13}$ and R$^{17}$ are, independently, hydrogen atom, C$_1$-C$_8$ alkyl group, C$_1$-C$_8$ fluoroalkyl group, —C(R')(R")—OR$^{19}$ group, —(CH$_2$)$_j$—CO$_2$R$^7$ group, —(CH$_2$)$_j$—CN group, —(CH$_2$)$_j$—C(=O)R' group, —(CH$_2$)$_j$CONR'R" group or —(CH$_2$)$_j$—Aryl group, wherein j is 0, 1 or 2, wherein Aryl is phenyl group, pyridyl group, pyrimidinyl, pyridazinyl group, furyl group, thenyl group, pyrazolinyl group, oxazolyl group, thiazolyl group, oxadiazolyl group or isoxazolyl group which may be substituted with halogen atom, C$_1$-C$_8$ alkyl group, hydroxy group, C$_1$-C$_8$ alkoxy group, nitro group or cyano group;

R$^7$ is hydrogen atom, alkali metal atom or C$_1$-C$_8$ alkyl group;

R' and R" are, independently, hydrogen atom or C$_1$-C$_8$ alkyl group, or R' and R" are taken together to form an alicyclic structure;

R$^{19}$ is hydrogen atom, or C$_1$-C$_8$ alkyl group optionally substituted with hydroxy group or ether group, or a pharmacologically acceptable ester or salt thereof, in an amount effective to treat or prevent said diseases.

11. A pharmaceutical composition for preventing or treating hypertension, congestive heart failure, renal failure, glaucoma or hyperuricemia which comprises as an active ingredient an imidazole derivative represented by the general formula:

wherein

Y is cyano group, 1H-tetrazol-5-yl group or alkali metal salt thereof, or —CO$_2$R$^7$ group;

$R^2$, $R^3$, $R^4$ and $R^5$ are, independently, hydrogen atom or $C_1$-$C_8$ alkyl group, or $R^2$ and $R^3$, or $R^4$ and $R^5$ are taken together to form =O bond;

is single bond or double bond;

$C(R^{13})$ $C(R^{14})$ $C(R^{15})$ $C(R^{17})$ is single bond, double bond or diene bond;

$R^{13}$, $R^{14}$, $R^{15}$ and $R^{17}$ are, independently, hydrogen atom, $C_1$-$C_8$ alkyl group, $C_1$-$C_8$ fluoroalkyl group, —C(R')(R")—OR$^{19}$ group, —(CH$_2$)$_j$—CO$_2$R$^7$ group, —(CH$_2$)$_j$—CN group, —(CH$_2$)$_j$—C(=O)R' group, —(CH$_2$)$_j$CONR'R" group or —(CH$_2$)$_j$—Aryl group, wherein j is 0, 1 or 2, wherein Aryl is phenyl group, pyridyl group, pyrimidinyl, pyridazinyl group, furyl group, thenyl group, pyrazolinyl group, oxazolyl group, thiazolyl group, oxadiazolyl group or isoxazolyl group which may be substituted with halogen atom, $C_1$-$C_8$ alkyl group, hydroxy group, $C_1$-$C_8$ alkoxy group, nitro group or cyano group;

$R^7$ is hydrogen atom, alkali metal atom or $C_1$-$C_8$ alkyl group;

R' and R" are, independently, hydrogen atom or $C_1$-$C_8$ alkyl group, or R' and R" are taken together to form an alicyclic structure;

$R^{19}$ is hydrogen atom, or $C_1$-$C_8$ alkyl group optionally substituted with hydroxy group or ether group, or a pharmacologically acceptable ester or salt thereof, in an amount effective to treat or prevent said diseases.

12. A pharmaceutical composition comprising
(a) a compound of claim 1, in an amount effective to partially or totally block the angiotensin II receptor; and
(b) a pharmaceutically acceptable carrier.

* * * * *